United States Patent
Heitzmann et al.

(10) Patent No.: US 11,925,578 B2
(45) Date of Patent: Mar. 12, 2024

(54) DRUG DELIVERY IMPLANTS WITH BI-DIRECTIONAL DELIVERY CAPACITY

(71) Applicant: GLAUKOS CORPORATION, San Clemente, CA (US)

(72) Inventors: Harold A. Heitzmann, Irvine, CA (US); Thomas W. Burns, Dana Point, CA (US); David S. Haffner, Mission Viejo, CA (US)

(73) Assignee: Glaukos Corporation, Aliso Viejo, CA (US)

( * ) Notice: Subject to any disclaimer, the term of this patent is extended or adjusted under 35 U.S.C. 154(b) by 48 days.

(21) Appl. No.: 15/756,925

(22) PCT Filed: Sep. 1, 2016

(86) PCT No.: PCT/US2016/049996
§ 371 (c)(1),
(2) Date: Mar. 1, 2018

(87) PCT Pub. No.: WO2017/040853
PCT Pub. Date: Mar. 9, 2017

(65) Prior Publication Data
US 2018/0303665 A1 Oct. 25, 2018

Related U.S. Application Data

(60) Provisional application No. 62/213,573, filed on Sep. 2, 2015.

(51) Int. Cl.
*A61F 9/00* (2006.01)
*A61K 9/00* (2006.01)
(Continued)

(52) U.S. Cl.
CPC .......... *A61F 9/0017* (2013.01); *A61K 9/0051* (2013.01); *A61F 9/00781* (2013.01);
(Continued)

(58) Field of Classification Search
CPC ................ A61F 9/0017; A61F 9/00781; A61F 2250/0067; A61F 2250/0068;
(Continued)

(56) References Cited

U.S. PATENT DOCUMENTS 663,670 A 12/1900 Wiswall
2,031,754 A 2/1936 Mills
(Continued)

FOREIGN PATENT DOCUMENTS

AU 200072059 A1 7/2001
AU 2004264913 12/2011
(Continued)

OTHER PUBLICATIONS

US 7,524,280 B2, 04/2009, Connors et al. (withdrawn)
(Continued)

*Primary Examiner* — Nathan R Price
*Assistant Examiner* — Tania Ismail
(74) *Attorney, Agent, or Firm* — Knobbe, Martens, Olson & Bear, LLP

(57) ABSTRACT

Certain aspects relate to drug delivery devices and methods for the treatment of ocular disorders requiring targeted and controlled administration of a drug to an interior portion of the eye. In several embodiments, the devices are capable of controlled release of two or more drugs, the release of each drug into a different ocular space (e.g., an ocular compartment versus an ocular fluid outflow pathway).

20 Claims, 87 Drawing Sheets

(51) Int. Cl.
*A61F 9/007* (2006.01)
*A61M 31/00* (2006.01)

(52) U.S. Cl.
CPC .......... *A61F 2250/0067* (2013.01); *A61F 2250/0068* (2013.01); *A61K 9/00* (2013.01); *A61K 9/0004* (2013.01); *A61K 9/0024* (2013.01); *A61K 9/009* (2013.01); *A61K 9/0092* (2013.01); *A61K 9/0097* (2013.01); *A61M 31/002* (2013.01)

(58) Field of Classification Search
CPC ...... A61K 9/0051; A61K 9/00; A61K 9/0004; A61K 9/0024; A61K 9/009; A61K 9/0097; A61K 9/0092; A61M 31/002
See application file for complete search history.

(56) References Cited

U.S. PATENT DOCUMENTS

| | | |
|---|---|---|
| 2,127,903 A | 8/1938 | Bowen |
| 3,159,161 A | 12/1964 | Ness |
| 3,416,530 A | 12/1968 | Ness |
| 3,710,795 A | 1/1973 | Higuchi et al. |
| 3,717,151 A | 2/1973 | Collett |
| 3,788,327 A | 1/1974 | Donowitz et al. |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Aklyama |
| 3,948,871 A | 4/1976 | Butterfield et al. |
| 3,949,750 A | 4/1976 | Freeman |
| 3,961,628 A | 6/1976 | Arnold |
| 4,030,480 A | 6/1977 | Meyer |
| 4,034,756 A | 7/1977 | Higuchi et al. |
| 4,037,604 A | 7/1977 | Newkirk |
| 4,043,346 A | 8/1977 | Mobley et al. |
| 4,093,708 A | 6/1978 | Zaffaroni et al. |
| 4,113,088 A | 9/1978 | Binkhorst |
| 4,168,697 A | 9/1979 | Cantekin |
| 4,175,563 A | 11/1979 | Arenberg et al. |
| 4,207,890 A | 6/1980 | Mamajek et al. |
| 4,328,803 A | 5/1982 | Pape |
| 4,402,681 A | 9/1983 | Haas et al. |
| 4,428,746 A | 1/1984 | Mendez |
| 4,449,974 A | 5/1984 | Messingschlager |
| 4,450,150 A | 5/1984 | Sidman |
| 4,457,757 A | 7/1984 | Molteno |
| 4,468,216 A | 8/1984 | Muto |
| 4,501,274 A | 2/1985 | Skjaerpe |
| 4,521,210 A | 6/1985 | Wong |
| 4,554,918 A | 11/1985 | White |
| 4,604,087 A | 8/1986 | Joseph |
| 4,632,842 A | 12/1986 | Karwoski et al. |
| 4,634,418 A | 1/1987 | Binder |
| 4,692,142 A | 9/1987 | Dignam et al. |
| 4,718,907 A | 1/1988 | Karwoski et al. |
| 4,722,724 A | 2/1988 | Schocket |
| 4,733,665 A | 3/1988 | Palmaz |
| 4,736,836 A | 4/1988 | Alongi et al. |
| 4,743,248 A | 5/1988 | Bartoo et al. |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,828,439 A | 5/1989 | Giannuzi |
| 4,846,172 A | 7/1989 | Berlin |
| 4,846,793 A | 7/1989 | Leonard et al. |
| 4,853,224 A | 8/1989 | Wong |
| 4,863,457 A | 9/1989 | Lee |
| 4,878,905 A | 11/1989 | Blass |
| 4,883,864 A | 11/1989 | Scholz |
| 4,886,488 A | 12/1989 | White |
| 4,936,825 A | 6/1990 | Ungerleider |
| 4,946,436 A | 8/1990 | Smith |
| 4,955,881 A | 9/1990 | Eckenhoff |
| 4,968,296 A | 11/1990 | Ritch et al. |
| 4,986,810 A | 1/1991 | Semrad |
| 4,997,652 A | 3/1991 | Wong |
| 5,005,577 A | 4/1991 | Frenekl |
| 5,017,381 A | 5/1991 | Maruyama et al. |
| 5,041,081 A | 8/1991 | Odrich |
| 5,073,163 A | 12/1991 | Lippman |
| 5,092,837 A | 3/1992 | Ritch et al. |
| 5,098,443 A | 3/1992 | Parel et al. |
| 5,116,327 A | 5/1992 | Seder et al. |
| 5,127,901 A | 7/1992 | Odrich |
| 5,128,145 A | 7/1992 | Edgren et al. |
| 5,139,502 A | 8/1992 | Berg et al. |
| 5,164,188 A | 11/1992 | Wong |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,246,451 A | 9/1993 | Trescony et al. |
| 5,248,231 A | 9/1993 | Denham et al. |
| 5,300,020 A | 4/1994 | L'Esperance, Jr. |
| 5,318,513 A | 6/1994 | Leib et al. |
| 5,324,280 A | 6/1994 | Wong et al. |
| 5,326,345 A | 7/1994 | Price, Jr. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,358,492 A | 10/1994 | Feibus |
| 5,360,399 A | 11/1994 | Stegmann |
| 5,364,374 A | 11/1994 | Morrison et al. |
| 5,370,607 A | 12/1994 | Memmen |
| 5,370,641 A | 12/1994 | O'Donnell, Jr. |
| 5,372,577 A | 12/1994 | Ungerleider |
| 5,378,474 A | 1/1995 | Morella et al. |
| 5,378,475 A | 1/1995 | Smith et al. |
| 5,380,290 A | 1/1995 | Makower et al. |
| 5,384,333 A | 1/1995 | Davis et al. |
| 5,397,300 A | 3/1995 | Baerveldt et al. |
| 5,433,701 A | 7/1995 | Rubinstein |
| 5,443,505 A | 8/1995 | Wong et al. |
| 5,454,796 A | 10/1995 | Krupin |
| 5,464,450 A | 11/1995 | Buscemi et al. |
| 5,466,233 A | 11/1995 | Weiner et al. |
| 5,476,445 A | 12/1995 | Baerveldt et al. |
| 5,486,165 A | 1/1996 | Stegmann |
| 5,500,465 A | 3/1996 | Krishnan et al. |
| 5,502,052 A | 3/1996 | DeSantis |
| 5,516,522 A | 5/1996 | Peyman et al. |
| 5,520,631 A | 5/1996 | Nordquist et al. |
| 5,547,993 A | 8/1996 | Miki |
| 5,558,629 A | 9/1996 | Baerveldt et al. |
| 5,558,630 A | 9/1996 | Fisher |
| 5,562,641 A | 10/1996 | Flomenblit et al. |
| RE35,390 E | 12/1996 | Smith |
| 5,599,534 A | 2/1997 | Himmelstein et al. |
| 5,626,558 A | 5/1997 | Suson |
| 5,626,559 A | 5/1997 | Solomon |
| 5,629,008 A | 5/1997 | Lee |
| 5,639,278 A | 6/1997 | Dereume et al. |
| 5,643,321 A | 7/1997 | McDevitt |
| 5,645,856 A | 7/1997 | Lacy et al. |
| 5,651,782 A | 7/1997 | Simon et al. |
| 5,652,014 A | 7/1997 | Galin et al. |
| 5,652,236 A | 7/1997 | Krauss |
| 5,663,205 A | 9/1997 | Ogawa et al. |
| 5,665,114 A | 9/1997 | Weadock et al. |
| 5,670,161 A | 9/1997 | Healy et al. |
| 5,676,679 A | 10/1997 | Simon et al. |
| 5,681,275 A | 10/1997 | Ahmed |
| 5,686,425 A | 11/1997 | Lee |
| 5,702,414 A | 12/1997 | Richter et al. |
| 5,702,419 A | 12/1997 | Berry et al. |
| 5,704,907 A | 1/1998 | Nordquist et al. |
| 5,709,854 A | 1/1998 | Griffith-Cima et al. |
| 5,713,844 A | 2/1998 | Peyman |
| 5,722,948 A | 3/1998 | Gross |

(56) References Cited

U.S. PATENT DOCUMENTS

| | | |
|---|---|---|
| 5,723,005 A | 3/1998 | Herrick |
| 5,725,493 A | 3/1998 | Avery et al. |
| 5,725,529 A | 3/1998 | Nicholson et al. |
| 5,733,327 A | 3/1998 | Igaki et al. |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,242 A | 6/1998 | Wong et al. |
| 5,766,243 A | 6/1998 | Christensen et al. |
| 5,767,079 A | 6/1998 | Glaser et al. |
| 5,773,019 A | 6/1998 | Ashton et al. |
| 5,785,674 A | 7/1998 | Mateen |
| 5,800,376 A | 9/1998 | Vaskelis |
| 5,807,302 A | 9/1998 | Wandel |
| 5,810,870 A | 9/1998 | Myers et al. |
| 5,814,620 A | 9/1998 | Robinson et al. |
| 5,824,071 A | 10/1998 | Nelson et al. |
| 5,824,072 A | 10/1998 | Wong |
| 5,830,171 A | 11/1998 | Wallace |
| 5,865,831 A | 2/1999 | Cozean et al. |
| 5,868,697 A | 2/1999 | Richter et al. |
| 5,869,079 A | 2/1999 | Wong et al. |
| 5,869,468 A | 2/1999 | Freeman |
| 5,879,319 A | 3/1999 | Pynson et al. |
| 5,882,327 A | 3/1999 | Jacob |
| 5,891,084 A | 4/1999 | Lee |
| 5,893,837 A | 4/1999 | Eagles et al. |
| 5,902,598 A | 5/1999 | Chen et al. |
| 5,908,449 A | 6/1999 | Bruchman et al. |
| 5,913,852 A | 6/1999 | Magram |
| 5,925,342 A | 7/1999 | Adorante et al. |
| 5,932,299 A | 8/1999 | Katoot |
| 5,952,378 A | 9/1999 | Stjerschantz et al. |
| 5,980,928 A | 11/1999 | Terry |
| 5,981,598 A | 11/1999 | Tatton |
| 6,004,302 A | 12/1999 | Brierley |
| 6,007,510 A | 12/1999 | Nigam |
| 6,007,511 A | 12/1999 | Prywes |
| 6,033,434 A | 3/2000 | Borghi |
| 6,050,970 A | 4/2000 | Baeverldt |
| 6,059,812 A | 5/2000 | Clerc et al. |
| 6,060,463 A | 5/2000 | Freeman |
| 6,063,116 A | 5/2000 | Kelleher |
| 6,063,396 A | 5/2000 | Kelleher |
| 6,077,299 A | 6/2000 | Adelberg et al. |
| 6,102,045 A | 8/2000 | Nordquist et al. |
| 6,110,912 A | 8/2000 | Kaufman et al. |
| 6,129,761 A | 10/2000 | Hubbell |
| 6,142,990 A | 11/2000 | Burk |
| 6,146,387 A | 11/2000 | Trott et al. |
| 6,159,458 A | 12/2000 | Bowman et al. |
| 6,165,210 A | 12/2000 | Lau et al. |
| 6,168,575 B1 | 1/2001 | Soltanpour |
| 6,174,305 B1 | 1/2001 | Mikus et al. |
| 6,186,974 B1 | 2/2001 | Allan et al. |
| 6,196,993 B1 | 3/2001 | Cohan et al. |
| 6,217,895 B1 | 4/2001 | Guo et al. |
| 6,228,873 B1 | 5/2001 | Brandt et al. |
| 6,231,597 B1 | 5/2001 | Deem et al. |
| 6,231,600 B1 | 5/2001 | Zhong |
| 6,231,853 B1 | 5/2001 | Hillman et al. |
| 6,241,721 B1 | 6/2001 | Cozean et al. |
| 6,248,363 B1 | 6/2001 | Patel et al. |
| 6,251,090 B1 | 6/2001 | Avery et al. |
| 6,261,256 B1 | 7/2001 | Ahmed |
| 6,268,398 B1 | 7/2001 | Ghosh et al. |
| 6,274,138 B1 | 8/2001 | Bandman et al. |
| 6,290,684 B1 | 9/2001 | Herrick |
| 6,299,895 B1 | 10/2001 | Hammang et al. |
| 6,306,114 B1 | 10/2001 | Freeman et al. |
| 6,306,120 B1 | 10/2001 | Tan |
| 6,328,758 B1 | 12/2001 | Tornier et al. |
| 6,331,313 B1 | 12/2001 | Wong et al. |
| 6,348,042 B1 | 2/2002 | Warren, Jr. |
| 6,358,222 B1 | 3/2002 | Grundei |
| 6,363,938 B2 | 4/2002 | Saadat et al. |
| 6,369,116 B1 | 4/2002 | Wong et al. |
| 6,375,642 B1 | 4/2002 | Grieshaber et al. |
| 6,375,972 B1 | 4/2002 | Guo et al. |
| 6,378,526 B1 | 4/2002 | Bowman |
| 6,397,849 B1 | 6/2002 | Bowman et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,423,001 B1 | 7/2002 | Abreu |
| 6,436,427 B1 | 8/2002 | Hammang et al. |
| 6,443,893 B1 | 9/2002 | Schnakenberg et al. |
| 6,450,984 B1 | 9/2002 | Lynch et al. |
| 6,454,787 B1 | 9/2002 | Maddalo et al. |
| 6,455,062 B1 | 9/2002 | Olejnik et al. |
| 6,464,724 B1 | 10/2002 | Lynch et al. |
| 6,468,283 B1 | 10/2002 | Richter et al. |
| 6,494,857 B1 | 12/2002 | Neuhann |
| 6,503,231 B1 | 1/2003 | Prausnitz et al. |
| 6,506,411 B2 | 1/2003 | Hunter et al. |
| 6,508,779 B1 | 1/2003 | Suson |
| 6,517,483 B2 | 2/2003 | Park et al. |
| 6,524,275 B1 | 2/2003 | Lynch et al. |
| 6,533,768 B1 | 3/2003 | Hill |
| 6,533,769 B2 | 3/2003 | Homen |
| 6,544,249 B1 | 4/2003 | Yu et al. |
| 6,548,078 B2 | 4/2003 | Guo et al. |
| 6,551,618 B2 | 4/2003 | Baird et al. |
| 6,562,374 B1 | 5/2003 | Han et al. |
| 6,576,219 B2 | 6/2003 | Brandt et al. |
| 6,582,453 B1 | 6/2003 | Tran et al. |
| 6,585,753 B2 | 7/2003 | Eder et al. |
| 6,589,198 B1 | 7/2003 | Soltanpour et al. |
| 6,589,203 B1 | 7/2003 | Mitrev |
| 6,595,945 B2 | 7/2003 | Brown |
| 6,605,053 B1 | 8/2003 | Kamm et al. |
| 6,623,283 B1 | 9/2003 | Torigian et al. |
| 6,626,858 B2 | 9/2003 | Lynch et al. |
| 6,638,239 B1 | 10/2003 | Bergheim et al. |
| 6,649,184 B2 | 11/2003 | Hammang et al. |
| 6,656,490 B1 | 12/2003 | Steinemann et al. |
| 6,660,870 B1 | 12/2003 | Ruskinko et al. |
| 6,666,213 B2 | 12/2003 | Svadovskiy |
| 6,666,841 B2 | 12/2003 | Gharib et al. |
| 6,682,500 B2 | 1/2004 | Soltanpour et al. |
| 6,692,759 B1 | 2/2004 | Wong et al. |
| 6,693,093 B2 | 2/2004 | Chowdhary et al. |
| 6,699,211 B2 | 3/2004 | Savage |
| 6,699,493 B2 | 3/2004 | Wong |
| 6,712,764 B2 | 3/2004 | Jeffries et al. |
| 6,726,666 B2 | 4/2004 | de Juan, Jr. |
| 6,726,918 B1 | 4/2004 | Wong et al. |
| D490,152 S | 5/2004 | Myall et al. |
| 6,730,056 B1 | 5/2004 | Ghaem et al. |
| 6,736,791 B1 | 5/2004 | Tu et al. |
| 6,758,837 B2 | 7/2004 | Peclat et al. |
| 6,764,698 B1 | 7/2004 | Byun et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,893,413 B2 | 5/2005 | Martin |
| 6,939,298 B2 | 9/2005 | Brown et al. |
| 6,939,299 B1 | 9/2005 | Petersen et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,981,958 B1 | 1/2006 | Gharib et al. |
| 6,998,137 B2 | 2/2006 | Shih et al. |
| 7,033,603 B2 | 4/2006 | Nelson et al. |
| 7,048,946 B1 | 5/2006 | Wong et al. |
| 7,083,802 B2 | 8/2006 | Peyman |
| 7,094,225 B2 | 8/2006 | Tu et al. |
| 7,094,226 B2 | 8/2006 | Yaacobi |
| 7,101,402 B2 | 9/2006 | Phelps et al. |
| 7,101,567 B1 | 9/2006 | Sano et al. |
| 7,135,009 B2 | 11/2006 | Tu et al. |
| 7,144,616 B1 | 12/2006 | Unger et al. |

(56) References Cited

U.S. PATENT DOCUMENTS

| | | |
|---|---|---|
| 7,163,543 B2 | 1/2007 | Smedley et al. |
| 7,182,747 B2 | 2/2007 | Kwon |
| 7,186,232 B1 | 3/2007 | Smedley et al. |
| 7,192,412 B1 | 3/2007 | Zhou et al. |
| 7,192,484 B2 | 3/2007 | Chappa et al. |
| 7,195,774 B2 | 3/2007 | Carvalho et al. |
| 7,220,238 B2 | 5/2007 | Lynch et al. |
| 7,226,435 B2 | 6/2007 | Darnell |
| 7,252,006 B2 | 8/2007 | Tai et al. |
| 7,261,529 B2 | 8/2007 | Persyn et al. |
| 7,273,475 B2 | 9/2007 | Tu et al. |
| 7,294,115 B1 | 11/2007 | Wilk |
| 7,297,130 B2 | 11/2007 | Bergheim et al. |
| 7,331,984 B2 | 2/2008 | Tu et al. |
| 7,364,564 B2 | 4/2008 | Sniegowski et al. |
| 7,402,156 B2 | 7/2008 | Kiehlbauch et al. |
| 7,431,710 B2 | 10/2008 | Tu et al. |
| 7,445,793 B2 | 11/2008 | Niwa et al. |
| 7,488,303 B1 | 2/2009 | Haffner et al. |
| 7,494,487 B2 | 2/2009 | Timm |
| 7,496,174 B2 | 2/2009 | Gertner et al. |
| 7,513,893 B2 | 4/2009 | Soroudi |
| RE40,722 E | 6/2009 | Chappa |
| 7,563,241 B2 | 7/2009 | Tu et al. |
| 7,563,255 B2 | 7/2009 | Adamis et al. |
| 7,585,517 B2 | 9/2009 | Cooper et al. |
| 7,592,016 B2 | 9/2009 | Wong et al. |
| 7,638,137 B2 | 11/2009 | Rathjen et al. |
| 7,641,627 B2 | 1/2010 | Camras et al. |
| 7,678,065 B2 | 3/2010 | Haffner et al. |
| 7,678,078 B1 | 3/2010 | Peyman et al. |
| 7,680,244 B2 | 3/2010 | Gertner et al. |
| 7,680,245 B2 | 3/2010 | Gertner |
| 7,695,135 B1 | 4/2010 | Rosenthal |
| 7,697,663 B2 | 4/2010 | Gertner |
| 7,708,711 B2 | 5/2010 | Tu et al. |
| 7,709,049 B2 | 5/2010 | Chappa |
| 7,749,528 B2 | 7/2010 | DeCarvalho et al. |
| 7,776,024 B2 | 8/2010 | Santini et al. |
| 7,794,751 B2 | 9/2010 | Chudzik et al. |
| 7,811,252 B2 | 10/2010 | Dacquay et al. |
| 7,811,268 B2 | 10/2010 | Maldon Ado Bas |
| 7,815,592 B2 | 10/2010 | Coroneo |
| 7,822,175 B2 | 10/2010 | Gertner |
| 7,846,468 B2 | 12/2010 | Wong |
| 7,850,637 B2 | 12/2010 | Lynch et al. |
| 7,857,782 B2 | 12/2010 | Tu et al. |
| 7,862,531 B2 | 1/2011 | Yaron et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,887,517 B2 | 2/2011 | Santos et al. |
| 7,887,521 B2 | 2/2011 | Dacquey et al. |
| 7,951,155 B2 | 5/2011 | Smedley et al. |
| 7,953,203 B2 | 5/2011 | Gertner et al. |
| 7,958,840 B2 | 6/2011 | Chappa |
| 7,967,772 B2 | 6/2011 | McKenzie et al. |
| 7,978,819 B2 | 7/2011 | Gertner et al. |
| 7,985,415 B2 | 7/2011 | Giroux |
| 7,997,460 B2 | 8/2011 | Pardes et al. |
| 8,007,459 B2 | 8/2011 | Haffner et al. |
| D645,489 S | 9/2011 | Gille et al. |
| D645,490 S | 9/2011 | Gille et al. |
| 8,012,136 B2 | 9/2011 | Collins, Jr. et al. |
| 8,034,016 B2 | 10/2011 | Yaron et al. |
| 8,034,105 B2 | 10/2011 | Stegmann et al. |
| 8,059,784 B2 | 11/2011 | Gertner |
| 8,060,211 B2 | 11/2011 | Greenberg et al. |
| 8,062,244 B2 | 11/2011 | Tu et al. |
| 8,062,657 B2 | 11/2011 | Edelman et al. |
| 8,070,290 B2 | 12/2011 | Gille et al. |
| 8,071,120 B2 | 12/2011 | Wong |
| 8,073,105 B2 | 12/2011 | Gertner et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,152,752 B2 | 4/2012 | Lynch et al. |
| 8,235,053 B2 | 8/2012 | Sanchez et al. |
| 8,241,656 B2 | 8/2012 | Chudzik et al. |
| 8,267,882 B2 | 9/2012 | Euteneuer et al. |
| 8,267,995 B2 | 9/2012 | Castillejos |
| 8,273,050 B2 | 9/2012 | Bergheim et al. |
| 8,273,366 B2 | 9/2012 | Chauhan et al. |
| 8,277,830 B2 | 10/2012 | De Juan, Jr. et al. |
| 8,282,593 B2 | 10/2012 | Dacey, Jr. et al. |
| 8,298,578 B2 | 10/2012 | De Juan, Jr. et al. |
| 8,333,726 B2 | 12/2012 | Rapaki et al. |
| 8,333,742 B2 | 12/2012 | Bergheim et al. |
| 8,337,445 B2 | 12/2012 | Tu et al. |
| 8,343,086 B2 | 1/2013 | Dacey, Jr. et al. |
| 8,348,877 B2 | 1/2013 | Tu et al. |
| 8,366,652 B2 | 2/2013 | Dacey et al. |
| 8,388,568 B2 | 3/2013 | Lynch et al. |
| 8,404,269 B2 | 3/2013 | Snyder et al. |
| 8,414,517 B2 | 4/2013 | Dacey, Jr. et al. |
| 8,414,518 B2 | 4/2013 | Schieber et al. |
| 8,419,673 B2 | 4/2013 | Rickard |
| 8,425,929 B2 | 4/2013 | Huang et al. |
| 8,439,972 B2 | 5/2013 | Badawi et al. |
| 8,440,216 B2 | 5/2013 | Huang et al. |
| 8,444,589 B2 | 5/2013 | Silvestrini |
| 8,452,391 B2 | 5/2013 | Roy |
| 8,454,582 B2 | 6/2013 | deJuan et al. |
| 8,486,031 B2 | 7/2013 | Bogdan |
| 8,486,052 B2 | 7/2013 | Varner et al. |
| 8,506,515 B2 | 8/2013 | Burns et al. |
| 8,529,492 B2 | 9/2013 | Luke et al. |
| 8,545,431 B2 | 10/2013 | Rickard |
| 8,579,846 B2 | 11/2013 | Tu et al. |
| 8,579,848 B2 | 11/2013 | Field et al. |
| 8,585,631 B2 | 11/2013 | Dacquay |
| 8,585,664 B2 | 11/2013 | Dos Santos et al. |
| 8,603,024 B2 | 12/2013 | Bohm et al. |
| 8,617,094 B2 | 12/2013 | Smedley et al. |
| 8,642,066 B2 | 2/2014 | Abe et al. |
| 8,656,958 B2 | 2/2014 | Unger et al. |
| 8,657,804 B2 | 2/2014 | Horne et al. |
| 8,721,580 B2 | 5/2014 | Rickard et al. |
| 8,753,305 B2 | 6/2014 | Field et al. |
| 8,771,217 B2 | 7/2014 | Lynch et al. |
| 8,771,220 B2 | 7/2014 | Nissan |
| 8,801,648 B2 | 8/2014 | Bergheim et al. |
| 8,808,219 B2 | 8/2014 | Bergheim et al. |
| 8,808,224 B2 | 8/2014 | Rickard |
| 8,814,820 B2 | 8/2014 | Bergheim et al. |
| 8,840,578 B2 | 9/2014 | Dos Santos et al. |
| 8,864,701 B2 | 10/2014 | Dos Santos et al. |
| 8,882,781 B2 | 11/2014 | Smedley et al. |
| 8,956,320 B2 | 2/2015 | Ovchinnikov et al. |
| 8,986,240 B2 | 3/2015 | Dos Santos et al. |
| 8,998,838 B2 | 4/2015 | Yalamanchili |
| 9,022,967 B2 | 5/2015 | Oliver et al. |
| 9,066,782 B2 | 6/2015 | Tu et al. |
| 9,072,588 B2 | 7/2015 | Bohm et al. |
| 9,125,721 B2 | 9/2015 | Field |
| 9,132,034 B2 | 9/2015 | Dos Santos |
| 9,155,653 B2 | 10/2015 | Field |
| 9,155,654 B2 | 10/2015 | Tu et al. |
| 9,173,775 B2 | 11/2015 | Haffner et al. |
| 9,220,632 B2 | 12/2015 | Smedley et al. |
| 9,226,851 B2 | 1/2016 | Gunn |
| 9,283,115 B2 | 3/2016 | Lind et al. |
| 9,289,324 B2 | 3/2016 | Johnson et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,585,789 B2 | 3/2017 | Silvestrini et al. |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,603,741 B2 | 3/2017 | Berlin |

(56) References Cited

U.S. PATENT DOCUMENTS

| | | |
|---|---|---|
| 9,636,255 B2 | 5/2017 | Haffner et al. |
| 9,668,915 B2 | 6/2017 | Haffner et al. |
| 9,730,638 B2 | 8/2017 | Haffner et al. |
| 9,789,001 B2 | 10/2017 | Tu et al. |
| 9,827,143 B2 | 11/2017 | Lynch |
| 9,833,357 B2 | 12/2017 | Berlin |
| 9,962,290 B2 | 5/2018 | Burns et al. |
| 9,987,472 B2 | 6/2018 | Tu et al. |
| 9,993,368 B2 | 6/2018 | Bergheim et al. |
| D833,008 S | 11/2018 | Kalina, Jr. et al. |
| 10,159,601 B2 | 12/2018 | Berlin |
| 10,188,551 B2 | 1/2019 | Rangel-Friedman et al. |
| 10,206,813 B2 | 2/2019 | Haffner et al. |
| D846,738 S | 4/2019 | Kalina, Jr. et al. |
| 10,245,178 B1 | 4/2019 | Heitzmann et al. |
| 10,271,989 B2 | 4/2019 | Haffner et al. |
| 10,285,853 B2 | 5/2019 | Rangel-Friedman et al. |
| 10,285,856 B2 | 5/2019 | Tu et al. |
| 10,406,029 B2 | 9/2019 | Tu et al. |
| 10,485,701 B2 | 11/2019 | Haffner et al. |
| 10,485,702 B2 | 11/2019 | Bergheim et al. |
| 10,492,950 B2 | 12/2019 | Lynch et al. |
| 10,499,809 B2 | 12/2019 | Kalina, Jr. et al. |
| 10,517,759 B2 | 12/2019 | Crimaldi et al. |
| 10,568,762 B2 | 2/2020 | Lynch et al. |
| D886,997 S | 6/2020 | Kalina, Jr. et al. |
| 10,674,906 B2 | 6/2020 | Kalina, Jr. et al. |
| 10,813,789 B2 | 10/2020 | Haffner et al. |
| D901,683 S | 11/2020 | Kalina, Jr. et al. |
| 10,828,195 B2 | 11/2020 | Burns et al. |
| 10,828,473 B2 | 11/2020 | Haffner et al. |
| 10,959,941 B2 | 3/2021 | Haffner |
| 11,019,996 B2 | 6/2021 | Kalina, Jr. et al. |
| 11,019,997 B2 | 6/2021 | Kalina, Jr. et al. |
| 11,116,625 B2 | 9/2021 | Kalina, Jr. |
| D938,585 S | 12/2021 | Kalina, Jr. et al. |
| 11,197,780 B2 | 12/2021 | Haffner et al. |
| 11,253,394 B2 | 2/2022 | Haffner et al. |
| 11,318,043 B2 | 5/2022 | Heitzmann et al. |
| 11,376,040 B2 | 7/2022 | Kalina, Jr. et al. |
| 11,426,306 B2 | 8/2022 | Haffner et al. |
| 11,523,938 B2 | 12/2022 | Rangel-Friedman et al. |
| 11,559,430 B2 | 1/2023 | Crimaldi et al. |
| 11,564,833 B2 | 1/2023 | Burns et al. |
| 11,744,458 B2 | 9/2023 | Kalina, Jr. et al. |
| 2001/0000527 A1 | 4/2001 | Yaron et al. |
| 2001/0053873 A1 | 12/2001 | Schaaf et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0052640 A1 | 5/2002 | Bigus et al. |
| 2002/0071866 A1 | 6/2002 | Geerke |
| 2002/0082591 A1 | 6/2002 | Haefliger |
| 2002/0087111 A1 | 7/2002 | Ethier et al. |
| 2002/0099434 A1 | 7/2002 | Buscemi et al. |
| 2002/0102307 A1 | 8/2002 | Guo et al. |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0111601 A1 | 8/2002 | Thompson |
| 2002/0111603 A1 | 8/2002 | Cheikh |
| 2002/0127250 A1 | 9/2002 | Guo et al. |
| 2002/0128704 A1 | 9/2002 | Daum et al. |
| 2002/0133168 A1 | 9/2002 | Smedley et al. |
| 2002/0143284 A1 | 10/2002 | Tu et al. |
| 2002/0156413 A1 | 10/2002 | Williams et al. |
| 2002/0169468 A1 | 11/2002 | Brown |
| 2002/0176844 A1 | 11/2002 | Ng et al. |
| 2002/0177856 A1 | 11/2002 | Richter et al. |
| 2002/0182185 A1 | 12/2002 | Wong |
| 2002/0188282 A1 | 12/2002 | Greenberg |
| 2002/0193725 A1 | 12/2002 | Odrich |
| 2002/0197298 A1 | 12/2002 | Yaacobi |
| 2003/0003129 A1 | 1/2003 | Yaacobi |
| 2003/0004209 A1 | 1/2003 | Hunter et al. |
| 2003/0010638 A1 | 1/2003 | Hansord et al. |
| 2003/0018295 A1 | 1/2003 | Henley et al. |
| 2003/0019833 A1 | 1/2003 | Unger et al. |
| 2003/0021828 A1 | 1/2003 | Guo et al. |
| 2003/0055372 A1 | 3/2003 | Lynch et al. |
| 2003/0060752 A1 | 3/2003 | Bergheim et al. |
| 2003/0060873 A1 | 3/2003 | Gertner et al. |
| 2003/0064088 A1 | 4/2003 | Carvalho et al. |
| 2003/0079329 A1 | 5/2003 | Yaron et al. |
| 2003/0083646 A1 | 5/2003 | Sirhan et al. |
| 2003/0093063 A1 | 5/2003 | Carr et al. |
| 2003/0095995 A1 | 5/2003 | Wong et al. |
| 2003/0097117 A1 | 5/2003 | Buono |
| 2003/0097151 A1 | 5/2003 | Smedley et al. |
| 2003/0108588 A1 | 6/2003 | Chen et al. |
| 2003/0119000 A1 | 6/2003 | Polansky |
| 2003/0135149 A1 | 7/2003 | Cullen et al. |
| 2003/0139729 A1 | 7/2003 | Stegmann et al. |
| 2003/0139784 A1 | 7/2003 | Morimoto et al. |
| 2003/0143274 A1 | 7/2003 | Viegas et al. |
| 2003/0153863 A1 | 8/2003 | Patel |
| 2003/0175324 A1 | 9/2003 | Robinson et al. |
| 2003/0176854 A1 | 9/2003 | Rodstrom |
| 2003/0181848 A1 | 9/2003 | Bergheim et al. |
| 2003/0187384 A1 | 10/2003 | Bergheim et al. |
| 2003/0195438 A1 | 10/2003 | Petillo |
| 2003/0203003 A1 | 10/2003 | Nelson et al. |
| 2003/0208163 A1 | 11/2003 | Yaron et al. |
| 2003/0211071 A1 | 11/2003 | Bologna et al. |
| 2003/0212383 A1 | 11/2003 | Cote et al. |
| 2003/0215528 A1* | 11/2003 | Graham ................. A61K 31/00 424/718 |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0013702 A1 | 1/2004 | Glover |
| 2004/0018238 A1 | 1/2004 | Shukla |
| 2004/0022853 A1 | 2/2004 | Ashton et al. |
| 2004/0024345 A1 | 2/2004 | Gharib et al. |
| 2004/0034357 A1* | 2/2004 | Beane ..................... A61L 31/16 606/232 |
| 2004/0057979 A1 | 3/2004 | Wong et al. |
| 2004/0059248 A1 | 3/2004 | Messner et al. |
| 2004/0076676 A1 | 4/2004 | Tojo et al. |
| 2004/0082939 A1 | 4/2004 | Berlin |
| 2004/0088048 A1 | 5/2004 | Richter et al. |
| 2004/0092548 A1 | 5/2004 | Embleton et al. |
| 2004/0092856 A1 | 5/2004 | Dahan |
| 2004/0092911 A1 | 5/2004 | Yaacobi |
| 2004/0102729 A1 | 5/2004 | Haffner et al. |
| 2004/0111050 A1 | 6/2004 | Smedley et al. |
| 2004/0111080 A1 | 6/2004 | Harper et al. |
| 2004/0115268 A1 | 6/2004 | Ashton et al. |
| 2004/0127843 A1 | 7/2004 | Tu et al. |
| 2004/0131654 A1 | 7/2004 | Yaacobi |
| 2004/0131655 A1 | 7/2004 | Yaacobi |
| 2004/0137059 A1 | 7/2004 | Nivaggioli et al. |
| 2004/0147870 A1 | 7/2004 | Burns et al. |
| 2004/0151714 A1 | 8/2004 | Soll |
| 2004/0154946 A1 | 8/2004 | Solovay et al. |
| 2004/0162545 A1 | 8/2004 | Brown et al. |
| 2004/0163652 A1 | 8/2004 | Watson |
| 2004/0175410 A1 | 9/2004 | Ashton et al. |
| 2004/0176341 A1 | 9/2004 | Chou et al. |
| 2004/0176737 A1 | 9/2004 | Henley et al. |
| 2004/0180075 A1 | 9/2004 | Robinson et al. |
| 2004/0186533 A1 | 9/2004 | Greenberg et al. |
| 2004/0186534 A1 | 9/2004 | Shadduck |
| 2004/0193095 A1 | 9/2004 | Shadduck |
| 2004/0193262 A1 | 9/2004 | Shadduck |
| 2004/0208909 A1 | 10/2004 | Brubaker et al. |
| 2004/0208910 A1 | 10/2004 | Ashton et al. |
| 2004/0210181 A1 | 10/2004 | Vass et al. |
| 2004/0210185 A1 | 10/2004 | Tu et al. |
| 2004/0215126 A1 | 10/2004 | Ahmed |
| 2004/0216749 A1 | 11/2004 | Tu |
| 2004/0219181 A1 | 11/2004 | Viscasillas |
| 2004/0220537 A1 | 11/2004 | Embleton et al. |

(56) References Cited

U.S. PATENT DOCUMENTS

| | | |
|---|---|---|
| 2004/0225250 A1 | 11/2004 | Yablonski |
| 2004/0249404 A1 | 12/2004 | Haefliger |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk, Jr. et al. |
| 2004/0260228 A1 | 12/2004 | Lynch et al. |
| 2005/0008673 A1 | 1/2005 | Snyder et al. |
| 2005/0038498 A1 | 2/2005 | Dubrow et al. |
| 2005/0042293 A1 | 2/2005 | Jackson et al. |
| 2005/0049578 A1 | 3/2005 | Tu et al. |
| 2005/0055075 A1 | 3/2005 | Pinchuk et al. |
| 2005/0064010 A1 | 3/2005 | Cooper et al. |
| 2005/0069893 A1 | 3/2005 | Flammer et al. |
| 2005/0107734 A1 | 5/2005 | Coroneo |
| 2005/0112175 A1 | 5/2005 | Yaacobi |
| 2005/0119601 A9 | 6/2005 | Lynch et al. |
| 2005/0119737 A1 | 6/2005 | Bene et al. |
| 2005/0125003 A1 | 6/2005 | Pinchuk et al. |
| 2005/0137538 A1 | 6/2005 | Kunzler et al. |
| 2005/0159660 A1 | 7/2005 | Montegrande et al. |
| 2005/0165368 A1 | 7/2005 | Py et al. |
| 2005/0171490 A1 * | 8/2005 | Weaver ............... A61M 39/02 604/247 |
| 2005/0171507 A1 | 8/2005 | Christian et al. |
| 2005/0175708 A1 | 8/2005 | Carrasquillo et al. |
| 2005/0181018 A1 | 8/2005 | Peyman |
| 2005/0182350 A1 | 8/2005 | Nigam |
| 2005/0184004 A1 | 8/2005 | Rodgers et al. |
| 2005/0186245 A1 | 8/2005 | Hunter et al. |
| 2005/0186279 A1 | 8/2005 | Guo et al. |
| 2005/0192527 A1 | 9/2005 | Gharib et al. |
| 2005/0208102 A1 | 9/2005 | Schultz |
| 2005/0209549 A1 | 9/2005 | Bergheim et al. |
| 2005/0222537 A1 | 10/2005 | Dinsmoor et al. |
| 2005/0232972 A1 | 10/2005 | Odrich |
| 2005/0240143 A1 | 10/2005 | Dohlman |
| 2005/0244461 A1 | 11/2005 | Nivaggioli et al. |
| 2005/0244464 A1 | 11/2005 | Hughes |
| 2005/0244465 A1 | 11/2005 | Nivaggioli et al. |
| 2005/0244467 A1 | 11/2005 | Nivaggioli et al. |
| 2005/0244470 A1 | 11/2005 | Hughes et al. |
| 2005/0244475 A1 | 11/2005 | Edelman et al. |
| 2005/0244477 A1 | 11/2005 | Hughes et al. |
| 2005/0244500 A1 | 11/2005 | Whitcup et al. |
| 2005/0244506 A1 | 11/2005 | Burke et al. |
| 2005/0249710 A1 | 11/2005 | Wong |
| 2005/0250788 A1 | 11/2005 | Tu et al. |
| 2005/0261624 A1 | 11/2005 | Wilcox |
| 2005/0261641 A1 | 11/2005 | Warchol et al. |
| 2005/0267397 A1 | 12/2005 | Bhalla |
| 2005/0267398 A1 | 12/2005 | Protopsaltis et al. |
| 2005/0273033 A1 | 12/2005 | Grahn et al. |
| 2005/0276841 A1 | 12/2005 | Davis et al. |
| 2005/0277864 A1 | 12/2005 | Haffner et al. |
| 2005/0281861 A1 | 12/2005 | Hughes et al. |
| 2005/0287188 A1 | 12/2005 | Anderson et al. |
| 2005/0288619 A1 | 12/2005 | Savage |
| 2006/0009498 A1 | 1/2006 | Whitcup |
| 2006/0020248 A1 | 1/2006 | Prescott |
| 2006/0020253 A1 | 1/2006 | Prescott |
| 2006/0021623 A1 | 2/2006 | Varner et al. |
| 2006/0024350 A1 | 2/2006 | Miller et al. |
| 2006/0032507 A1 | 2/2006 | Tu |
| 2006/0034929 A1 | 2/2006 | Brubaker |
| 2006/0036207 A1 | 2/2006 | Koonmen et al. |
| 2006/0039952 A1 | 2/2006 | Yaacobi |
| 2006/0039979 A1 | 2/2006 | Yamada et al. |
| 2006/0062826 A1 | 3/2006 | Brubaker et al. |
| 2006/0067978 A1 | 3/2006 | Heiler et al. |
| 2006/0069340 A1 | 3/2006 | Simon |
| 2006/0074375 A1 | 4/2006 | Bergheim et al. |
| 2006/0079828 A1 | 4/2006 | Brown |
| 2006/0083772 A1 | 4/2006 | DeWitt et al. |
| 2006/0084907 A1 | 4/2006 | Bergheim et al. |
| 2006/0084952 A1 | 4/2006 | Pallikaris et al. |
| 2006/0089590 A1 | 4/2006 | Powell et al. |
| 2006/0100408 A1 | 5/2006 | Higuchi et al. |
| 2006/0110429 A1 | 5/2006 | Reiff et al. |
| 2006/0116626 A1 | 6/2006 | Smedley et al. |
| 2006/0129129 A1 | 6/2006 | Smith |
| 2006/0135918 A1 | 6/2006 | LaRuffa |
| 2006/0136022 A1 | 6/2006 | Wong, Jr. et al. |
| 2006/0155300 A1 | 7/2006 | Stamper et al. |
| 2006/0167435 A1 | 7/2006 | Adamis et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200097 A1 | 9/2006 | Humayun et al. |
| 2006/0200113 A1 | 9/2006 | Haffner et al. |
| 2006/0210604 A1 | 9/2006 | Dadey et al. |
| 2006/0216329 A1 | 9/2006 | Peyman |
| 2006/0235367 A1 | 10/2006 | Takashima et al. |
| 2006/0241749 A1 | 10/2006 | Tu et al. |
| 2006/0246112 A1 | 11/2006 | Snyder et al. |
| 2006/0246145 A1 | 11/2006 | Chang et al. |
| 2006/0253151 A1 | 11/2006 | Nun |
| 2006/0257450 A1 | 11/2006 | Mudumba et al. |
| 2006/0257451 A1 | 11/2006 | Varner et al. |
| 2006/0258994 A1 | 11/2006 | Avery |
| 2006/0264453 A1 | 11/2006 | Mudumba et al. |
| 2006/0270968 A1 | 11/2006 | Greenberg et al. |
| 2006/0276739 A1 | 12/2006 | Brown |
| 2006/0292222 A1 | 12/2006 | Jonasse |
| 2007/0004998 A1 | 1/2007 | Rodgers et al. |
| 2007/0021653 A1 | 1/2007 | Hattenbach et al. |
| 2007/0026037 A1 | 2/2007 | Kloke et al. |
| 2007/0026048 A1 | 2/2007 | Greeberg |
| 2007/0031472 A1 | 2/2007 | Huang et al. |
| 2007/0031473 A1 | 2/2007 | Peyman |
| 2007/0032734 A1 | 2/2007 | Najafi et al. |
| 2007/0038174 A1 | 2/2007 | Hopkins |
| 2007/0059336 A1 | 3/2007 | Hughes et al. |
| 2007/0073390 A1 | 3/2007 | Lee |
| 2007/0078371 A1 | 4/2007 | Brown et al. |
| 2007/0088014 A1 | 4/2007 | Edelman et al. |
| 2007/0088432 A1 | 4/2007 | Solovay et al. |
| 2007/0092570 A1 | 4/2007 | Missel et al. |
| 2007/0093740 A1 | 4/2007 | Shetty |
| 2007/0106199 A1 | 5/2007 | Krivoy et al. |
| 2007/0106200 A1 | 5/2007 | Levy |
| 2007/0112263 A1 | 5/2007 | Fink et al. |
| 2007/0112318 A1 | 5/2007 | Leahy et al. |
| 2007/0118065 A1 | 5/2007 | Pinchuk et al. |
| 2007/0118066 A1 | 5/2007 | Pinchuk et al. |
| 2007/0123767 A1 | 5/2007 | Montegrande et al. |
| 2007/0123812 A1 | 5/2007 | Pinchuk et al. |
| 2007/0129623 A1 | 6/2007 | Fleischman et al. |
| 2007/0154621 A1 | 7/2007 | Raad |
| 2007/0156079 A1 | 7/2007 | Brown |
| 2007/0179426 A1 | 8/2007 | Selden |
| 2007/0185468 A1 | 8/2007 | Prywes |
| 2007/0190111 A1 | 8/2007 | Robinson et al. |
| 2007/0191863 A1 | 8/2007 | De Juan, Jr. et al. |
| 2007/0197957 A1 | 8/2007 | Hunter et al. |
| 2007/0202186 A1 | 8/2007 | Yamamoto et al. |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0212395 A1 | 9/2007 | Donello et al. |
| 2007/0212397 A1 | 9/2007 | Roth |
| 2007/0219632 A1 | 9/2007 | Castillejos |
| 2007/0233037 A1 | 10/2007 | Gifford, III et al. |
| 2007/0244442 A1 | 10/2007 | Chowhan |
| 2007/0249984 A1 | 10/2007 | Molteno |
| 2007/0260201 A1 | 11/2007 | Prausnitz et al. |
| 2007/0260203 A1 | 11/2007 | Donello et al. |
| 2007/0268340 A1 | 11/2007 | Dacquay et al. |
| 2007/0269487 A1 | 11/2007 | de Juan et al. |
| 2007/0270744 A1 | 11/2007 | Dacquay et al. |
| 2007/0270748 A1 | 11/2007 | Dacquay et al. |
| 2007/0270768 A1 | 11/2007 | Dacquay et al. |

(56) References Cited

U.S. PATENT DOCUMENTS

| | | |
|---|---|---|
| 2007/0270777 A1 | 11/2007 | Dacquay et al. |
| 2007/0276315 A1 | 11/2007 | Haffner |
| 2007/0282244 A1 | 12/2007 | Tu et al. |
| 2007/0282245 A1 | 12/2007 | Tu et al. |
| 2007/0292470 A1 | 12/2007 | Thornton |
| 2007/0292474 A1 | 12/2007 | Hsu et al. |
| 2007/0292596 A1 | 12/2007 | Chappa et al. |
| 2007/0293807 A1 | 12/2007 | Lynch et al. |
| 2007/0293820 A1 | 12/2007 | Dacquay et al. |
| 2007/0293872 A1 | 12/2007 | Peyman |
| 2007/0293873 A1 | 12/2007 | Chang |
| 2007/0298068 A1 | 12/2007 | Badawi et al. |
| 2007/0298073 A1 | 12/2007 | Whitcup et al. |
| 2007/0298074 A1 | 12/2007 | Robinson et al. |
| 2007/0299516 A1 | 12/2007 | Cui et al. |
| 2008/0027304 A1 | 1/2008 | Pardo et al. |
| 2008/0038316 A1 | 2/2008 | Wong, Jr. et al. |
| 2008/0039769 A1 | 2/2008 | Peyman |
| 2008/0039792 A1 | 2/2008 | Meng et al. |
| 2008/0039931 A1 | 2/2008 | Jelle et al. |
| 2008/0045878 A1 | 2/2008 | Bergheim et al. |
| 2008/0045911 A1 | 2/2008 | Borgia et al. |
| 2008/0051680 A1 | 2/2008 | Luebcke |
| 2008/0057101 A1 | 3/2008 | Roorda |
| 2008/0057102 A1 | 3/2008 | Roorda |
| 2008/0057103 A1 | 3/2008 | Roorda |
| 2008/0057123 A1 | 3/2008 | Grenier et al. |
| 2008/0058704 A1 | 3/2008 | Hee et al. |
| 2008/0058793 A1 | 3/2008 | Pilla et al. |
| 2008/0063687 A1 | 3/2008 | Chou et al. |
| 2008/0063898 A1 | 3/2008 | Lally et al. |
| 2008/0071252 A1 | 3/2008 | Santini, Jr. et al. |
| 2008/0075753 A1 | 3/2008 | Chappa |
| 2008/0081064 A1 | 4/2008 | Jelle et al. |
| 2008/0082078 A1 | 4/2008 | Berlin |
| 2008/0086101 A1 | 4/2008 | Freilich |
| 2008/0089923 A1 | 4/2008 | Burkstrand et al. |
| 2008/0095822 A1 | 4/2008 | Maquet et al. |
| 2008/0097379 A1 | 4/2008 | Daquay et al. |
| 2008/0097390 A1 | 4/2008 | Daquay et al. |
| 2008/0107694 A1 | 5/2008 | Trogden et al. |
| 2008/0108932 A1 | 5/2008 | Rodgers |
| 2008/0108934 A1 | 5/2008 | Berlin |
| 2008/0112923 A1 | 5/2008 | Hughes et al. |
| 2008/0113031 A1 | 5/2008 | Moodley et al. |
| 2008/0114076 A1 | 5/2008 | Asgharian et al. |
| 2008/0125691 A1 | 5/2008 | Yaron et al. |
| 2008/0125712 A1 | 5/2008 | Dacquay et al. |
| 2008/0131372 A1 | 6/2008 | Huang et al. |
| 2008/0131481 A1 | 6/2008 | Hughes |
| 2008/0131482 A1 | 6/2008 | Hughes |
| 2008/0131484 A1 | 6/2008 | Robinson et al. |
| 2008/0131486 A1 | 6/2008 | Huang et al. |
| 2008/0138382 A1 | 6/2008 | Huang et al. |
| 2008/0138408 A1 | 6/2008 | Venkatesh et al. |
| 2008/0140024 A1 | 6/2008 | Yaacobi |
| 2008/0145405 A1 | 6/2008 | Kunzler et al. |
| 2008/0145406 A1 | 6/2008 | Asgharian et al. |
| 2008/0147021 A1 | 6/2008 | Jani |
| 2008/0152694 A1 | 6/2008 | Lobl et al. |
| 2008/0231485 A1 | 6/2008 | Huang et al. |
| 2008/0161741 A1 | 7/2008 | Bene et al. |
| 2008/0161907 A1 | 7/2008 | Chen et al. |
| 2008/0167600 A1 | 7/2008 | Peyman |
| 2008/0172014 A1 | 7/2008 | Whitcup et al. |
| 2008/0177153 A1 | 7/2008 | Bachman et al. |
| 2008/0177220 A1 | 7/2008 | Lindgren et al. |
| 2008/0181928 A1 | 7/2008 | Hokimi-Mehr et al. |
| 2008/0181929 A1 | 7/2008 | Robinson et al. |
| 2008/0183123 A1 | 7/2008 | Behar-Cohen et al. |
| 2008/0200860 A1 | 8/2008 | Tu et al. |
| 2008/0208334 A1 | 8/2008 | Jinkerson et al. |
| 2008/0208557 A1 | 8/2008 | Katano |
| 2008/0210322 A1 | 9/2008 | Unger et al. |
| 2008/0221501 A1 | 9/2008 | Cote et al. |
| 2008/0228127 A1 | 9/2008 | Burns et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0236669 A1 | 10/2008 | Unger et al. |
| 2008/0241222 A1 | 10/2008 | Whitcup et al. |
| 2008/0241223 A1 | 10/2008 | Nivaggio et al. |
| 2008/0243243 A1 | 10/2008 | Williams et al. |
| 2008/0243247 A1 | 10/2008 | Poley et al. |
| 2008/0260803 A1 | 10/2008 | Hughes et al. |
| 2008/0277007 A1 | 11/2008 | Unger et al. |
| 2008/0286336 A1 | 11/2008 | Shiah et al. |
| 2008/0286338 A1 | 11/2008 | Rosenthal et al. |
| 2008/0289710 A1 | 11/2008 | Unger et al. |
| 2008/0292679 A1 | 11/2008 | Lyons et al. |
| 2008/0306429 A1 | 12/2008 | Shields et al. |
| 2008/0318843 A1 | 12/2008 | Schultz et al. |
| 2009/0003525 A1 | 1/2009 | Gertner et al. |
| 2009/0036768 A1 | 2/2009 | Seehusen et al. |
| 2009/0036818 A1 | 2/2009 | Grahn et al. |
| 2009/0043250 A1 | 2/2009 | Gonnelli |
| 2009/0043321 A1 | 2/2009 | Conston et al. |
| 2009/0047256 A1 | 2/2009 | Bettinger et al. |
| 2009/0060981 A1 | 3/2009 | Chauhan |
| 2009/0069648 A1 | 3/2009 | Irazoqui et al. |
| 2009/0074786 A1 | 3/2009 | Dor et al. |
| 2009/0076436 A2 | 3/2009 | Gharib et al. |
| 2009/0082321 A1 | 3/2009 | Edelman et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0092654 A1 | 4/2009 | de Juan, Jr. et al. |
| 2009/0093780 A1 | 4/2009 | Tuitupou et al. |
| 2009/0112190 A1 | 4/2009 | Boyden et al. |
| 2009/0118702 A1 | 5/2009 | Lazar |
| 2009/0123515 A1 | 5/2009 | Taylor et al. |
| 2009/0123546 A1 | 5/2009 | Ashton et al. |
| 2009/0132040 A1 | 5/2009 | Frion et al. |
| 2009/0137992 A1 | 5/2009 | Mallakrishnan |
| 2009/0138081 A1 | 5/2009 | Bergheim et al. |
| 2009/0142413 A1 | 6/2009 | Allen et al. |
| 2009/0143752 A1 | 6/2009 | Higuchi et al. |
| 2009/0148498 A1 | 6/2009 | Libin et al. |
| 2009/0149947 A1 | 6/2009 | Frohwitter |
| 2009/0151422 A1 | 6/2009 | Unger et al. |
| 2009/0155338 A1 | 6/2009 | Conway et al. |
| 2009/0157087 A1 | 6/2009 | Wei et al. |
| 2009/0162417 A1 | 6/2009 | Eellis |
| 2009/0177138 A1 | 7/2009 | Brown et al. |
| 2009/0177182 A1 | 7/2009 | Hickingbotham et al. |
| 2009/0196903 A1 | 8/2009 | Kilman |
| 2009/0196906 A1 | 8/2009 | Spada et al. |
| 2009/0204053 A1 | 8/2009 | Nissan et al. |
| 2009/0209945 A1 | 8/2009 | Lobl et al. |
| 2009/0214619 A1 | 8/2009 | Reiff et al. |
| 2009/0220572 A1 | 9/2009 | Deschatelets et al. |
| 2009/0220573 A1 | 9/2009 | Kaufman |
| 2009/0227933 A1 | 9/2009 | Karageozian |
| 2009/0227934 A1 | 9/2009 | Eutenever et al. |
| 2009/0240215 A1 | 9/2009 | Humayun et al. |
| 2009/0246252 A1 | 10/2009 | Arps et al. |
| 2009/0264861 A1 | 10/2009 | Jain et al. |
| 2009/0270308 A1 | 10/2009 | Libin et al. |
| 2009/0274877 A1 | 11/2009 | Chan et al. |
| 2009/0275924 A1 | 11/2009 | Lattanzio et al. |
| 2009/0280155 A1 | 11/2009 | Chappa et al. |
| 2009/0280158 A1 | 11/2009 | Butuner |
| 2009/0286773 A1 | 11/2009 | Spada et al. |
| 2009/0287136 A1 | 11/2009 | Castillejos |
| 2009/0287274 A1 | 11/2009 | De Rodder |
| 2009/0294345 A1 | 12/2009 | Kelly et al. |
| 2009/0306585 A1 | 12/2009 | Pang et al. |
| 2009/0306595 A1 | 12/2009 | Shih et al. |
| 2009/0306608 A1 | 12/2009 | Li et al. |
| 2009/0312742 A1 | 12/2009 | Pang et al. |
| 2009/0326432 A1 | 12/2009 | Schmidt et al. |
| 2010/0004581 A1 | 1/2010 | Brigatti et al. |
| 2010/0004635 A1 | 1/2010 | Lin et al. |
| 2010/0004639 A1 | 1/2010 | Pang et al. |

(56) References Cited

U.S. PATENT DOCUMENTS

| | | |
|---|---|---|
| 2010/0015195 A1 | 1/2010 | Jain et al. |
| 2010/0025613 A1 | 2/2010 | Tai et al. |
| 2010/0030136 A1 | 2/2010 | Dacquay et al. |
| 2010/0040670 A1 | 2/2010 | Odrich et al. |
| 2010/0042209 A1 | 2/2010 | Guarnieri |
| 2010/0056977 A1 | 3/2010 | Wandel |
| 2010/0056979 A1 | 3/2010 | Smedley et al. |
| 2010/0057003 A1 | 3/2010 | Dos Santos |
| 2010/0057055 A1 | 3/2010 | Camras et al. |
| 2010/0068141 A1 | 3/2010 | Kaushal et al. |
| 2010/0069842 A1 | 3/2010 | Dos Santos et al. |
| 2010/0087774 A1 | 4/2010 | Haffner et al. |
| 2010/0092536 A1 | 4/2010 | Hunter et al. |
| 2010/0100054 A1 | 4/2010 | Cormier et al. |
| 2010/0106073 A1 | 4/2010 | Haffner et al. |
| 2010/0114006 A1 | 5/2010 | Baerveldt |
| 2010/0114039 A1 | 5/2010 | Gazzini |
| 2010/0114309 A1 | 5/2010 | Peyman |
| 2010/0119519 A1 | 5/2010 | Peyman |
| 2010/0119580 A1 | 5/2010 | Guo et al. |
| 2010/0119694 A1 | 5/2010 | Guo et al. |
| 2010/0121342 A1 | 5/2010 | Schieber et al. |
| 2010/0124565 A1 | 5/2010 | Spada et al. |
| 2010/0125237 A1 | 5/2010 | Schocket |
| 2010/0129424 A9 | 5/2010 | Byrne et al. |
| 2010/0137780 A1 | 6/2010 | Singh et al. |
| 2010/0145180 A1 | 6/2010 | Abreu |
| 2010/0152676 A1 | 6/2010 | Clements |
| 2010/0152699 A1 | 6/2010 | Ferrari et al. |
| 2010/0158980 A1 | 6/2010 | Kopczynski et al. |
| 2010/0160870 A1 | 6/2010 | Clements et al. |
| 2010/0168644 A1 | 7/2010 | Brown |
| 2010/0173866 A1 | 7/2010 | Hee et al. |
| 2010/0175767 A1 | 7/2010 | Unger et al. |
| 2010/0185138 A1 | 7/2010 | Yaron et al. |
| 2010/0189765 A1 | 7/2010 | Erickson et al. |
| 2010/0189817 A1 | 7/2010 | Kruger et al. |
| 2010/0191103 A1 | 7/2010 | Stamper et al. |
| 2010/0191329 A1 | 7/2010 | Badawi et al. |
| 2010/0203155 A1 | 8/2010 | Wei et al. |
| 2010/0204325 A1 | 8/2010 | Blanda et al. |
| 2010/0204699 A1 | 8/2010 | Wei et al. |
| 2010/0211044 A1 | 8/2010 | Dacquay et al. |
| 2010/0222733 A1 | 9/2010 | Schieber et al. |
| 2010/0222752 A1 | 9/2010 | Collins, Jr. et al. |
| 2010/0225061 A1 | 9/2010 | Bath |
| 2010/0233241 A1 | 9/2010 | Leahy et al. |
| 2010/0234791 A1 | 9/2010 | Lynch et al. |
| 2010/0234817 A1 | 9/2010 | Nazzaro et al. |
| 2010/0239635 A1 | 9/2010 | McClain et al. |
| 2010/0239637 A1 | 9/2010 | Ciolino et al. |
| 2010/0241046 A1 | 9/2010 | Pinchuk et al. |
| 2010/0241055 A1 | 9/2010 | Dacey, Jr. et al. |
| 2010/0247606 A1 | 9/2010 | Robinson et al. |
| 2010/0249691 A1 | 9/2010 | Van Der Mooren et al. |
| 2010/0249692 A1 | 9/2010 | Dacey, Jr. et al. |
| 2010/0255061 A1 | 10/2010 | De Juan, Jr. et al. |
| 2010/0256578 A1 | 10/2010 | Lust et al. |
| 2010/0256597 A1 | 10/2010 | Prausnitz et al. |
| 2010/0261646 A1 | 10/2010 | Lavik et al. |
| 2010/0266664 A1 | 10/2010 | Asgharian et al. |
| 2010/0274224 A1 | 10/2010 | Jain et al. |
| 2010/0274258 A1 | 10/2010 | Silvestrini et al. |
| 2010/0274259 A1 | 10/2010 | Yaron et al. |
| 2010/0278898 A1 | 11/2010 | Hughes et al. |
| 2010/0318034 A1 | 12/2010 | Goncalves |
| 2010/0331796 A1 | 12/2010 | Leahy et al. |
| 2011/0009874 A1 | 1/2011 | Wardle et al. |
| 2011/0009958 A1 | 1/2011 | Wardle et al. |
| 2011/0022007 A1 | 1/2011 | Li et al. |
| 2011/0046536 A1 | 2/2011 | Stegmann et al. |
| 2011/0046728 A1 | 2/2011 | Shareef et al. |
| 2011/0053905 A1 | 3/2011 | Guo et al. |
| 2011/0054418 A1 | 3/2011 | Pugh et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0076318 A1 | 3/2011 | Hughes et al. |
| 2011/0091520 A1 | 4/2011 | Huang et al. |
| 2011/0092878 A1 | 4/2011 | Tu et al. |
| 2011/0098627 A1 | 4/2011 | Wilcox |
| 2011/0098632 A1 | 4/2011 | Behar-Cohen et al. |
| 2011/0098640 A1 | 4/2011 | Horne et al. |
| 2011/0098809 A1 | 4/2011 | Wardle et al. |
| 2011/0104155 A1 | 5/2011 | Rekik |
| 2011/0105987 A1 | 5/2011 | Bergheim et al. |
| 2011/0106006 A1 | 5/2011 | Martin et al. |
| 2011/0112352 A1 | 5/2011 | Pilla et al. |
| 2011/0112470 A1 | 5/2011 | Lingenfelder et al. |
| 2011/0112475 A1 | 5/2011 | Benson |
| 2011/0118649 A1 | 5/2011 | Stegmann et al. |
| 2011/0118835 A1 | 5/2011 | Silvestrini et al. |
| 2011/0125090 A1 | 5/2011 | Peyman |
| 2011/0129516 A1 | 6/2011 | Jacob et al. |
| 2011/0129541 A1 | 6/2011 | Chen et al. |
| 2011/0130831 A1 | 6/2011 | Badawi et al. |
| 2011/0144559 A1 | 6/2011 | Lafdi et al. |
| 2011/0152767 A1 | 6/2011 | Pinedjian |
| 2011/0166500 A1 | 7/2011 | Roy |
| 2011/0172528 A1 | 7/2011 | Gertner |
| 2011/0172587 A1 | 7/2011 | Santini, Jr. et al. |
| 2011/0182966 A1 | 7/2011 | Robinson et al. |
| 2011/0196487 A1 | 8/2011 | Badawi et al. |
| 2011/0202020 A1 | 8/2011 | Lazar |
| 2011/0207987 A1 | 8/2011 | DiCarlo et al. |
| 2011/0224597 A1 | 9/2011 | Stegmann et al. |
| 2011/0238036 A1 | 9/2011 | Ashton |
| 2011/0238075 A1 | 9/2011 | Clauson et al. |
| 2011/0244010 A1 | 10/2011 | Doshi |
| 2011/0244014 A1 | 10/2011 | Williams et al. |
| 2011/0245753 A1 | 10/2011 | Sunalp |
| 2011/0248671 A1 | 10/2011 | Dos Santos et al. |
| 2011/0251568 A1 | 10/2011 | Beeley et al. |
| 2011/0257623 A1 | 10/2011 | Marshall et al. |
| 2011/0288396 A1 | 11/2011 | Iyengar et al. |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0022505 A1 | 1/2012 | Dacquay et al. |
| 2012/0035146 A1 | 2/2012 | Wong et al. |
| 2012/0035524 A1 | 2/2012 | Silvestrini |
| 2012/0035528 A1 | 2/2012 | Coppeta et al. |
| 2012/0059349 A1 | 3/2012 | Kuo et al. |
| 2012/0059461 A1 | 3/2012 | Badawi et al. |
| 2012/0071809 A1 | 3/2012 | Tu et al. |
| 2012/0078158 A1 | 3/2012 | Haffner et al. |
| 2012/0078224 A1 | 3/2012 | Lerner et al. |
| 2012/0078362 A1 | 3/2012 | Haffner et al. |
| 2012/0083765 A1 | 4/2012 | LaBelle |
| 2012/0089072 A1 | 4/2012 | Cunningham, Jr. |
| 2012/0089073 A1 | 4/2012 | Cunningham, Jr. |
| 2012/0089113 A1 | 4/2012 | Ambati et al. |
| 2012/0100187 A1 | 4/2012 | Chappa et al. |
| 2012/0107371 A1 | 5/2012 | Zion et al. |
| 2012/0109040 A1 | 5/2012 | Smedley et al. |
| 2012/0130467 A1 | 5/2012 | Selden et al. |
| 2012/0136322 A1 | 5/2012 | Alster et al. |
| 2012/0157487 A1 | 6/2012 | Yuan et al. |
| 2012/0165933 A1 | 6/2012 | Haffner et al. |
| 2012/0177717 A1 | 7/2012 | Abe et al. |
| 2012/0179087 A1 | 7/2012 | Schieber et al. |
| 2012/0179122 A1 | 7/2012 | Eilat et al. |
| 2012/0184892 A1 | 7/2012 | Bigler et al. |
| 2012/0197217 A1 | 8/2012 | Coldren |
| 2012/0203160 A1 | 8/2012 | Kahook et al. |
| 2012/0238994 A1 | 9/2012 | Nazzaro et al. |
| 2012/0245505 A1 | 9/2012 | Robinson et al. |
| 2012/0253300 A1 | 10/2012 | Kaufman |
| 2012/0257167 A1 | 10/2012 | Gille et al. |
| 2012/0259195 A1 | 10/2012 | Haffner et al. |
| 2012/0265149 A1 | 10/2012 | Lerner et al. |

(56) References Cited

U.S. PATENT DOCUMENTS

| | | |
|---|---|---|
| 2012/0277733 A1 | 11/2012 | Pang et al. |
| 2012/0289883 A1 | 11/2012 | Meng et al. |
| 2012/0302861 A1 | 11/2012 | Marshall et al. |
| 2012/0310072 A1 | 12/2012 | Grieshaber |
| 2012/0321719 A1 | 12/2012 | McDonnell et al. |
| 2012/0323159 A1 | 12/2012 | Wardle et al. |
| 2013/0004651 A1 | 1/2013 | Fu-Giles |
| 2013/0006164 A1 | 1/2013 | Yaron et al. |
| 2013/0006165 A1 | 1/2013 | Eutenener et al. |
| 2013/0017244 A1 | 1/2013 | Huang et al. |
| 2013/0017262 A1 | 1/2013 | Mullen et al. |
| 2013/0018295 A1 | 1/2013 | Haffner et al. |
| 2013/0018296 A1 | 1/2013 | Bergheim et al. |
| 2013/0018360 A1 | 1/2013 | Dockendorf et al. |
| 2013/0023838 A1 | 1/2013 | Leahy et al. |
| 2013/0053794 A1 | 2/2013 | Cadden et al. |
| 2013/0060227 A1 | 3/2013 | Singh et al. |
| 2013/0062809 A1 | 3/2013 | Ellis |
| 2013/0071349 A1 | 3/2013 | Robinson et al. |
| 2013/0071462 A1 | 3/2013 | Jarrett et al. |
| 2013/0079701 A1 | 3/2013 | Schieber et al. |
| 2013/0090534 A1 | 4/2013 | Burns et al. |
| 2013/0090612 A1 | 4/2013 | De Juan, Jr. et al. |
| 2013/0102949 A1 | 4/2013 | Baerveldt |
| 2013/0110125 A1 | 5/2013 | Silvestrini et al. |
| 2013/0116523 A1 | 5/2013 | Jung et al. |
| 2013/0142858 A1 | 6/2013 | Kopczynski et al. |
| 2013/0144128 A1 | 6/2013 | De Juan, Jr. et al. |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0150779 A1 | 6/2013 | Field |
| 2013/0150959 A1 | 6/2013 | Shieber et al. |
| 2013/0156840 A1 | 6/2013 | Basinger et al. |
| 2013/0158381 A1 | 6/2013 | Rickard |
| 2013/0158462 A1 | 6/2013 | Wardle et al. |
| 2013/0158561 A1 | 6/2013 | Bhagat |
| 2013/0165840 A1 | 6/2013 | Orge |
| 2013/0172804 A1 | 7/2013 | Schieber et al. |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0253528 A1 | 9/2013 | Haffner et al. |
| 2013/0281910 A1 | 10/2013 | Tu et al. |
| 2013/0289467 A1 | 10/2013 | Haffner et al. |
| 2013/0310930 A1 | 11/2013 | Tu et al. |
| 2014/0034607 A1 | 2/2014 | Meng et al. |
| 2014/0035184 A1 | 2/2014 | Nivaggioli et al. |
| 2014/0037746 A1 | 2/2014 | Ashton et al. |
| 2014/0039456 A1 | 2/2014 | Lerner |
| 2014/0046437 A1 | 2/2014 | Renke |
| 2014/0052046 A1 | 2/2014 | Peartree et al. |
| 2014/0135712 A1 | 5/2014 | Horne et al. |
| 2014/0234389 A1 | 8/2014 | Shiah et al. |
| 2014/0294986 A1 | 10/2014 | Liu et al. |
| 2014/0303544 A1 | 10/2014 | Haffner et al. |
| 2015/0118279 A1 | 4/2015 | Ghebremeskel et al. |
| 2015/0223981 A1 | 8/2015 | Smedley et al. |
| 2015/0342875 A1 | 12/2015 | Haffner |
| 2015/0374546 A1 | 12/2015 | Hill |
| 2016/0045363 A1 | 2/2016 | Haffner et al. |
| 2016/0354245 A1 | 8/2016 | Horvath et al. |
| 2016/0354309 A1 | 12/2016 | Heitzman et al. |
| 2017/0135857 A1 | 5/2017 | Hafner et al. |
| 2017/0281409 A1 | 10/2017 | Haffner et al. |
| 2018/0021170 A1 | 1/2018 | Haffner et al. |
| 2018/0028361 A1 | 2/2018 | Haffner et al. |
| 2018/0085065 A1 | 3/2018 | Haffner et al. |
| 2018/0161205 A1 | 6/2018 | Tu et al. |
| 2018/0177633 A1 | 6/2018 | Haffner et al. |
| 2018/0256393 A1 | 9/2018 | Yamamoto et al. |
| 2018/0280194 A1 | 10/2018 | Heitzmann et al. |
| 2018/0303752 A1 | 10/2018 | Haffner |
| 2018/0325732 A1 | 11/2018 | Burns et al. |
| 2018/0333296 A1 | 11/2018 | Heitzmann et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0083307 A1 | 3/2019 | Burns et al. |
| 2019/0083313 A1 | 3/2019 | Berlin |
| 2019/0091012 A1 | 3/2019 | Kalina, Jr. |
| 2019/0104936 A1 | 4/2019 | Gunn et al. |
| 2019/0105077 A1 | 4/2019 | Kalina, Jr. et al. |
| 2019/0125581 A1 | 5/2019 | Heitzmann et al. |
| 2019/0224046 A1 | 7/2019 | Heitzmann et al. |
| 2019/0314199 A1 | 10/2019 | Haffner et al. |
| 2019/0321220 A1 | 10/2019 | Rangel-Friedman et al. |
| 2019/0321225 A1 | 10/2019 | Smedley et al. |
| 2019/0321226 A1 | 10/2019 | Haffner et al. |
| 2020/0000635 A1 | 1/2020 | Lerner |
| 2020/0155349 A1 | 5/2020 | Haffner et al. |
| 2020/0179171 A1 | 6/2020 | Crimaldi et al. |
| 2020/0214560 A1 | 7/2020 | Kalina, Jr. et al. |
| 2020/0214561 A1 | 7/2020 | Kalina, Jr. et al. |
| 2020/0367745 A1 | 11/2020 | Kalina, Jr. et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2021/0369447 A1 | 12/2021 | Kalina, Jr. |
| 2022/0000663 A1 | 1/2022 | Haffner et al. |
| 2022/0015628 A1 | 1/2022 | Kalina, Jr. et al. |
| 2022/0119350 A1 | 4/2022 | Murphy et al. |
| 2022/0233349 A1 | 7/2022 | Haffner et al. |
| 2022/0233354 A1 | 7/2022 | Haffner et al. |
| 2022/0313486 A1 | 10/2022 | Heitzmann et al. |
| 2022/0330979 A1 | 10/2022 | Kalina, Jr. et al. |
| 2023/0053931 A1 | 2/2023 | Haffner et al. |
| 2023/0090539 A1 | 3/2023 | Haffner et al. |
| 2023/0157868 A1 | 5/2023 | Haffner et al. |
| 2023/0210694 A1 | 7/2023 | Crimaldi et al. |

FOREIGN PATENT DOCUMENTS

| | | |
|---|---|---|
| AU | 2009251058 B2 | 12/2013 |
| CA | 2244646 A1 | 2/1999 |
| CA | 2442652 | 1/2011 |
| CA | 2683224 C | 12/2014 |
| CA | 2830555 | 4/2015 |
| CA | 2762536 | 11/2020 |
| CH | 92111244 | 7/1993 |
| CN | 101396335 A | 4/2009 |
| DE | 19840047 A1 | 3/2000 |
| DE | 10127666 A1 | 1/2003 |
| EP | 0180708 | 5/1986 |
| EP | 0387155 | 9/1990 |
| EP | 0613383 B1 | 8/1997 |
| EP | 0858788 A1 | 8/1998 |
| EP | 1100462 A2 | 5/2001 |
| EP | 1296645 A2 | 4/2003 |
| EP | 1339438 A2 | 9/2003 |
| EP | 1420716 A1 | 5/2004 |
| EP | 1477187 A1 | 11/2004 |
| EP | 1534363 A2 | 6/2005 |
| EP | 1550471 A1 | 7/2005 |
| EP | 1592407 | 11/2005 |
| EP | 1621219 A2 | 2/2006 |
| EP | 1637126 A2 | 3/2006 |
| EP | 1521573 | 1/2008 |
| EP | 1977724 A1 | 10/2008 |
| EP | 2260803 | 12/2010 |
| EP | 2260804 | 12/2010 |
| EP | 2263621 | 12/2010 |
| EP | 2351589 | 8/2011 |
| EP | 2982354 | 2/2016 |
| EP | 2985012 | 2/2016 |
| EP | 2902018 | 11/2016 |
| EP | 2967993 | 4/2019 |
| ES | 2048986 | 4/1994 |

(56) References Cited

FOREIGN PATENT DOCUMENTS

| | | |
|---|---|---|
| FR | 2553658 A1 | 4/1985 |
| FR | 2710269 A1 | 3/1995 |
| FR | 2721499 | 12/1995 |
| FR | 2757068 A1 | 6/1998 |
| GB | 2296663 A | 7/1996 |
| JP | 2001-507969 | 1/2003 |
| JP | 2003-520077 | 7/2003 |
| JP | 2003-275327 | 9/2003 |
| JP | 2003-530964 | 10/2003 |
| JP | 2004-500220 | 1/2004 |
| JP | 2005-512607 | 5/2005 |
| JP | 3703721 | 7/2005 |
| JP | 2007-501066 | 1/2007 |
| JP | 2008-500878 | 1/2008 |
| JP | 4031836 | 1/2008 |
| JP | 2009-056324 | 3/2009 |
| JP | 2009-523540 | 6/2009 |
| JP | 2009-532132 | 9/2009 |
| JP | 2010-509003 | 3/2010 |
| JP | 4688444 | 2/2011 |
| JP | 2011-092765 | 5/2011 |
| JP | 2011-520805 | 7/2011 |
| JP | 2011-522575 | 8/2011 |
| JP | 2011-522695 | 8/2011 |
| JP | 2012-516224 | 7/2012 |
| JP | 2012-198134 | 9/2012 |
| JP | 2012-527318 | 11/2012 |
| JP | 2013-063308 | 4/2013 |
| JP | 5255402 | 4/2013 |
| JP | 5323011 | 7/2013 |
| JP | 2013-208434 | 10/2013 |
| JP | 2014-504732 | 2/2014 |
| JP | 2014-193366 | 10/2014 |
| JP | 2014-236980 | 12/2014 |
| JP | 2014-240022 | 12/2014 |
| JP | 2016-511108 | 4/2016 |
| JP | 2020-075162 | 5/2020 |
| RU | 2022539 C1 | 11/1994 |
| RU | 2143250 | 12/1999 |
| WO | WO 89/00869 A1 | 2/1989 |
| WO | WO 91/18568 A1 | 12/1991 |
| WO | WO 92/00112 | 1/1992 |
| WO | WO 1992/19294 | 11/1992 |
| WO | WO 94/02081 | 2/1994 |
| WO | WO 94/13234 | 6/1994 |
| WO | WO 95/08310 A1 | 3/1995 |
| WO | WO 95/013765 A1 | 5/1995 |
| WO | WO 96/20742 A1 | 7/1996 |
| WO | WO 96/038174 A1 | 12/1996 |
| WO | WO 98/23237 A1 | 6/1998 |
| WO | WO 1998/030181 A1 | 7/1998 |
| WO | WO 98/35639 A1 | 8/1998 |
| WO | WO 98/37831 | 9/1998 |
| WO | WO 1999/11244 | 3/1999 |
| WO | WO 99/26567 A1 | 6/1999 |
| WO | WO 99/30641 A1 | 6/1999 |
| WO | WO 99/56637 | 11/1999 |
| WO | WO 00/007565 A2 | 2/2000 |
| WO | WO 00/13627 A1 | 3/2000 |
| WO | WO 00/037056 A2 | 6/2000 |
| WO | WO 00/64390 A1 | 11/2000 |
| WO | WO 00/64391 A1 | 11/2000 |
| WO | WO 00/64393 A1 | 11/2000 |
| WO | WO 00/67687 A1 | 11/2000 |
| WO | WO 2000/64389 | 11/2000 |
| WO | WO 00/72788 A1 | 12/2000 |
| WO | WO 01/41685 | 6/2001 |
| WO | WO 01/50943 A2 | 7/2001 |
| WO | WO 2001/78631 | 10/2001 |
| WO | WO 01/080825 A2 | 11/2001 |
| WO | WO 01/97727 | 12/2001 |
| WO | WO 02/002076 A2 | 1/2002 |
| WO | WO 02/36052 | 5/2002 |
| WO | WO 02/043785 A2 | 6/2002 |
| WO | WO 2002/053129 | 7/2002 |
| WO | WO 2002/074052 | 9/2002 |
| WO | WO 02/080811 | 10/2002 |
| WO | WO 2002/087418 | 11/2002 |
| WO | WO 2002/089699 | 11/2002 |
| WO | WO 2003/015659 | 2/2003 |
| WO | WO 03/020172 A1 | 3/2003 |
| WO | WO 2003/073968 | 9/2003 |
| WO | WO 04/006890 A1 | 1/2004 |
| WO | WO 2004/014218 | 2/2004 |
| WO | WO 2004/043231 | 5/2004 |
| WO | WO 2004/043435 | 5/2004 |
| WO | WO 04/066871 | 8/2004 |
| WO | WO 03/061625 | 9/2004 |
| WO | WO 2004/073552 | 9/2004 |
| WO | WO 04/098565 A2 | 11/2004 |
| WO | WO 2004/093761 A1 | 11/2004 |
| WO | WO 2005/016418 | 2/2005 |
| WO | WO 2005/105197 | 11/2005 |
| WO | WO 2005/107664 A2 | 11/2005 |
| WO | WO 2005/110362 | 11/2005 |
| WO | WO 05/117780 | 12/2005 |
| WO | WO 06/014434 A2 | 2/2006 |
| WO | WO 2006/036715 | 4/2006 |
| WO | WO 07/084582 | 7/2007 |
| WO | WO 2007/087061 | 8/2007 |
| WO | WO 2007/115259 A2 | 10/2007 |
| WO | WO 2007/130393 | 11/2007 |
| WO | WO 2008/005873 | 1/2008 |
| WO | WO 2008/060359 | 5/2008 |
| WO | WO 2008/061043 | 5/2008 |
| WO | WO 2008/083118 | 7/2008 |
| WO | WO 2008/094989 A2 | 8/2008 |
| WO | WO 08/157614 A2 | 12/2008 |
| WO | WO 2009/012406 | 1/2009 |
| WO | WO 2009/035562 | 3/2009 |
| WO | WO 2009/035571 A2 | 3/2009 |
| WO | WO 09/063222 A2 | 5/2009 |
| WO | WO 09/097468 A2 | 8/2009 |
| WO | WO 09/126569 | 10/2009 |
| WO | WO 09/137085 | 11/2009 |
| WO | WO 2009/151543 | 12/2009 |
| WO | WO 10/006053 A1 | 1/2010 |
| WO | WO 10/065970 | 6/2010 |
| WO | WO 10/078063 A1 | 7/2010 |
| WO | WO 2010/077987 | 7/2010 |
| WO | WO 10/093945 A3 | 8/2010 |
| WO | WO 10/135369 | 11/2010 |
| WO | WO 10/141729 | 12/2010 |
| WO | WO 11/127064 A2 | 10/2011 |
| WO | WO 2012/019136 | 2/2012 |
| WO | WO 12/071476 | 5/2012 |
| WO | WO 13/022801 | 2/2013 |
| WO | WO 2013/040079 | 3/2013 |
| WO | WO 2013/119843 A1 | 8/2013 |
| WO | WO 2013/148275 | 10/2013 |
| WO | WO 2014/150292 A1 | 9/2014 |
| WO | WO 2014/151070 | 9/2014 |
| WO | WO 2014/164569 | 10/2014 |
| WO | WO 2015/073571 | 5/2015 |
| WO | WO 2015/184173 | 12/2015 |
| WO | WO 2016/023116 | 2/2016 |
| WO | WO 2016/042163 A2 | 3/2016 |
| WO | WO 2016/154066 | 9/2016 |
| WO | WO 2016/187355 | 11/2016 |
| WO | WO 2017/015633 | 1/2017 |
| WO | WO 2017/040853 | 3/2017 |
| WO | WO 2017/040855 | 3/2017 |
| WO | WO 2017/053885 | 3/2017 |
| WO | WO 2017/087713 | 5/2017 |
| WO | WO 2017/184881 | 10/2017 |
| WO | WO 2019/036025 A2 | 2/2019 |
| WO | WO 2019/070385 | 4/2019 |

(56) References Cited

FOREIGN PATENT DOCUMENTS

| WO | WO 2019/200336 | 10/2019 |
|----|----------------|---------|
| WO | WO 2020/172615 | 8/2020  |

OTHER PUBLICATIONS

Emi, Kazayuki, et al., Hydrostatic Pressure of the Suprachoroidal Space, Investigative Ophthalmology & Visual Science, vol. 30, No. 2, Feb. 1989 (pp. 233-239).

Katz, L. Jay, MD, A Call for Innovative Operations for Glaucoma, Arch Ophthalmology, Mar. 2000, vol. 118, pp. 412-413.

International Preliminary Report on Patentability in PCT/US2016/053570 dated Mar. 27, 2018.

Alexander, L., et al., Disistronic Polioviruses as Expression Vectors for Foreign Genes. 1994. Aids Research and Human Retroviruses. vol. 10, Supplement 2, S57-S60.

Bae, et al., "In vitro experiment of the pressure regulating valve for a glaucoma implant", Journal of Micromechanics and Microengineering 13.5, 13:613-619, No. 5, Sep. 2003.

Cairns, J.E., "Trabeculectomy: Preliminary report of a new method", Am. J. Ophthalmology, 66:673-79 (1968).

"Changing Perspectives in Glaucoma Management," Innovations in Glaucoma 2010.

Chen, et al., "Trabeculetomy combined with implantation of sil-icon rubber slice for intractable glaucoma", Eye Science, 18:95-98, vol. 2, Jun. 2002.

Chen, P.-J., Rodger, D.C., Meng, E., Humayun, M.S., Tai, Y.-C., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.

Fine, Ben S., et al., "A Clinicopathologic Study of Four Cases of Primary Open-Angle Glaucoma Compared to Normal Eyes", American Journal of Ophthalmology, vol. 91, No. 1, 1981, pp. 88-105.

Fiore, P.M., et al., Use of neodymium: YAG laser to open an occluded molteno tube, Ophthalmic Surgery, May 1989; 20(5): 373-74.

Gimbel, H.V., et al., "Small incision trabeculotomy combined with phacoemulsificatin and intraocular lens implantation", J Cataract Refract Surg, vol. 19:92-96 (Jan. 1993).

Gothwal, et al., "Migration of seton into the anterior chamber", Eye, 16:85-97, 2002.

Hoskins, H. Dunbar, et al., Diagnosis and Therapy of the Glaucomas, Chapter 4: Aqueous Humor Outflow, 61 edition, pp. 41-66 (1989) (28 pages).

Huang, Morgan C., et al., Intermediate-term Clinical Experience with the Ahmed Glaucoma Valve Implant, 127 Am. J. Ophthalmol. 27 (Jan. 1999).

Johnson, et al., Schlemm's Canal Becomes Smaller After Successful Filtration Surgery, (reprinted) ARCM Ophthalmol/vol. 118, Sep. 2000 (www.archophthalmol.com) p. 1251-1256.

Jordon, et al., "A Novel Approach to Suprachoroidal Drainage for the Surgical Treatment of Intractable Glaucoma," J Glaucoma 15(3): 200-205 (2006).

Kampik, Anselm Franz Grehn, Nutzen und Risiken Augenärzticher Therapie, Hauptreferate der XXXIII, Essener Fortbildung für Augenärzte, Dec. 1998. (English translated version enclosed Benefits and Risks of Ophthalmological Therapy).

Katuri, Kalyan C., Asrani, Sanjay and Ramasubramanian, Melur K., "Intraocular Pressure Monitoring Sensors", IEEE Sensors Journal, vol. 8, No. 1, Jan. 2008, 8 pp.

Kershner, Robert, "Nonpenetrating trabulectomy with placement of a collagen drainage device", J. Cataract Refract. Sug., 21:608-611 (1995).

Klemm, A. Balazs, J. Draeger, R. Wiezorrek, Experimental use of space-retaining substances with extended duration: functional and morphological results, Graefe's Arch Clin Exp Ophthalmol (1995) 233:592-597.

Krupin, Theodore, et al., Filtering valve implant surgery for eyes with neovascular glaucoma, 89 Am. J. Ophthalmol. 338 (Mar. 1980).

Mermoud, A., et al., "Comparison of deep sclerectomy with collagen implant and trabeculectomy in open-angle glaucoma", J. Cataract Refract. Surg., vol. 25, No. 3, Mar. 1999, pp. 323-331 (abstract only).

Miyazaki, Akiko, et al., Postoperative Results of Combined Trabeculotomy, Phacoemulsification and Intraocular Lens Implantation With Self-Sealing Wound, Japanese Journal of Ophthalmic Surgery, 1997, pp. 537-542, vol. 10, No. 4.

Molteno, A.C.B., et al., Implants for draining neovascular glaucoma, 61 Br. J. Ophthalmol. 120 (1977).

Moses, Robert A., M.D .; Circumferential Flow in Schlemm's Canal; American Journal of Ophthalmology, Sep. 1979, vol. 88, No. 3, Part II, :pp. 585-591.

Nguyen, Quang H., et al., Complications of Baerveldt Glaucoma Drainage Implants, 116 Arch. Ophthalmol. 571 (May 1998).

Notice of Opposition filed Jul. 26, 2017 in EP Application No. EP 2260804.

Online encyclopedia article "Hyaluronan," section on "Medical Applications" accessed Monday, Sep. 27, 2010. http://en.wikipedia.org/wiki/Hyaluronic_acid.

Refojo, "Current status of biomaterials in ophthalmology", Survey of ophthalmology, 26:257-265, No. 5, 1982.

Rizq, et al., Intraocular Pressure Measurement at the Choroid Surface: A Feasibility Study with Implications for Implantable Microsystems, Br J Ophthalmol 2001; 85:868-871, Jul. 2001.

Saxena, Sandeep. "Clinical Ophthalmology". 2011. pp. 245.

Schocket, Investigations of the Reasons for Success and Failure in the Anterior Shunt-to-the Encircling-Band Procedure in the Treatment of Refractory Glaucoma, Tr. Am. Ophth. Soc., 84:743 (1986).

Scott, et al., "Use of glaucoma drainage devices in the management of glaucoma associated with aniridia", American Journal of Ophthalmology, 135:155-159, No. 2, Feb. 1, 2003.

Shields, M. Bruce, MD, A Study Guide for Glaucoma: Aqueous Humor Dynamics, Copyright 1982, pp. 6-43.

Stefansson, J., "An Operation for Glaucoma", American J. Ophthalmology, 8:681-693 (1925).

Tham, et al., "Incisional surgery for angle closure glaucoma", Seminars in Ophthalmology, 17:92-99, No. 2, Jun. 2002.

Topouzis, Fotis, et al., Follow-up of the Original Cohort With the Ahmed Glaucoma Valve Implant, 128 Am. J. Ophthalmol. 198 (Aug. 1999).

"Transcend Medical CyPass® System—Instructions for Use," (Release date Apr. 29, 2013).

Tripathi, et al., Functional Anatomy of the Anterior Chamber Angle, Biomedical Foundation of Ophthalmology, vol. 1, Chapter 10,pp. 1-74; edited by Thomas Dune and Edward Jaeger, Revised Edition, 1983,—Harper & Row, Publishers.

Tun, et al., Assessment of Trabecular Meshwork Width Using Swept Source Optical Coherence Tomography, 251:6 Graefes Arch. Clin. Exp. Ophthalmol. 1587 (2013).

Wagner, Justin A., Edwards, Aurélie, and Schuman, Joel S., Characterization of Uveoscleral Outflow in Enucleated Porcine Eyes Perfused Under Constant Pressure, Invest Ophthalmol Vis Sci. Sep. 2004; 45(9): 3203-3206 (9 pages).

Walter, et al., Development of a Completely Encapsulated Intraocular Pressure Sensor, Ophthalmic Research Nov.-Dec. 2000; 32:278-284.

Webster's Third New International Dictionary of the English Language (Unabridged), definitions of "deploy" and "deployment", p. 605 (2002) (4 pages).

Wilcox, Michael J. et al. "Hypothesis for Improving Accessory Filtration by Using Geometry", J. Glaucoma, vol. 3, No. 3, pp. 244-247 (1994).

Wilcox et al., Latest Research: Tear Biomarkers, Jun. 29, 2011, 5 pages.

Wilcox, Michael J. et al. "Performance of a New, Low-volume, High-Surface Area Aqueous Shunt in Normal Rabbit Eyes", J. Glaucoma, vol. 9, No. 1, pp. 74-82 (Feb. 2000).

(56) References Cited

OTHER PUBLICATIONS

Wilson, Ellen D., "Implants offer choices for glaucoma surgeons", EW Glaucoma, Oct. 11, 1999, website "http://www.eyeorld.org/sep99/999p60.asp".
Yan, et al., "Schlemm's Canal and Trabecular Meshworkin Eyes with Primary Open Angle Glaucoma: A Comparative Study Using High-Frequency", PLOS One, 15 pages, Jan. 4, 2016.
Rejection Decision in Chinese Application No. 201610177795.2 dated Jan. 9, 2019.
Examination Report in Australian Application No. 2018229507 dated Oct. 2, 2019.
Examination Report in Australian Application No. 2018229507 dated Mar. 20, 2019.
Search Report in European Application No. 10778286.4 dated Dec. 8, 2017.
International Search Report and Written Opinion in PCT/US2014/065283 dated Feb. 18, 2015.
Examination Report in Australian application No. 2015266850, dated Feb. 12, 2019.
Examination Report in Australian Application No. 2020201236, dated Jul. 8, 2020.
Bucciarelli, Patrice D., "Working Model is Next Step in Team's Long Journey to Commercial Product", Healthfirst, Business First of Louisville, louisville.bizjournals.com, Feb. 27, 2004.
Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL.
Ianchulev, Chapter 3: Suprachoroidal Space as a Therapeutic Target, in J.R. Samples & I.I.K. Ahmed (eds.), Surgical Innovations in Glaucoma 33 (Springer Science+Business Media 2014).
Supplementary European Search Report in related European application No. 04779911.9, dated Jul. 18, 2007, 3 pp.
Office Action in related European application No. 04779911.9, dated Apr. 17, 2009, 4 pp.
Office Action in corresponding EP Application No. 04779911.9 dated Sep. 30, 2010, 4 pp.
Extended Search Report in European Application No. 18153863.8 dated Jun. 5, 2018.
International Search Report and Written Opinion in PCT/US2011/061967 dated Jun. 28, 2012.
International Search Report and Written Opinion for PCT/US2014/022858, dated Jun. 25, 2014.
International Preliminary Report on Patentability, PCT/US2014/022858, dated Sep. 15, 2015.
International Search Report and Written Opinion in PCT/US2016/049996 dated Dec. 16, 2016.
International Preliminary Report on Patentability in PCT/US2016/049996 dated Mar. 6, 2018.
Examination Report in Japanese Application No. 2016-221183 dated Feb. 8, 2019.
Office Action in Japanese Application No. 2018-211032 dated Nov. 6, 2019.
https://entokey.com/gonioscopy-2/ Uploaded Oct. 2016.
Jain et al., "Development of polyvinyl alcohol-gelatin membranes for antibiotic delivery in the eye", Drug Development and Industrial Pharmacy, 2011, Informa Healthcare USA, Inc., 12 pages.
Second Office Action in Chinese Application No. 201080032278.7 dated Nov. 15, 2014.
Office Action in European Application No. 18153863.8 dated Oct. 19, 2018.
Canadian Office Action for Application No. 2,901,476, dated Nov. 13, 2020, in 5 pages.
Extended Search Report in European Application No. 18183395.5 dated Nov. 14, 2018.
International Search Report and Written Opinion, PCT/US2017/028665, dated Jul. 31, 2017.
International Preliminary Report on Patentability, PCT/US2017/028665, dated Oct. 23, 2018.
Rejection Decision in Japanese Application No. 2012-511975 dated Jan. 9, 2015.

* cited by examiner

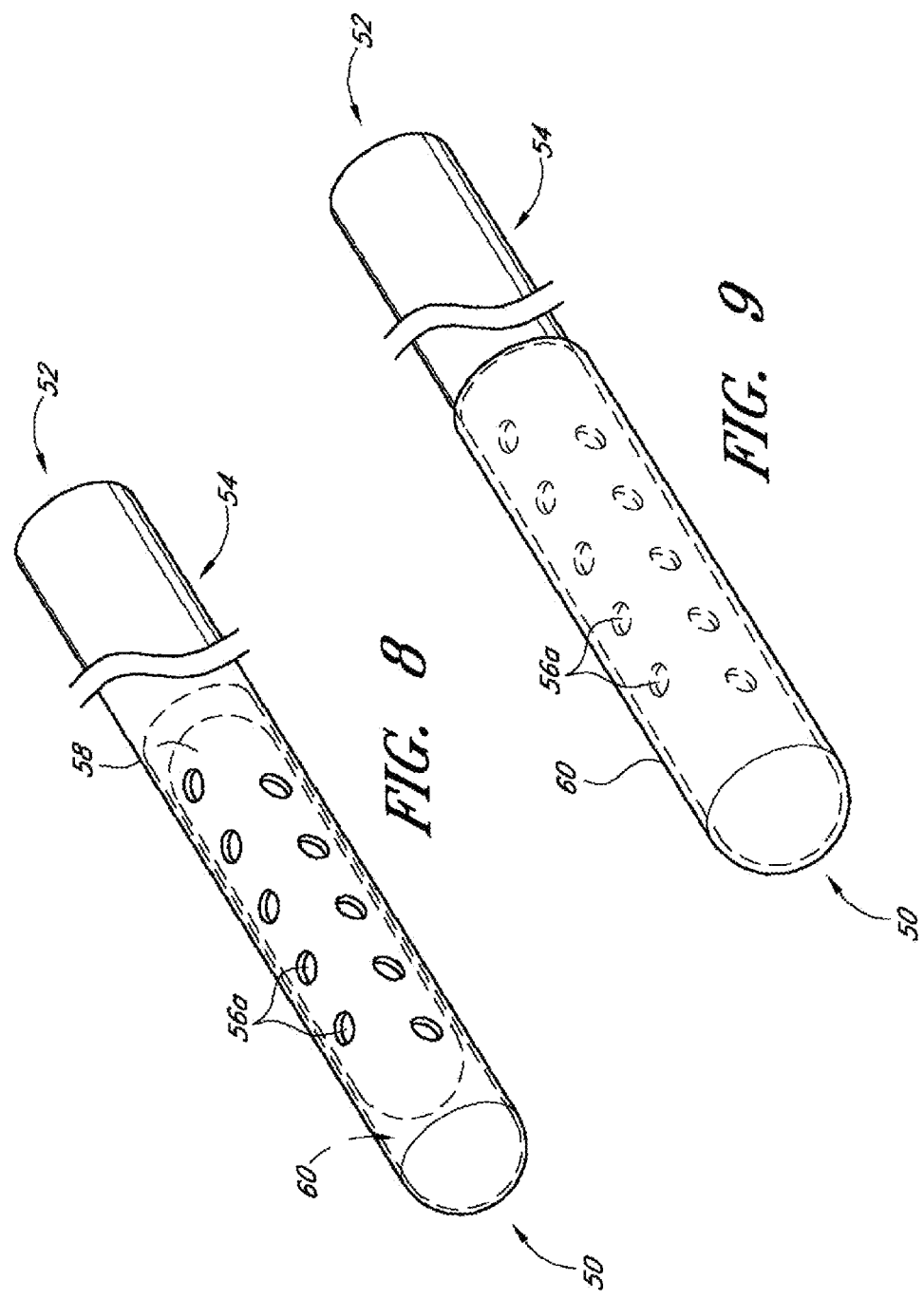

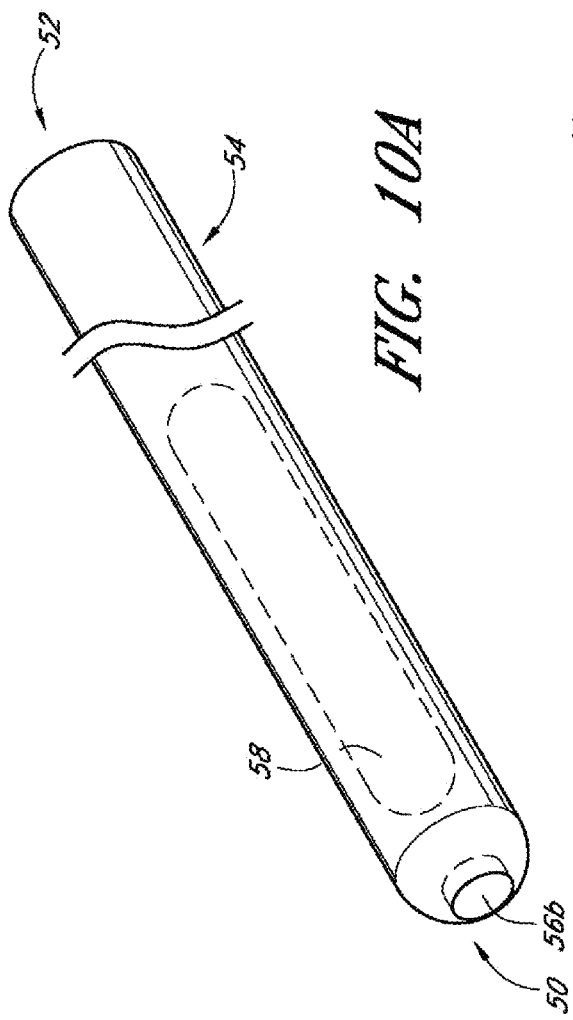
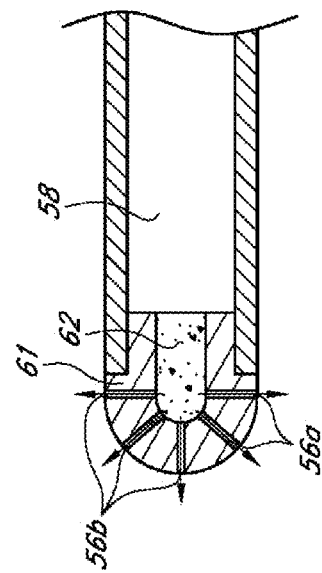
FIG. 10A
FIG. 10B

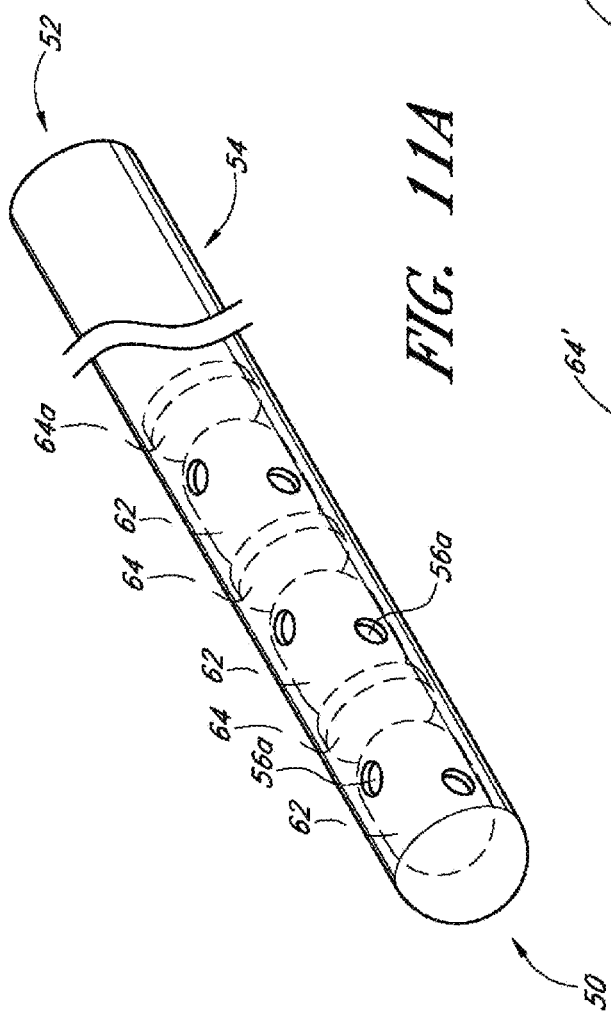
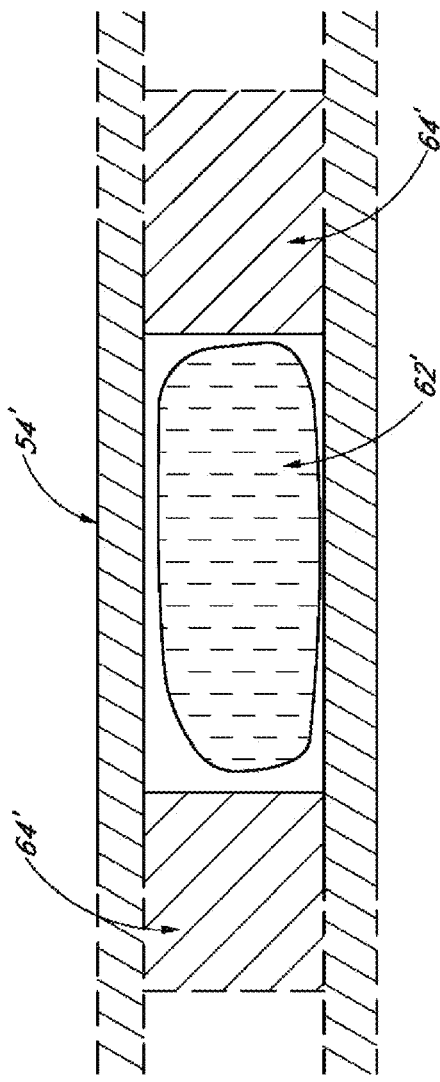
FIG. 11A
FIG. 11B

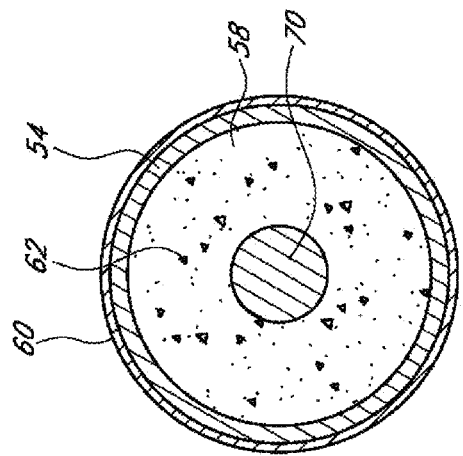
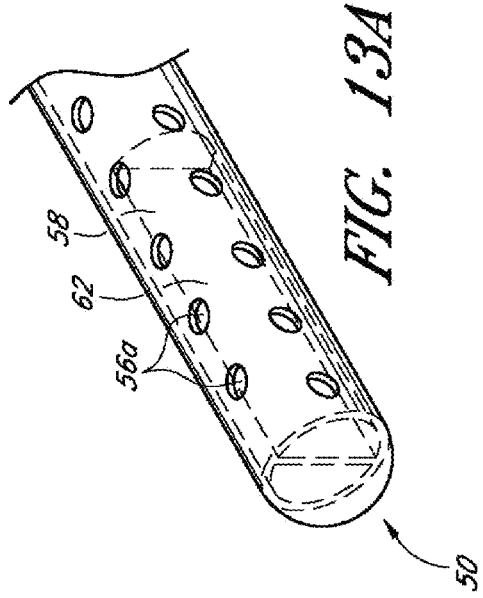
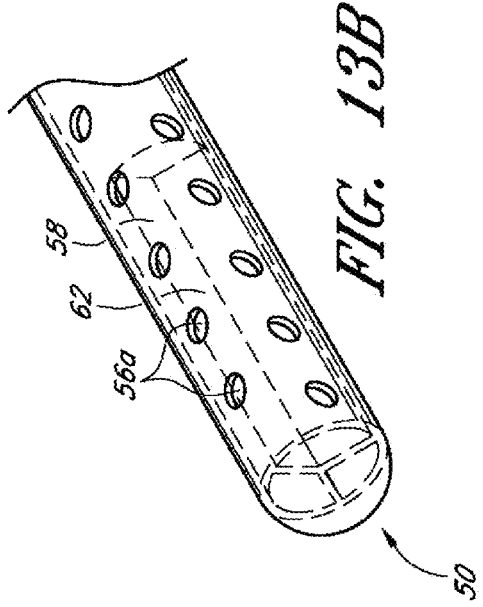

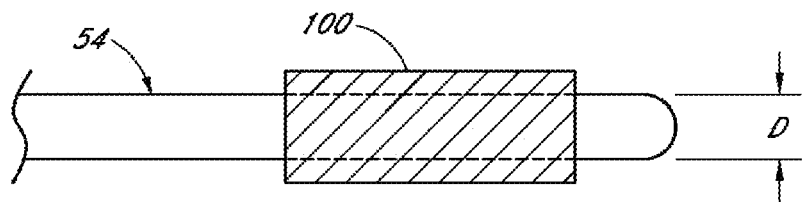
FIG. 19L
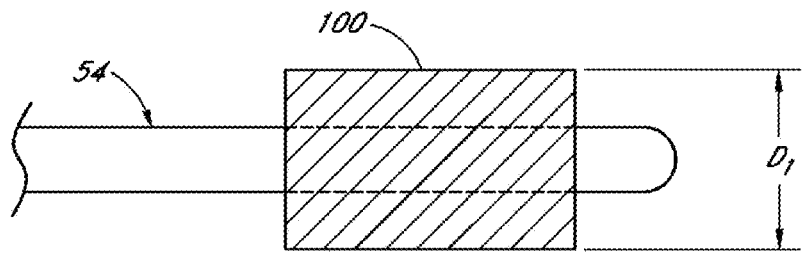
FIG. 19M
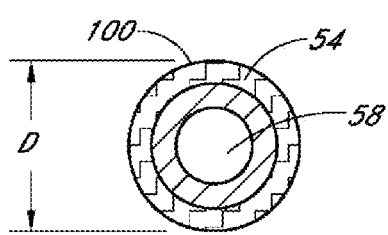 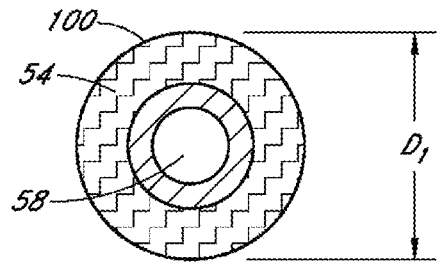
FIG. 19N    FIG. 19O
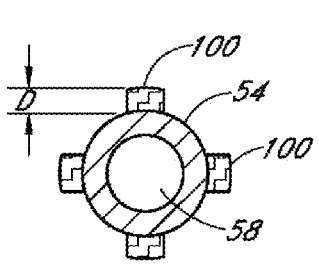 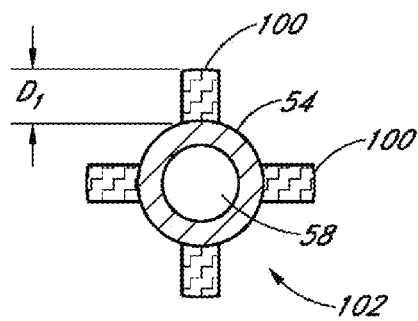
FIG. 19P    FIG. 19Q

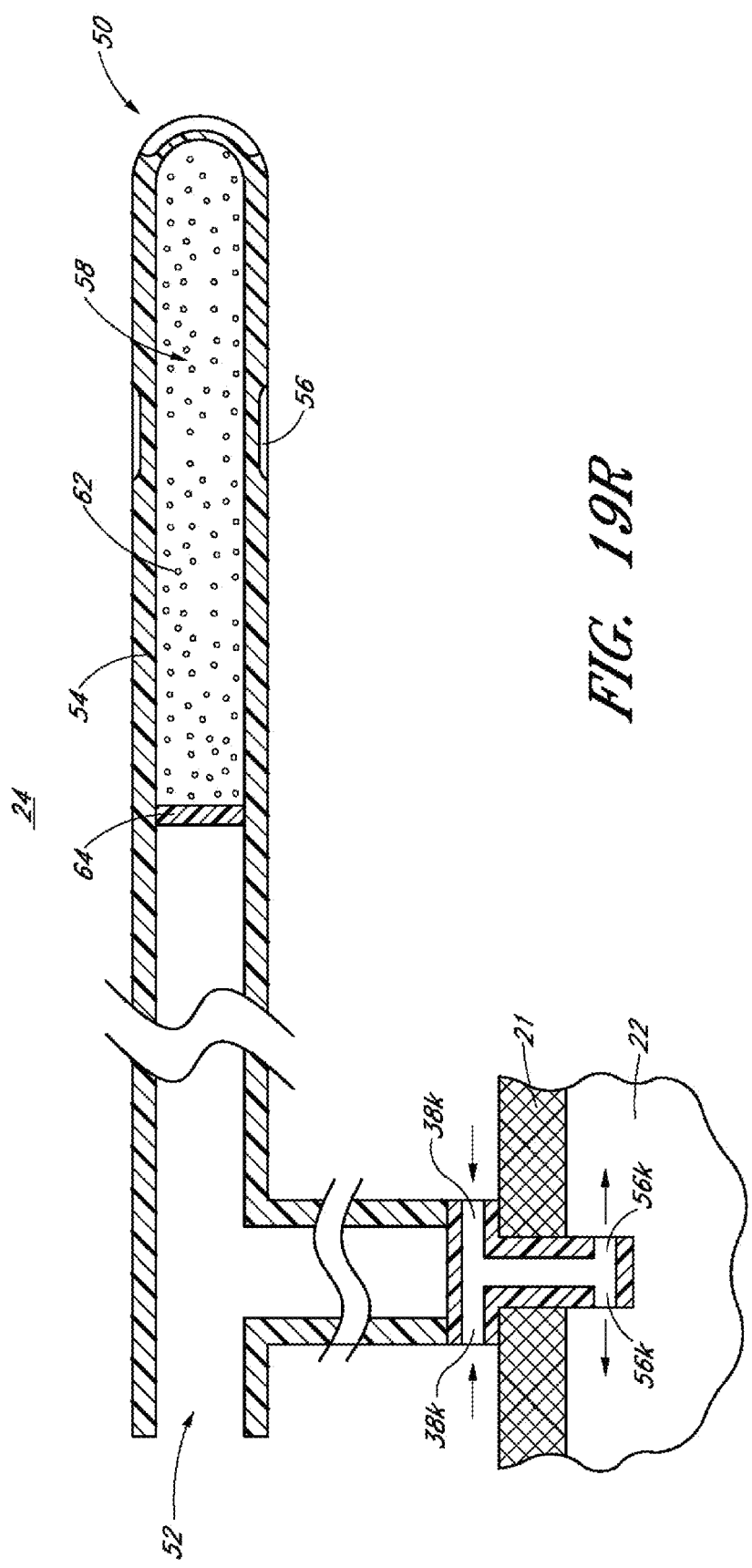

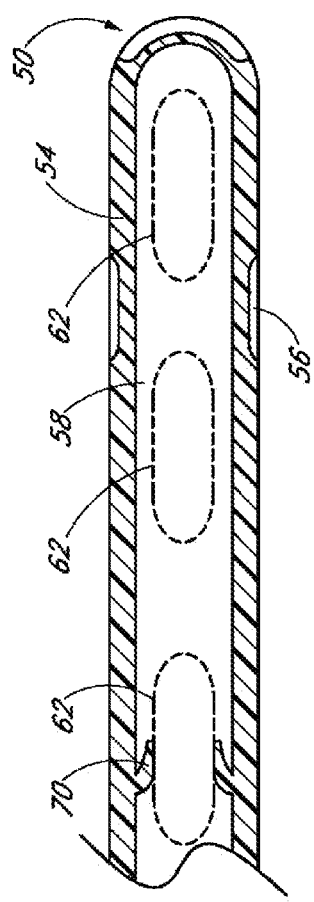
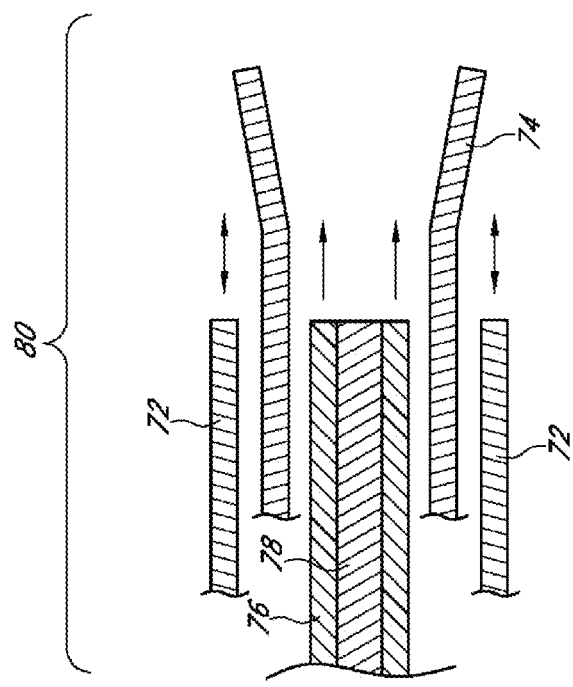
FIG. 20C

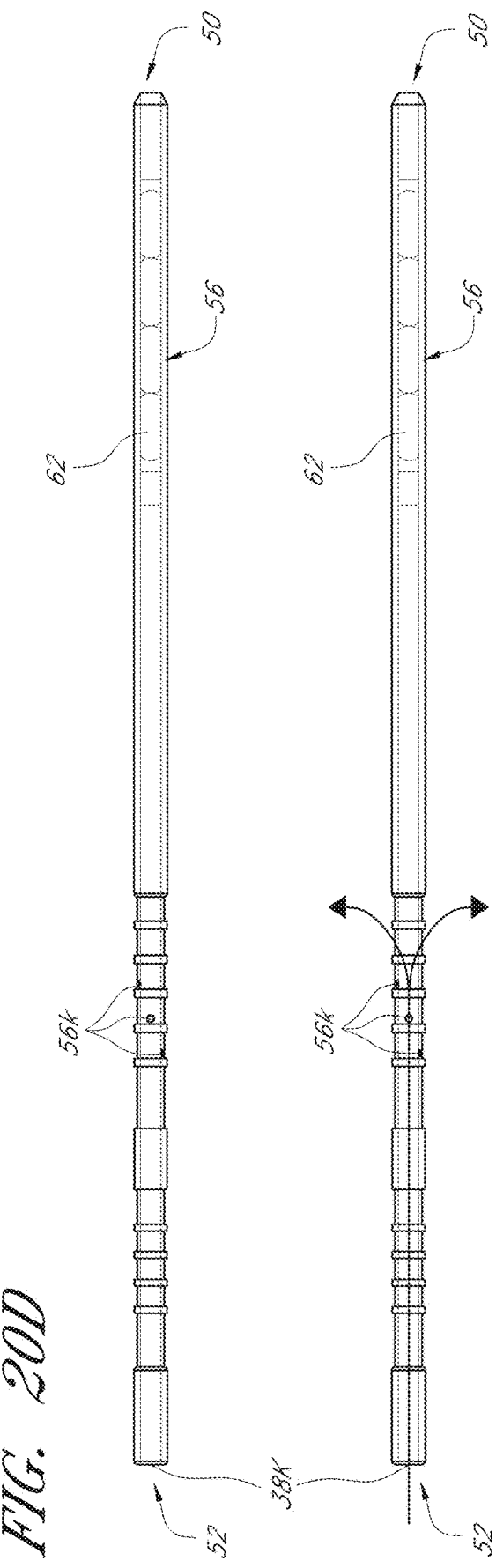

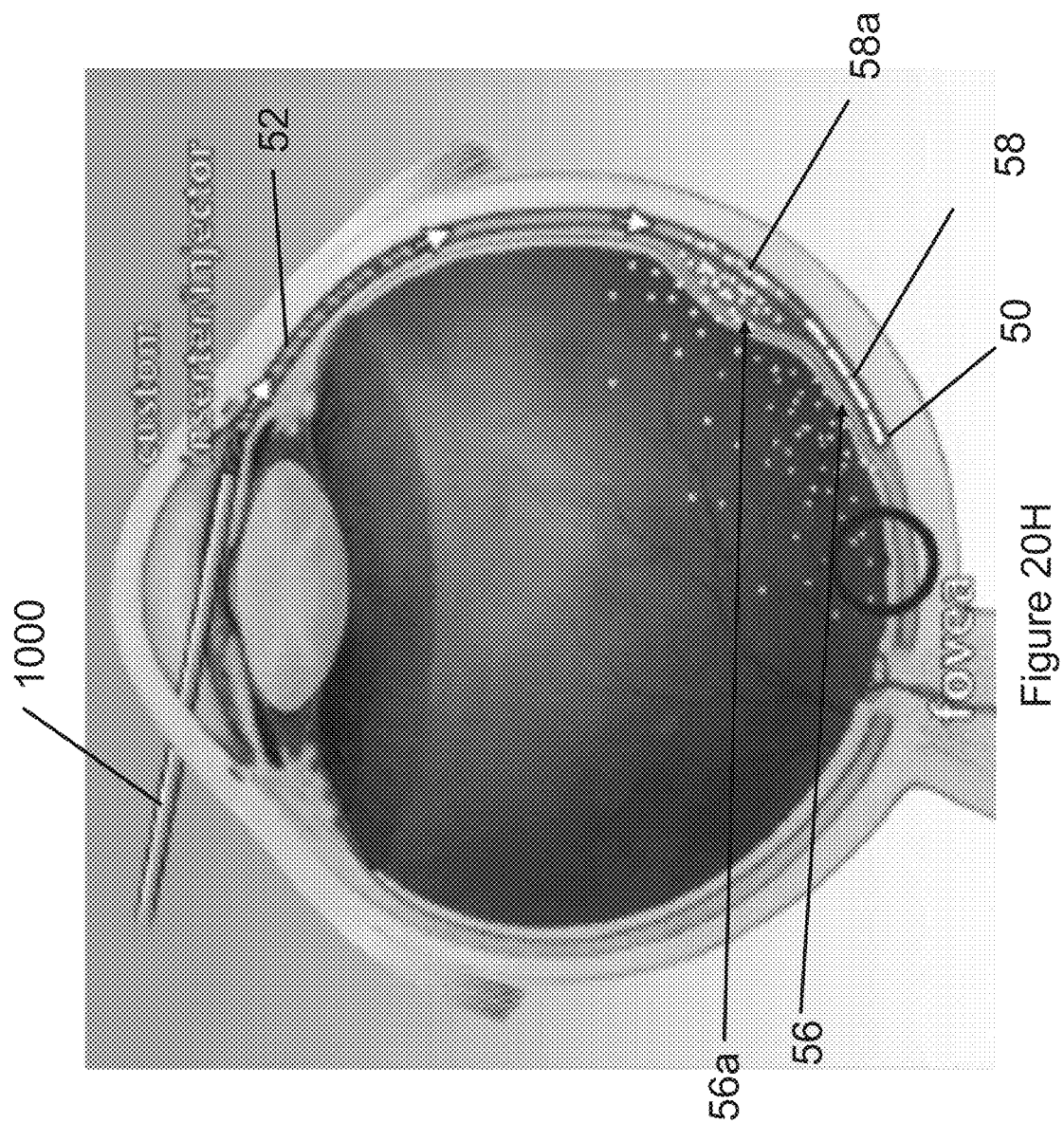

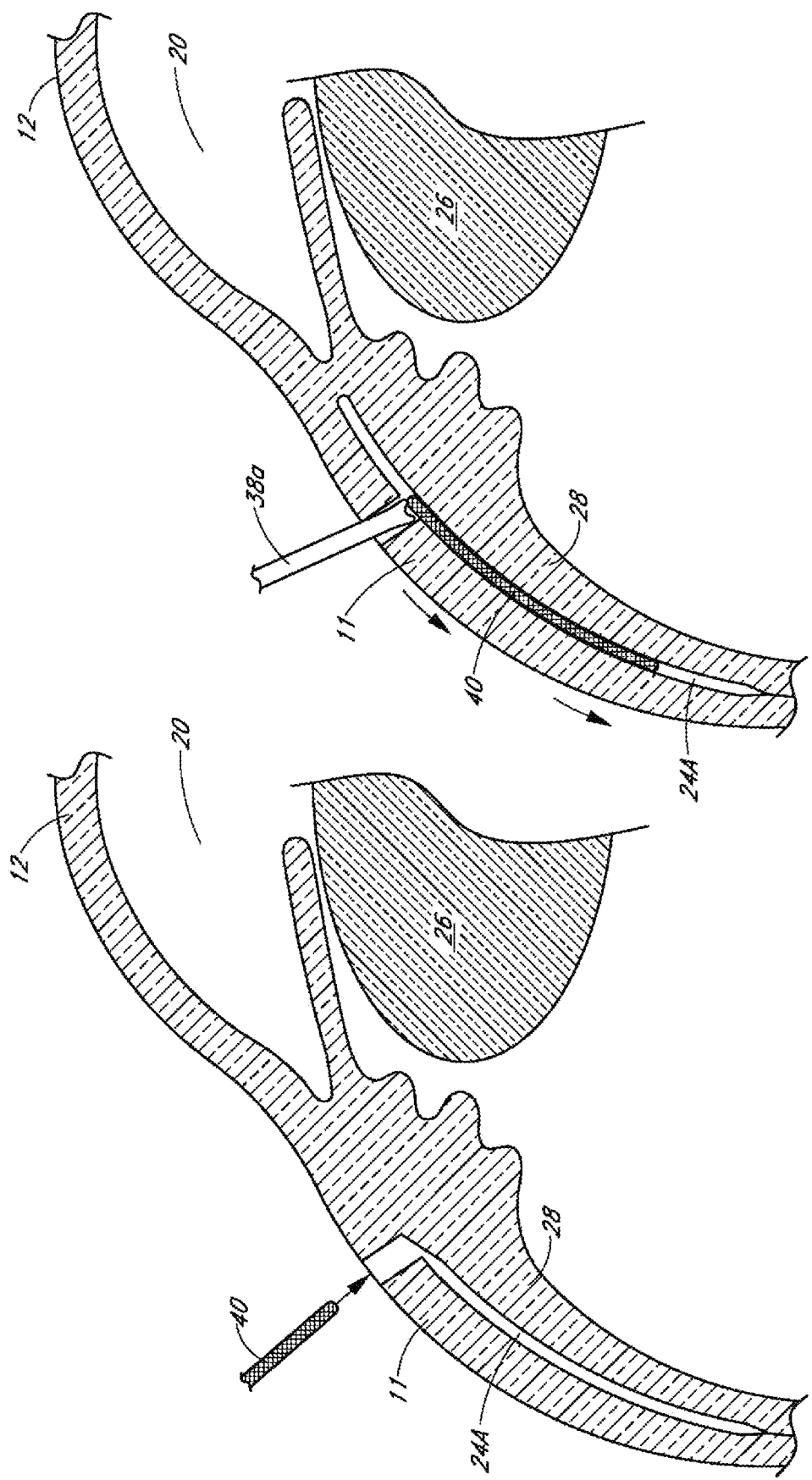

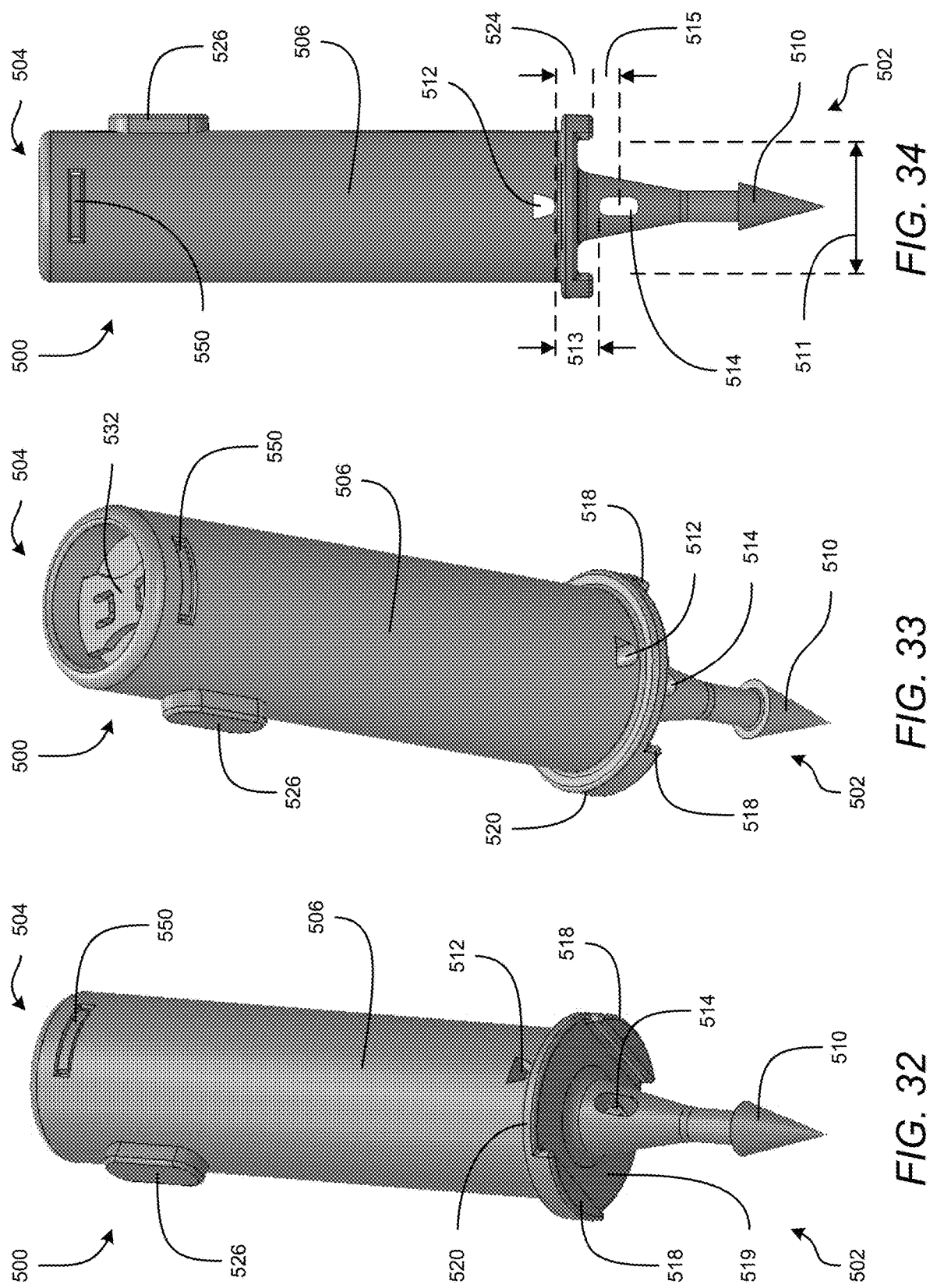

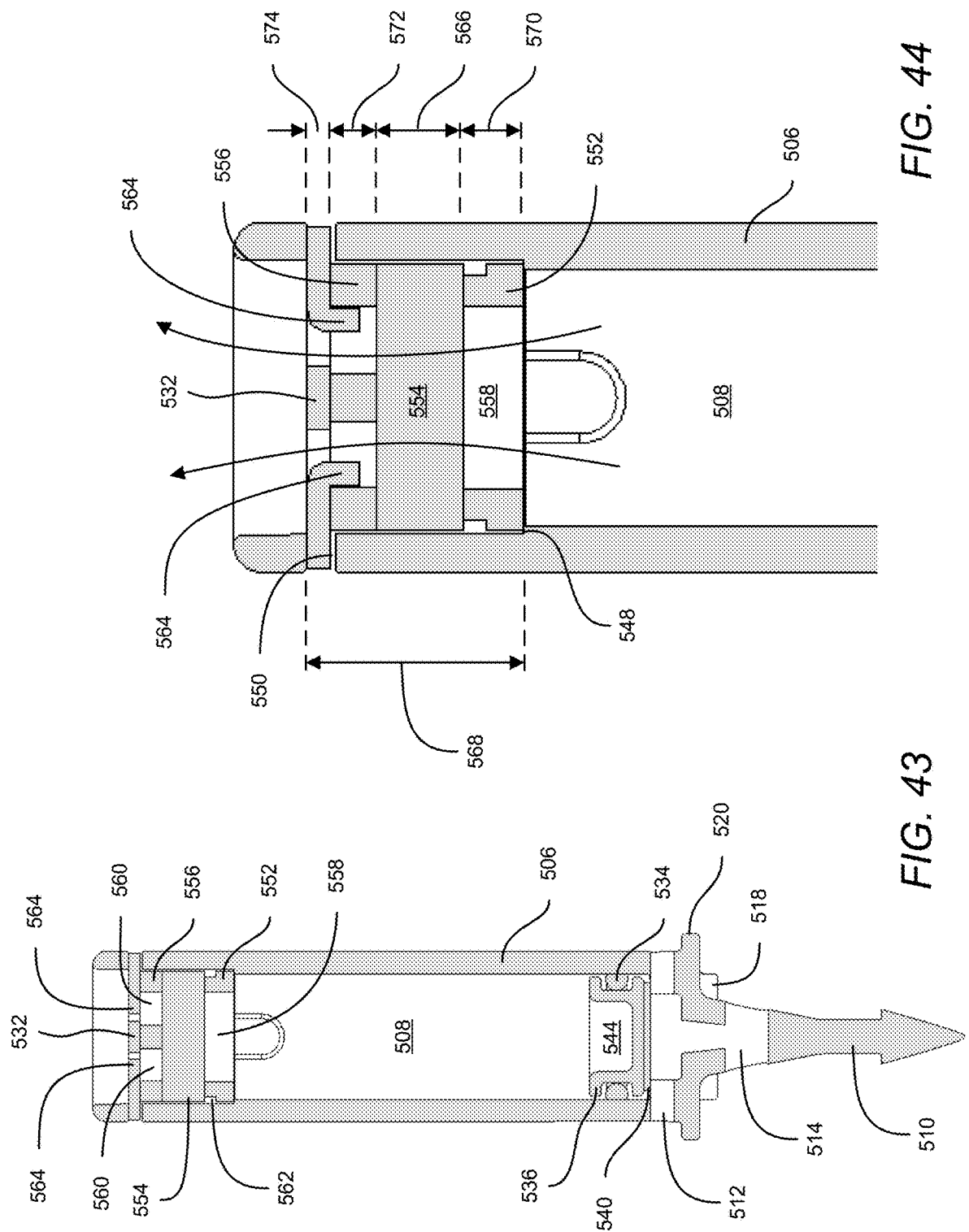

DRUG DELIVERY IMPLANTS WITH BI-DIRECTIONAL DELIVERY CAPACITY

RELATED CASES

This application is the U.S. National Phase application under 35 U.S.C. § 371 of International Application PCT/US2016/049996, filed on Sep. 1, 2016, which claims the benefit of U.S. Provisional Application Nos. 62/213,573, filed Sep. 2, 2015, the entire contents of each of which is incorporated by reference herein.

BACKGROUND

Field

This disclosure relates to implantable intraocular drug delivery devices structured to provide targeted and/or controlled release of a drug to a desired intraocular target tissue and methods of using such devices for the treatment of ocular diseases and disorders. In certain embodiments, this disclosure relates to a treatment of increased intraocular pressure wherein aqueous humor is permitted to flow out of an anterior chamber of the eye through a surgically implanted pathway. In certain embodiments, this disclosure also relates particularly to a treatment of ocular diseases with drug delivery devices affixed to the eye, such as to fibrous tissue within the eye.

Description of the Related Art

The mammalian eye is a specialized sensory organ capable of light reception and is able to receive visual images. The retina of the eye consists of photoreceptors that are sensitive to various levels of light, interneurons that relay signals from the photoreceptors to the retinal ganglion cells, which transmit the light-induced signals to the brain. The iris is an intraocular membrane that is involved in controlling the amount of light reaching the retina. The iris consists of two layers (arranged from anterior to posterior), the pigmented fibrovascular tissue known as a stroma and pigmented epithelial cells. The stroma connects a sphincter muscle (sphincter pupillae), which contracts the pupil, and a set of dilator muscles (dilator pupillae) which open it. The pigmented epithelial cells block light from passing through the iris and thereby restrict light passage to the pupil.

Numerous pathologies can compromise or entirely eliminate an individual's ability to perceive visual images, including trauma to the eye, infection, degeneration, vascular irregularities, and inflammatory problems. The central portion of the retina is known as the macula. The macula, which is responsible for central vision, fine visualization and color differentiation, may be affected by age related macular degeneration (wet or dry), diabetic macular edema, idiopathic choroidal neovascularization, or high myopia macular degeneration, among other pathologies.

Other pathologies, such as abnormalities in intraocular pressure, can affect vision as well. Aqueous humor is a transparent liquid that fills at least the region between the cornea, at the front of the eye, and the lens and is responsible for producing a pressure within the ocular cavity. Normal intraocular pressure is maintained by drainage of aqueous humor from the anterior chamber by way of a trabecular meshwork which is located in an anterior chamber angle, lying between the iris and the cornea or by way of the "uveoscleral outflow pathway." The "uveoscleral outflow pathway" is the space or passageway whereby aqueous exits the eye by passing through the ciliary muscle bundles located in the angle of the anterior chamber and into the tissue planes between the choroid and the sclera, which extend posteriorly to the optic nerve. About two percent of people in the United States have glaucoma, which is a group of eye diseases encompassing a broad spectrum of clinical presentations and etiologies but unified by increased intraocular pressure. Glaucoma causes pathological changes in the optic nerve, visible on the optic disk, and it causes corresponding visual field loss, which can result in blindness if untreated. Increased intraocular pressure is the only risk factor associated with glaucoma that can be treated, thus lowering intraocular pressure is the major treatment goal in all glaucomas, and can be achieved by drug therapy, surgical therapy, or combinations thereof.

Many pathologies of the eye progress due to the difficulty in administering therapeutic agents to the eye in sufficient quantities and/or duration necessary to ameliorate symptoms of the pathology. Often, uptake and processing of the active drug component of the therapeutic agent occurs prior to the drug reaching an ocular target site. Due to this metabolism, systemic administration may require undesirably high concentrations of the drug to reach therapeutic levels at an ocular target site. This can not only be impractical or expensive, but may also result in a higher incidence of side effects. Topical administration is potentially limited by limited diffusion across the cornea, or dilution of a topically applied drug by tear-action. Even those drugs that cross the cornea may be unacceptably depleted from the eye by the flow of ocular fluids and transfer into the general circulation. Thus, a means for ocular administration of a therapeutic agent in a controlled and targeted fashion would address the limitations of other delivery routes.

SUMMARY

In several embodiments, there is provided a combination drug device that has a reservoir filled with therapeutic agent to treat the distal pathways of the conventional aqueous outflow system between the Schlemm's canal and the aqueous veins, inclusive. In several embodiments, the device is implanted such that its inflow orifice collects aqueous from the anterior chamber of the eye, and directs it to Schlemm's canal, driven by the natural pressure differential. While the aqueous is passing through the device, it contacts a membrane, which is in turn in contact with a drug reservoir. Because of the drug concentration gradient across the membrane thickness, drug is eluted into the aqueous stream, and then carried to the outflow pathways where it becomes bioavailable to reduce the pressure drop from Schlemm's canal to aqueous veins, which is typically 3-6 mm Hg. Various drug candidates include, but are not limited to, vasodilators such as nitric oxide (nitroglycerine), caffeine, niacin, alprostadil, hydralazine, minoxidil, nesiridite, etc. In several embodiments, optionally, two reservoirs can be utilized to elute two agents one as described above into the distal outflow pathways, and a second glaucoma medication (prostaglandin, beta blocker, kinase inhibitor, for example) to elute into the anterior chamber as a second or combination treatment. Various embodiments disclosed herein can relate to a drug delivery ocular implant. In several embodiments, the implant comprises an outer shell having a proximal end and a distal end. The outer shell can be shaped to define an interior chamber. The implant can include a first and a second drug positioned within the outer shell (though 3, 4, 5 or more drugs can optionally be positioned within the outer shell). The implant can include a drug barrier within the interior chamber, the drug barrier separating the interior chamber into a first subchamber and a second subchamber. In some embodiments, the first drug is positioned within the first subchamber. In some embodiments, the second drug is positioned within the second subchamber. In additional embodiments, a plurality of drug barriers are used, creating a plurality of subchambers.

In some embodiments, the implant includes a first drug release element configured to release the first drug from the interior chamber. The first drug release element can include at least one or more of a distal seal member and a proximal seal member. The distal seal member can include at least one opening. The proximal seal member can include at least one opening. A membrane can be compressed between the distal seal member and the proximal seal member. In some embodiments, the implant can include a retainer configured to retain the drug release element in place relative to the outer shell.

In some embodiments, the first drug release element is configured such that the drug passes through the at least one opening in the distal seal member, through the compressed membrane, through the at least one opening in the proximal seal member, and out the proximal end of the outer shell.

In some embodiments, the implant includes a second drug release element configured to release the second drug from the interior chamber. The second drug release element can include a membrane positioned in fluid communication with the second drug within the interior chamber and in fluid communication with an inlet and outlet fluid flow pathway configured to conduct ocular fluid from an ocular chamber to a physiological fluid outflow pathway. In some embodiments, the second drug release element is optionally constructed in the same manner as the first drug release element, and vice versa.

In some embodiments, the physiological fluid outflow pathway is Schlemm's Canal. In some embodiments, the first drug comprises a prostaglandin analog. In some embodiments, the prostaglandin analog is selected from the group consisting of bimatoprost, latanoprost, travoprost, unoprostone, and mixtures thereof.

In some embodiments, the second drug comprises a vasodilator. In some embodiments, the vasodilator comprises nitric oxide, a nitric oxide precursor, a nitric oxide analog or a nitric oxide derivative. In some embodiments, the nitric oxide precursor comprises L-arginine. In some embodiments, the nitric oxide precursor comprises SNAP, hydroxylamine and/or sodium nitroprusside.

In some embodiments, the implant includes one or more enzymes that generate nitric oxide. In some embodiments, the drug barrier is impermeable to the first and second drug. In some embodiments, the drug barrier is optionally positioned to make the first subchamber and the second subchamber equal in volume.

In several embodiments, implants are provided that comprise an impermeable barrier positioned within the interior lumen that divides the lumen into two compartments, each compartment housing a separate therapeutic agent. In such embodiments, there is additionally provided a drug eluting regulating membrane at both the distal and proximal regions of the implant, e.g., an elution controlling membrane for the first compartment and an elution controlling membrane for the second compartment. Depending on the embodiment, the elution controlling membranes may be the same material, or may be different materials, based on the characteristics of the drug positioned within each interior compartment. Additionally, each of the membranes may have different elution characteristics, depending on the therapeutic agent housed within each compartment. In some embodiments, the implants allow for bidirectional drug elution, e.g., drug elution from the proximal portion of the implant, as well as drug elution from the distal portion of the implant. In several embodiments, this bidirectional drug elution allows two different regions of the eye to be treated concurrently. In some embodiments two different aspects of an ocular disorder are treated, while in some embodiments a side effect of one of the therapeutic agents is lessened by the administration of the second therapeutic agent.

In some embodiments, the implant need not be configured to elute from the proximal region, but rather may be configured to elute only from the distal region. In some embodiments, implants can be delivered in combinations of proximal eluting, distal eluting, and proximal+distal eluting configurations.

In some embodiments, the first drug comprises a prostaglandin analog. In several embodiments the prostaglandin analog is selected from the group consisting of bimatoprost, latanoprost, travoprost and unoprostone. In several embodiments, the prostaglandin analog is positioned within the more proximally positioned interior chamber of an implant having two chambers and thus, the prostaglandin analog is positioned such that it elutes from the implant into the anterior chamber of the eye. In several embodiments, the second drug positioned within the second interior chamber comprises a vasodilator. Vasodilator compounds that are released from the implant, in several embodiments, act on the trabecular meshwork, and its integrated vasculature, to increase blood flow in and around the trabecular meshwork. In some embodiments, this increase blood flow facilitates passage of ocular fluid through the trabecular meshwork and into a physiological fluid outflow pathway. Suitable vasodilators include, but are not limited to, endothelium derived hyperpolarizing factor (EDHF), cyclic GMP-dependent protein kinase, nitric oxide, epinephrine, histamine, prostacyclin, prostaglandin D2, prostaglandin E2, vasoactive intestinal peptide (VIP), adenosine, L-arginine, bradykinin, substance P, niacin, platelet activating factor, or precursors or derivatives of any of the agent listed above. In particular embodiments, nitric oxide, or precursor or derivatives thereof, is released from the implant. In several embodiments, a multicomponent composition suitable for generating nitric oxide in vivo is positioned within the second chamber of an implant. For example, one or more of the enzymes that functions to convert L-arginine to nitric oxide as well as L-arginine can be positioned within the second chamber of an implant. Thus, nitric oxide can be generated in vivo, close to its site of action, which in some embodiments addresses the relatively short half-life of nitric oxide. In several embodiments endothelial nitric oxide synthase, neuronal nitric oxide synthase, and/or inducible nitric oxide synthase positioned within the implant, along with L-arginine. In alternative embodiments the implant can house L-arginine as the second therapeutic agent and the natives enzymes responsible for converting L-arginine to nitric oxide within the eye are leveraged to generate nitric oxide as the L-arginine is eluted from the implant. In several embodiments, S-nitroso-N-acetylpenicillamine (SNAP), hydroxylamine, and/or sodium nitroprusside can be positioned within the implant to generate nitric oxide. Additionally, in several embodiments, supplemental compounds can be included in the implant that facilitate the production of additional nitric oxide, for example, by regeneration of L-arginine (thereby allowing further production of nitric oxide by conversion of the regenerated L-arginine).

In several embodiments, one or more compounds that inhibit the breakdown of nitric oxide, or otherwise prolong its half-life are also included in the implant. For example in several embodiments, phosphodiesterase inhibitors are used, such as for example inhibitors of phosphodiesterase type 5 (or other PDE types). In several embodiments one or more of sildenafil, tadalafil, and vardenafil are used. Other embodiments involve the use of molecules that are downstream of nitric oxide in a nitric oxide signaling pathway. For example, in several embodiments, cyclic GMP is eluted from the implant. Addition nitric oxide-releasing agents include, but are not limited to, sydnonimines, organic nitrites, sodium nitroprusside, nucleophyle-NO adducts and 5-nitrosothiols. Additional embodiments involve the introduction of agents that facilitate nitric oxide production. For example, inducers of iNOS are used in several embodiments. Such compounds include, but are not limited to interferons or interferon-like molecules (e.g., IFN-gamma), interleukins, tumor necrosis factor and the like are eluted from the implant. In some embodiments, other molecules with vasodilator function are eluted, such as, endothelin-1.

BRIEF DESCRIPTION OF THE DRAWINGS

These and other features, aspects, and advantages of the present disclosure will now be described with reference to the drawings of embodiments, which embodiments are intended to illustrate and not to limit the disclosure. One of ordinary skill in the art would readily appreciated that the features depicted in the illustrative embodiments are capable of combination in manners that are not explicitly depicted, but are both envisioned and disclosed herein.

FIG. 8 illustrates the distal portion of a drug delivery implant in accordance with embodiments disclosed herein.

FIG. 9 illustrates the distal portion of another drug delivery implant in accordance with embodiments disclosed herein.

FIGS. 10A-10G illustrate other drug delivery implants in accordance with embodiments disclosed herein.

FIGS. 11A-11B illustrate various embodiments of implants as disclosed herein that house one or more drug-containing pellets within the implant.

FIGS. 13A-13C illustrate drug delivery implants in accordance with embodiments disclosed herein.

FIGS. 20A-20C illustrate a rechargeable drug delivery device in accordance with embodiments disclosed herein.

FIGS. 20D and 20E depict various features of elongate delivery devices in accordance with several embodiments disclosed herein.

FIGS. 20G-20I illustrate various implantation configurations of drug delivery devices in accordance with embodiments disclosed herein.

FIGS. 27A-27D illustrate a cross-sectional view an eye during the steps of one embodiment of a method for implanting drug delivery devices as disclosed herein.

FIG. 32 is a distal perspective view of an example embodiment of a drug delivery ocular implant.

FIG. 33 is a proximal perspective view of the implant of FIG. 32.

FIG. 34 is a side view of the implant of FIG. 32.

FIG. 43 is a cross-sectional view of the implant of FIG. 32.

FIG. 44 is a partial cross-sectional view of the implant of FIG. 32.

DETAILED DESCRIPTION

Figure 1:
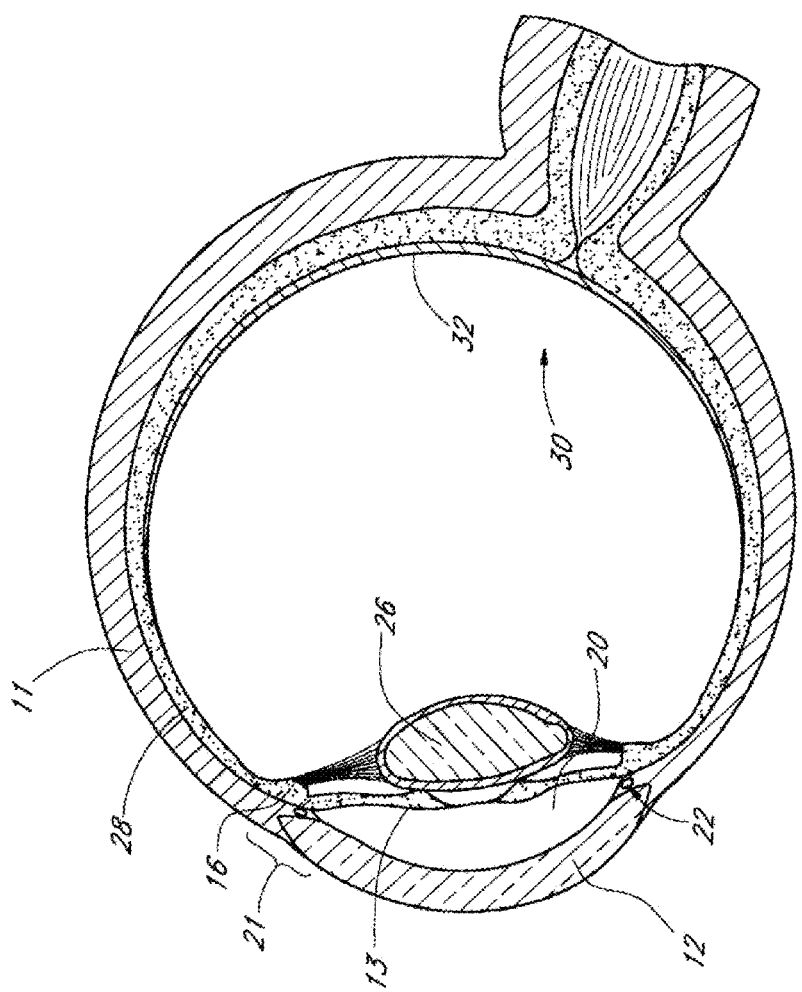
FIG. 1 illustrates a schematic cross sectional view of an eye.

Achieving local ocular administration of a drug may require direct injection or application, but could also include the use of a drug eluting implant, a portion of which, could be positioned in close proximity to the target site of action within the eye or within the chamber of the eye where the target site is located (e.g., anterior chamber, posterior chamber, or both simultaneously). Use of a drug eluting implant could also allow the targeted delivery of a drug to a specific ocular tissue, such as, for example, the macula, the retina, the ciliary body, the optic nerve, or the vascular supply to certain regions of the eye. Use of a drug eluting implant could also provide the opportunity to administer a controlled amount of drug for a desired amount of time, depending on the pathology. For instance, some pathologies may require drugs to be released at a constant rate for just a few days, others may require drug release at a constant rate for up to several months, still others may need periodic or varied release rates over time, and even others may require periods of no release (e.g., a "drug holiday"). Further, implants may serve additional functions once the delivery of the drug is complete. Implants may maintain the patency of a fluid flow passageway within an ocular cavity, they may function as a reservoir for future administration of the same or a different therapeutic agent, or may also function to maintain the patency of a fluid flow pathway or passageway from a first location to a second location, e.g. function as a stent. Conversely, should a drug be required only acutely, an implant may also be made completely biodegradable.

Implants according to the embodiments disclosed herein preferably do not require an osmotic or ionic gradient to release the drug(s), are implanted with a device that minimizes trauma to the healthy tissues of the eye which thereby reduces ocular morbidity, and/or may be used to deliver one or more drugs in a targeted and controlled release fashion to treat multiple ocular pathologies or a single pathology and its symptoms. However, in certain embodiments, an osmotic or ionic gradient is used to initiate, control (in whole or in part), or adjust the release of a drug (or drugs) from an implant. In some embodiments, osmotic pressure is balanced between the interior portion(s) of the implant and the ocular fluid, resulting in no appreciable gradient (either osmotic or ionic). In such embodiments, variable amounts of solute are added to the drug within the device in order to balance the pressures.

As used herein, "drug" refers generally to one or more drugs that may be administered alone, in combination and/or compounded with one or more pharmaceutically acceptable excipients (e.g. binders, disintegrants, fillers, diluents, lubricants, drug release control polymers or other agents, etc.), auxiliary agents or compounds as may be housed within the implants as described herein. The term "drug" is a broad term that may be used interchangeably with "therapeutic agent" and "pharmaceutical" or "pharmacological agent" and includes not only so-called small molecule drugs, but also macromolecular drugs, and biologics, including but not limited to proteins, nucleic acids, antibodies and the like, regardless of whether such drug is natural, synthetic, or recombinant. Drug may refer to the drug alone or in combination with the excipients described above. "Drug" may also refer to an active drug itself or a prodrug or salt of an active drug.

As used herein, "patient" shall be given its ordinary meaning and shall also refer to mammals generally. The term "mammal", in turn, includes, but is not limited to, humans, dogs, cats, rabbits, rodents, swine, ovine, and primates, among others. Additionally, throughout the specification ranges of values are given along with lists of values for a particular parameter. In these instances, it should be noted that such disclosure includes not only the values listed, but also ranges of values that include whole and fractional values between any two of the listed values.

In several embodiments, a biocompatible drug delivery ocular implant is provided that comprises an outer shell that is shaped to define at least one interior lumen that houses a drug for release into an ocular space. The outer shell is polymeric in some embodiments, and in certain embodiments is substantially uniform in thickness, with the exception of areas of reduced thickness, through which the drug more readily passes from the interior lumen to the target tissue. In other words, a region of drug release may be created by virtue of the reduced thickness. In several other embodiments the shell of the implant comprises one or more regions of increased drug permeability (e.g., based on the differential characteristics of portions of the shell such as materials, orifices, etc.), thereby creating defined regions from which the drug is preferentially released. In other embodiments, if the material of the outer shell is substantially permeable to a drug, the entire outer shell can be a region of drug release. In yet another embodiment, portions of the outer shell that surround where the drug is placed in the interior lumen or void of the device may be considered a region of drug release. For example, if the drug is loaded toward the distal end or in the distal portion of the device (e.g. the distal half or distal ⅔ of the device), the distal portion of the device will be a region of drug release as the drug will likely elute preferentially through those portions of the outer shell that are proximate to the drug. Therefore, as used herein, the term "region of drug release" shall be given its ordinary meaning and shall include the embodiments disclosed in this paragraph, including a region of drug permeability or increased drug permeability based on the characteristics of a material and/or the thickness of the material, one or more orifices or other passageways through the implant (also as described below), regions of the device proximate to the drug and/or any of these features in conjunction with one or more added layers of material that are used to control release of the drug from the implant. Depending on the context, these terms and phrases may be used interchangeably or explicitly throughout the present disclosure.

In some embodiments, the implant body comprises a fluid flow pathway. In some embodiments, the implant optionally comprises a retention feature. In some embodiments, the drug is encapsulated, coated, or otherwise covered with a biodegradable coating, such that the timing of initial release of the drug is controlled by the rate of biodegradation of the coating. In some embodiments, such implants are advantageous because they allow a variable amount of drug to be introduced (e.g., not constrained by dimensions of an implant shell) depending on the type and duration of therapy to be administered. In some embodiments having a shunt feature the shunt feature works in conjunction with the drug to treat one or more symptoms of the disease or condition affecting the patient. For example, in some embodiments, the shunt removes fluid from the anterior chamber while the drug simultaneously reduces the production of ocular fluid. In other embodiments, as discussed herein, the shunt counteracts one or more side effects of administration of a particular drug (e.g., the shunt drains ocular fluid that was produced by the actions of the drug).

Following implantation at the desired site within the eye, drug is released from the implant in a targeted and controlled fashion, based on the design of the various aspects of the implant, preferably for an extended period of time. The implant and associated methods disclosed herein may be used in the treatment of pathologies requiring drug administration to the posterior chamber of the eye, the anterior chamber of the eye, or to specific tissues within the eye, such as the macula, the ciliary body or other ocular target tissues.

FIG. 1 illustrates the anatomy of an eye, which includes the sclera 11, which joins the cornea 12 at the limbus 21, the iris 13 and the anterior chamber 20 between the iris 13 and the cornea 12. The eye also includes the lens 26 disposed behind the iris 13, the ciliary body 16 and Schlemm's canal 22. The eye also includes a uveoscleral outflow pathway, which functions to remove a portion of fluid from the anterior chamber, and a suprachoroidal space positioned between the choroid 28 and the sclera 11. The eye also includes the posterior region 30 of the eye which includes the macula 32.

General

In some embodiments functioning as a drug delivery device alone, the implant is configured to deliver one or more drugs to anterior region of the eye in a controlled fashion while in other embodiments the implant is configured to deliver one or more drugs to the posterior region of the eye in a controlled fashion. In still other embodiments, the implant is configured to simultaneously deliver drugs to both the anterior and posterior region of the eye in a controlled fashion. In yet other embodiments, the configuration of the implant is such that drug is released in a targeted fashion to a particular intraocular tissue, for example, the macula or the ciliary body. In certain embodiments, the implant delivers drug to the ciliary processes and/or the posterior chamber. In certain other embodiments, the implant delivers drug to one or more of the ciliary muscles and/or tendons (or the fibrous band). In some embodiments, implants deliver drug to one or more of Schlemm's canal, the trabecular meshwork, the episcleral veins, the lens cortex, the lens epithelium, the lens capsule, the sclera, the scleral spur, the choroid, the suprachoroidal space, retinal arteries and veins, the optic disc, the central retinal vein, the optic nerve, the macula, the fovea, and/or the retina. In still other embodiments, the delivery of drug from the implant is directed to an ocular chamber generally. It will be appreciated that each of the embodiments described herein may target one or more of these regions, and may also optionally be combined with a shunt feature (described below).

In several embodiments, the implant comprises an outer shell. In some embodiments, the outer shell is tubular and/or elongate, while in other embodiments, other shapes (e.g., round, oval, cylindrical, etc.) are used. In certain embodiments, the outer shell is not biodegradable, while in others, the shell is optionally biodegradable. In several embodiments, the shell is formed to have at least a first interior lumen. In certain embodiments, the first interior lumen is positioned at or near the distal end of the device. In other embodiments, a lumen may run the entire length of the outer shell. In some embodiments, the lumen is subdivided. In certain embodiments, the first interior lumen is positioned at or near the proximal end of the device. In those embodiments additionally functioning as a shunt, the shell may have one or more additional lumens within the portion of the device functioning as a shunt.

In several embodiments, the drug (or drugs) is positioned within the interior lumen (or lumens) of the implant shell. In several embodiments, the drug is preferentially positioned within the more distal portion of the lumen. In some embodiments, the distal-most 15 mm of the implant lumen (or lumens) house the drug (or drugs) to be released. In some embodiments, the distal-most 10 mm, including 1, 2, 3, 4, 5, 6, 7, 8, and 9 mm of the interior lumen(s) house the drug to be released. In several embodiments, the drug is preferentially positioned within the more proximal portion of the lumen.

In some embodiments, the drug diffuses through the shell and into the intraocular environment. In several embodiments, the outer shell material is permeable or semi-permeable to the drug (or drugs) positioned within the interior lumen, and therefore, at least some portion of the total elution of the drug occurs through the shell itself, in addition to that occurring through any regions of increased permeability, reduced thickness, orifices etc. The term "permeable" and related terms (e.g. "impermeable" or "semi permeable") are used herein to refer to a material being permeable to some degree (or not permeable) to one or more drugs or therapeutic agents and/or ocular fluids. The term "impermeable" does not necessarily mean that there is no elution or transmission of a drug through a material, instead such elution or other transmission is negligible or very slight, e.g. less than about 3% of the total amount, including less than about 2% and less than about 1%.

In some embodiments, the implant is dimensioned such that, following implantation, the distal end of the implant is located sufficiently close to the macula that the drug delivered by the implant reaches the macula. In some embodiments incorporating a shunt feature, the implant is dimensioned such that when the distal end of the implant is positioned sufficiently near the macula, the proximal end of the implant extends into the anterior chamber of the eye. In those embodiments, outflow ports in the implant, described in more detail below, are positioned such that the aqueous humor will be drained into the uveoscleral outflow pathway or other physiological outflow pathway.

In some embodiments, the shunt feature works in conjunction with the drug delivery function to potentiate the therapeutic effects of the delivered agent. In other embodiments, the therapeutic effects of the delivered agent may be associated with unwanted side effects, such as fluid accumulation or swelling. In some embodiments, the shunt feature functions ameliorate the side effects of the delivered agent. It shall be appreciated that the dimensions and features of the implants disclosed herein may be tailored to attain targeted and/or controlled delivery to various regions of the eye while still allowing communication with a physiological outflow pathway.

For example, in some embodiments, the implant is dimensioned such that following implantation the distal end of the implant is located in the suprachoroidal space and the proximal end of the implant is located in the anterior chamber of the eye. In several embodiments, the drug eluted from the implant elutes from the proximal end of the implant into the anterior chamber. In some embodiments incorporating a shunt feature, one or more outflow ports in the implant are positioned such that aqueous humor will drain into the uveoscleral pathway. In several embodiments, aqueous humor will drain from the anterior chamber to the suprachoroidal space.

The delivery instruments, described in more detail below, may be used to facilitate delivery and/or implantation of the drug delivery implant to the desired location of the eye. The delivery instrument may be used to place the implant into a desired position, such as the inferior portion of the iris, the suprachoroidal space near the macula, in a position extending from the anterior chamber to the suprachoroidal space, or other intraocular region. The design of the delivery instruments may take into account, for example, the angle of implantation and the location of the implant relative to an incision. For example, in some embodiments, the delivery instrument may have a fixed geometry, be shape-set, or actuated. In some embodiments, the delivery instrument may have adjunctive or ancillary functions, such as for example, injection of dye and/or viscoelastic fluid, dissection, or use as a guidewire. As used herein, the term "incision" shall be given its ordinary meaning and may also refer to a cut, opening, slit, notch, puncture or the like.

In certain embodiments the drug delivery implant may contain one or more drugs which may or may not be compounded with a bioerodible polymer or a bioerodible polymer and at least one additional agent. In still other embodiments, the drug delivery implant is used to sequentially deliver multiple drugs. Additionally, certain embodiments are constructed using different outer shell materials, and/or materials of varied permeability to generate a tailored drug elution profile. Certain embodiments are constructed using different numbers, dimensions and/or locations of orifices in the implant shell to generate a tailored drug elution profile. Certain embodiments are constructed using different polymer coatings and different coating locations on the implant to generate a tailored drug elution profile. Some embodiments elute drug at a constant rate, others yield a zero-order release profile. Yet other embodiments yield variable elution profiles. Still other embodiments are designed to stop elution completely or nearly completely for a predetermined period of time (e.g., a "drug holiday") and later resume elution at the same or a different elution rate or elution concentration. Some such embodiments elute the same therapeutic agent before and after the drug holiday while other embodiments elute different therapeutic agents before and after the drug holiday.

Drug Delivery Implants

The present disclosure relates to ophthalmic drug delivery implants which, following implantation at an implantation site, provide controlled release of one or more drugs to a desired target region within the eye, the controlled release being for an extended, period of time. Various embodiments of the implants are shown in FIGS. 2-20 and will be referred to herein.

Figure 2:
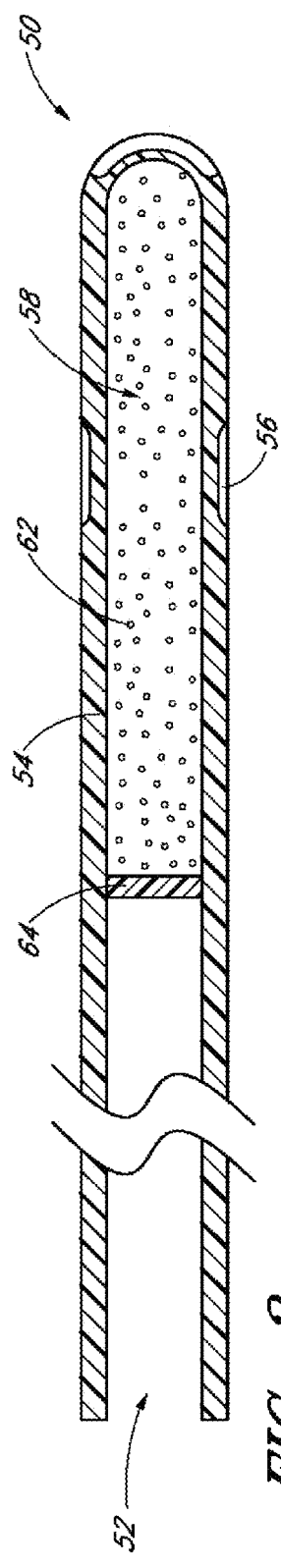
FIG. 2 illustrates a drug delivery device in accordance with embodiments disclosed herein.

FIG. 2 depicts a cross sectional schematic of one embodiment of an implant in accordance with the description herein. The implant comprises an outer shell 54 made of one or more biocompatible materials. The outer shell of the implant is manufactured by extrusion, drawing, injection molding, sintering, micro machining, laser machining, and/or electrical discharge machining, or any combination thereof. Other suitable manufacturing and assembly methods known in the art may also be used. In several embodiments, the outer shell is tubular in shape, and comprises at least one interior lumen 58. In some embodiments the interior lumen is defined by the outer shell and a partition 64. In some embodiments, the partition is impermeable, while in other embodiments the partition is permeable or semi-permeable. In some embodiments, the partition allows for the recharging of the implant with a new dose of drug(s). In some other embodiments, other shell shapes are used, yet still produce at least one interior lumen. In several embodiments the outer shell of the implant 54 is manufactured such that the implant has a distal portion 50 and a proximal portion 52. In several embodiments, the thickness of the outer shell 54 is substantially uniform. In other embodiments the thickness varies in certain regions of the shell. Depending on the desired site of implantation within the eye, thicker regions of the outer shell 54 are positioned where needed to maintain the structural integrity of the implant.

In some embodiments, the implant is made of a flexible material. In other embodiments, a portion of the implant is made from flexible material while another portion of the implant is made from rigid material. In some embodiments, the implant comprises one or more flexures (e.g., hinges). In some embodiments, the drug delivery implant is pre-flexed, yet flexible enough to be contained within the straight lumen of a delivery device.

In several embodiments the majority of the surface of the outer shell of the implant is substantially impermeable to ocular fluids. In several embodiments, the majority of the surface of the outer shell of the implant is also substantially impermeable to the drug 62 housed within the interior lumen of the implant (discussed below). In other embodiments, the outer shell is semi-permeable to drug and/or ocular fluid and certain regions of the implant are made less or more permeable by way of coatings or layers or impermeable (or less permeable) material placed within or on the outer shell.

In several embodiments, the outer shell also has one or more regions of drug release 56. In some embodiments the regions of drug release are of reduced thickness compared to the adjacent and surrounding thickness of the outer shell. In some embodiments, the regions of reduced thickness are formed by one or more of ablation, stretching, etching, grinding, molding and other similar techniques that remove material from the outer shell (See FIG. 6F). In other embodiments the regions of drug release are of a different thickness (e.g., some embodiments are thinner and other embodiments are thicker) as compared to the surrounding outer shell, but are manufactured with an increased permeability to one or more of the drug 62 and ocular fluid. In still other embodiments, the outer shell is uniform or substantially uniform in thickness but constructed with materials that vary in permeability to ocular fluid and drugs within the lumen. As such, these embodiments have defined regions of drug release from the implant.

Figure 3A:
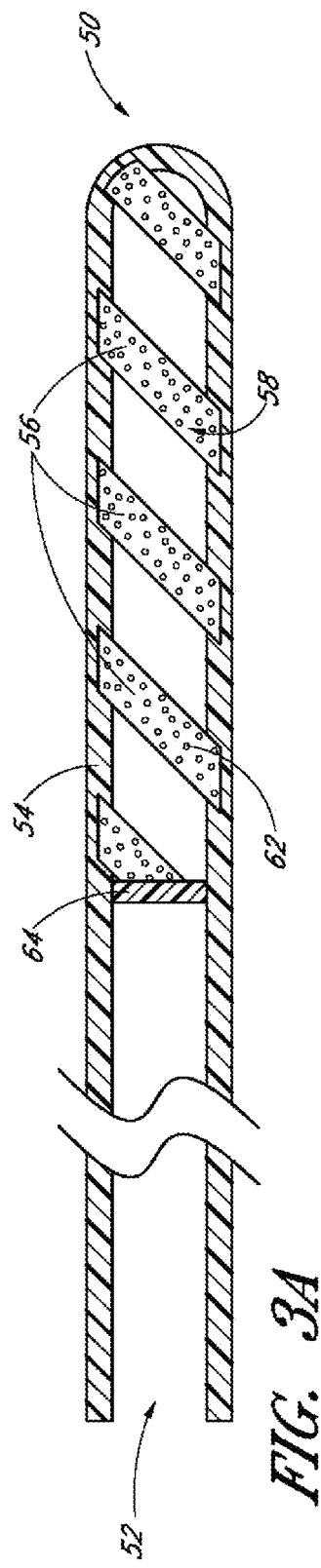
FIGS. 3A and 3B illustrate drug delivery devices in accordance with embodiments disclosed herein.
Figure 3B:
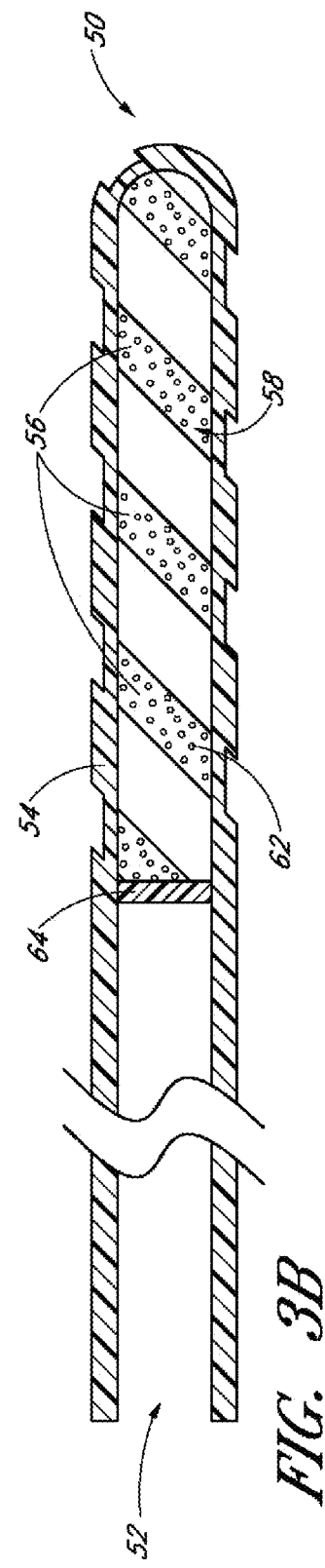

The regions of drug release may be of any shape needed to accomplish sufficient delivery of the drug to a particular target tissue of the eye. For example, in FIG. 2, the regions 56 are depicted as defined areas of thinner material. FIG. 3A depicts the regions of drug release used in other embodiments, namely a spiral shape of reduced thickness 56. In some embodiments, the spiral is on the interior of the implant shell (i.e., the shell is rifled; see FIG. 3A). In other embodiments, spiral is on the exterior of the shell (see FIG. 3B). In other embodiments, the region of drug release is shaped as circumferential bands around the implant shell.

Figure 4:
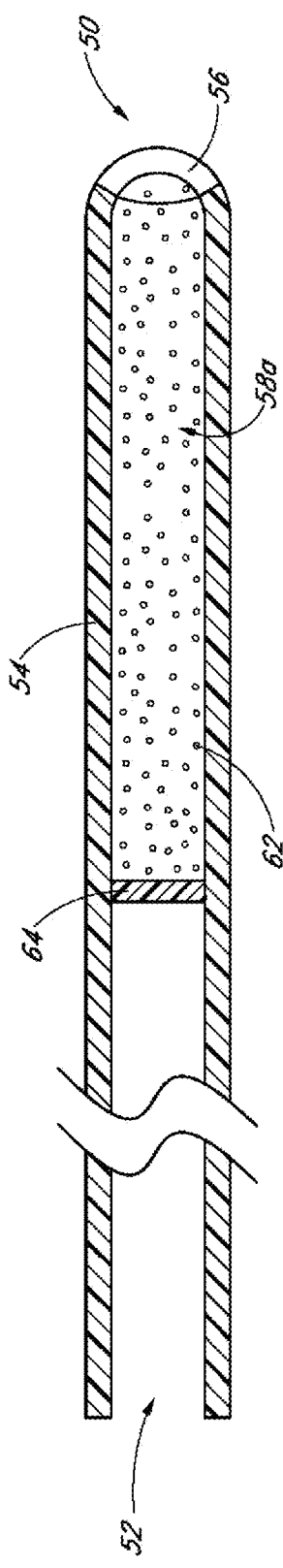
FIG. 4 illustrates a drug delivery device in accordance with embodiments disclosed herein.

FIG. 4 depicts another embodiment, wherein a region of drug release is located at the distal-most portion of the implant. Certain such embodiments are used when more posterior regions of the eye are to be treated. Alternatively, or in conjunction with the embodiment of FIG. 4, the proximal portion of the implant may also have a region of drug release at or near the proximal-most portion. In other embodiments, the regions of drug release are uniformly or substantially uniformly distributed along the distal and/or proximal portions of the implant. In some embodiments, the regions of drug release are located at or near the distal end of the implant or, in alternative embodiments at or near the proximal end of the implant (or in still additional embodiments, at or near both the proximal and distal ends). In certain embodiments, the implants (based on the regions of drug release (based on thickness/permeability, orifices, layers etc.) are strategically placed to create a differential pattern of drug elution from the implant, depending on the target tissue to be treated after implantation. In some embodiments, the regions of drug release are configured to preferentially elute drug from the distal end of the implant. In some such embodiments, the regions of drug release are strategically located at or near a target tissue in the more posterior region of the eye after the implantation procedure is complete. In some embodiments, the regions of drug release are configured to preferentially elute drug from the proximal end of the implant. In some such embodiments, the regions of drug release are strategically located at or near a target tissue in the anterior chamber of the eye after the implantation procedure is complete. As discussed in more detail below, in several embodiments, the regions of drug release comprise one (or more) orifices that allow communication between an interior lumen of the implant and the environment in which the implant is implanted. It shall also be appreciated from the disclosure herein that, in certain embodiments, combinations of regions of drug release (as described above) may be combined with one or more orifices and/or coatings (below) in order to tailor the drug release profile. Similarly, the embodiments described above and depicted in FIGS. 2-4 can be adapted to be implanted into the punctum of a subject, as described in more detail herein.

The implant in some embodiments includes a distal portion located at the distal end of the implant. In some embodiments, the distal portion is sufficiently sharp to pierce eye tissue near the scleral spur of the eye. The distal portion can be sufficiently blunt so as not to substantially penetrate scleral tissue of the eye. In some embodiments, the implant has a generally sharpened forward end and is self-trephinating, i.e., self-penetrating, so as to pass through tissue without pre-forming an incision, hole, or aperture. The sharpened forward end can be, for example, conical or tapered. The taper angle of the sharpened end is, for example, about 30°±15° in some embodiments. In some embodiments, the radius of the tip of the distal end is about 70 microns to about 200 microns. In embodiments comprising a shunt, discussed further herein, an outlet opening is formed at the distal end of the shunt and the distal portion gradually increases in cross-sectional size in the proximal direction, preferably at a generally constant taper or radius, or in a parabolic manner.

In some embodiments, the implant has a cap or tip at one or both ends. A distal end cap can include a tissue-piercing end. In some embodiments the cap has a conically shaped tip. In other embodiments, the cap can have a tapered angle tip. The tip can be sufficiently sharp to pierce eye tissue near the scleral spur of the eye. The tip can also be sufficiently blunt so as not to substantially penetrate scleral tissue of the eye. In some embodiments, the conically shaped tip facilitates delivery of the shunt to the desired location. In embodiments comprising a shunt, the distal end cap has one or more outlet openings to allow fluid flow. Each of the one or more outlet openings can communicate with at least one of the one or more lumens.

In some embodiments, the implant has a substantially constant cross-sectional shape through most of its length. Alternatively, the implant can have portions of reduced or enlarged cross-sectional size (e.g., diameter) along its length. In some embodiments, the distal end of the implant has a tapered portion, or a portion having a continually decreasing radial dimension with respect to the lumen axis along the length of the axis. The tapered portion preferably in some embodiments terminates with a smaller radial dimension at the distal end. During implantation, the tapered portion can operate to form, dilate, and/or increase the size of an incision or puncture created in the tissue. The tapered portion may have a diameter of about 30-gauge to about 23-gauge, and preferably about 25-gauge.

Figure 5:
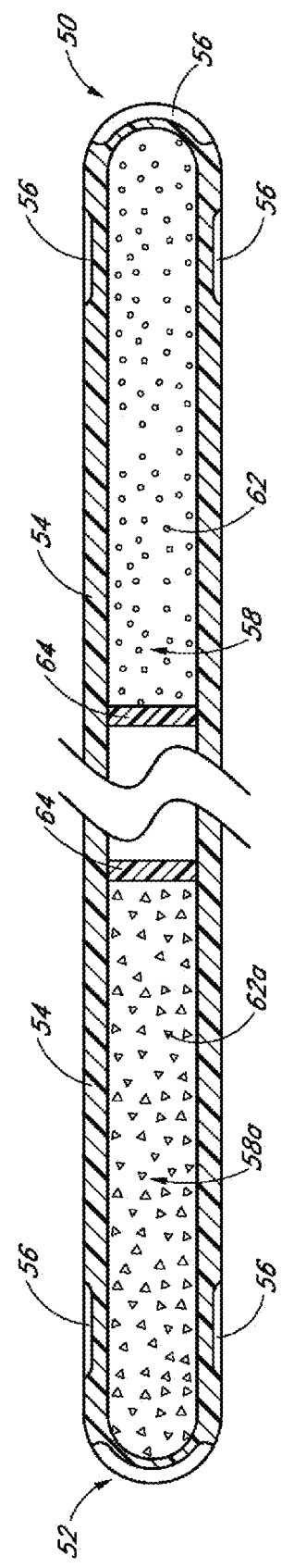
FIG. 5 illustrates a drug delivery device in accordance with embodiments disclosed herein.

In several embodiments, lumens are present in both the proximal and distal portions of the implant (see FIGS. 5; 58a and 58, respectively). In such embodiments both the proximal 52 and the distal portion 50 of the implant have one or more regions of drug release. In some such embodiments the proximal and distal portions of the implant house two different drugs 62a (proximal) and 62 (distal) in the lumens. See FIG. 5. In other embodiments, the proximal and distal portion of the implant may house the same drugs, or the same drug at different concentrations or combined with alternate excipients. It will be appreciated that the placement of the regions of drug release, whether within the proximal portion, distal portion, or both portions of the implant, are useful to specifically target certain intraocular tissues. For example, placement of the region of drug release at the distal most portion of the implant, is useful, in some embodiments, for specifically targeting drug release to particular intraocular regions, such as the macula. In other embodiments, the regions of drug release are placed to specifically release drug to other target tissues, such as the ciliary body, the retina, the vasculature of the eye, or any of the ocular targets discussed above or known in the art. In some embodiments, the specific targeting of tissue by way of specific placement of the region of drug release reduces the amount of drug needed to achieve a therapeutic effect. In some embodiments, the specific targeting of tissue by way of specific placement of the region of drug release reduces non-specific side effects of an eluted drug. In some embodiments, the specific targeting of tissue by way of specific placement of the region of drug release increases the overall potential duration of drug delivery from the implant.

Figure 6A:
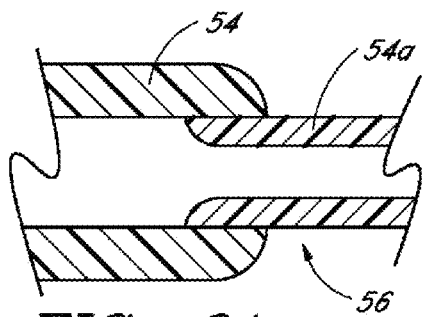
FIGS. 6A-6I illustrate various aspects of a drug delivery device in accordance with embodiments disclosed herein.
Figure 6E:
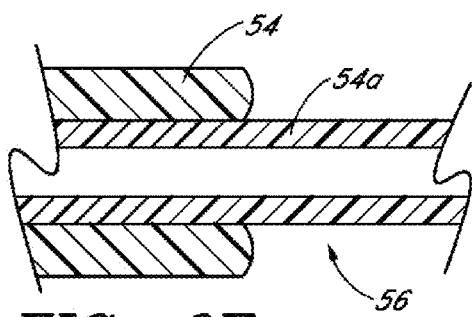
Figure 6B:
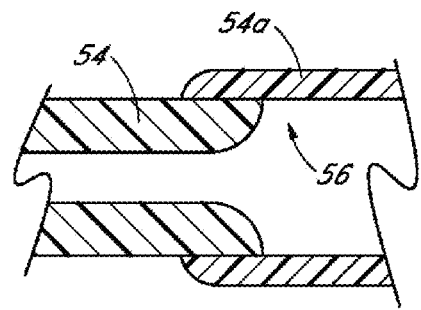
Figure 6F:
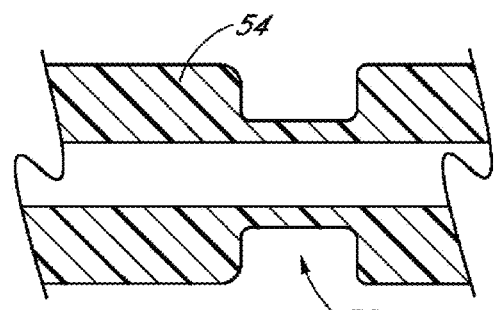
Figure 6C:
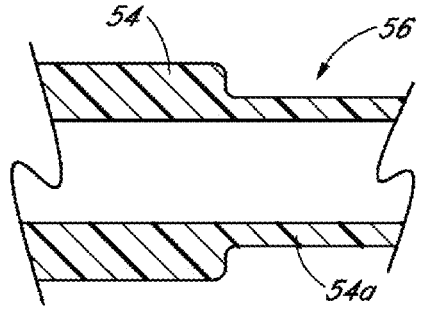
Figure 6G:
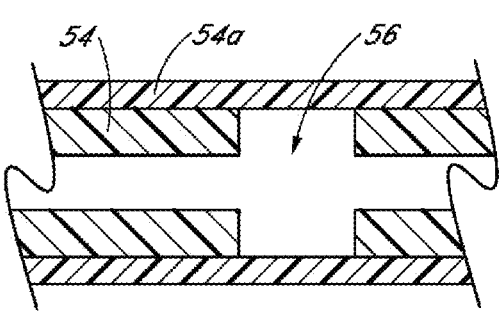
Figure 6D:
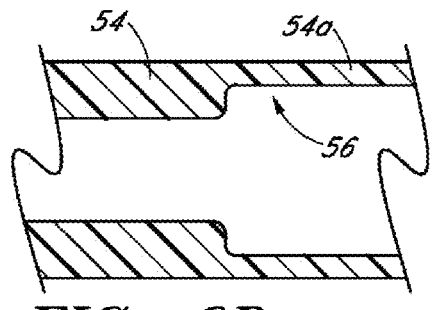

Regardless of their shape and location(s) on the outer shell of the implant, the regions of drug release are of a defined and known area. The defined area assists in calculating the rate of drug elution from the implant (described below). FIGS. 6A-I represent certain embodiments of the region of drug release. FIGS. 6A and B depict overlapping regions of a thicker 54 and thinner 54a portion of the outer shell material with the resulting formation of an effectively thinner region of material, the region of drug release 56. FIGS. 6C and 6D depict joinder of thicker 54 with thinner 54a portions of the outer shell material. FIG. 6E depicts a thicker sleeve of outer shell material overlapping at least in part with a thinner shell material. FIG. 6G depicts a "tube within a tube" design, wherein a tube with a first thickness 54 is encased in a second tube with a second thickness 54a. In the embodiment shown in FIG. 6G, and in certain other embodiments, the break or gap in the shell with a first thickness 54, does not communicate directly with the external environment.

Figure 6H:
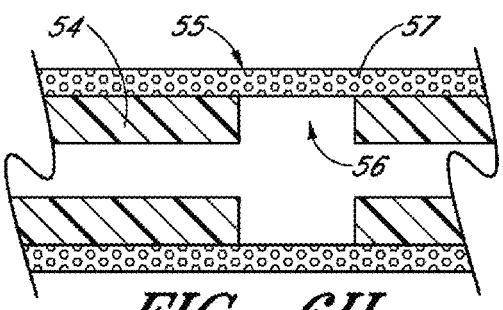

FIG. 6H depicts an embodiment wherein the region of drug release is bordered both by the outer shell 54 and by a substantially impermeable matrix material 55 having a communicating particulate matter 57 dispersed within the impermeable matrix. In some such embodiments, the communicating particulate matter comprises hydrogel particles, for example, polyacrylamide, cross-linked polymers, poly2-hydroxyethylmethacrylate (HEMA) polyethylene oxide, polyAMPS and polyvinylpyrrolidone, or naturally derived hydrogels such as agarose, methylcellulose, hyaluronan. Other hydrogels known in the art may also be used. In some embodiments, the impermeable material is silicone. In other embodiments, the impermeable material may be Teflon®, flexible graphite, silicone rubber, silicone rubber with fiberglass reinforcement, Neoprene®, fiberglass, cloth inserted rubber, vinyl, nitrile, butyl, natural gum rubber, urethane, carbon fiber, fluoroelastomer, and or other such impermeable or substantially impermeable materials known in the art. In this and other embodiments disclosed herein, terms like "substantially impermeable" or "impermeable" should be interpreted as relating to a material's relative impermeability with regard to the drug of interest. This is because the permeability of a material to a particular drug depends upon characteristics of the material (e.g. crystallinity, hydrophilicity, hydrophobicity, water content, porosity) and also to characteristics of the drug.

Figure 6I:
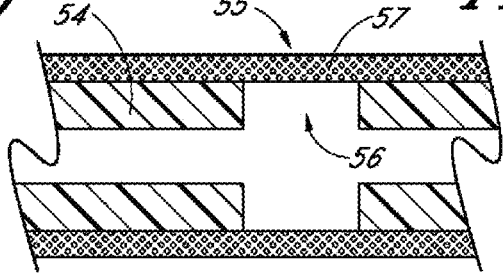

FIG. 6I depicts another embodiment wherein the region of drug release is bordered both by the outer shell 54 and by an impermeable matrix material 55, such as silicone having a communicating particulate matter 57 dispersed within the impermeable matrix. In other embodiments, the impermeable material may be Teflon®, flexible graphite, polydimethylsiloxane and other silicone elastomers, Neoprene®, fiberglass, cloth inserted rubber, vinyl, nitrile, butyl, natural gum rubber, urethane, carbon fiber, fluoroelastomer, and or other such impermeable or substantially impermeable materials known in the art. In several embodiments, the communicating particulate matter is compounded with the impermeable matrix material during implant manufacturing. The resultant matrix is impermeable until placed in a solvent that causes the communicating particulate matter to dissolve. In several embodiments, the communicating particles are salt crystals (for example, sodium bicarbonate crystals or sodium chloride crystals). In other embodiments, other soluble and biocompatible materials may be used as the communicating particulate matter. Preferred communicating particulate matter is soluble in a solvent such as water, saline, ocular fluid, or another biocompatible solvent that would not affect the structure or permeability characteristics of the impermeable matrix. It will be appreciated that certain embodiments, the impermeable matrix material compounded with a communicating particulate matter has sufficient structural integrity to form the outer shell of the implant (i.e., no additional shell material is necessary).

In certain embodiments, the communicating particles are extracted with a solvent prior to implantation. The extraction of the communicating particles thus creates a communicating passageway within the impermeable material. Pores (or other passages) in the impermeable material allow ocular fluid to pass into the particles, which communicate the fluid into the lumen of implant. Likewise, the particles communicate the drug out of the lumen of the implant and into the target ocular tissue.

In contrast to a traditional pore or orifice (described in more detail below), embodiments such as those depicted in FIGS. 6H and 6I communicate drug from the lumen of the implant to the ocular tissue through the communicating particles or through the resultant vacancy in the impermeable matrix after dissolution of the particle. In several embodiments, the regions of drug release are employed on implants adapted to be implanted into the punctum of a subject, as described in more detail herein. For example, in several implant embodiments configured for treatment of glaucoma, the punctal implant has regions of drug release positioned along the proximal portion of the implant, but not at the proximal end. This advantageously allows release of the therapeutic agent from the implant, but prevents the drainage of tears from washing the drug down the nasolacrimal duct. See also, FIGS. 7-9.

Figure 7:
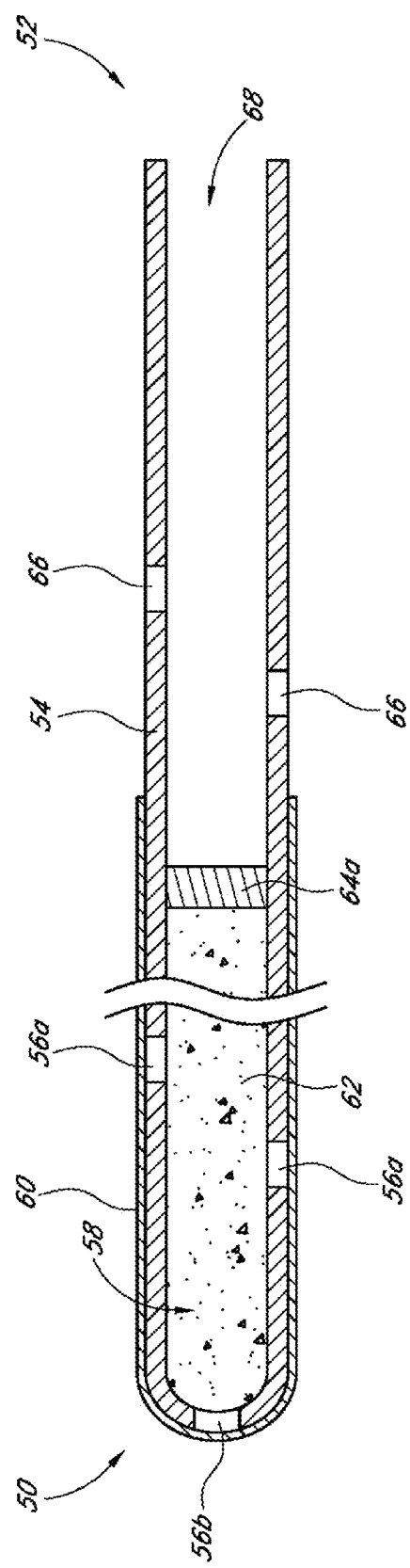
FIG. 7 illustrates a cross sectional view of drug delivery implant in accordance with embodiments disclosed herein.

In several embodiments, the region of drug release comprises one or more orifices. It shall be appreciated that certain embodiments utilize regions of drug release that are not orifices, either alone or in combination with one or more orifices in order to achieve a controlled and targeted drug release profile that is appropriate for the envisioned therapy. FIG. 7 shows a cross sectional schematic of one embodiment of an implant in accordance with the description herein. While the drug is represented as being placed within the lumen 58 in FIG. 7, it has been omitted from several other Figures, so as to allow clarity of other features of those embodiments. It should be understood, however, that all embodiments herein optionally include one or more drugs.

In several embodiments, the implant further comprises a coating 60 which may be positioned in various locations in or on the implant as described below. In some embodiments, the coating 60 is a polymeric coating. FIG. 8 depicts an implant wherein the coating 60 is positioned inside the implant, but enveloping the therapeutic agent housed within the lumen, while FIG. 9 depicts the coating 60 on the exterior of the shell 54. Some other embodiments may comprise implants with non-polymeric coatings in place of, or in addition to a polymeric coating. The coating is optionally biodegradable. Some other embodiments may comprise an implant made entirely of a biodegradable material, such that the entire implant is degraded over time. In some embodiments, the coating is placed over the entire implant (e.g., enveloping the implant) while in other embodiments only a portion of the implant is covered. In some embodiments, the coating is on the exterior surface of the implant. In some embodiments, the coating is placed on the luminal wall within the implant. Similarly, in some embodiments in which the coating is positioned inside the implant, the coating covers the entire inner surface of the lumen, while in other embodiments, only a portion of the inner surface is covered. It shall be appreciated that, in addition to the regions of drug release described above, implants according to several embodiments, disclosed herein combine regions of drug release with one or more coatings in order to control drug release characteristics.

In other embodiments, the outer shell may contain one or more orifice(s) 56b in the distal tip of the implant, as shown in FIGS. 10A and 10B. In other embodiments, the outer shell contains one or more orifice(s) in the proximal tip of the implant, such as for example drug elution and/or fluid influx (e.g., for dissolution of drug housed within the implant and/or for shunting of fluid to a fluid outflow pathway). The shape and size of the orifice(s) can be selected based on the desired elution profile. Still other embodiments comprise a combination of a distal orifice and multiple orifices placed more proximally on the outer shell. Additional embodiments comprise combinations of distal orifices, proximal orifices on the outer shell and/or regions of drug release as described above (and optionally one or more coatings). Additional embodiments have a closed distal end. In such embodiment the regions of drug release (based on thickness/permeability of the shell, orifices, coatings, placement of the drug, etc.) are arranged along the long axis of the implant. Such a configuration is advantageous in order to reduce the amount of tissue damage caused by the advancing distal end that occurs during the several embodiments of the implantation procedures disclosed herein.

Figure 10C:
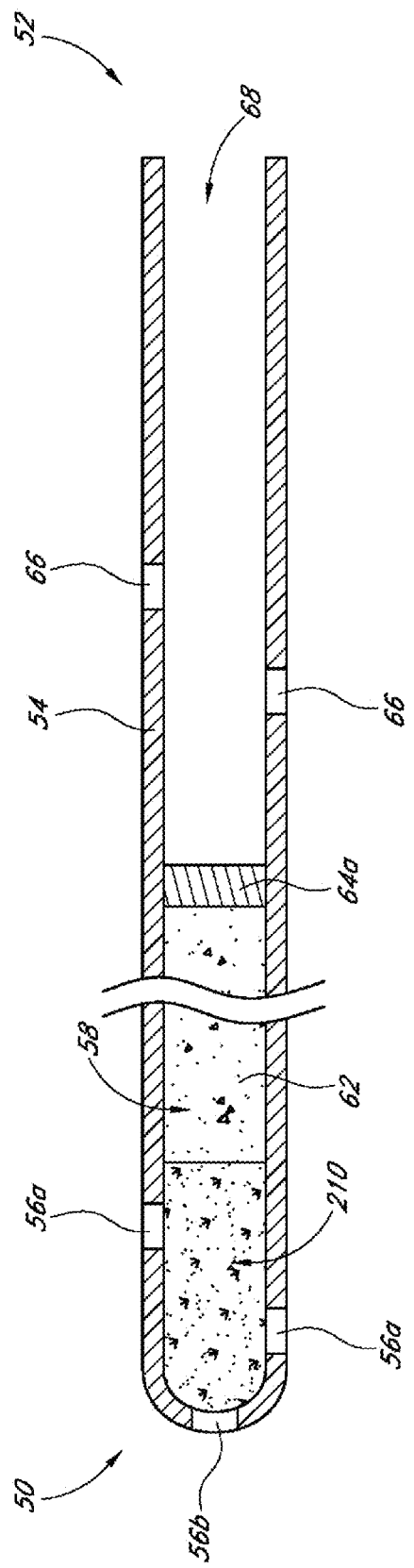
Figure 10D:
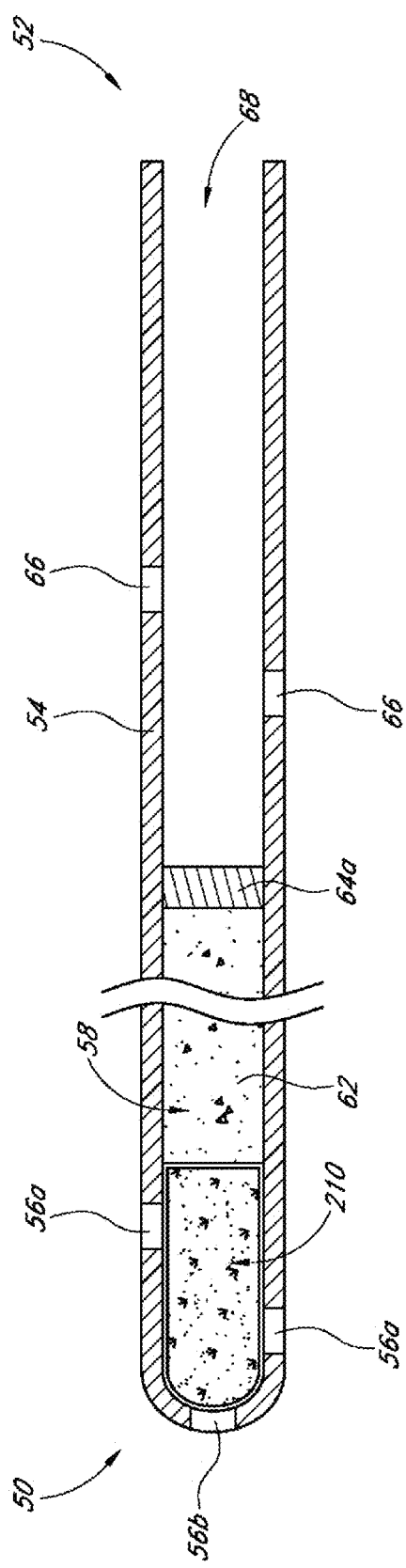
Figure 10E:
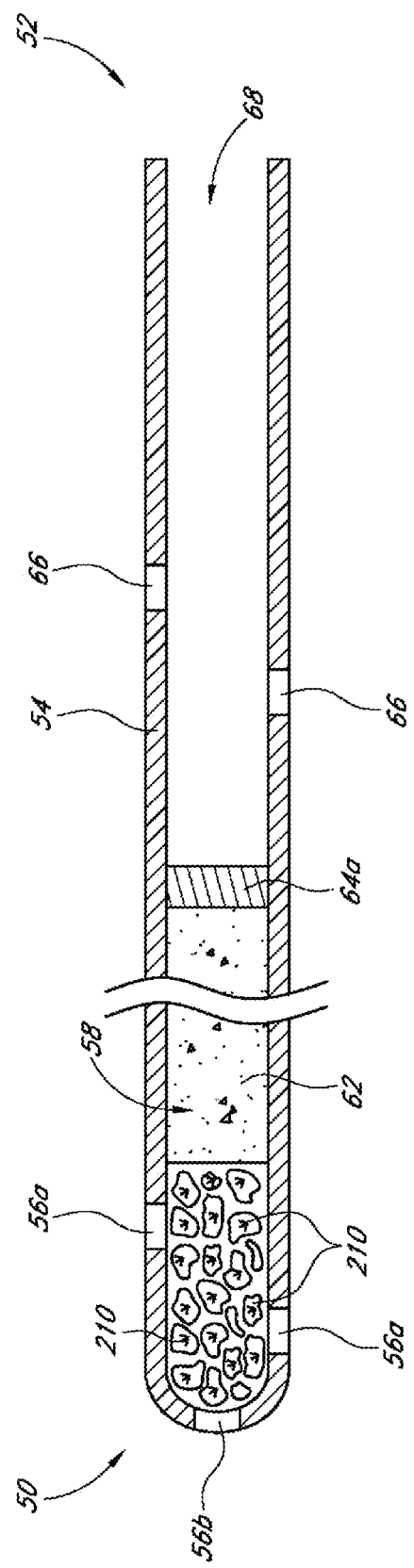
Figure 10F:
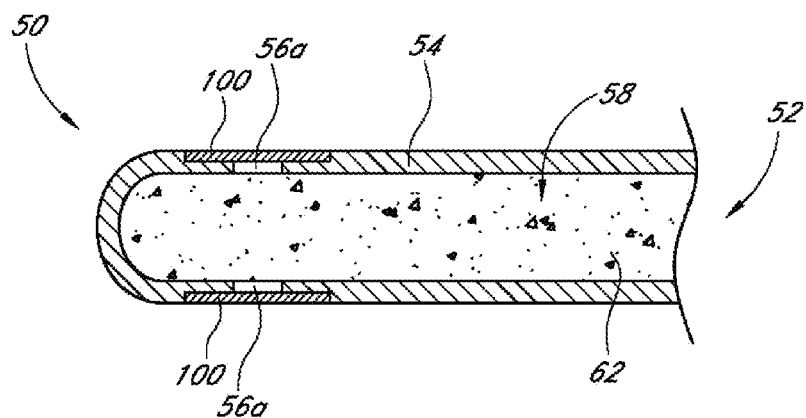
Figure 10G:
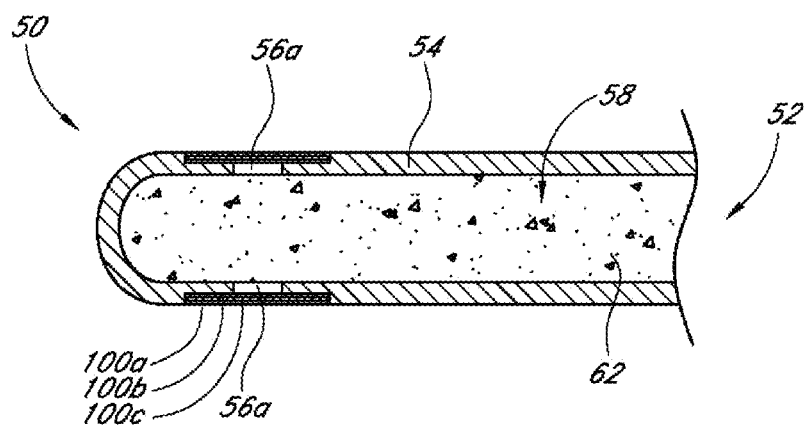

In several embodiments, an additional structure or structures within the interior of the lumen partially controls the elution of the drug from the implant. In some embodiments, a proximal barrier 64a is positioned proximally relative to the drug 62 (FIGS. 7 and 10C). An optional shunt feature may also be included which comprises outflow apertures 66 in communication with a proximal inflow lumen 68 located in the proximal region 52 of the implant. In addition to the layer or layers of permeable or semi-permeable material may be used to envelope the drug discussed above, FIG. 10C depicts an internal plug 210 that is be located between the drug 62 and the various orifices 56a and 56b in certain embodiments. In such embodiments, the internal plug need not completely surround the drug. In some embodiments, the biomaterial of the internal plug 210 differs from that of the shell 54, while in some embodiments the material of the internal plug 210 is the same material as that of the shell 54. Suitable materials for the internal plug include, but are not limited to, agarose or hydrogels such as polyacrylamide, polymethyl methacrylate, or HEMA (hydroxyethyl methacrylate). In additional any material disclosed herein for use in the shell or other portion of the implant may be suitable for the internal plug, in certain embodiments.

In such embodiments where the material is the same, the physical characteristics of the material used to construct 210 are optionally different than that of the shell 54. For example, the size, density, porosity, or permeability of the material of 210 may differ from that of the shell 54. In some embodiments, the internal plug is formed in place (i.e. within the interior lumen of the implant), for example by polymerization, molding, or solidification in situ of a dispensed liquid, powder, or gel. In other embodiments, the internal plug is preformed external to the shell placed within the shell prior to implantation. In such embodiments, tailored implants are constructed in that the selection of a pre-formed internal plug may be optimized based on a particular drug, patient, implant, or disease to be treated. In several embodiments, the internal plug is biodegradable or bioerodible, while in some other embodiments, the internal plug is durable (e.g., not biodegradable or bioerodible).

In several other embodiments, the internal plug 210 may be more loosely fit into the interior lumen of the shell which may allow flow or transport of the drug around the plug. See FIG. 10D. In still other embodiments, the internal plug may comprise two or more pieces or fragments. See FIG. 10E.

In several embodiments, the orifices 56a are covered (wholly or partially) with one or more elution membranes 100 that provide a barrier to the release of drug 62 from the interior lumen 58 of the implant shell 54. See FIG. 10F. In several embodiments, the elution membrane is permeable to the therapeutic agent, to bodily fluids or to both. In some embodiments the membrane is elastomeric and comprises silicone. In other embodiments, the membrane is fully or partially coated with a biodegradable or bioerodible material, allowing for control of the inception of entry of bodily fluid, or egress of therapeutic agent from the implant. In certain embodiments, the membrane is impregnated with additional agents that are advantageous, for example an anti-fibrotic agent, a vasodilator, an anti-thrombotic agent, or a permeability control agent. In addition, in certain embodiments, the membrane comprises one or more layers 100a, 100b, and 100c in FIG. 10G, for example, allowing a specific permeability to be developed.

Similar to the internal plug and regions of drug release described above, the characteristics of the elution membrane at least partially define the release rate of the therapeutic agent from the implant. Thus, the overall release rate of drug from the implant may be controlled by the physical characteristics of the implant, including, but not limited to, the area and volume of the orifices, the surface area of any regions of drug release, the size and position of any internal plug with respect to both the drug and the orifices and/or regions of drug release, and the permeability of any layers overlaying any orifices or regions of drug release to the drug and bodily fluids.

In some embodiments, multiple pellets 62 of single or multiple drug(s) are placed end to end within the interior lumen of the implant (FIG. 11A). In some other embodiments a partition 64 is employed to seal therapeutic agents from one another when contained within the same implant inner lumen. In some embodiments, the partition 64 bioerodes at a specified rate. In some embodiments, the partition 64 is incorporated into the drug pellet and creates a seal against the inner dimension of the shell of the implant 54 in order to prevent drug elution in an unwanted direction. In certain embodiments further comprising a shunt, a partition may be positioned distal to the shunt outlet holes, which are described in more detail below.

An additional non-limiting embodiment of a drug pellet-containing implant is shown in FIG. 11B (in cross section). In certain embodiments, the pellets are micro-pellets 62' (e.g., micro-tablets). As shown generally in FIG. 11B, the micro-pellet 62' can be housed within a compartment defined by endpieces or partitions 64'. While shown in FIG. 11B as dimensioned to hold one micro-tablet of therapeutic agent 62', it shall be appreciated that, in some embodiments, the lumen 58' may be dimensioned to hold a plurality of micro-tablets comprising the same or differing therapeutic agents. Advantageously, such embodiments employed an extruded shell and one or more micro-pellets allow the release of the therapeutic agents from the implant, in a controlled fashion, without the therapeutic agent being exposed to the elevated temperatures that are often required for extrusion. Rather, the shell may first be extruded and then loaded with micro-pellets once temperatures are normalized.

As discussed in more detail herein, each tablet comprises a therapeutic agent (also referred to herein as an active pharmaceutical ingredient (API)) optionally combined with one or more excipients. Excipients may include, among others, freely water soluble small molecules (e.g., salts) in order to create an osmotic pressure gradient across the wall of tubing 54'. In some embodiments, such a gradient increases stress on the wall, and decreases the time to release drug.

The in vivo environment into which several embodiments of the implants disclosed herein are positions may be comprised of a water-based solution (such as aqueous humor or blood plasma) or gel (such as vitreous humor). Water from the surrounding in vivo environment may, in some embodiments, diffuse through semipermeable or fenestrated stent walls into the drug reservoir (e.g., one or more of the interior lumens, depending on the embodiment). Water collecting within the drug-containing interior lumen then begins dissolving a small amount of the tablet or drug-excipient powder. The dissolution process continues until a solution is formed within the lumen that is in osmotic equilibrium with the in vivo environment.

In additional embodiments, osmotic agents such as saccharides or salts are added to the drug to facilitate ingress of water and formation of the isosmotic solution. With relatively insoluble drugs, for example corticosteroids, the isosmotic solution may become saturated with respect to the drug in certain embodiments. In certain such embodiments, saturation can be maintained until the drug supply is almost exhausted. In several embodiments, maintaining a saturated condition is particularly advantageous because the elution rate will tend to be essentially constant, according to Fick's Law.

Several embodiments of the implant may also comprise a shunt in addition to functioning as a drug delivery device. The term "shunt" as used herein is a broad term, and is to be given its ordinary and customary meaning to a person of ordinary skill in the art (and it is not to be limited to a special or customized meaning), and refers without limitation to the portion of the implant defining one or more fluid passages for transport of fluid from a first, often undesired location, to one or more other locations. In some embodiments, the shunt can be configured to provide a fluid flow path for draining aqueous humor from the anterior chamber of an eye to an outflow pathway to reduce intraocular pressure, such as is depicted generally in FIG. 12A. In other embodiments the shunt can be configured to provide a fluid flow path for draining aqueous humor to an outflow pathway. Still other embodiments can be configured to drain ocular fluid or interstitial fluid from the area in and around the eye to a remote location. Yet other combination drug delivery-shunt implants may be configured to drain physiological fluid from a first physiologic site to a second site (which may be physiologic or external to a patient). In still additional embodiments, the shunt additionally (or alternatively) functions to provide a bulk fluid environment to facilitate the dilution and/or elution of the drug.

The shunt portion of the implant can have an inflow portion 68 and one or more outflow portions 66. As described above, the outflow portion may be disposed at or near the proximal end 52 of the implant. While not illustrated, in some embodiments a shunt outflow portion may be disposed at or near the distal end of the implant with the inflow portion residing a different location (or locations) on the implant. In some embodiments, when the implant is deployed, the inflow portion may be sized and configured to reside in the anterior chamber of the eye and the outflow portion may be sized and configured to reside in the supraciliary or suprachoroidal space. In some embodiments, the outflow portion may be sized and configured to reside in the supraciliary region of the uveoscleral outflow pathway, the suprachoroidal space, other part of the eye, or within other physiological spaces amenable to fluid deposition.

In some embodiments, at least one lumen extends through the shunt portion of the implant. In some embodiments, there is at least one lumen that operates to conduct the fluid through the shunt portion of the implant. In certain embodiments, each lumen extends from an inflow end to an outflow end along a lumen axis. In some embodiments the lumen extends substantially through the longitudinal center of the shunt. In other embodiments, the lumen can be offset from the longitudinal center of the shunt.

In implants additionally comprising a shunt in the proximal portion of the device, the first (most proximal) outflow orifice on the implant is positioned between 1 and 10 mm from the anterior chamber of the subject. In some embodiments additionally comprising a shunt in the proximal portion of the device, the first (most proximal) outflow orifice on the implant is positioned preferably between 2 and 5 mm from the anterior chamber of the subject. Additional outflow orifices may be positioned in more distal locations, up to or beyond the point where the interior lumen housing the drug or therapeutic agent begins.

In some embodiments comprising a shunt, a shunt inflow portion preferably is disposed at or near a proximal end of the implant and a shunt outflow portion preferably is disposed at or near a distal end of the shunt. When implanted, in several embodiments, the shunt inflow portion is sized and configured to reside in the anterior chamber of the eye and the shunt outflow portion is sized and configured to reside in the uveoscleral outflow pathway. In some embodiments, the shunt outflow portion is sized and configured to reside in the supraciliary region of the uveoscleral outflow pathway or in the suprachoroidal space. Multiple outflow points may be used in a single device, depending on the embodiment.

In some embodiments, the flow path through the implant is configured to regulate the flow rate to reduce the likelihood of hypotony in the eye. In some embodiments, the intraocular pressure is maintained at about 8 mm Hg. In other embodiments, the intraocular pressure is maintained at pressures less than about 8 mm Hg, for example the intraocular pressure may be maintained between about 6 mm Hg and about 8 mm Hg. In other embodiments, the intraocular pressure is maintained at pressures greater than about 8 mm Hg. For example, the intraocular pressure may be maintained between about 8 mm Hg and about 18 mm Hg, and more preferably between 8 mm Hg and 16 mm Hg, and most preferably not greater than 12 mm Hg. In some embodiments, the flow rate can be limited to about 2.5 µL/min or less. In some embodiments, the flow rate can be limited to between about 1.9 µL/min and about 3.1 µL/min.

For example, the Hagen-Poisseuille equation suggests that a 4 mm-long shunt at a flow rate of 2.5 µL/min should have an inner diameter of 52 micrometers to create a pressure gradient of 5 mm Hg above the pressure in the suprachoroidal space.

Figure 12A:
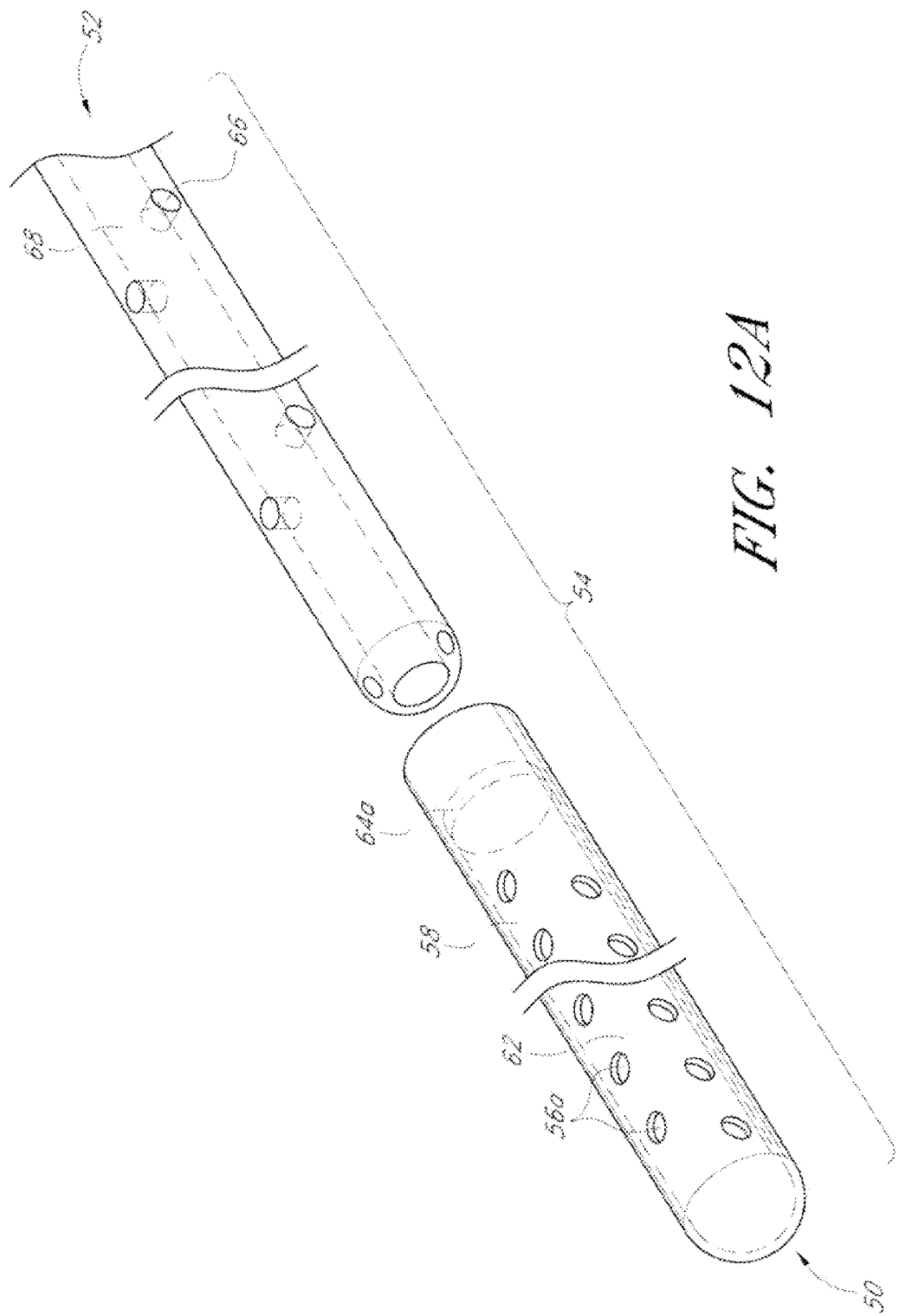
FIG. 12A illustrates another drug delivery implant incorporating a shunt in accordance with embodiments disclosed herein.
Figure 12C:
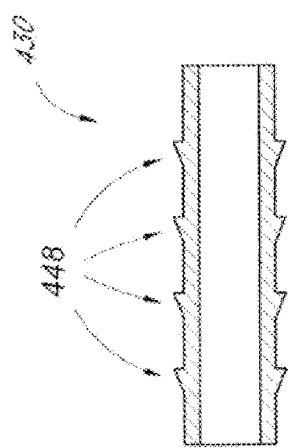
FIG. 12C illustrates a cross-sectional view of an embodiment of retention features disposed on a drug delivery implant in accordance with embodiments disclosed herein.
Figure 12B:
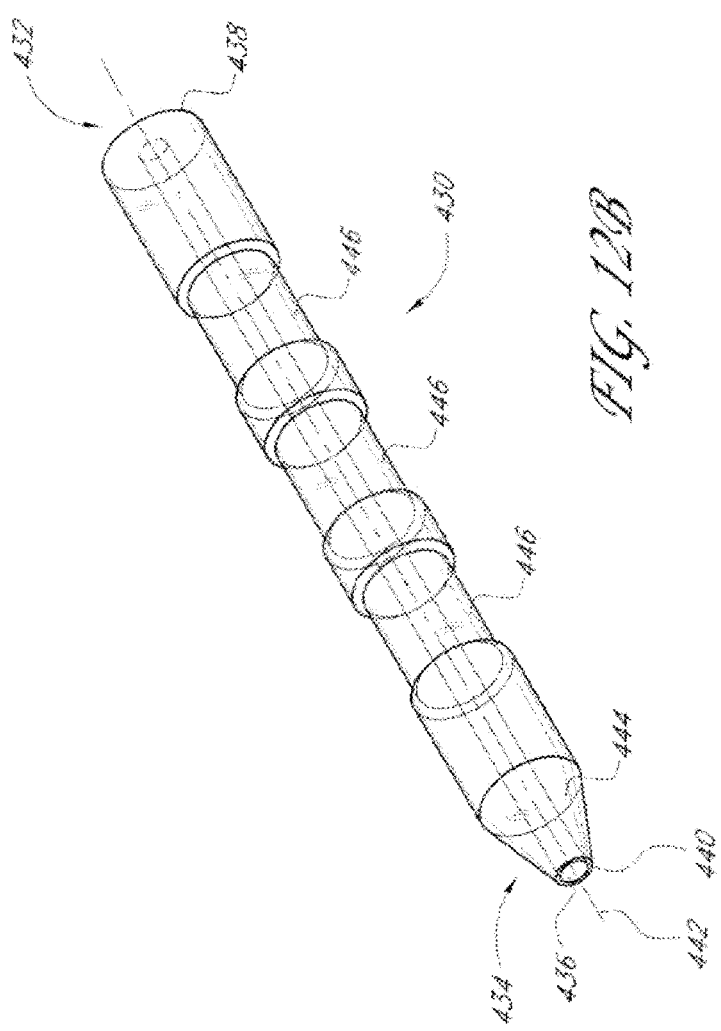
FIG. 12B illustrates a further drug delivery implant incorporating a shunt in accordance with embodiments disclosed herein.

FIG. 12B illustrates another embodiment of a drug eluting implant 430 comprising a shunt that is operable to drain fluid from the anterior chamber to the uveoscleral outflow pathway (e.g., the suprachoroidal space). The drug eluting implant 430 can comprise at least one interior lumen 436 extending therethrough, wherein at least a first active drug can be placed. The interior lumen 436 of the implant 430 can communicate with an inflow portion 432 and an outflow portion 434. When implanted, the inflow portion 432 is sized and configured to reside in the anterior chamber of the eye and the outflow portion 434 is sized and configured to reside in the uveoscleral outflow pathway. The first active drug can elute from the inflow portion 432 into the anterior chamber to treat a target ocular tissue. As the first active drug elutes from the interior lumen 436 into the anterior chamber, fluid can be conducted through the interior lumen 436 if the implant.

The implant 430 preferably has an outer diameter that will permit the implant 430 to fit within a 21-gauge or 23-gauge needle or hollow instrument during implantation; however, larger or smaller gauge instruments may also be used. The implant 430 can also have a diameter that is designed for delivery with larger needles. For example, the implant 430 can also be delivered with 18-, 19- or 20-gauge needles. The implant 430 can have a constant diameter through most of its length. In some embodiments, the implant 430 comprises retention features 446 that operate to mechanically lock or anchor the implant 430 in place when implanted. In some embodiments, the retention features 446 comprise portions of reduced diameter, e.g., annular grooves, between the proximal end 438 and the distal end 440. In some embodiments, the retention features 446 comprise barbs or other projections, which extend from the outer surface of the implant 430, to inhibit migration of the implant 430 from its implanted position, as described above.

As shown in FIG. 12C, for example, some embodiments of an implant 430 have a plurality of annular ribs 448 formed on an exterior surface of the implant 430. The annular ribs 448 can be spaced longitudinally along the implant 430 between the proximal end 438 and the distal end 440. Spacing between the annular ribs 448 can be regular or irregular.

The outflow portion 434 of the implant 430 preferably is disposed at or near the distal end 440 of the implant 430. In the embodiment illustrated in FIG. 12B, the outflow portion 434 has a tapered portion 444; however, it may also have other shapes (e.g. semi-sphere, a paraboloid, a hyperboloid) with a continually decreasing radial dimension with respect to the lumen axis 442 along the length of the axis 442. The tapered portion 444 preferably terminates with a smaller radial dimension at the outflow end 440. During implantation, the tapered portion 444 can operate to form, dilate, and/or increase the size of, an incision or puncture created in the tissue. For example, the distal end 440 can operate as a trocar to puncture or create an incision in the tissue. Following advancement of the distal end 440 of the implant 430, the tapered portion 444 can be advanced through the puncture or incision. The tapered portion 444 will operate to stretch or expand the tissue around the puncture or incision to accommodate the increasing size of the tapered portion 444 as it is advanced through the tissue.

The tapered portion 444 can also facilitate proper location of the implant 430 into the supraciliary or suprachoroidal spaces. For example, the implant 430 is preferably advanced through the tissue within the anterior chamber angle during implantation. This tissue typically is fibrous or porous, which is relatively easy to pierce or cut with a surgical device, such as the tip of the implant 430. The implant 430 can be advanced through this tissue and abut against the sclera once the implant 430 extends into the uveoscleral outflow pathway. As the implant 430 abuts against the sclera, the tapered portion 444 preferably provides a generally rounded edge or surface that facilitates sliding of the implant 430 within the suprachoroidal space along the interior wall of the sclera. For example, as the implant 430 is advanced into the uveoscleral outflow pathway and against the sclera, the implant 430 will likely be oriented at an angle with respect to the interior wall of the sclera. As the tip of the implant 430 engages the sclera, the tip preferably has a radius that will permit the implant 430 to slide along the sclera instead of piercing or substantially penetrating the sclera. As the implant 430 slides along the sclera, the tapered portion 444 will provide an edge against which the implant 430 can abut against the sclera and reduce the likelihood that the implant 430 will pierce the sclera.

Once the implant 430 is implanted in position with the inflow portion 432 residing in the anterior chamber and the outflow portion 434 residing in the uveoscleral outflow pathway, the first active drug can elute from the lumen 436 of the implant 430 into the anterior chamber and aqueous humor can flow from the anterior chamber to the uveoscleral outflow pathway through the lumen 436 of the implant 430. The flow of fluid is preferably restricted by the size of the lumen 436, which produces a capillary effect that limits the fluid flow for given pressures. The capillary effect of the lumen allows the shunt to restrict flow and provides a valveless regulation of fluid flow. The flow of fluid through the implant 430 is preferably configured to be restricted to a flow rate that will reduce the likelihood of hypotony in the eye. For example, in some embodiments, the flow rate can be limited to about 2.5 µL/min or less. In some embodiments the flow rate can be limited to between about 1.9 µL/min and about 3.1 µL/min. In other applications, a plurality of implants 430 can be used in a single eye to elute at least a first drug into the anterior chamber and to conduct fluid from the anterior chamber to the uveoscleral outflow pathway. In such applications, the cumulative flow rate through the implants preferably is within the range of about 1.9 µL/min to about 3.1 µL/min, although the flow rate for each of the implants can be significantly less than about 2.5 µL/min. For example, if an application called for implantation of five implants, then each implant 430 can be configured to have a flow rate of about 0.5 µL/min.

While the lumen 436 is depicted in FIG. 4 as extending substantially through the longitudinal center of the implant 430, in some embodiments, the lumen can be offset from the longitudinal center of the shunt. For example, while FIG. 4 depicts the implant 430 as having a tapered portion 444 that terminates substantially where the tapered portion 444 meets the lumen 436, the lumen 436 can be offset from the center of the implant 430 such that lumen 436 opens along one of the sides of the tapered portion 444. Accordingly, the tapered portion 444 can terminate at a location offset from the lumen axis 442 and can extend beyond the point at which the interior lumen 436 and the exterior tapered portion 444 meet. Additionally, the lumen 436 can vary in direction along its length.

In some embodiments, the implant comprises one or more lumens or sub-lumens, as described further herein. In some embodiments, at least a first active drug is placed in at least one sub-lumen. The sub-lumen can have a closed distal end or can have an outlet located in or near the distal end to allow fluid to flow from the anterior chamber to the uveoscleral outflow pathway. In some embodiments, at least one sub-lumen does not contain any active drugs and is configured exclusively to allow fluid to drain from the anterior chamber to the uveoscleral outflow pathway.

The implant 430 preferably comprises any of the materials described herein. The implant 430 can be fabricated through conventional micro machining techniques or through procedures commonly used for fabricating optical fibers. For example, in some embodiments, the implant 430 is drawn with a bore, or lumen, extending therethrough. In some embodiments, the tapered portion 444 at the outflow portion 434 can be constructed by shearing off an end tubular body. This can create a tapered portion 444 that can be used to puncture or incise the tissue during implantation and dilate the puncture or incision during advancement of the implant 430. Other materials can be used for the implant 430 of FIG. 4, and other methods of manufacturing the implant 430 can also be used. For example, the implant 430 can be constructed of metals or plastics, and the implants can be machined with a bore that is drilled as described above.

The implant 430 of FIG. 4 represents an implant having a construction that provides for the opportunity to vary the size of the implant 430 or the lumen 436. The implant 430 also need not have a unitary configuration; that is, be formed of the same piece of material. For example, a proximal portion of the implant can be formed of glass drawn to have at least one small diameter lumen. A distal portion of the implant can be a cap formed of a different material. The cap can include a tissue-piercing end and one or more outlet openings. Each of the one or more outlet openings communicates with at least one of the one or more lumens in the proximal portion. In one preferred mode, the cap has a conically shaped tip with a plurality of outlet openings disposed proximal of the tip's distal end.

In some embodiments, the implant has a proximal end cap. For example, an O-ring cap with a region of drug release (as discussed more fully herein and with reference to FIGS. 18K and 18M) can be located over the proximal end of the implant to allow for drug elution into the anterior chamber of the eye. In other embodiments, a crimp cap comprising a region of drug release (as discussed more fully herein and with reference to FIGS. 18L and 18N) is located over the proximal end of the implant. Regions of the crimp cap can be compressible such that the cap can be securely placed on, and sealed to, the body of the implant. The regions of drug release are further permeable to aqueous humor to allow for drainage of aqueous humor from the anterior chamber and through the lumen of the implant. In some embodiments, the cap comprises one or more orifices or layers in place of, or in addition to, regions of drug release based on thickness and/or permeability of the cap material. The one or more orifices or layers can be permeable to aqueous humor to allow for drainage from the anterior chamber. In some embodiments, a coating is placed within the cap to cover an orifice therein. The coating may comprise a membrane or layer of semi-permeable polymer. In some embodiments, the coating has a defined thickness, and thus a defined and known permeability to various drugs and ocular fluid. In some embodiments, the coating is placed in other locations, including on the exterior of the cap, within the orifice, or combinations thereof.

In some embodiments, the implant is formed with one or more dividers positioned longitudinally within the outer shell, creating multiple additional sub-lumens within the interior lumen of the shell. The divider(s) can be of any shape (e.g. rectangular, cylindrical) or size that fits within the implant so as to form two or more sub-lumens, and may be made of the same material or a different material than the outer shell, including one or more polymers, copolymers, metal, or combinations thereof. In one embodiment, a divider is made from a biodegradable or bioerodible material. The multiple sub-lumens may be in any configuration with respect to one another. In some embodiments, a single divider may be used to form two sub-lumens within the implant shell. See e.g., FIG. 13A. In some embodiments, the two sub-lumens are of equal dimension. In other embodiments the divider may be used to create sub-lumens that are of non-equivalent dimensions. In still other embodiments, multiple dividers may be used to create two or more sub-lumens within the interior of the shell. In some embodiments the lumens may be of equal dimension. See, e.g. FIG. 13B. Alternatively, the dividers may be positioned such that the sub-lumens are not of equivalent dimension.

In some embodiments, one or more of the sub-lumens formed by the dividers may traverse the entire length of the implant. In some embodiments, one or more of the sub-lumens may be defined of blocked off by a transversely, or diagonally placed divider or partition. The blocked off sub-lumens may be formed with any dimensions as required to accommodate a particular dose or concentration of drug.

In some embodiments comprising a shunt, one or more lumens extend through the shunt to form at least a portion of the flow path. Preferably, there is at least one lumen that operates to conduct the fluid through the shunt. Each lumen preferably extends from an inflow end to an outflow end along a lumen axis. In some embodiments the lumen extends substantially through the longitudinal center of the shunt. In other embodiments, the lumen can be offset from the longitudinal center of the shunt.

Figure 14:
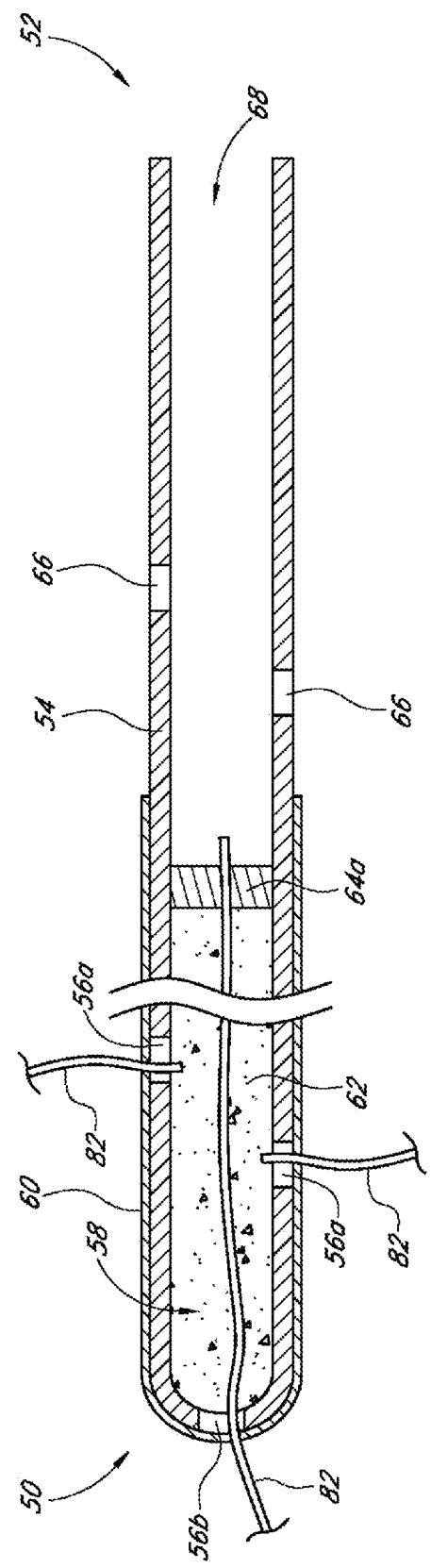
FIG. 14 illustrates a drug delivery implant in accordance with embodiments disclosed herein.
Figure 15:
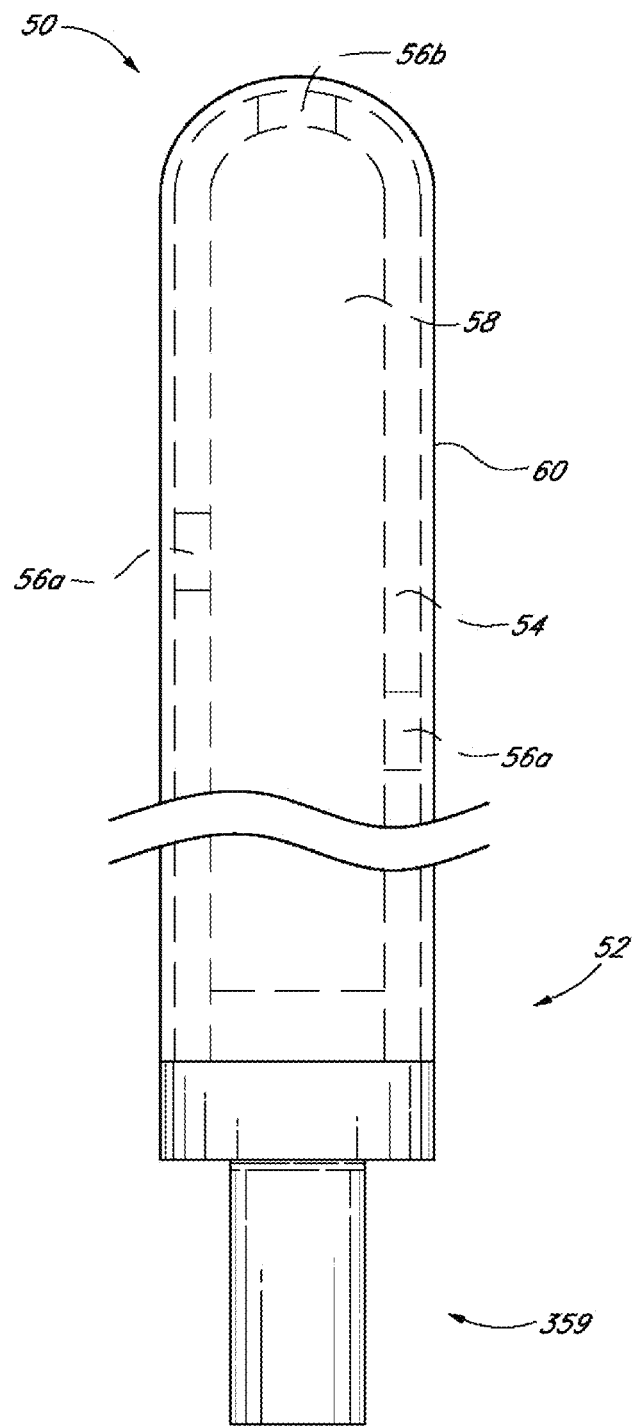
FIG. 15 illustrates an illustrative embodiment of a drug delivery implant and retention protrusion.
Figure 16:
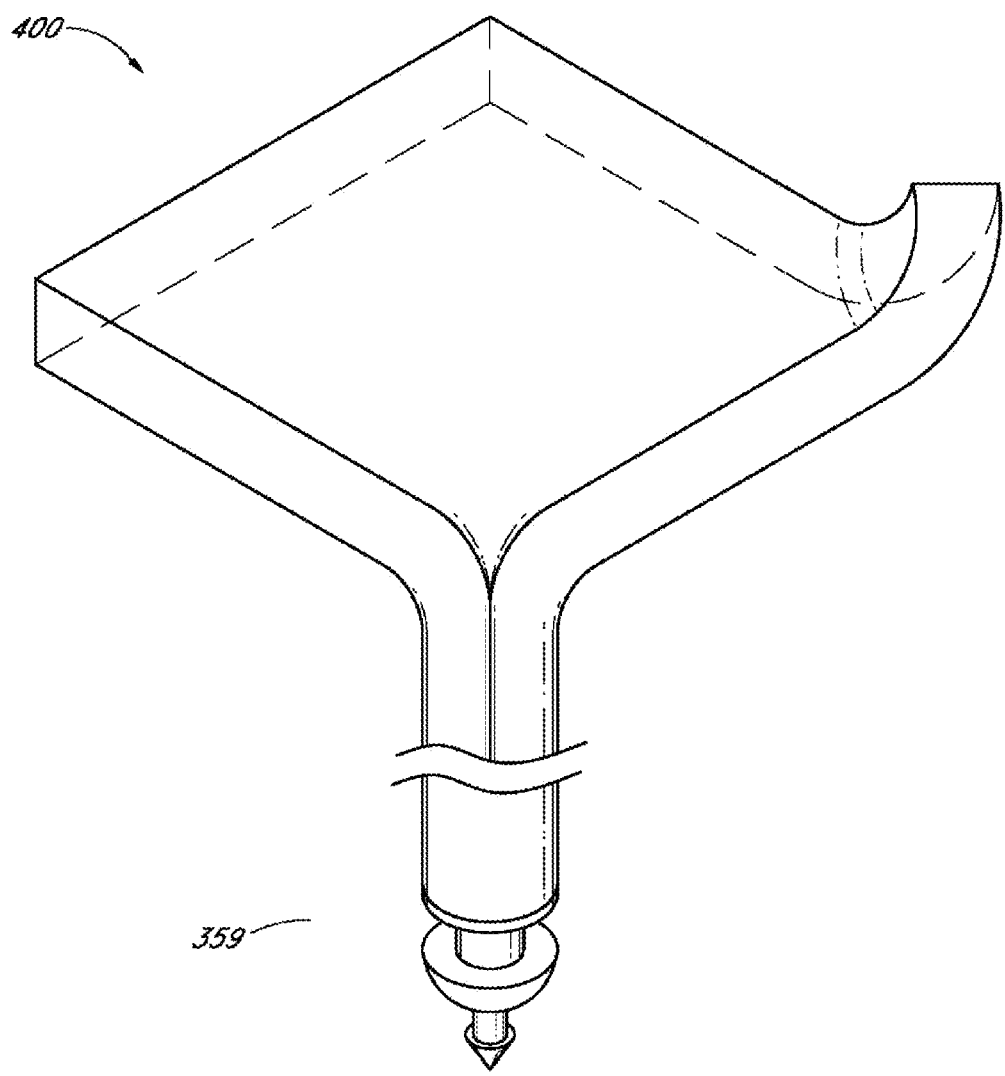
FIG. 16 illustrates an embodiment of a drug delivery implant in accordance with embodiments disclosed herein.
Figure 17:
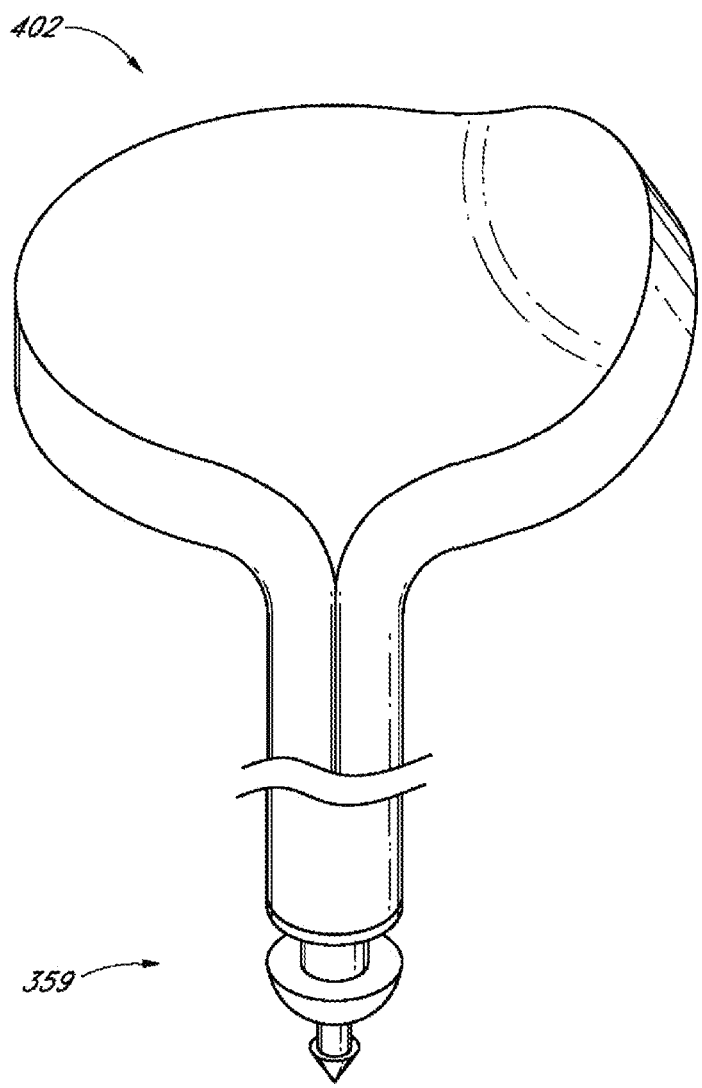
FIG. 17 illustrates another embodiment of a drug delivery implant in accordance with embodiments disclosed herein.

In some embodiments, a wick 82 is included in the implant (FIG. 14). FIG. 15 shows a cross sectional schematic of one embodiment of an implant in accordance with the description herein and further comprising a retention protrusion 359 for anchoring the implant to ocular tissue. While depicted in FIG. 15, and other Figures, as having the distal portion being the implant end and the proximal portion being the retention protrusion 359 end, in some embodiments, depending on the site and orientation of implantation, the distal portion and proximal portion may be reversed relative to the orientation in FIG. 15. Additionally, while the illustrated implant depicts the presence of orifices that pass through the outer shell, it shall be appreciated that embodiments of the implants comprising regions of drug release based on thickness and/or permeability of the shell material can also be used in conjunction with a retention feature. Moreover, implants comprising combinations of one or more orifices, one or more layers of permeable and/or semi-permeable material, and one or more areas of drug release based on thickness and/or permeability of the shell material are used in several embodiments.

In several embodiments, implants comprise a sheet 400 and a retention protrusion 359. See FIG. 16. In other embodiments, a disc 402 (FIG. 17) is used in place of a sheet. In several embodiments, the sheet or disc is flexible.

For delivery of some embodiments of the sheet or disc implants, the sheets or discs are dimensioned such that they can be rolled, folded, or otherwise packaged within a delivery instrument. The implant is dimensioned, in some embodiments, to be affixed (e.g., tethered) to the iris and float within the aqueous of the anterior chamber. In this context, the term "float" is not meant to refer to buoyancy of the implant, but rather that the sheet surface of the implant is movable within ocular fluid of the anterior chamber to the extent allowed by the retention protrusion. In certain embodiments, such implants are not tethered to an intraocular tissue and are free floating within the eye. In certain embodiments, the implant can be adhesively fixed to the iris with a biocompatible adhesive. In some embodiments, a biocompatible adhesive may be pre-activated, while in others, contact with ocular fluid may activate the adhesive. Still other embodiments may involve activation of the adhesive by an external stimulus, after placement of the implant, but prior to withdrawal of the delivery apparatus. Examples of external stimuli include, but are not limited to heat, ultrasound, and radio frequency, or laser energy. In certain embodiments, affixation of the implant to the iris is preferable due to the large surface area of the iris. In other embodiments, the implant is flexible with respect to a retention protrusion affixed to the iris, but is not free floating. Embodiments as disclosed herein are affixed to the iris in a manner that allows normal light passage through the pupil.

Figure 18A:
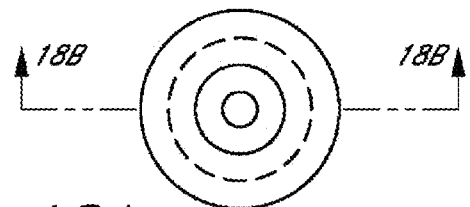
FIGS. 18A-18U illustrate various drug delivery devices in accordance with embodiments disclosed herein.
Figure 18B:
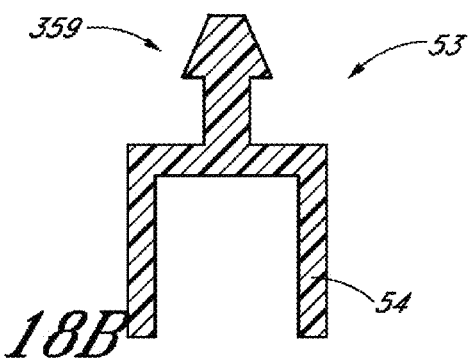
Figure 18C:
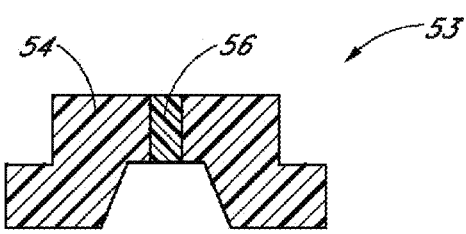
Figure 18D:
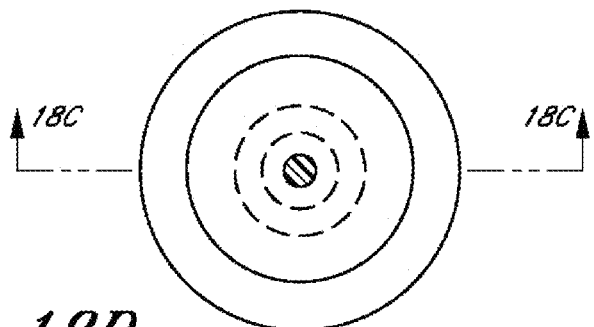
Figure 18E:
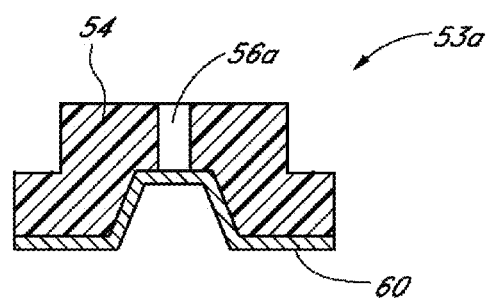
Figure 18F:
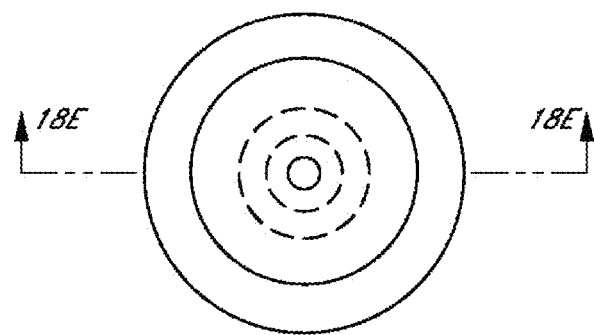
Figure 18G:
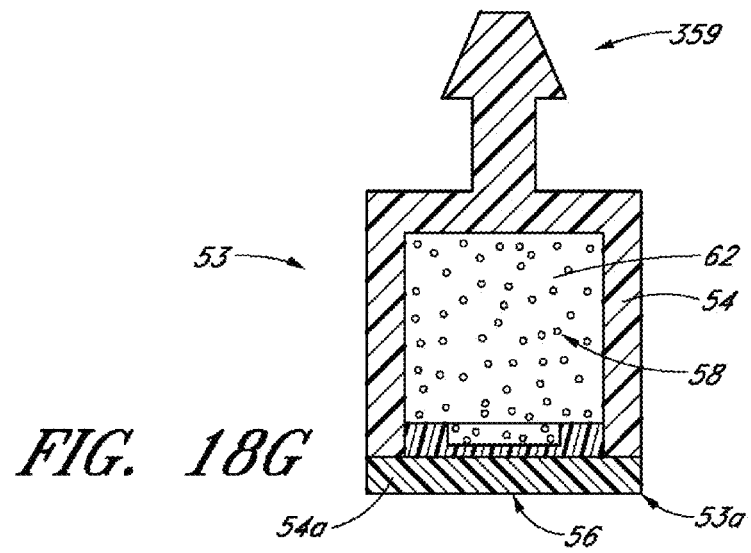
Figure 18H:
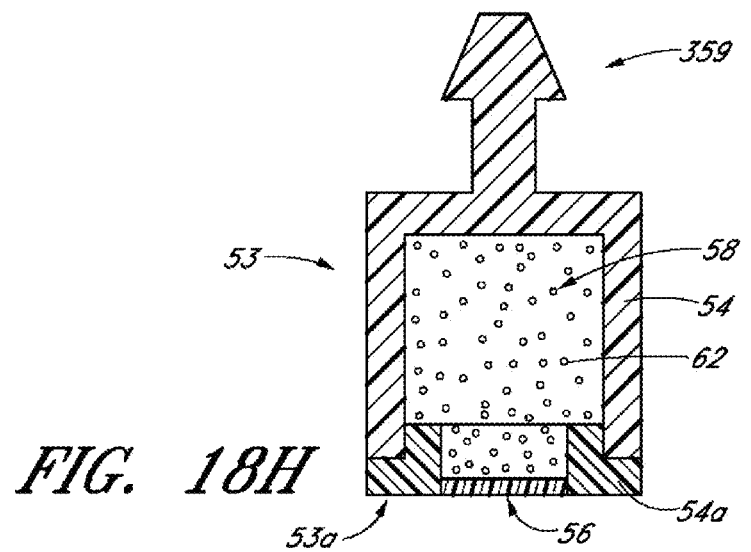
Figure 18I:
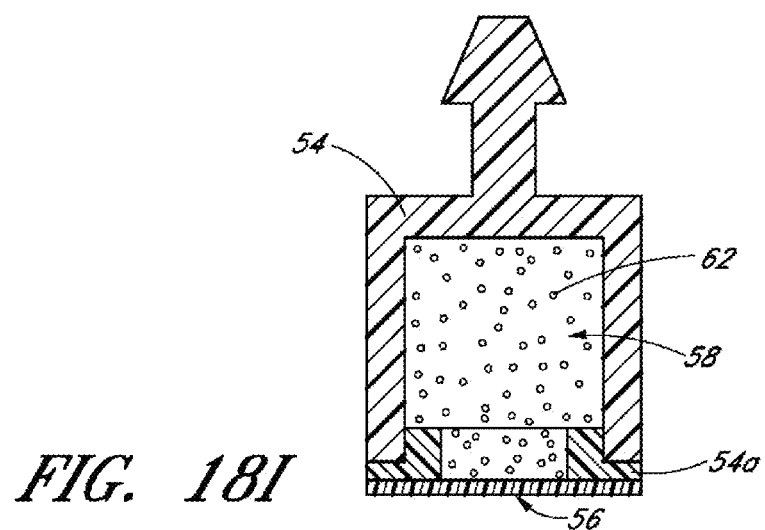
Figure 18J:
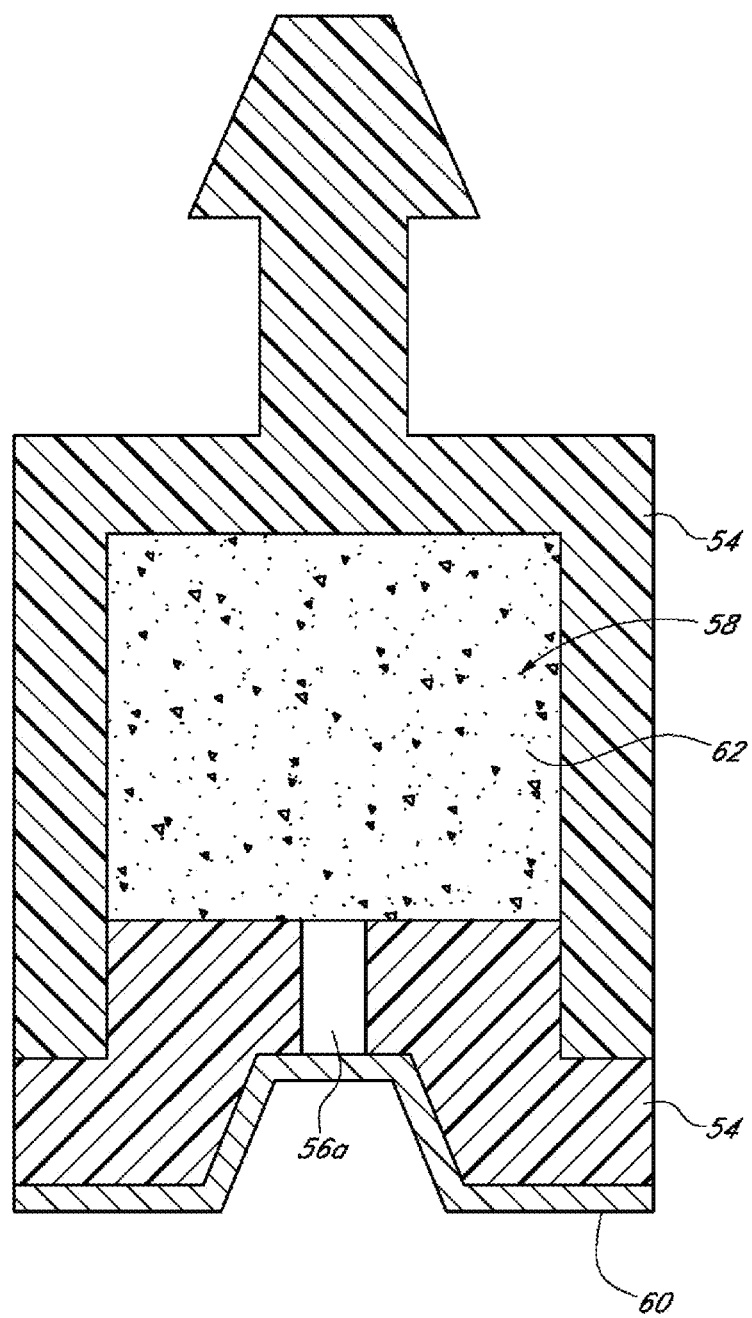

As discussed above, several embodiments disclosed herein employ multiple materials of varying permeability to control the rate of drug release from an implant. FIGS. 18A-18Q depict additional implant embodiments employing materials with varied permeability to control the rate of drug release from the implant. FIG. 18A shows a top view of the implant body 53 depicted in FIG. 18B. The implant body 53 comprises the outer shell 54 and retention protrusion 359. While not explicitly illustrated, it shall be appreciated that in several embodiments, implants comprising a body and a cap are also constructed without a retentions protrusion. FIG. 18C depicts an implant cap 53a, which, in some embodiments, is made of the same material as the outer shell 54. In other embodiments, the cap 53 is made of a different material from the outer shell. A region of drug release 56 is formed in the cap through the use of a material with permeability different from that of the shell 54. It shall also be appreciated that implants comprising a body and a cap (and optionally a retention protrusion) may be constructed with orifices through the body or the cap, may be constructed with layers or coatings of permeable or semi-permeable material covering all or a portion of any orifices, and may also be constructed with combinations of the above and regions of drug release based on thickness and/or permeability of the shell material. See 18E-18F.

FIGS. 18G-18J depict assembled implants according to several embodiments disclosed herein. The implant body 53 is joined with the implant cap 53a, thereby creating a lumen 58 which is filled with a drug 62. In some embodiments, the material of the implant body 54 differs from that of the cap 54a. Thus, the assembly of a cap and body of differing materials creates a region of drug release 56.

Figure 18K:
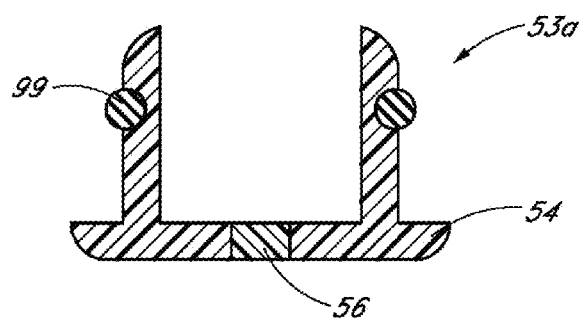
Figure 18L:
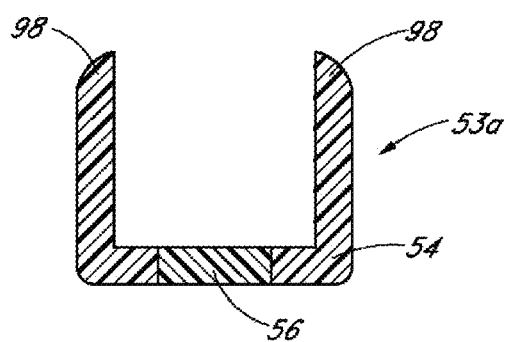
Figure 18M:
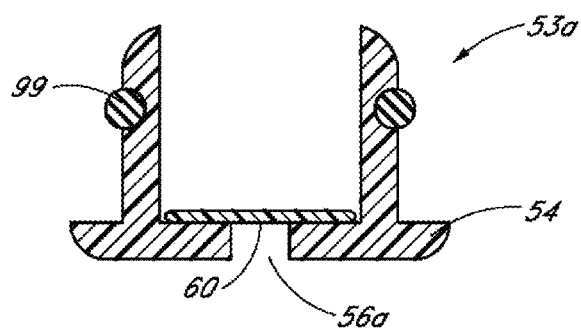
Figure 18N:
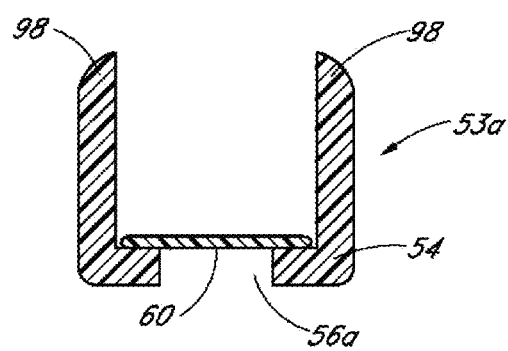
Figure 180:
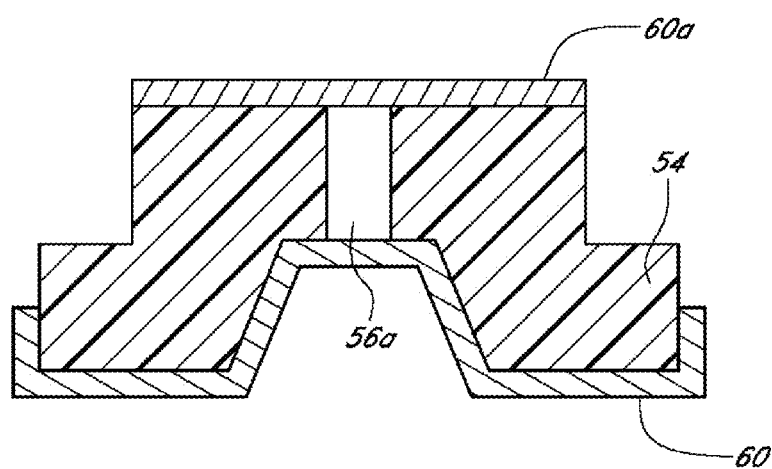

Additional non-limiting embodiments of caps are shown in FIGS. 18K and 18L. In FIG. 18K, an O-ring cap 53a with a region of drug release 56 is shown in cross-section. In other embodiments there may be one or more regions of drug release in the cap. An o-ring 99 (or other sealing mechanism) is placed around the cap such that a fluid impermeable seal is made between the cap and the body of the implant when assembled. In FIG. 18L, a crimp cap is shown. The outer shell of the cap comprises regions that are compressible 98 such that the cap is securely placed on, and sealed to, the body of the implant. As discussed above, certain embodiments employ orifices and layers in place of, or in addition to regions of drug release based on thickness and/or permeability of the shell material. FIG. 18M depicts an O-ring cap 53a shown in cross-section. A coating 60 is placed within the outer shell 54 of the cap and covering an orifice 56a. In other embodiments there may be one or more orifices in the cap. In some embodiments, the coating 60 comprises a membrane or layer of semi-permeable polymer. In some embodiments, the coating 60 has a defined thickness, and thus a defined and known permeability to various drugs and ocular fluid. In FIG. 18N, a crimp cap comprising an orifice and a coating is shown. While the coatings are shown positioned within the caps, it shall be appreciated that other locations are used in some embodiments, including on the exterior of the cap, within the orifice, or combinations thereof (See FIG. 18O).

Figure 18P:
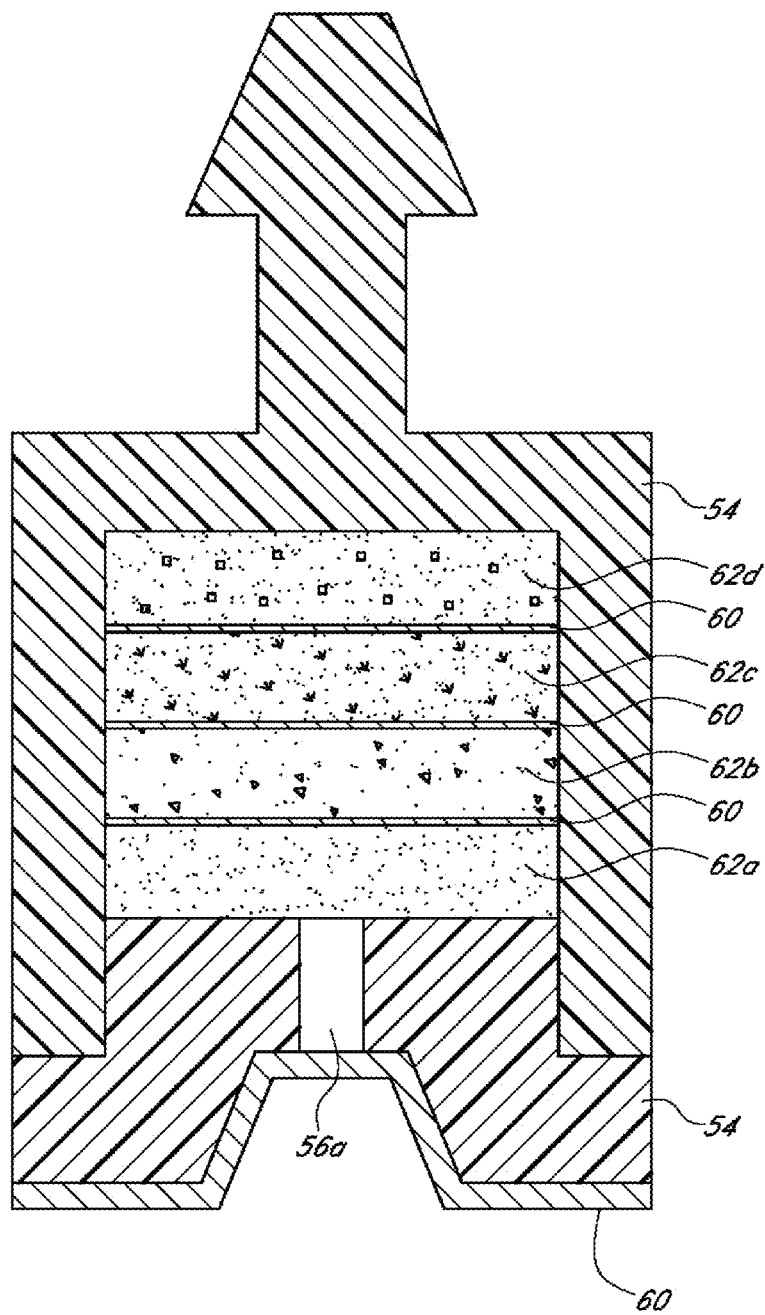
Figure 18Q:
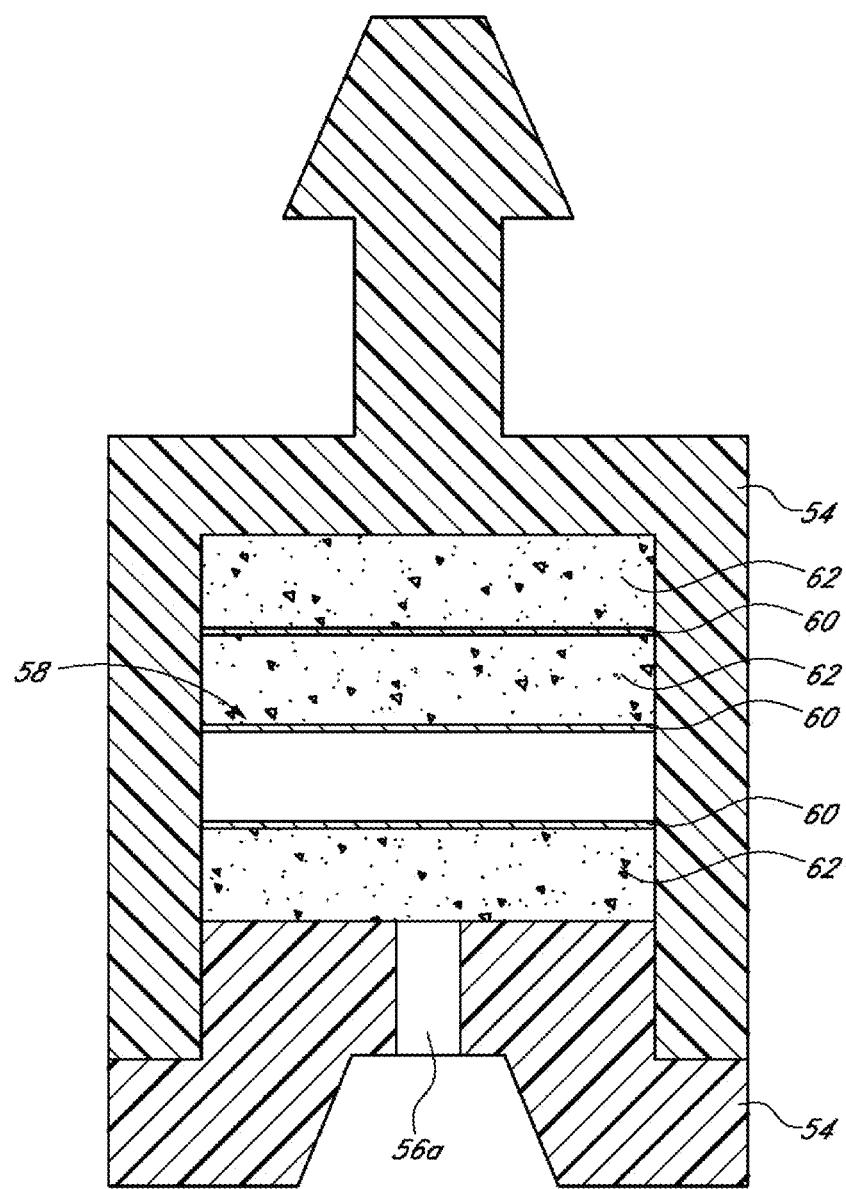

Additionally, as shown in FIGS. 18P and 18Q, in certain embodiments, coatings are employed within the drug material such that layers are formed. Coatings can separate different drugs 62a, 62b, 62c, 62d within the lumen (FIG. 18P). In certain embodiments, coatings are used to separate different concentration of the same drug (FIG. 18Q). It shall be appreciated that such internal layers are also useful in embodiments comprising regions of drug release (either alone or in combination with other drug release elements disclosed herein, e.g., orifices). In certain embodiments, the layers create a particularly desired drug elution profile. For example, use of slow-eroding layers is used to create periods of reduced drug release or drug "holidays." Alternatively, layers may be formulated to create zero order (or other kinetic profiles) as discussed in more detail below.

In each of the embodiments depicted in the Figures, as well as other embodiments, the coatings or outer layers of shell material may be formed by spraying, dipping, or added by some other equivalent means known in the art. Thus, in some embodiments, the permeability of the region of drug release or layer(s) covering an orifice (and hence the elution rate) will be at least partially defined by the materials used in manufacturing the implant, the coatings (if any) on the implant, and the effective thickness of implant outer shell.

Figure 18R:
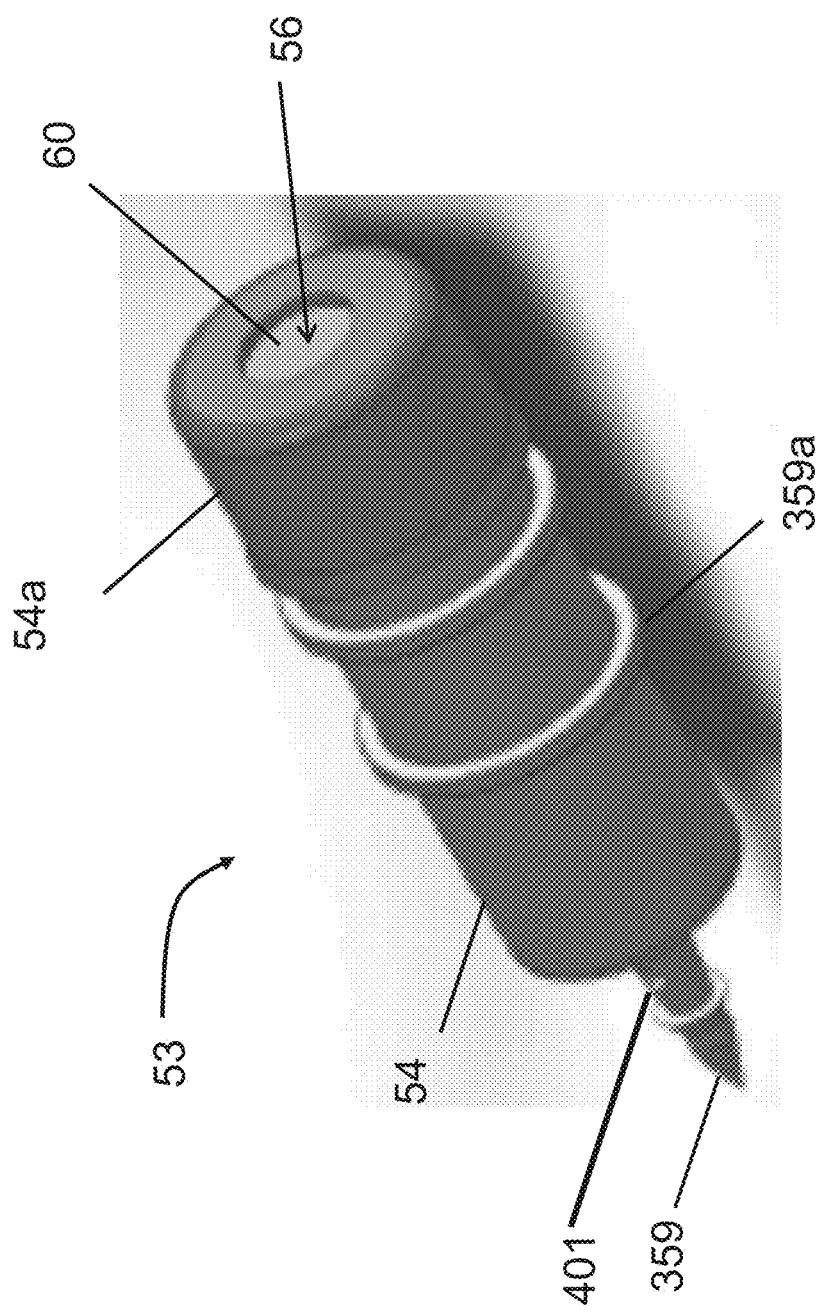

Additionally, in several embodiments, one or more portions of the implant are manufactured separately, then combined for a final implant that is ready for insertion to a target site (e.g., an assembled cap and implant shell). As shown, for example, in FIG. 18R, the implant 53, in several embodiments, comprises an implant shell 54, a separate cap 54a (which is shown for clarity in a different shade, but is optionally constructed of the same or of different material as compared to the implant shell). Any of the various cap configurations can be used with any of the implant shells (adjusting, of course, for dimensions that allow interaction between the components). As shown in FIG. 18R, the cap 54a comprises a central aperture, thereby creating a region of drug release 56. In several embodiments, the assembly of certain such embodiments exploit the elastic or semi-elastic characteristics of the membrane 60 through which the drug (or drugs) housed within the implant will elute. Advantageously, in several embodiments, the elastic properties of the membrane 60 allow the cap of an implant to be press fit onto the implant shell, and then retained by the pressure provided against the cap by the elastic rebound of the membrane (e.g., a "self-lock" feature). Thus, the membrane 60, in several embodiments, not only serves to define the release rate of the drug (or drugs), it also functions as a gasket to seal the interior portions of the implant from the outer environment, thus limiting the fluid communication between interior and exterior portions to that occurring through the membrane 60. As discussed in more detail below with respect to the possible materials from which the outer shell is constructed, the membrane 60 is (depending on the embodiment) constructed of similar materials, or combinations thereof. For example, the membrane 60, in one embodiment, comprises ethylene vinyl acetate, while in another embodiment, the membrane comprises silicone or other partially or semi-permeable materials material, homopolymers, polymer blends and copolymers, such as random copolymers and block copolymers, polyethylene, polyurethane, polyethersulfone, polyamide, poly(carbonate urethane), poly(ether urethane), silicone poly(carbonate urethane), silicone poly (ether urethane), PurSil™, Elasthane™, CarboSil™ and/or Bionate™. The selection of the membrane material and its dimensions (e.g., its thickness) are derived, at least in part, by the therapeutic agent of choice.

Figure 18S:
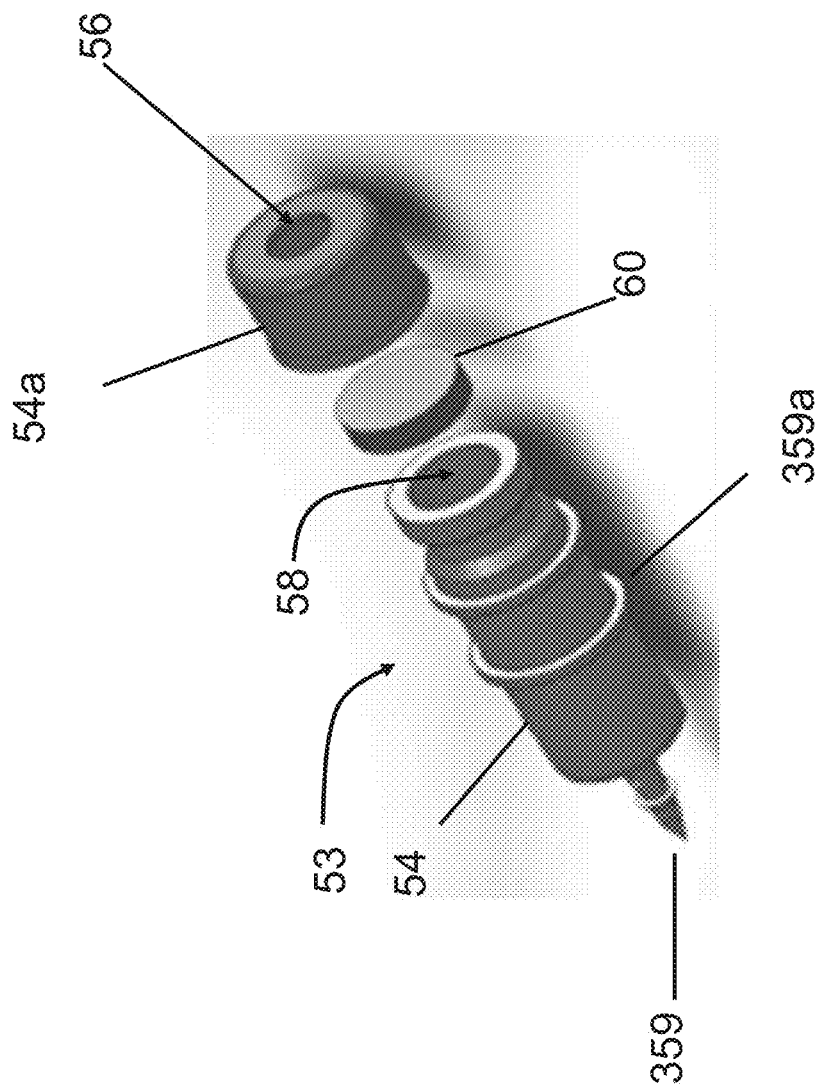

FIG. 18S depicts an exploded view of one embodiment of the implants disclosed herein. The implant 53 comprises, for example, a retention protraction 359 at one end in order to anchor the implant into a target tissue. The implant comprises at least one internal lumen 58 to house a therapeutic agent (or agents). As discussed above, the implant further comprises a cap 54a and an membrane 60, which when assembled together create a region of drug release 56 that is tailored (based on the membrane) to a particular therapeutic drug (or drugs) of interest.

In various embodiments, the thickness of the membrane 60 (taken in conjunction with the particular therapeutic agent or agents of choice) ranges from about 30 to about 200 µm in thickness, including about 30 to about 200 µm, about 50 to about 200 µm, about 70 to about 200 µm, about 90 to about 200 µm, about 30 to about 100 µm, about 30 to about 115 µm, about 50 to about 125 µm, about 63 to about 125 µm, about 84 to about 110 µm, about 57 to about 119 µm, and overlapping ranges thereof. In several embodiments, the thickness of the membrane 60 also defines, at least in part, the elution rate of the drug (or drugs) of interest.

As discussed herein, the elution rate of the drug is controlled, depending on the embodiment, to allow drug release over a desired time frame. For example, in several embodiments, the duration of drug release, depending on the embodiment, ranges from several months to several years, e.g., about 6 to about 12 months, about 12 to about 18 months, about 18 to about 24 months, about 24 to about 30 months, about 30 to about 36 months, etc.

Figure 18T:
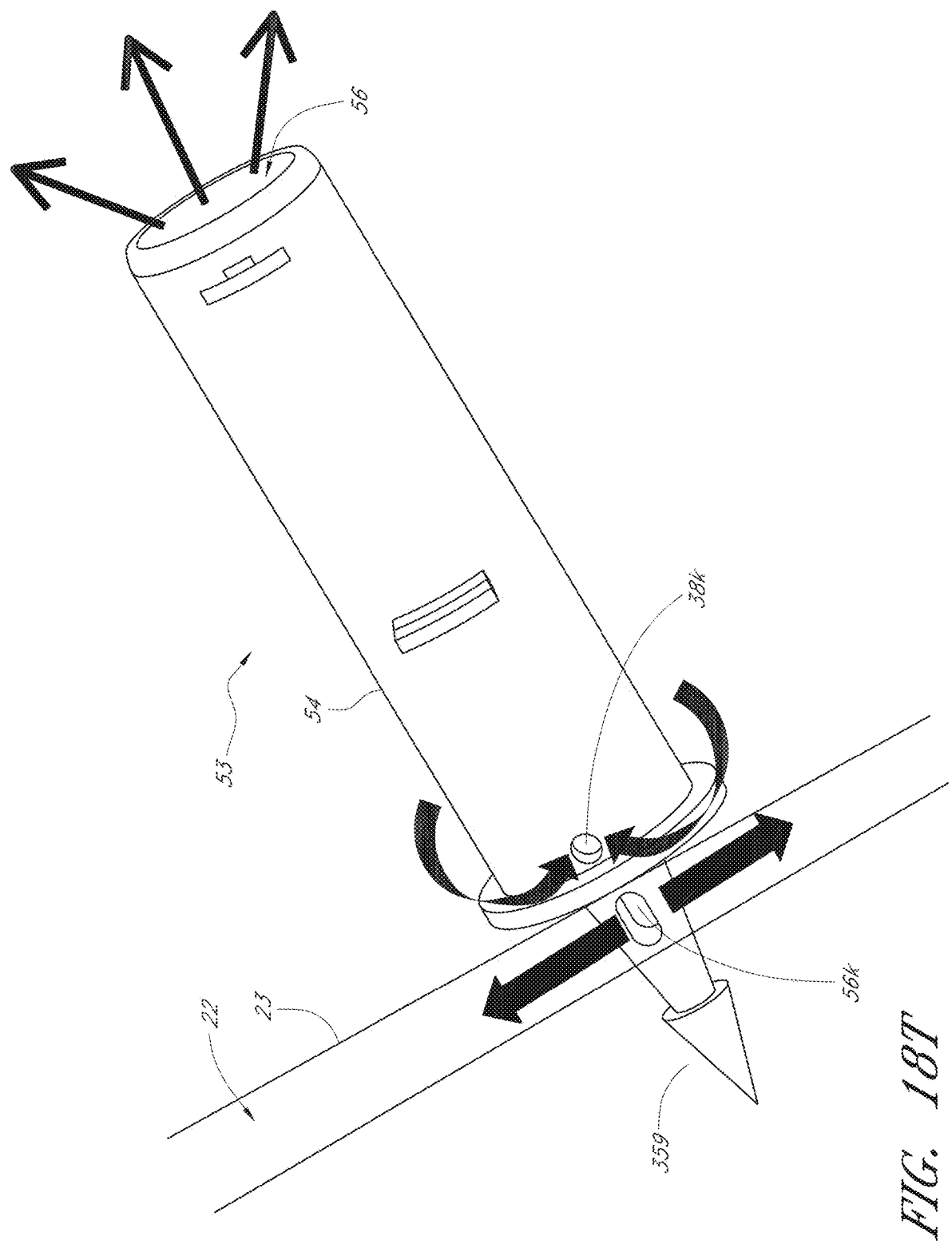

FIG. 18T depicts another embodiment in which the implant 53 further comprises at least one inflow pathway 38k and at least one fluid outflow pathway 56k. Other fluid inflow/outflow configurations are described in detail elsewhere here (e.g., see FIGS. 19R-19Y). As shown in FIG. 18T, a retention protrusion 359 anchors the implant in the ocular tissue such that the implant rests at or near the trabecular meshwork 23 and the fluid outflow pathway 56k allows ocular fluid to be directed through the implant (via fluid inflow pathway 38k) and to a physiological outflow space, shown here as Schlemm's canal 22. Similar to those embodiments described above, there is a region of drug release 56 which allows drug elution to a target tissue(s) of interest). It shall be appreciated that any of the various fluid inflow/outflow configurations can readily be adapted for use with any of the variety of implant bodies disclosed herein. Likewise, any of the retention protrusions are ready configurable for use with any of the implant shells, depending on the target tissue, the drug to be delivered, the desired drug delivery duration, and the like. For example, while the implant shown in FIG. 18T is depicted as having a spike-like or barb-like retention protrusion, the implant can also be configured with, for example, a threaded region as depicted in FIG. 19C.

Figure 18U:
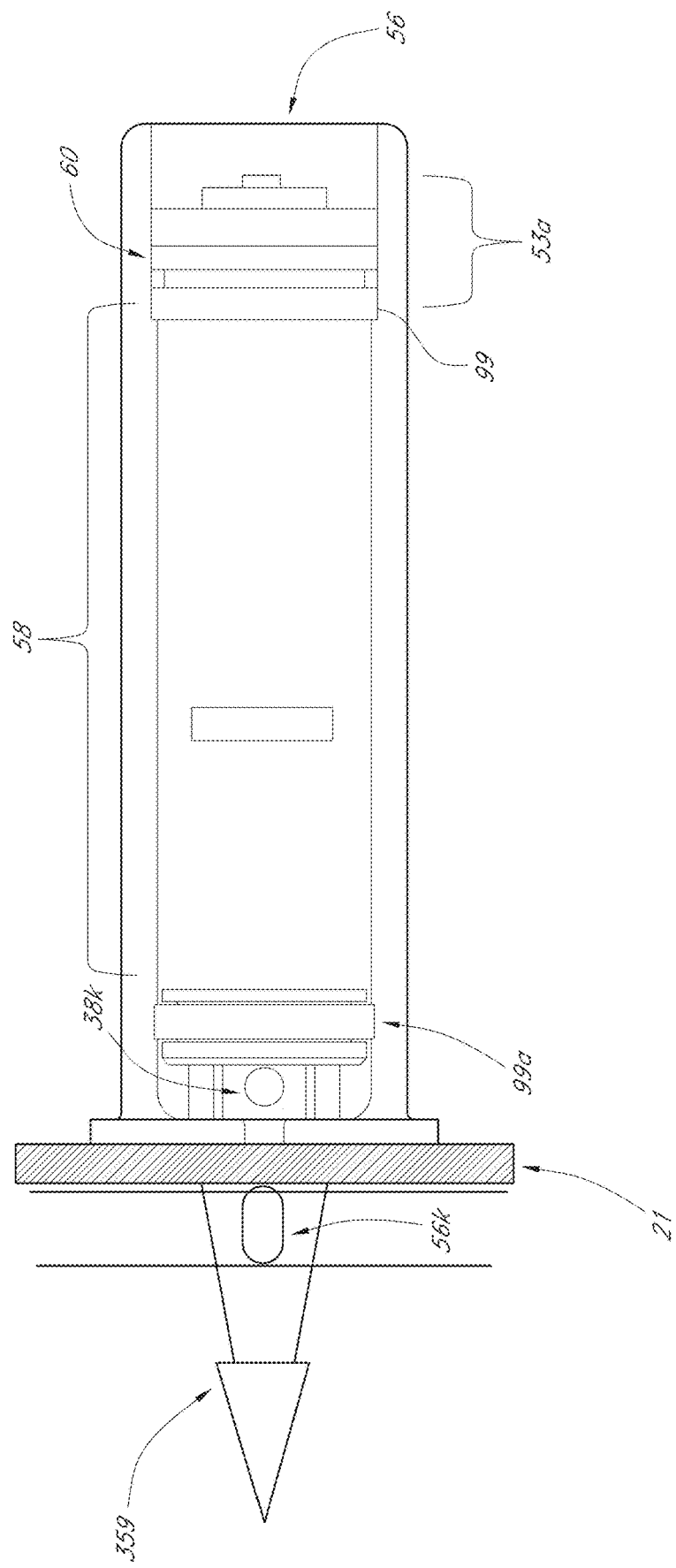

FIG. 18U depicts a cross sectional view of one embodiment of an implant having fluid inflow 38K and fluid outflow pathways 56k. As shown, the implant comprises a lumen 58 for containing drug to be delivered to a target tissue via elution through a membrane 60 and out of the implant via the region of drug release 56. One embodiment of a cap structure 53a is shown, into which the membrane 60 is integrated. To ensure that ocular fluid passes into the implant to dissolve drug (and drug flows out of the implant) only through the membrane 60 (which ensures controlled release) the cap 53 comprises a seal 99. Similarly, to prevent intrusion of ocular fluid into the implant from the portion adjacent to the inflow pathway 38k, an additional lower seal 99a is placed distal to the drug containing lumen 58. In several embodiments, the various features that allow for controlled release of a therapeutic agent (or agents) from the implant can be adapted to be implanted into the punctum of a subject, as described in more detail herein.

During manufacture of the implants of certain embodiments, one or more interior lumen 58 is formed within the outer shell of the implant. In some embodiments, an interior lumen is localized within the proximal portion of the implant, while in other embodiments, an interior lumen runs the entire length or any intermediate length of the implant. Some embodiments consist of a single interior lumen, while others comprise two or more interior lumens. In some embodiments, one or more of the internal lumens may communicate with an ocular chamber or region, e.g., the anterior chamber. In some embodiments, implants are dimensioned to communicate with more than one ocular chamber or region. In some embodiments, both the proximal and the distal end of the implant are positioned within a single ocular chamber or region, while in other embodiments, the ends of the implant are positioned in different ocular chambers or regions.

A drug 62 is housed within the interior lumen 58 of the implant. The drug 62 comprises a therapeutically effective agent against a particular ocular pathology as well as any additional compounds needed to prepare the drug in a form with which the drug is compatible. In some embodiments, one or more of the internal lumens may contain a different drug or concentration of drug, which may be delivered simultaneously (combination therapy) or separately. In some preferred embodiments, an interior lumen is sized in proportion to a desired amount of drug to be positioned within the implant. The ultimate dimensions of an interior lumen of a given embodiment are dictated by the type, amount, and desired release profile of the drug or drugs to be delivered and the composition of the drug(s).

In some embodiments, multiple pellets 62 of single or multiple drug(s) are placed within an interior lumen of the implant. In some embodiments an impermeable partition 64 is used to seal drug(s) within the lumen, such that the sole route of exit from the implant is through the region of drug release. In some embodiments, the impermeable partition 64 may bioerode at a specified rate. In some embodiments, the impermeable partition 64 is incorporated into the drug pellet and creates a seal against the inner dimension of the shell of the implant 54. In other embodiments, more than one impermeable partition is used within a lumen, thereby creating sub-lumens, which may contain different drugs, the same drug at a different concentration, or the same or another drug compounded with different excipients etc. In such embodiments, sequential drug release or release of two agents that are inert within the implant and active when co-mingled outside their respective sub-lumens may be achieved.

In several embodiments, micro-tablets provide an advantage with respect to the amount of an agent that can be packed, tamped, or otherwise placed into an implant disclosed herein. The resultant implant comprising micro-tablets, in some embodiments, thus comprises therapeutic agent at a higher density than can be achieved with non-micro-tablet forms. As described herein, some embodiments of the devices disclosed herein are rechargeable, and as such, the size of micro-tablets is advantageous. In some embodiments, the loading and/or recharging of a device is accomplished with a syringe/needle, through which the therapeutic agent is delivered In some embodiments, the micro-tablets may be introduced into the eye directly, such as into the vitreous cavity, using a syringe or cannula.

In one embodiment, micro-tablets with the above properties, or any combination thereof, are made using known techniques in the art including tableting, lyophilization, granulation (wet or dry), flaking, direct compression, molding, extrusion, and the like. Moreover, as discussed below, alterations in the above-discussed characteristics can be used to tailor the release profile of the micro-tableted therapeutic agent from an implant.

In several embodiments, the therapeutic agent is a protein, and in such embodiments, drying and/or tabletization should be completed under conditions (e.g., temperature, acid/base, etc.) that do not adversely affect the biological activity of the therapeutic agent. To assist in maintenance of biological activity of micro-pelleted therapeutic agents, in some embodiments, protein therapeutics are formulated with a stabilizing agent (e.g., mannitol, trehalose, starch, or other poly-hydroxy polymer) to maintain the structure (and therefore activity) of the therapeutic protein.

Punctal Implants

In several embodiments, the implants are configured specifically for use (e.g., implantation) in the punctum of the eye of a subject (e.g., the upper and/or lower punctum of the upper and/or lower canaliculus, respectively). The puncta function to collect tears that are released onto the surface of the eye by the lacrimal glands. However, in some individuals tear production is reduced, blocked, decreased, or otherwise insufficient to maintain an adequate level of moisture on the eye (or eyes). Damage to the corneal surface of the eye can result if the moisture on the eye remains reduced. When functioning normally (e.g., in a patient with normal tear production), the puncta convey the tear fluid to the lacrimal sac, which then allows it to drain through the nasolacrimal duct to the inner nose. One treatment for dry eye or similar syndromes is implantation of punctual plugs. Once implanted the plugs function to block the drainage of tear fluid, thereby increasing the retention of tear fluid on the eye. However, several of the implant embodiments disclosed herein advantageously allow the supplementation of the physical blockage of tear drainage with the delivery of one or more therapeutic agents to the eye in order to treat one or more aspects of reduced tear production. Thus, in several embodiments, one or more therapeutic agents are positioned in the implant in order to increase tear production and/or treat a symptom of dry eye, including, but not limited to, reduction in swelling, irritation of the eye and surrounding tissues and/or inflammation. Additional symptoms that are reduced, ameliorated, and in some cases eliminated include stinging or burning of the eye, a sandy or gritty feeling as if something is in the eye, episodes of excess tears following very dry eye periods, a stringy discharge from the eye, pain and redness of the eye, temporary or extended episodes of blurred vision, heavy eyelids, reduced ability to cry, discomfort when wearing contact lenses, decreased tolerance of reading, working on the computer, or any activity that requires sustained visual attention, and eye fatigue.

In several embodiments, the implants advantageously obviate the need for additional topical agents (e.g., ointments, artificial tears, etc.). In several embodiments, however, the implants are configured (e.g., have a particular drug release profile) to work synergistically with one or more of such agents. For example, in several embodiments, the implant is configured to deliver a constant dosage of a therapeutic agent over time to treat a damaged or diseased eye, and a subject with them implants in place can also use artificial tears, for example, to further enhance the efficacy of the agent delivered from the implant.

In several embodiments, the agents delivered from the implant are used for treatment of another ocular disorder, such as glaucoma, ocular hypertension, and/or elevated intraocular pressure.

Advantageously, as discussed herein, several embodiments of the implants configured for punctual placement allows metered delivery of one or more therapeutic agents; that is, delivery at a constant rate, thereby reducing the peaks and valleys of therapeutic agent concentration as occurs with topical administration (e.g., via eyedrop).

Any of the relevant features disclosed herein can be applied to the embodiments configured for use in the punctum. For example, the dimensions of the implants, their shape, their drug release characteristics, and the like can be configured for use in the punctum. In several embodiments, the plugs can be tailored to the punctal dimensions of a particular subject. Moreover, the plugs can be configured to be removable or, in several embodiments, permanent (e.g., capable of being recharged). In several embodiments, the punctal implants comprise at least a first active agent that is loaded, at least in part, preferentially in the proximal region of the implant (e.g., such that the agent is released to the tear film of the subject) with the distal region of the implant positioned within the within the lacrimal ducts. In several such embodiments, the implant is specifically adapted to prevent unintended release of the active agent (or agents) from the distal portion of the implant. In some such embodiments, a plug (e.g., an impermeable occlusive member), a membrane (e.g., a membrane with little to no permeability to the active agent/agents), and/or a valve (e.g., a one-way valve) prevent elution in a distal region of the device.

In several embodiments, the use of a valve or plug enables flushing of the implant. For example, if there is a need to replace the therapeutic agent (e.g., with a different agent or a different dose of the same agent) it may be beneficial to substantially remove any remaining agent within the implant. In such instances, the plug can be removed and the implant flushed from a proximal to distal direction, allowing the therapeutic agent remaining in the implant to be flushed down the nasolacrimal duct. Thereafter the implant can be reloaded with another dose, another agent, and the like. Similarly, flushing the implant can be performed when a valve is positioned in the distal region of the implant, the valve being opened by pressure exerted on it from the flushing procedure and preventing backflow of the flushed agent into the implant.

In several embodiments, an implant and method for treating an eye with latanoprost or other therapeutic agent(s) is provided, the method comprising inserting a distal end of an implant into at least one punctum of the eye and positioning the implant such that the proximal portion of the implant delivers latanoprost or other therapeutic agent(s) to the tear fluid adjacent the eye. In several embodiments, delivery of the latanoprost or other therapeutic agent(s) is inhibited distally of the proximal end.

Figure 19A:
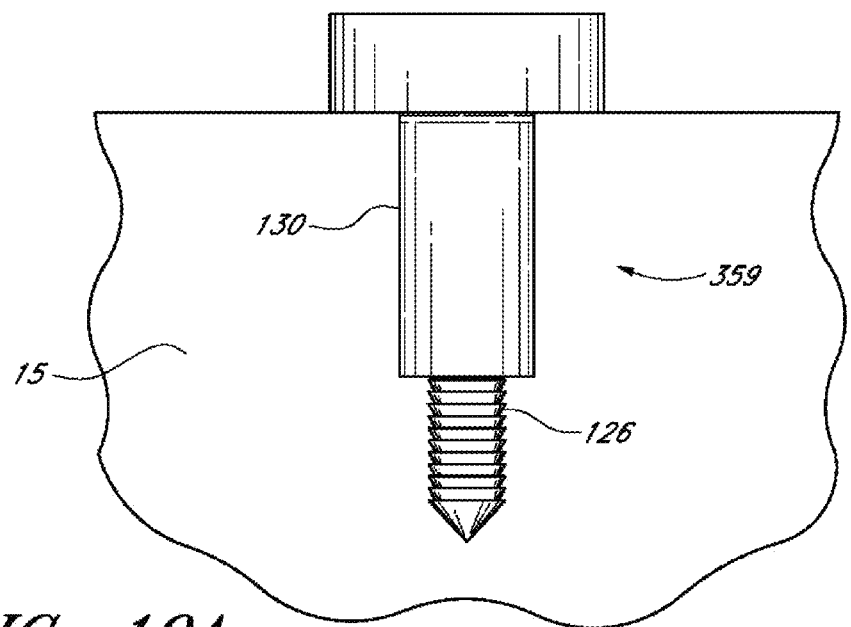
FIGS. 19A-19Y illustrate various anchor elements used in several embodiments disclosed herein.
Figure 19B:
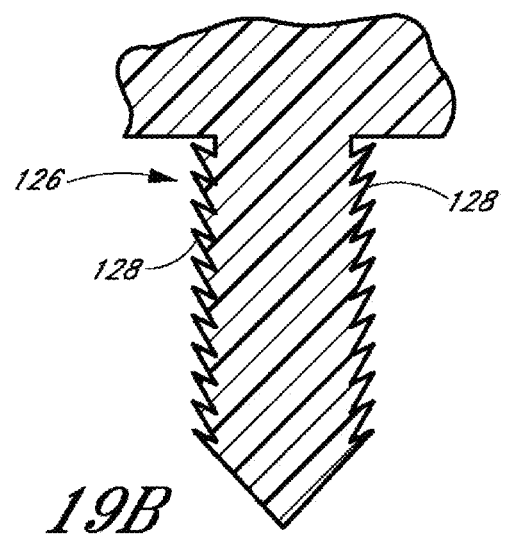
Figure 19C:
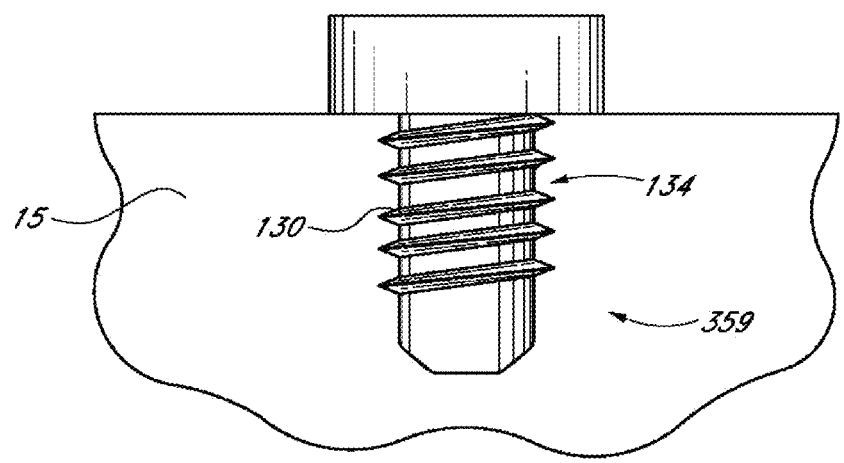
Figure 19D:
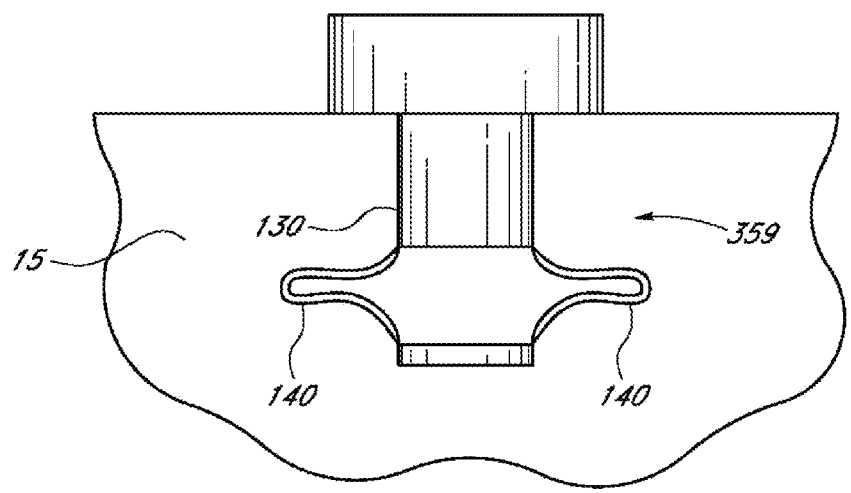
Figure 19E:
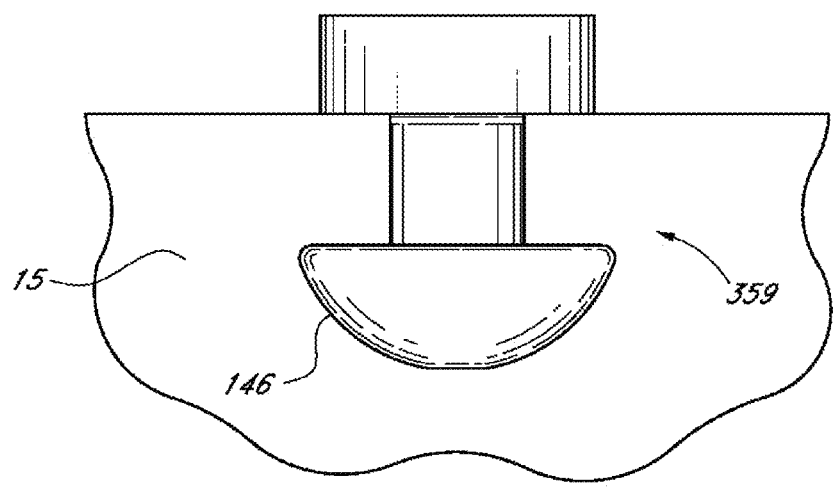
Figure 19F:
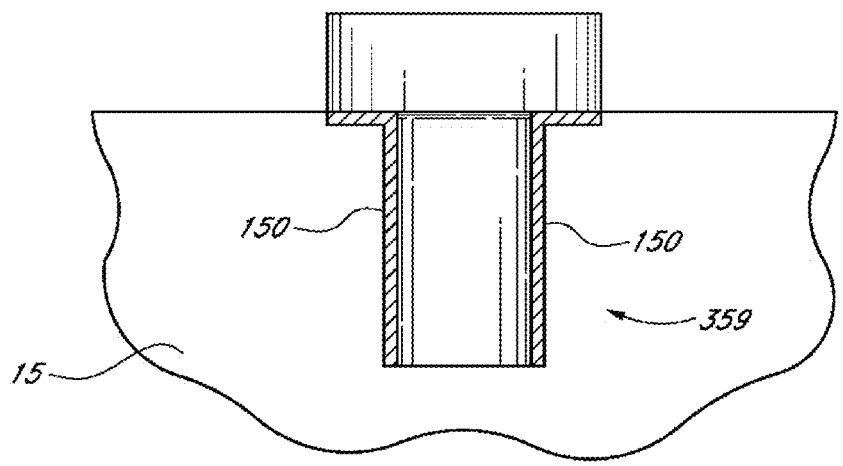
Figure 19G:
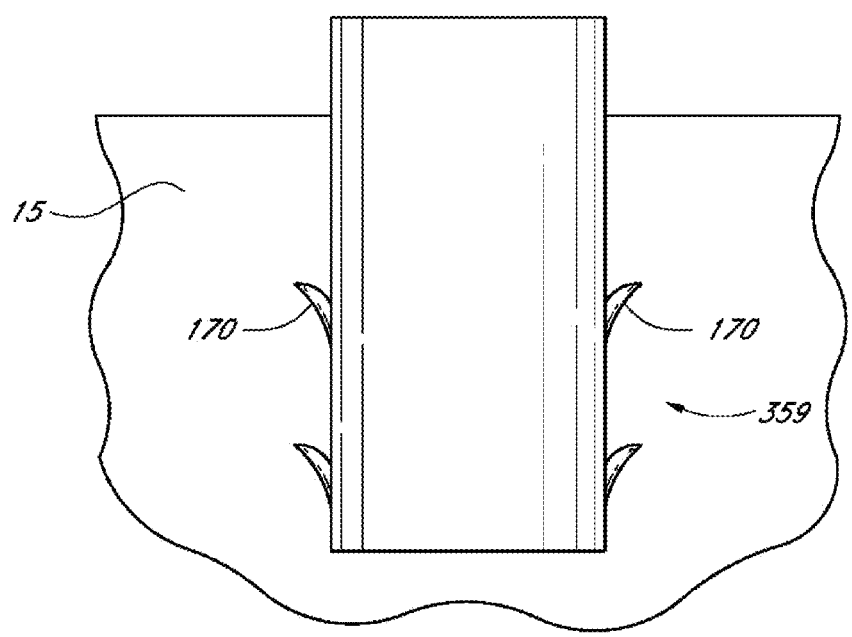
Figure 19H:
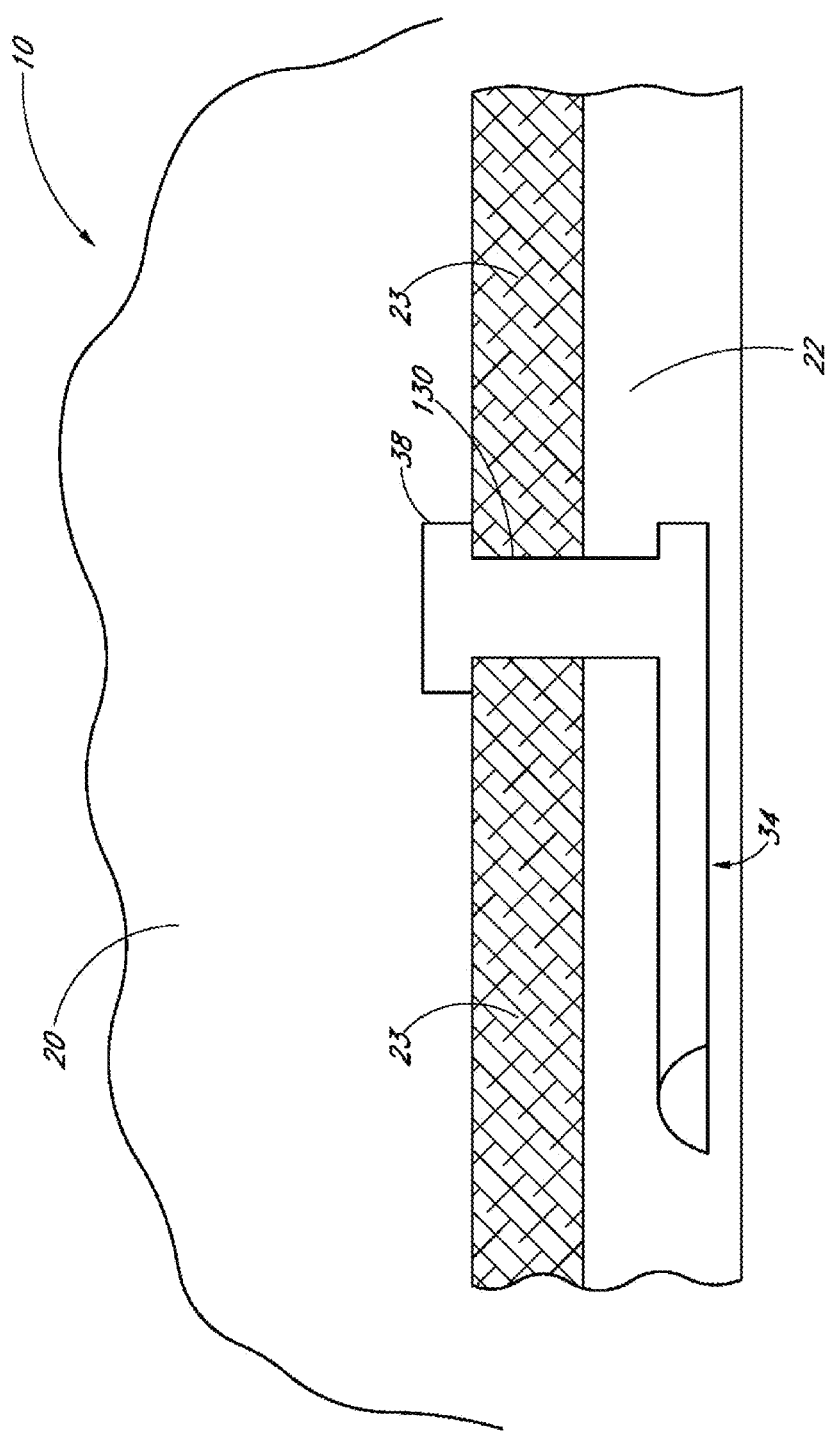
Figure 19I:
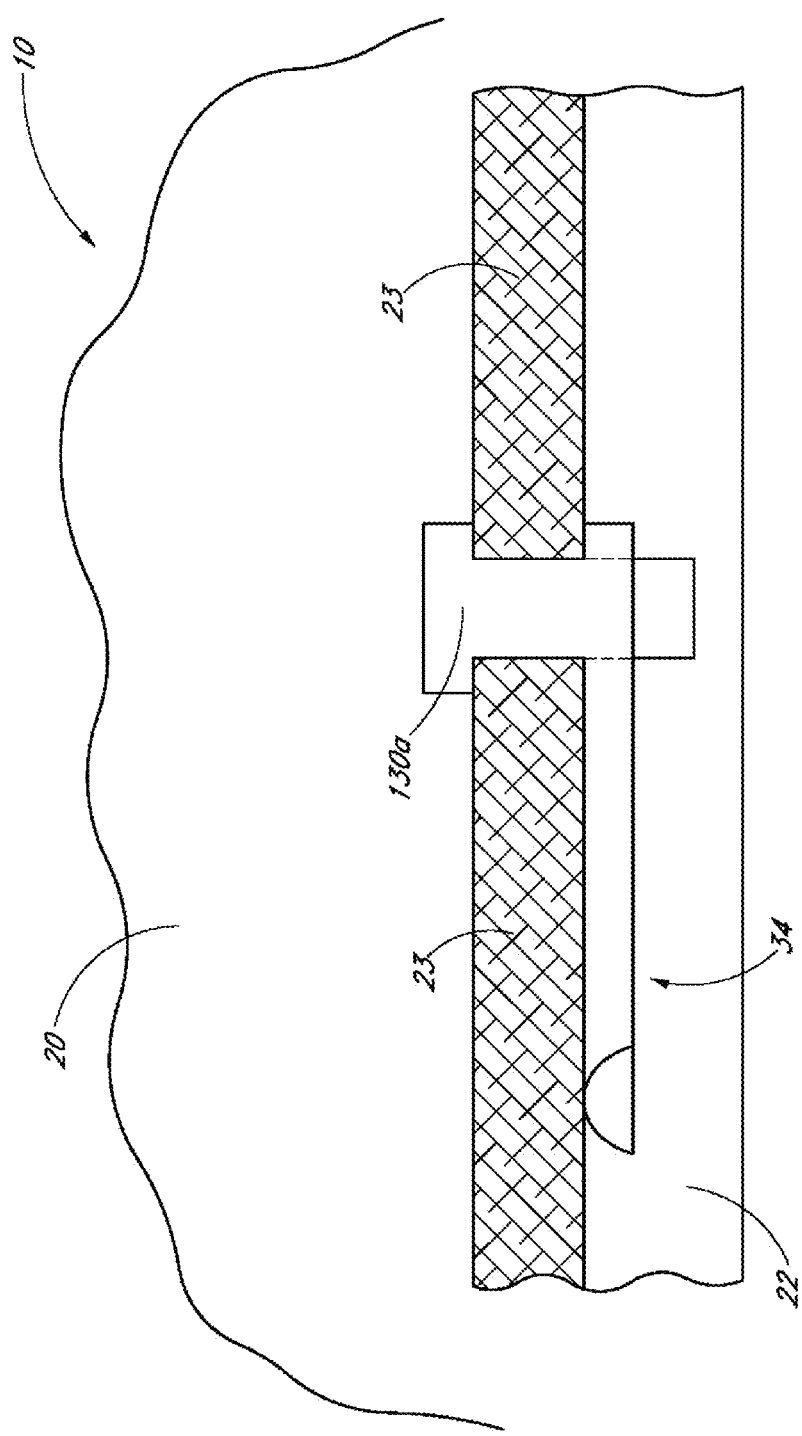
Figure 19J:
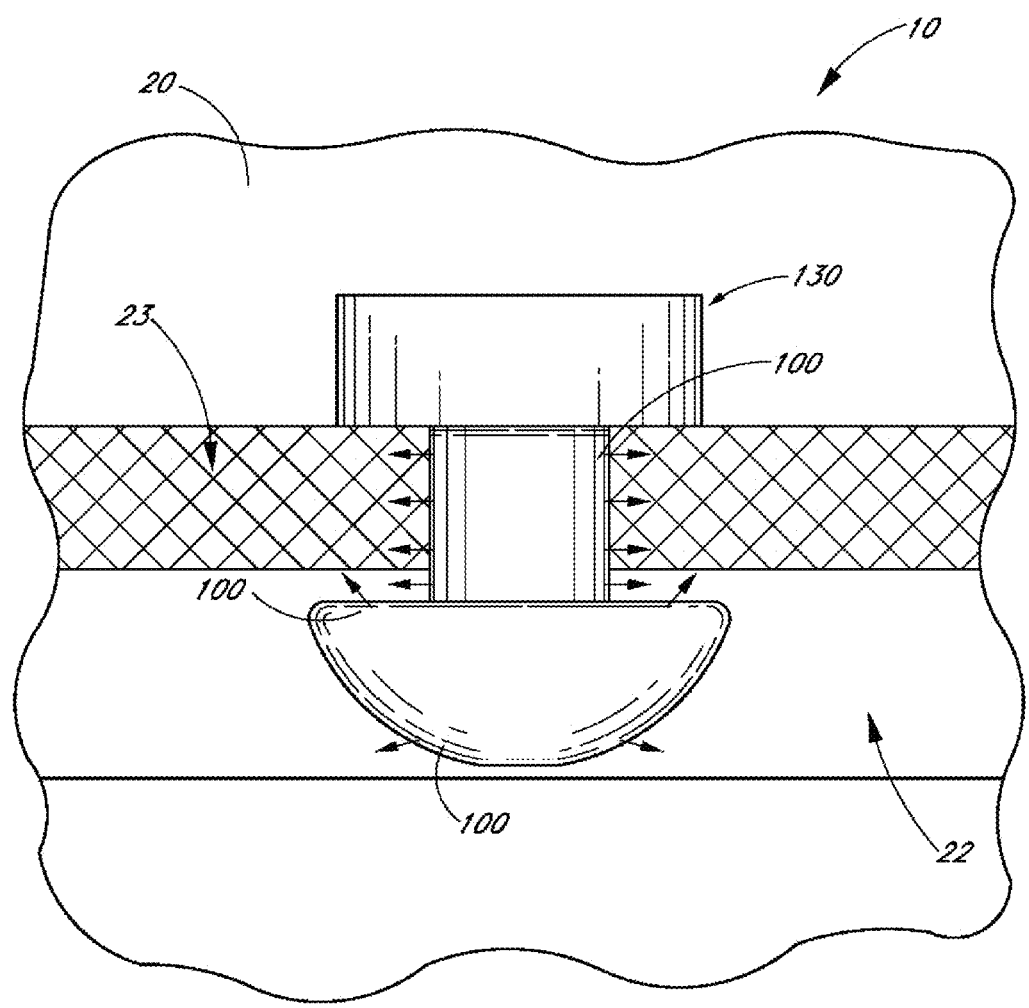
Figure 19K:
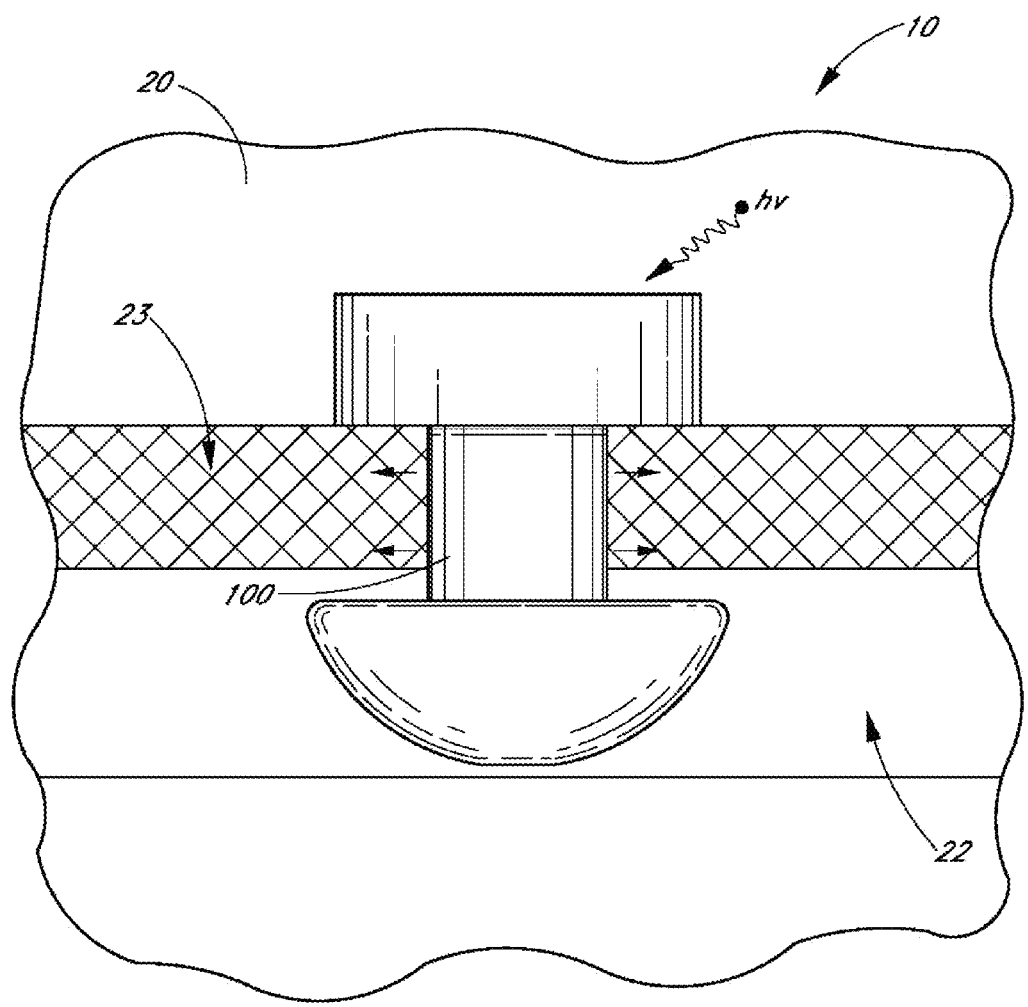
Figure 19S:
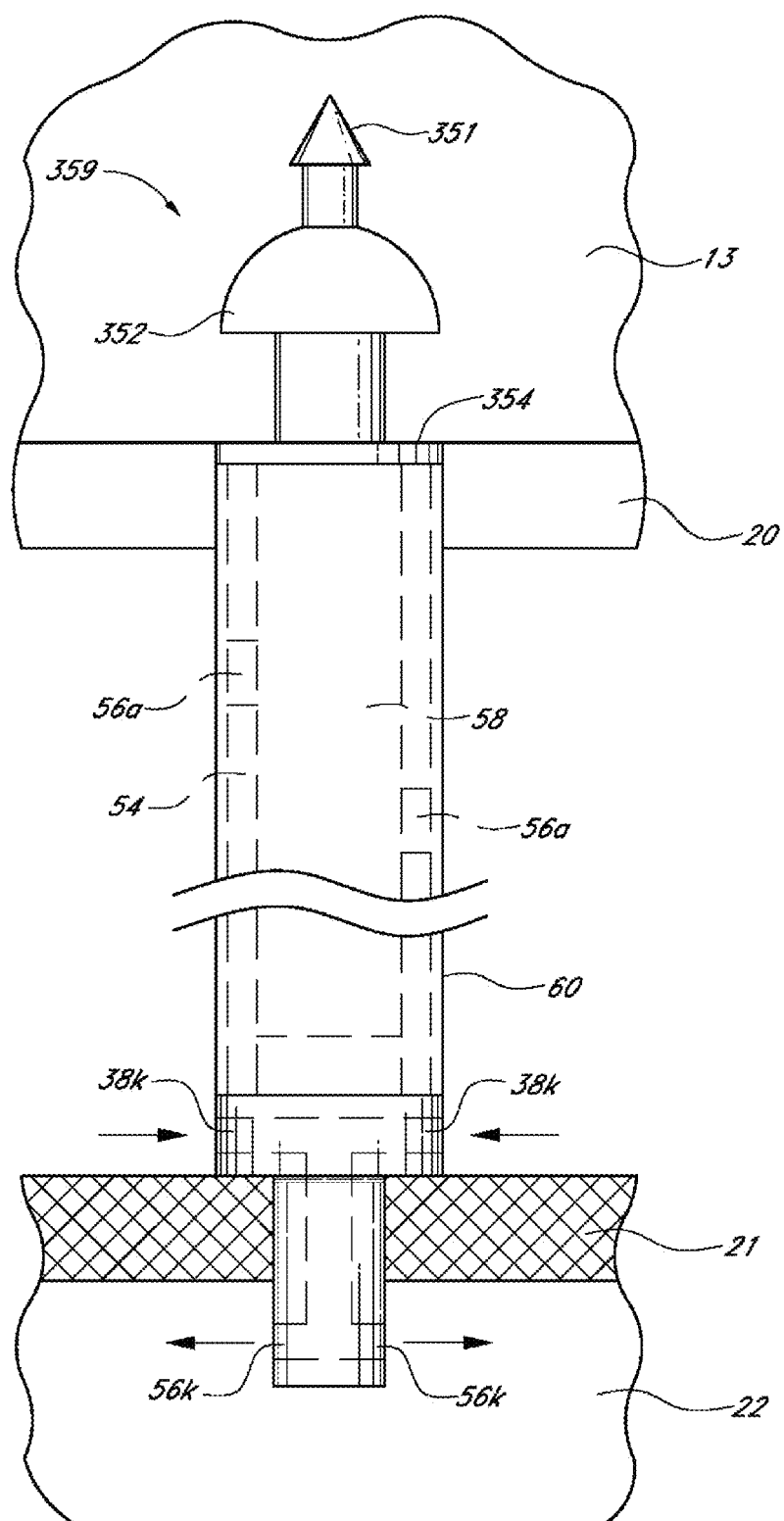
Figure 19T:
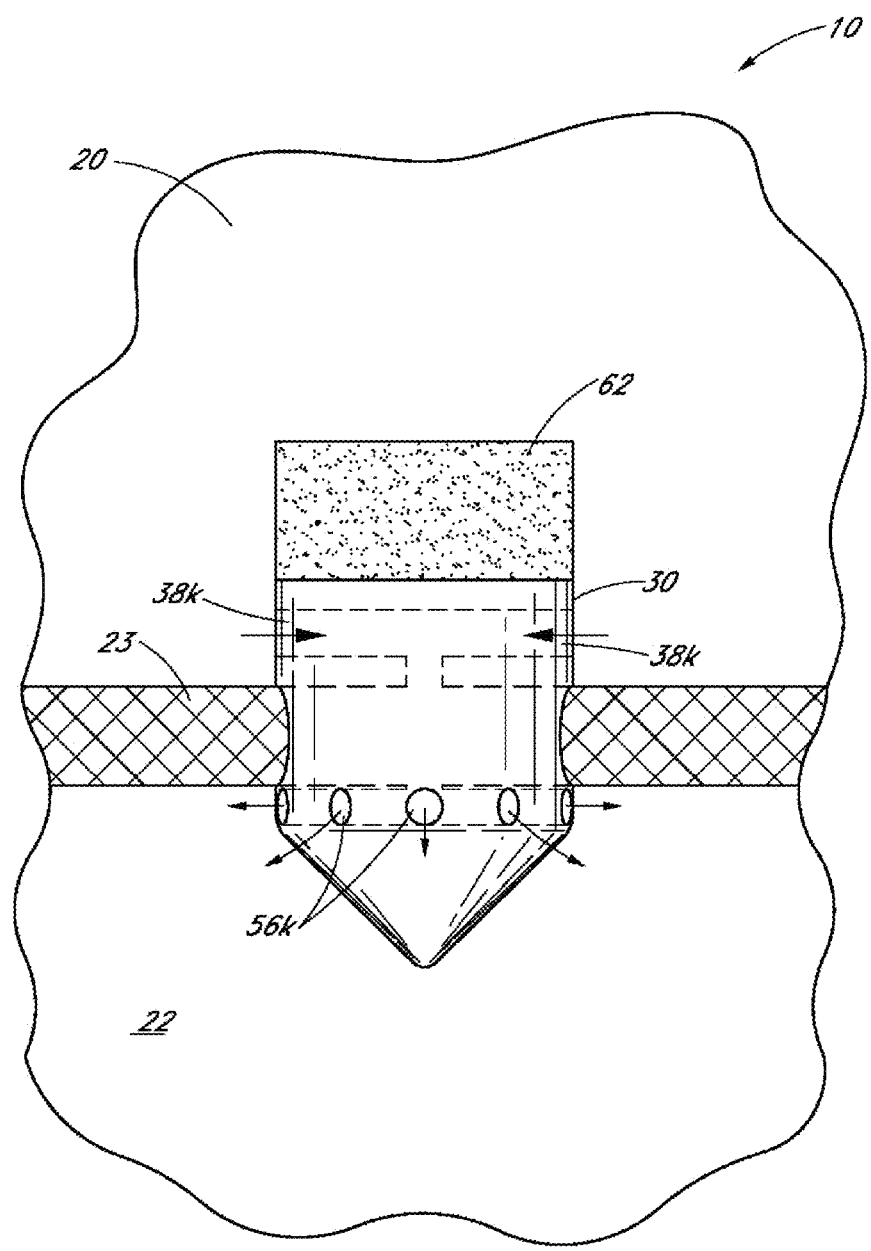
Figure 19U:
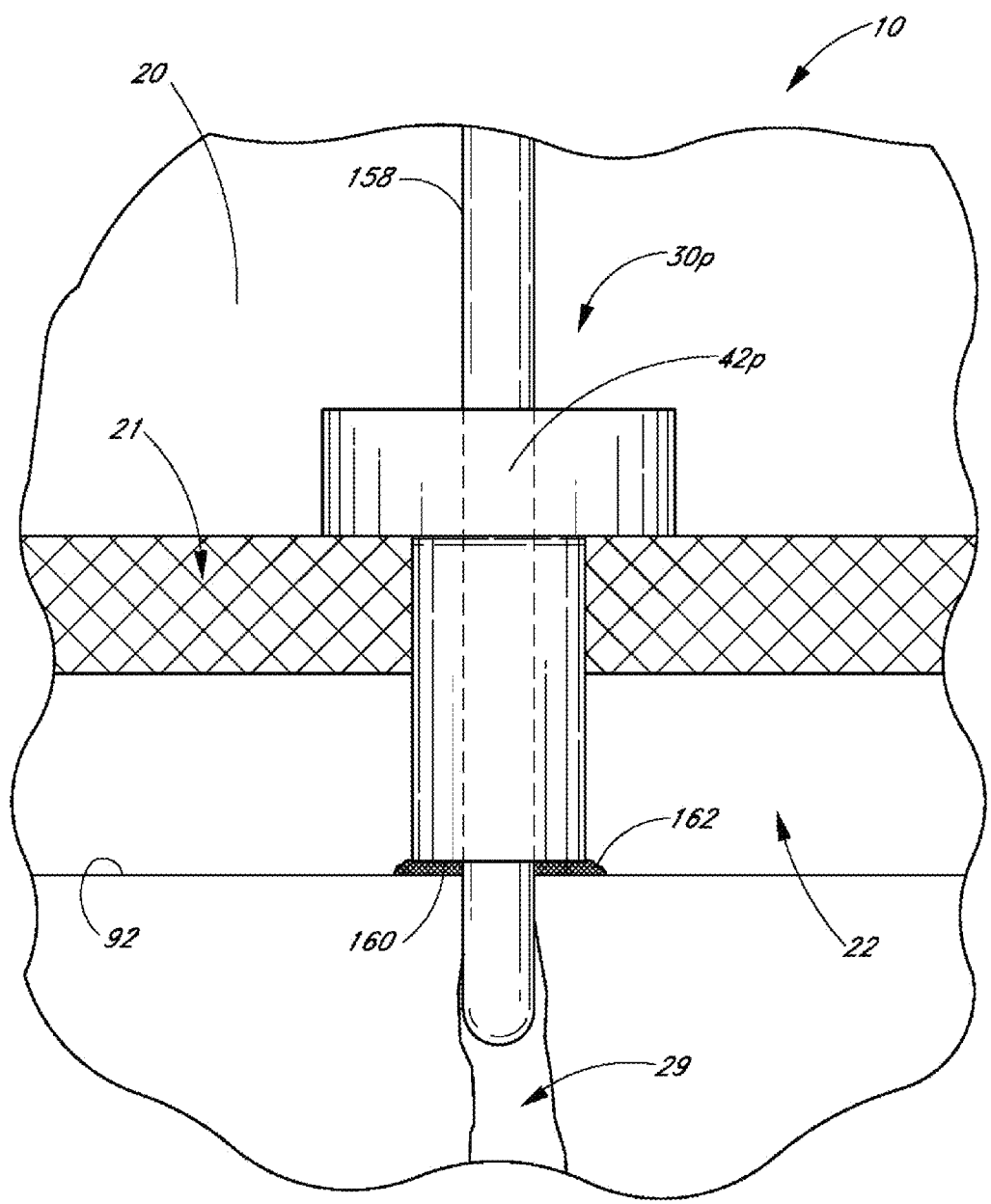
Figure 19V:
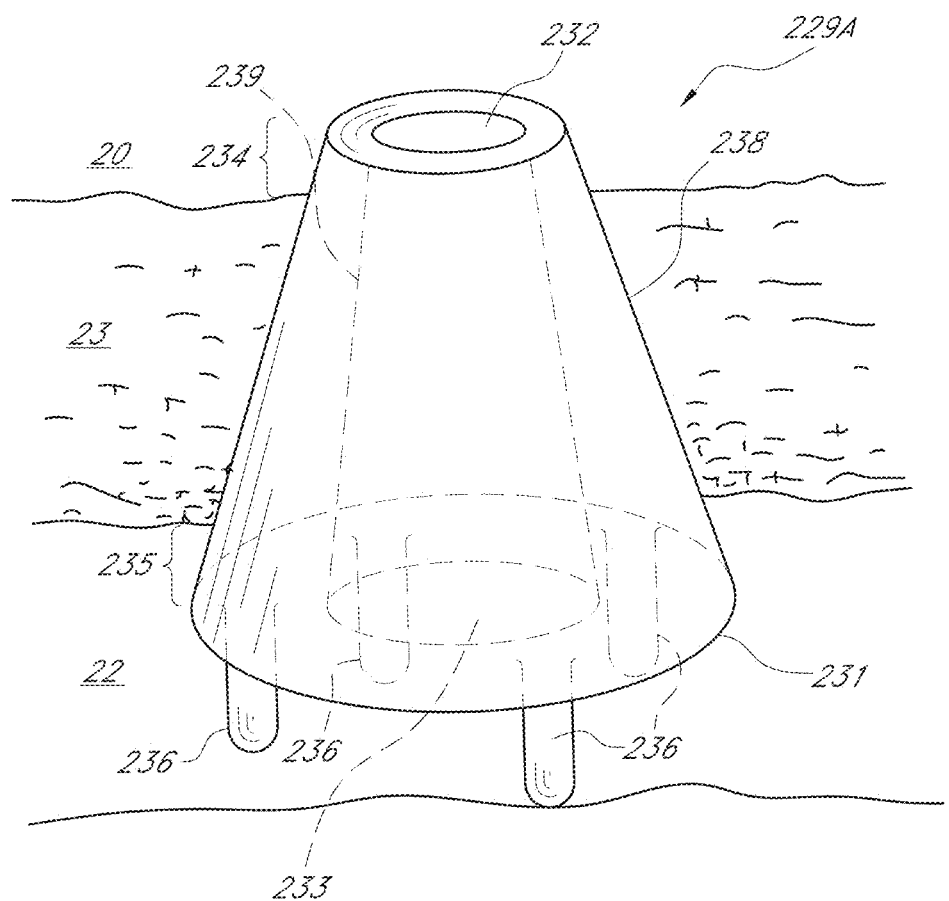
Figure 19W:
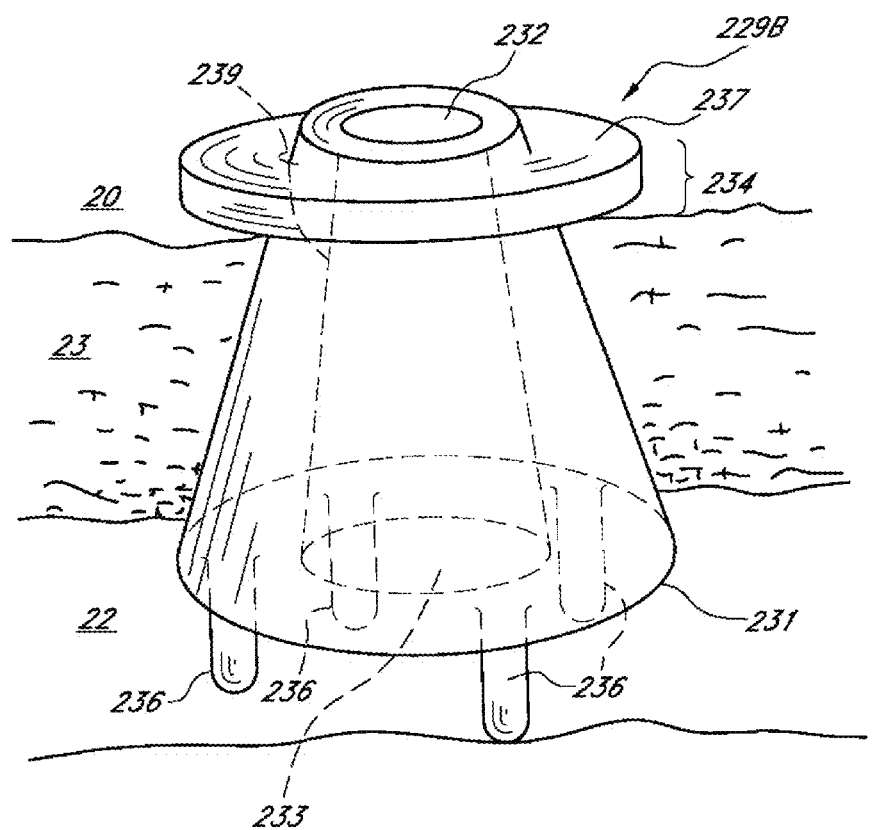

FIGS. 19A-19W illustrate embodiments of drug various embodiments of retention protrusions. As used herein, retention protrusion is to be given its ordinary meaning and may also refer to any mechanism or anchor element that allows an implant to become affixed, anchored, or otherwise attached, either permanently or transiently, to a suitable target intraocular tissue (represented generally as 15 in FIGS. 19A-19G). For example, a portion of an implant that comprises a biocompatible adhesive may be considered a retention protrusion, as may barbs, barbs with holes, screw-like elements, knurled elements, and the like. In some embodiments, implants are sutured to a target tissue. For example, in some embodiments, implants are sutured to the iris, preferably the inferior portion. It should be understood that any retention means may be used with any illustrated (and/or described) implant (even if not explicitly illustrated or described as such). In some embodiments, implants as described herein are wedged or trapped (permanently or transiently) based on their shape and/or size in a particular desirable ocular space. For example, in some embodiments, an implant (e.g., a suprachoroidal stent) is wedged within an ocular space (e.g., the suprachoroidal space) based on the outer dimensions of the implant providing a sufficient amount of friction against the ocular tissue to hold the implant in place.

Intraocular targets for anchoring of implants include, but are not limited to the fibrous tissues of the eye. In some embodiments, implants are anchored to the ciliary muscles and/or tendons (or the fibrous band). In some embodiments, implants are anchored into Schlemm's canal, the trabecular meshwork, the episcleral veins, the iris, the iris root, the lens cortex, the lens epithelium, the lens capsule, the sclera, the scleral spur, the choroid, the suprachoroidal space, the anterior chamber wall, or disposed within the anterior chamber angle. As used herein, the term "suprachoroidal space" shall be given its ordinary meaning and it will be appreciated that other potential ocular spaces exist in various regions of the eye that may be encompassed by the term "suprachoroidal space." For example, the suprachoroidal space located in the anterior region of the eye is also known as the supraciliary space, and thus, in certain contexts herein, use of "suprachoroidal space" shall be meant to encompass the supraciliary space.

The retention protrusions may be formulated of the same biocompatible material as the outer shell. In some embodiments the biodegradable retention protrusions are used. In alternate embodiments, one or more of the retention protrusions may be formed of a different material than the outer shell. Different types of retention protrusions may also be included in a single device.

In some embodiments, see for example FIG. 19A, the retention protrusion 359 may comprise a ridged pin 126 comprising a ridge 128 or series of ridges formed on the surface of a base portion 130. Such ridges may be formed in any direction on the surface of the implant including, but not limited to, biased from the long axis of the implant, spiraling around the implant, or encircling the implant (see, e.g. FIG. 19B). Likewise, the ridges may be distinct or contiguous with one another. Other anchoring elements may also be used, such as raised bumps; cylinders; deep threads 134, as shown in FIG. 19C; ribs 140, as shown in FIG. 19D; a rivet shaped base portion 146, as shown in FIG. 19E; biocompatible adhesive 150 encircling the retention element 359 where it passes through an ocular tissue, as shown in FIG. 19F; or barbs 170, as shown in FIG. 19G. In some embodiments, the retention protrusion is positioned within a pre-existing intraocular cavity or space, shown generally as 20. For example, as depicted in FIG. 19H, an elongated blade 34 resides within Schlemm's canal 22 and is attached to a base portion 130 that traverses the trabecular meshwork 21. In other embodiments, as depicted in FIG. 19I, based on the dimensions of intraocular spaces, which are well-known in the art, a shorter base 130a is used and attached to the elongated blade 34 residing within Schlemm's canal 22.

In certain embodiments, an expandable material 100 is used in conjunction with or in place of a physical retention protrusion. For example, in FIG. 19J, the base 130 is covered, in particular areas, with an expandable material 100. Upon contact with an appropriate solvent, which includes ocular fluid, the material expands (as depicted by the arrows), thus exerting pressure on the surrounding tissue, for example the trabecular meshwork 21 and base of Schlemm's canal 22 in FIG. 19J.

In some embodiments, an external stimulus is used to induce the expansion of the expandable material 100. As depicted in FIG. 19K, the base 130 is covered, in particular areas, with an expandable material 100. Upon stimulation by an external stimuli hv, the material expands (as depicted by the arrows), thus exerting pressure on the surrounding tissue, for example the trabecular meshwork 21 and base of Schlemm's canal 22 in FIG. 19K. Suitable external stimuli include, but are not limited to, light energy, electromagnetic energy, heat, ultrasound, radio frequency, or laser energy.

In several other embodiments, the expandable material 100, is coated or layered on the outer shell 54, which expands in response to contact with a solvent. See FIGS. 19L-19Q. In some embodiments, once the implant is fully positioned within the desired intraocular space, contact with bodily fluid causes the expandable material to swell, solidify or gel, or otherwise expand. (Compare dimension D to $D_1$ in FIGS. 19L-19Q). As a result, the expanded material exerts pressure on the surrounding ocular tissue, which secures in the implant in position. In several embodiments, such expandable materials (or other retention mechanisms) are employed on implants adapted to be implanted into the punctum of a subject, as described in more detail herein.

In some embodiments, the expanding material fills any voids between the implant shell and the surrounding intraocular tissue. In some such embodiments, the expanded material seals one portion of the implant off fills or otherwise seals the volume around the implant outer shell such that fluid is prevented from flowing around the implant, and must flow through the implant.

In other embodiments, such as those schematically depicted in FIGS. 19P and 19Q, the expandable material 100 is positioned on selected areas of the implant shell 54, such that the expanded material exerts pressure on the surrounding ocular tissue, but also maintains the patency of a natural ocular fluid passageway by the creation of zones of fluid flow 102 around the implant shell and expandable material. In still other embodiments, the expandable material can be positioned within the lumen of the implant, such that the expansion of the material assists or causes the lumen to be maintained in a patent state.

The expandable material can be positioned on the implant by dipping, molding, coating, spraying, or other suitable process known in the art.

In some embodiments, the expandable material is a hydrogel or similar material. Hydrogel is a three-dimensional network of cross-linked, hydrophilic polymer chains. The hydrophilicity of the polymer chains causes the hydrogel to swell in the presence of sufficient quantities of fluid. In other embodiments, the expandable material is foam, collagen, or any other similar biocompatible material that swells, solidifies or gels, or otherwise expands. In some embodiments, the expandable material begins to expand immediately on contact with an appropriate solvent. In other embodiments, expansion occurs after passage of a short period of time, such that the implant can be fully positioned in the desired target site prior to expansion of the material. Preferred solvents that induce expansion include water, saline, ocular fluid, aqueous humor, or another biocompatible solvents that would not affect the structure or permeability characteristics of the outer shell.

Although FIGS. 19L and 19M depict the expandable material as rectangular in cross-section, it will be appreciated that the cross-sectional shape can vary and may include circular, oval, irregular, and other shapes in certain embodiments. The relative expansion (change from dimension D to $D_1$) of the material is also controlled in several embodiments. In certain embodiments the D to $D_1$ change is greater than in other embodiments, while in some embodiments, a smaller D to $D_1$ change is realized upon expansion of the material.

FIGS. 19P and 19Q show side views of an implant having expandable anchoring elements 100 comprising projections extending radially outward from the body of the implant. In some such embodiments, the anchoring elements are individually connected to the implant body, while in other embodiments, they are interconnected by a sheath region that mounts over the implant body.

In selected embodiments, the implant and/or the retention protrusion additionally includes a shunt feature. The term "stent" may also be used to refer to a shunt. In some embodiments, the shunt can be configured to provide a fluid flow path for draining aqueous humor from the anterior chamber of an eye to an outflow pathway to reduce intraocular pressure, for example, as in FIGS. 19R-19T. In still other embodiments, the shunt feature of the implant may be positioned in any physiological location that necessitates simultaneous drug delivery and transport of fluid from a first physiologic site to a second site (which may be physiologic or external to a patient).

At least one lumen can extend through the shunt portion of the implant. In some embodiments, there is at least one lumen that operates to conduct the fluid through the shunt portion of the implant. In certain embodiments, each lumen extends from an inflow end to an outflow end along a lumen axis. In some embodiments the lumen extends substantially through the longitudinal center of the shunt. In other embodiments, the lumen can be offset from the longitudinal center of the shunt.

As discussed above, in some embodiments, a compressed pellet of drug not coated by an outer shell 62 is attached or otherwise coupled to an implant comprising a shunt and a retention feature. As depicted in FIG. 19T, the shunt portion of the implant comprises one or more inflow portions 38k and one or more outflow portions 56k. In some embodiments, the inflow portions are positioned in a physiological space that is distinct from the outflow portions. In some embodiments, such a positioning allows for fluid transport from a first location to a second location. For example, in some embodiments, when deployed intraocularly, the inflow portions are located in the anterior chamber and the outflow portions are located in Schlemm's canal 22. In this manner, ocular fluid that accumulates in the anterior chamber is drained from the anterior chamber into Schlemm's canal, thereby reducing fluid pressure in the anterior chamber. In other embodiments, the outflow portion may be sized and configured to reside in the supraciliary region of the uveoscleral outflow pathway, the suprachoroidal space, other part of the eye, or within other physiological spaces amenable to fluid deposition.

Additional embodiments comprising a shunt may be used to drain ocular fluid from a first location to different location. As depicted in FIG. 19U, a shunt 30p directs aqueous from the anterior chamber 20 directly into a collector channel 29 which empties into aqueous veins. The shunt 30p has a distal end 160 that rests against the back wall of Schlemm's canal. A removable alignment pin 158 is utilized to align the shunt lumen 42p with the collector channel 29.

In some embodiments, the shunt 30p is inserted through a previously made incision in the trabecular meshwork 23. In other embodiments, the shunt 30p may be formed with blade configuration to provide self-trephining capability. In these cases, the incision through the trabecular meshwork 23 is made by the self-trephining shunt device which has a blade at its base or proximate to the base.

As shown in FIG. 19V, a shunt extending between an anterior chamber 20 of an eye, through the trabecular meshwork 23, and into Schlemm's canal 22 of an eye can be configured to be axisymmetric with respect to the flow of aqueous therethrough. FIG. 19W illustrates a modification of the shunt 229A, identified generally by the reference numeral 229B. In this embodiment, the shunt 229B includes a flange 237 extending radially from the portion 234. Preferably, the flange 237 is configured to retain the first portion 234 within the anterior chamber 20. It is to be recognized that although generally, aqueous will flow from the anterior chamber 20 towards Schlemm's canal 22, the shunt 229A, 229B or any of the above-described shunts as well as other shunts described below, can provide for omni-directional flow of aqueous.

Figure 19X:
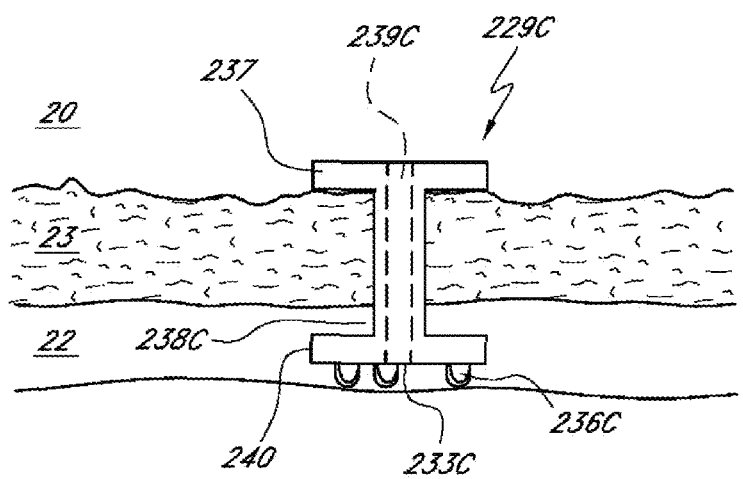

FIG. 19X illustrates another modification of the shunt 229A, identified generally by the reference numeral 229C. In this embodiment, the outer surface 238C is not conical. Rather, the outer surface 238C is cylindrical. The shunt 229C includes a flange 240 that can be the same size and shape as the flange 237. The legs 236C extend from the flange 240.

Figure 19Y:
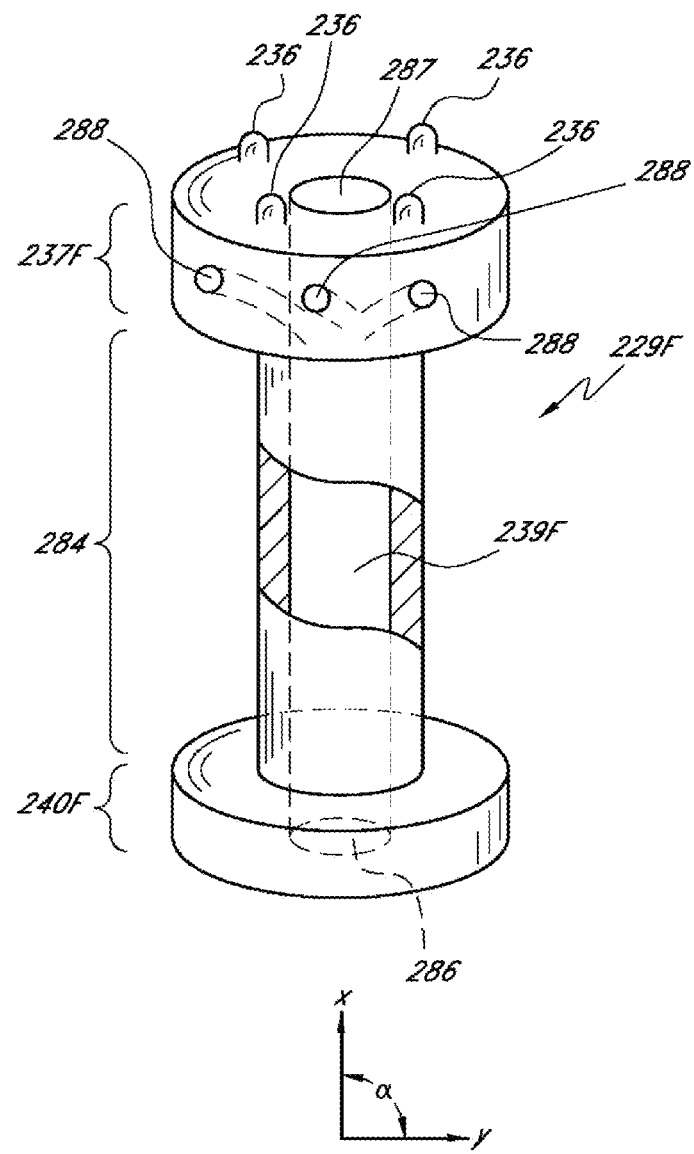

With reference to FIG. 19Y, another embodiment of an axisymmetric trabecular shunting device is illustrated therein and identified generally by the reference numeral 229F.

The shunt 229F comprises an inlet (proximal) section having a first flange 240F, an outlet (distal) section having a second flange 237F and a middle section 284 connecting the inlet section and the outlet section. A lumen 239F of the device 229F is configured to transport aqueous, liquid, or therapeutic agents between the inlet section and the outlet section.

A further advantage of such embodiments is provided where the outlet section 237F includes at least one opening 287, 288 suitably located for discharging substantially axisymmetrically the aqueous, liquid or therapeutic agents, wherein the opening 287, 288 is in fluid communication with the lumen 285 of the device 281. In the illustrated embodiment, the openings 288 extend radially from the lumen 285 and open at the outwardly facing surface around the periphery of the outlet flange 237F.

It should be understood that all such anchoring elements and retention protrusions may also be made flexible. It should also be understood that other suitable shapes can be used and that this list is not limiting. It should further be understood the devices may be flexible, even though several of the devices as illustrated in the Figures may not appear to be flexible. In those embodiments involving a rechargeable device, the retention protrusions not only serve to anchor the implant, but provide resistance to movement to allow the implant to have greater positional stability within the eye during recharging.

For the sake of clarity, only a small number of the possible embodiments of the implant have been shown with the various retention projections. It should be understood that any implant embodiment may be readily combined with any of the retention projections disclosed herein, and vice versa.

It will further be appreciated that, while several embodiments described above are shown, in some cases as being anchored within or to particular intraocular tissues, that each embodiment may be readily adapted to be anchored or deployed into or onto any of the target intraocular tissues disclosed herein or to other ocular tissues known in the art.

Additionally, while embodiments described both above and below include discussion of retention projections, it will be appreciated that several embodiments of the implants disclosed herein need not include a specific retention projection. Such embodiments are used to deliver drug to ocular targets which do not require a specific anchor point, and implants may simply be deployed to a desired intraocular space. Such targets include the vitreous humor, the ciliary muscle, ciliary tendons, the ciliary fibrous band, Schlemm's canal, the trabecular meshwork, the episcleral veins, the anterior chamber and the anterior chamber angle, the lens cortex, lens epithelium, and lens capsule, the ciliary processes, the posterior chamber, the choroid, and the suprachoroidal space. For example, in some embodiments, an implant according to several embodiments described herein is injected (via needle or other penetrating delivery device) through the sclera at a particular anatomical site (e.g., the pars plana) into the vitreous humor. Such embodiments need not be constructed with a retention protrusion, thus it will be appreciated that in certain embodiments, the use of a retention protrusion is optional for a particular target tissue.

Some embodiments disclosed herein are dimensioned to be wholly contained within the eye of the subject, the dimensions of which can be obtained on a subject to subject basis by standard ophthalmologic techniques. Upon completion of the implantation procedure, in several embodiments, the proximal end of the device may be positioned in or near the anterior chamber of the eye. The distal end of the implant may be positioned anywhere within the suprachoroidal space. In some embodiments, the distal end of the implant is near the limbus. In other embodiments, the distal end of the implant is positioned near the macula in the posterior region of the eye. In other embodiments, the proximal end of the device may be positioned in or near other regions of the eye. In some such embodiments, the distal end of the device may also be positioned in or near other regions of the eye. As used herein, the term "near" is used at times to as synonymous with "at," while other uses contextually indicate a distance sufficiently adjacent to allow a drug to diffuse from the implant to the target tissue. In still other embodiments, implants are dimensioned to span a distance between a first non-ocular physiologic space and a second non-ocular physiologic space.

In one embodiment, the drug delivery implant is positioned in the suprachoroidal space by advancement through the ciliary attachment tissue, which lies to the posterior of the scleral spur. The ciliary attachment tissue is typically fibrous or porous, and relatively easy to pierce, cut, or separate from the scleral spur with the delivery instruments disclosed herein, or other surgical devices. In such embodiments, the implant is advanced through this tissue and lies adjacent to or abuts the sclera once the implant extends into the uveoscleral outflow pathway. The implant is advanced within the uveoscleral outflow pathway along the interior wall of the sclera until the desired implantation site within the posterior portion of the uveoscleral outflow pathway is reached.

In some embodiments the total length of the implant is between 1 and 30 mm in length. In some embodiments, the implant length is between 2 and 25 mm, between 6 and 25 mm, between 8 and 25 mm, between 10 and 30 mm, between 15 and 25 mm or between 15 and 18 mm. In some embodiments the length of the implant is about 8, 9, 10, 11, 12, 13, 14, 15, 16, 17, 18, 19, 20, 21, 22, 23, 24, or 25 mm so that that the delivery device containing an implant can be inserted and advanced through the cornea to the iris and produce only a self-sealing puncture in the cornea, in some embodiments, the outer diameter of the implants are between about 100 and 600 microns. In some embodiments, the implant diameter is between about 150-500 microns, between about 125-550 microns, or about 175-475 microns. In some embodiments the diameter of the implant is about 100, 125, 150, 160, 170, 180, 190, 200, 225, 250, 275, 300, 325, 350, 375, 400, 425, 450, 460, 470, 475, 480, 490, or 500 microns. In some embodiments, the inner diameter of the implant is from about between 50-500 microns. In some embodiments, the inner diameter is between about 100-450 microns, 150-500 microns, or 75-475 microns. In some embodiments, the inner diameter is about 80, 90, 100, 110, 125, 150, 175, 200, 225, 250, 275, 300, 325, 350, 375, 400, 410, 420, 425, 430, 440, or 450 microns. In some embodiments, including but not limited to those in which the device is disc or wafer-shaped, the thickness is from about 25 to 250 microns, including about 50 to 200 microns, about 100 to 150 microns, about 25 to 100 microns, and about 100 to 250 microns. In several embodiments configured for implantation into the punctum, the implant ranges between about 0.5 and about 2.5 mm long (e.g., from the proximal end to the distal end). The length of the implant, in some embodiments, ranges from about 0.5 mm to about 0.7 mm, about 0.7 mm to about 0.9 mm, about 0.9 mm to about 1.0 mm, about 1.0 mm to about 1.1 mm, about 1.1 mm to about 1.2 mm, about 1.2 mm to about 1.3 mm, about 1.3 mm to about 1.35 mm, about 1.35 mm to about 1.4 mm, about 1.4 mm to about 1.45 mm, about 1.45 mm to about 1.5 mm, about 1.5 mm to about 1.55 mm, about 1.55 mm to about 1.6 mm, about 1.6 mm to about 1.65 mm, about 1.65 mm to about 1.7 mm, about 1.7 mm to about 1.9 mm, about 1.9 mm to about 2.1 mm, about 2.1 mm to about 2.3 mm, about 2.3 mm to about 2.5 mm, or lengths in between these ranges. In several embodiments, implants configured for implantation into the punctum have a diameter between about 0.2 mm and 2.0 mm, including about 0.2 mm to about 0.3 mm, about 0.3 mm to about 0.4 mm, about 0.4 mm to about 0.5 mm, about 0.5 mm to about 0.6 mm, about 0.5 mm to about 0.6 mm, about 0.6 mm to about 0.7 mm, about 0.7 mm to about 0.8 mm, about 0.8 mm to about 0.9 mm, about 0.9 mm to about 1.0 mm, about 1.0 mm to about 1.1 mm, about 1.1 mm to about 1.2 mm, about 1.2 mm to about 1.3 mm, about 1.3 mm to about 1.4 mm, about 1.4 mm to about 1.5 mm, about 1.5 mm to about 1.6 mm, about 1.6 mm to about 1.7 mm, about 1.7 mm to about 1.8 mm, about 1.8 mm to about 1.9 mm, about 1.9 mm to about 2.0 mm and diameters in between these ranges.

In further embodiments, any or all of the interior lumens formed during the manufacture of the implants may be coated with a layer of hydrophilic material, thereby increasing the rate of contact of ocular fluid with the therapeutic agent or agents positioned within the lumen. In one embodiment, the hydrophilic material is permeable to ocular fluid and/or the drug. Conversely, any or all of the interior lumens may be coated with a layer of hydrophobic material, to coordinately reduce the contact of ocular fluid with the therapeutic agent or agents positioned within the lumen. In one embodiment, the hydrophobic material is permeable to ocular fluid and/or the drug.

Figure 20A:
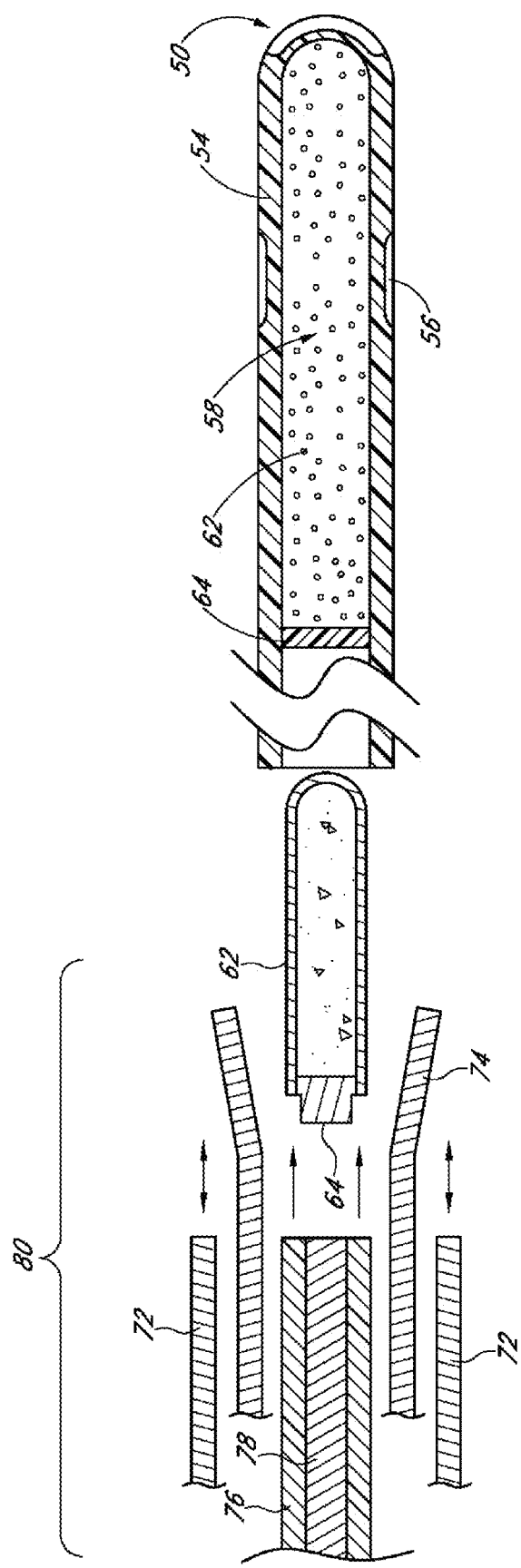
Figure 20B:
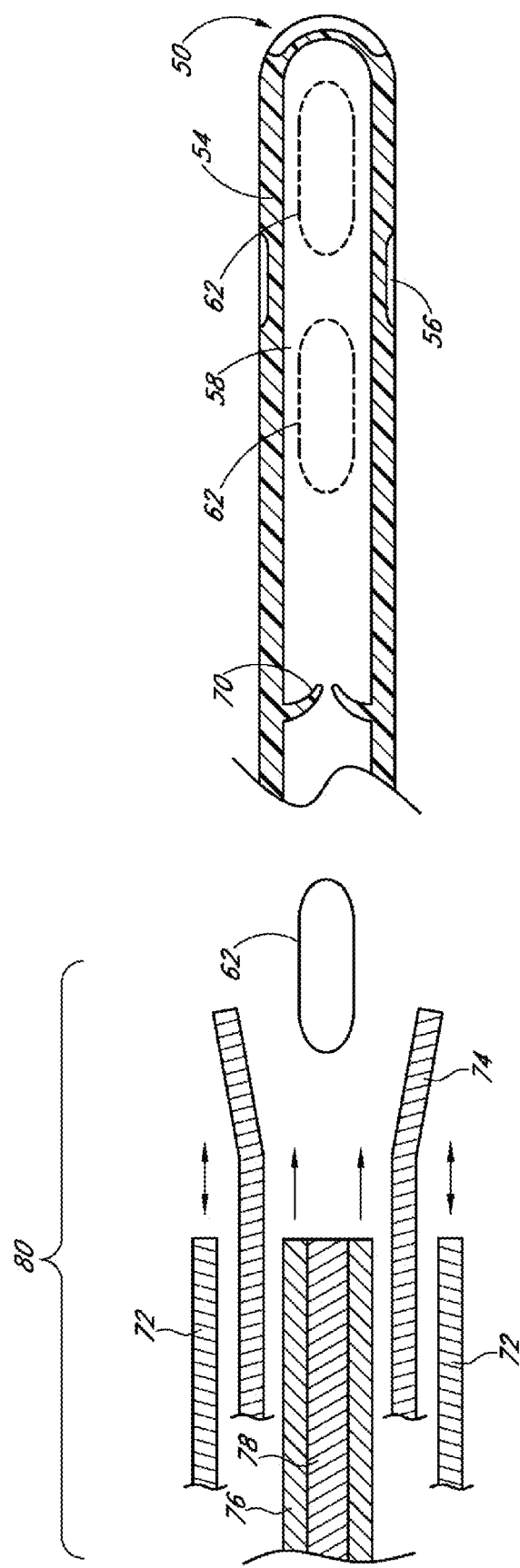

Selected embodiments of the drug delivery implants described herein allow for recharging of the implant, i.e. refilling the implant with additional (same or different) therapeutic agent. In the embodiments shown in FIGS. 20A-20C, the proximal end 52 of the implant is open and interacts with a recharging device 80. The recharging device 80 comprises a clamping sleeve 72 that houses flexible clamping grippers 74 that interacts with the proximal end 52 of the implant. A flexible pusher tube 76 that may be spring loaded contains a small internal recess 78 that holds the new therapeutic agent 62 for delivery to the implant lumen 58. In FIG. 20A, a new dose of agent, coated in a shell and capped with proximal barrier is inserted into the lumen of the implant. FIGS. 20B and 20C depict recharging the implant with multiple drug pellets. As schematically shown in FIGS. 20D and 20E, elongate implants can comprise a plurality of the features disclosed herein. For example, FIG. 20D depicts an elongate implant with a proximal 52 and distal end 50, containing a plurality of pellets of therapeutic agent 62. As discussed in more detail herein, the therapeutic agent, depending on the embodiment, may be in a variety of forms, such as pellets, micropellets, vesicles, micelles, or other membrane-like bound structures, oils, emulsions, gels, slurries, etc. The implant comprises a region of drug release 56. Moreover, the embodiments depicted in FIGS. 20D and 20E comprise fluid inflow 38k and outflow 56k pathways, thus allowing the combination of delivery of a therapeutic agent as well as directing fluid to an ocular fluid outflow pathway (e.g., Schlemm's canal).

Figure 20F:
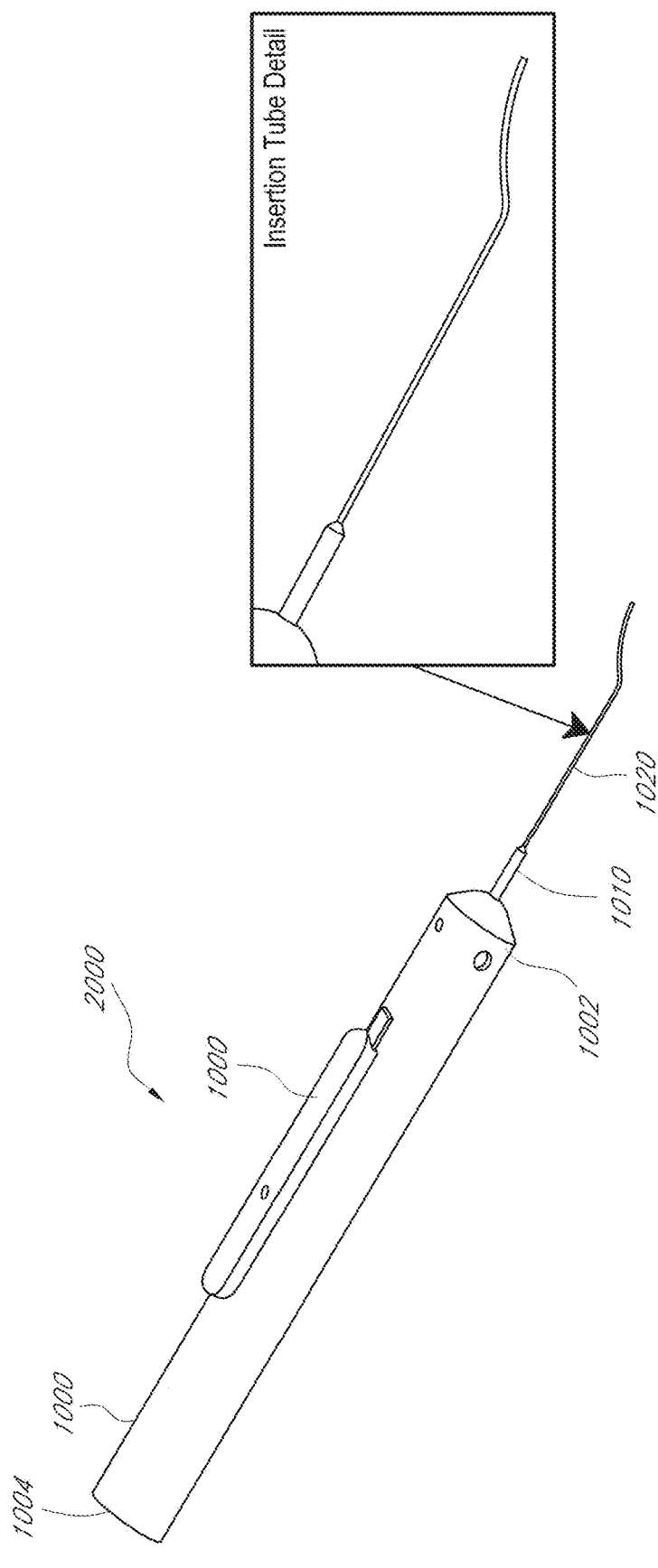
FIG. 20F illustrates one embodiment of a delivery device in accordance with embodiments disclosed herein.
Figure 20G:
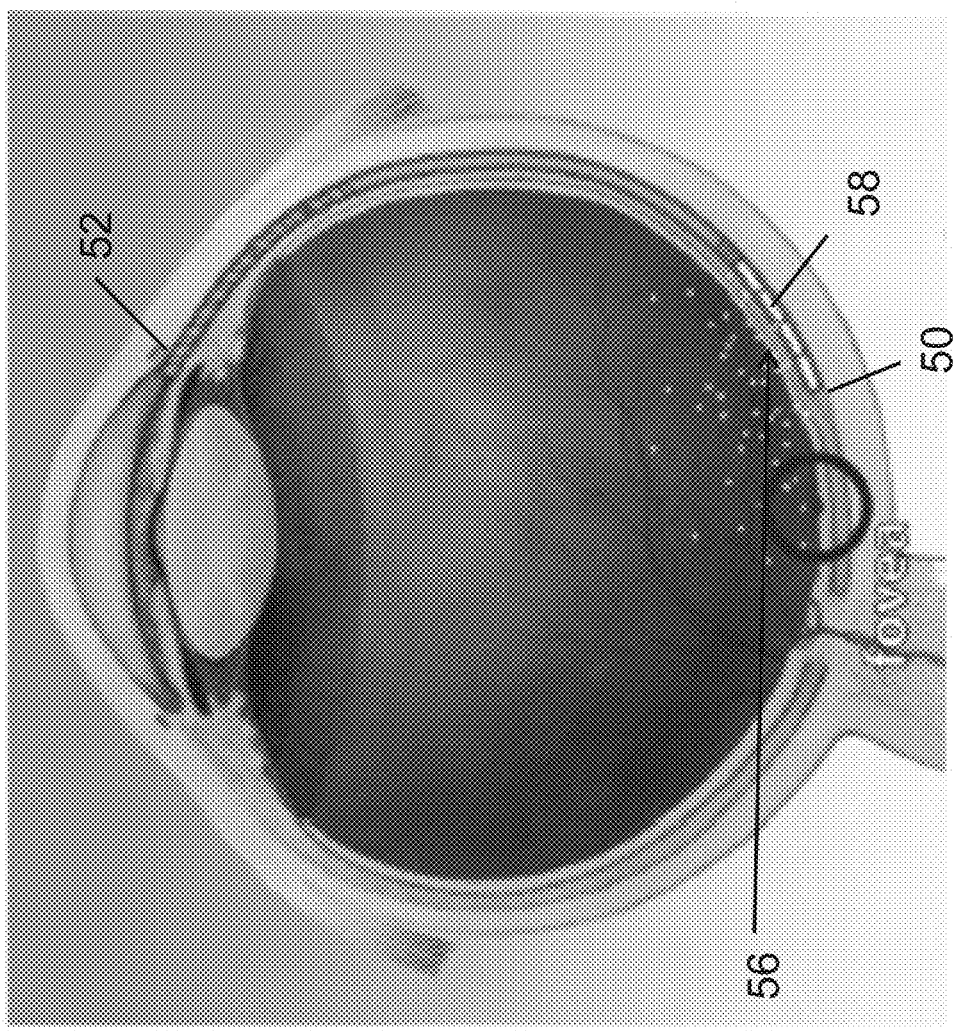

FIG. 20G schematically depicts an eye with one embodiment of an elongate implant positioned in accordance with several embodiments disclosed herein. As shown the proximal end of the implant 52 resides near the anterior portion of the eye, while the distal end of the implant 50 resides in a more posterior position. The implant can be implanted in the suprachoroidal space, in one embodiment, and positioned such that the region of drug release 56 allows the therapeutic agent 58 to elute from the implant in a posterior region of the eye. While not expressly depicted here, it shall be appreciated that the implant may, optionally, include the fluid inflow and outflow pathway described herein.

FIG. 20H depicts an additional configuration that is used in several embodiments. For example, in one embodiment the implant is positioned (e.g., via use of a custom inserter 1000) in the eye with the distal end 50 in a posterior portion of the eye and the proximal end 52 in a more anterior region. The implant depicted, and described in more detail elsewhere herein, comprises a plurality of regions of drug release, indicated as 56 and 56a, and a plurality of types of therapeutic agent, namely 58 and 58a in FIG. 20H. Several embodiments of such an implant are used when, for example, it is beneficial to provide a loading or bolus dose of a therapeutic agent (58a) for acute or relatively short term effects (perhaps, for example to reduce inflammation or risk of infection). Thereafter, a more long term formulation of the therapeutic agent (e.g., a pellet; 58) provides controlled drug release for a period of time beyond the acute effect. In several embodiments, such a configuration reduces complications with insertion of the device and reduces the time from insertion to reduction in one or more symptoms associated with the disease or disorder being treated.

Figure 20I:
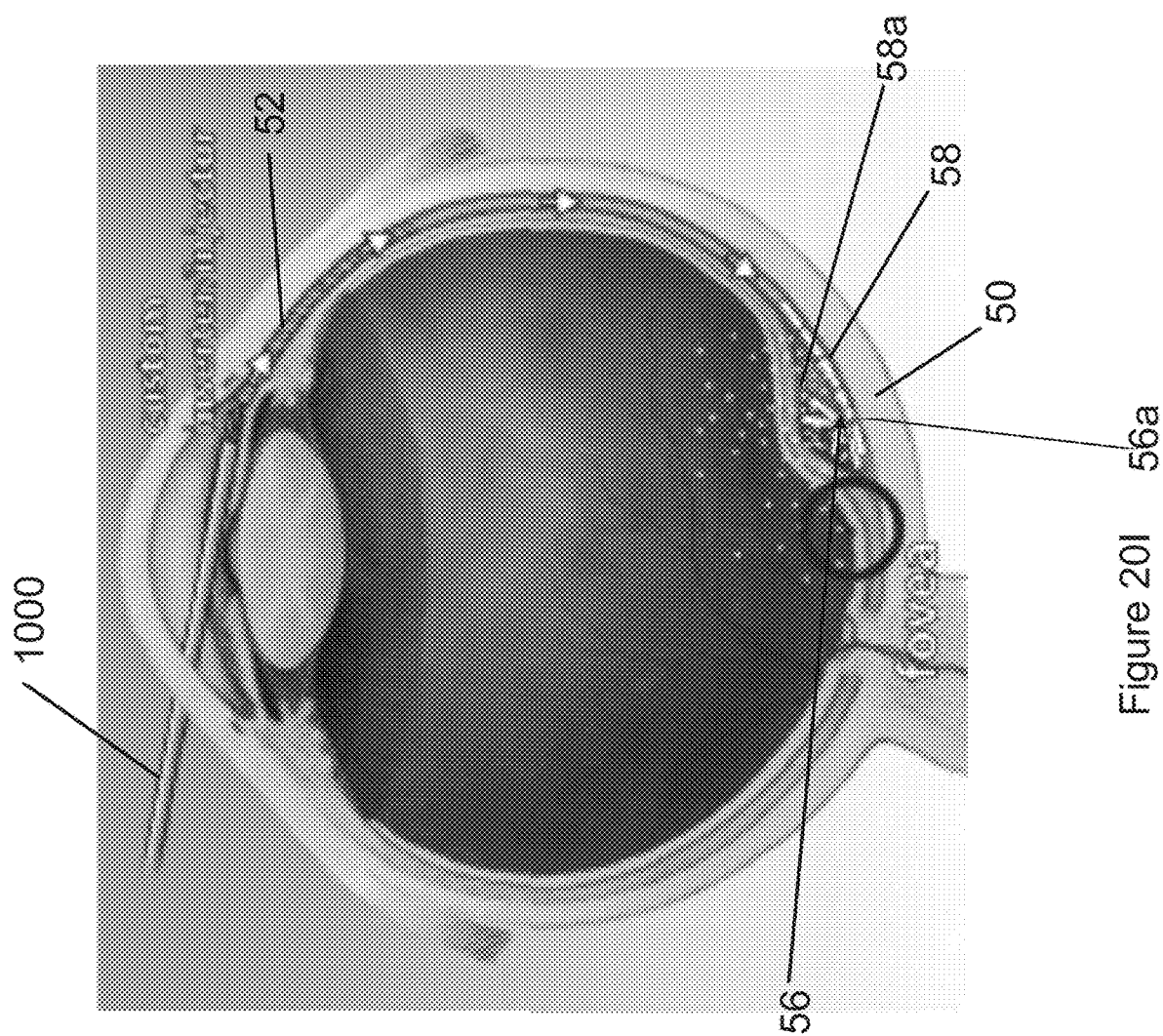
Figure 20J:
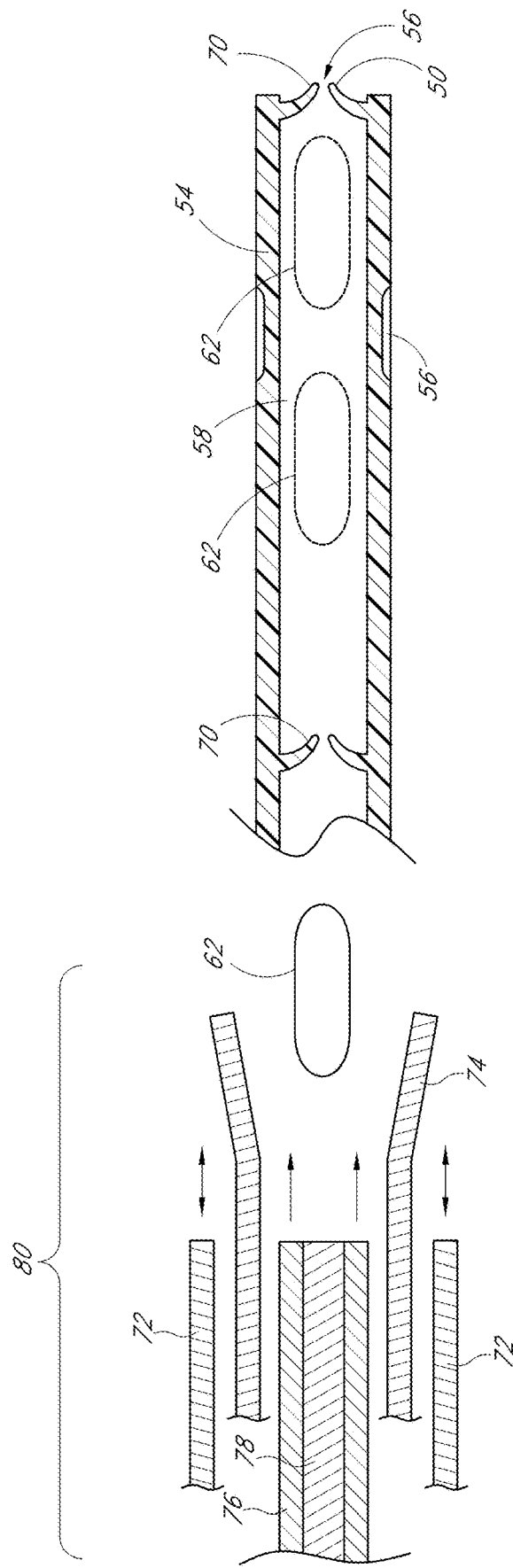
FIG. 20J illustrates an additional feature of the distal portion of certain drug delivery devices in accordance with embodiments disclosed herein.

FIG. 20I depicts yet another embodiment of an elongate device with an alternative drug elution strategy. Again the implant is positioned with the distal portion 50 in the posterior region of the eye. In the depicted embodiment, the regions of drug release 56 and 56a are positioned at or near the very distal end of the implant. The distal end is configured such that pellets of therapeutic agent 58, and or therapeutic agent in a different form (e.g., micropellets, vesicles, gel) or a different therapeutic agent (e.g., one that reduces or prevents a side effect due to the first therapeutic agent) are capable of being flushed out of the distal end of the implant. One schematic of such an implant is shown in FIG. 20J, wherein the distal end of the implant 50 comprises a region of drug release 56 that is generated by virtue of a one-way valve 70. In several embodiments, the valve comprises two or more flaps 70, open at the proximal end and reversibly closed at the distal end. The pressure provided on the proximal portion of the flaps induces the flaps to open and the drugs 58 and 58a are expelled (partially or completely) from the implant. In several embodiments, the flaps return to their closed (or substantially closed) position such that a seal is created to prevent backflow of ocular fluid (which may include expelled therapeutic agent) into the implant. In other embodiments, however, a fluid-tight seal is not formed. Other flap or sealing mechanisms are used, depending on the embodiment.

Such embodiments, are used, in several embodiments, during an initial implantation surgery. In such cases, flushing out the therapeutic agents 58 allows the agent 58 to be to fully exposed to the intraocular environment, which may hasten the therapeutic effects of the agent. Additionally, with the initial therapeutic agent 58 flushed out of the implant, the distal portion of the implant is open (e.g.,. not blocked with agent) for the delivery of a second therapeutic agent 58a. The flushing of the initial agent 58 from the device helps to ensure that the second agent (which, again, may reduce or prevent a side effect of the first agent) reaches the desired anatomical target tissue. If the device were not flushed and still contained the therapeutic agent 58, the second agent 58a would either have to move around the first agent within the implant or be eluted/flushed from the implant through side ports (which are more proximal, and thus farther from the posterior target tissue). Either approach may result in the second agent 58a failing to reach (at least in therapeutically effective concentrations) the desired target in the posterior region of the eye.

In additional embodiments, devices that are configured to allow flushing of their therapeutic drug contents out the distal end of the device are useful when assessing the efficacy and/or functionality of the device post-implantation. At such a time, it may be advantageous to be able to deliver a second agent (perhaps to ameliorate side effects) or a different concentration of an agent. This can thus be accomplished by flushing the implant with the second agent or a new concentration of a first agent.

In several embodiments, the agents 58a that are delivered secondarily and/or in conjunction with a flush of the first therapeutic agent 58 are in a fluid, semi-fluid, or fluid-like form. In several embodiments, microparticles that behave like a fluid (e.g., they have liquid-like flow properties) are used. In some embodiments, the secondary agent 58a is configured to have its own desired elution profile. In such cases, the secondary agent 58a is optionally housed or contained within a structure that allows for controlled release. In several embodiments, this comprises admixing the therapeutic agent with one or more polymers (e.g., creating a "matrix) that allows release of the therapeutic agent from the admixture with a known rate of elution. In several embodiments, the one or more polymers are selected such that they are readily intercovertible between a liquid or semi-liquid state and a solid or semi-solid state. In several embodiments, the interconversion is due to externally applied stimuli (e.g., radio frequency, light, etc.). In several embodiments, the interconversion is temperature or pressure induced. For example, in several embodiments, the polymers are liquid or semi-liquid at room temperature, but upon exposure to increased temperatures (e.g., physiological temperatures) become solid or semi-solid. In such a manner, the polymer matrix can be used to hold the therapeutic agent at a desired target site, thereby improving the accuracy of delivery and reduction of wash-out due to ocular fluid flow. In several embodiments, optionally, the polymers are biodegradable (such that repeated administration does not result in build-up of polymer at the delivery site). In several embodiments, the polymers are mixtures of polymers that are configured to mimic a membrane bound structure (e.g., a micelle or vesicle). In several such embodiments, the drug is intermixed with those polymers such that it is incorporated into the micelle or vesicle, and (based on the known characteristics of the polymers) elutes at a certain rate. Similarly, such micelles or vesicles are optionally mixed with a polymeric matrix that is readily intercovertible between a liquid or semi-liquid state and a solid or semi-solid state.

Figure 35A:
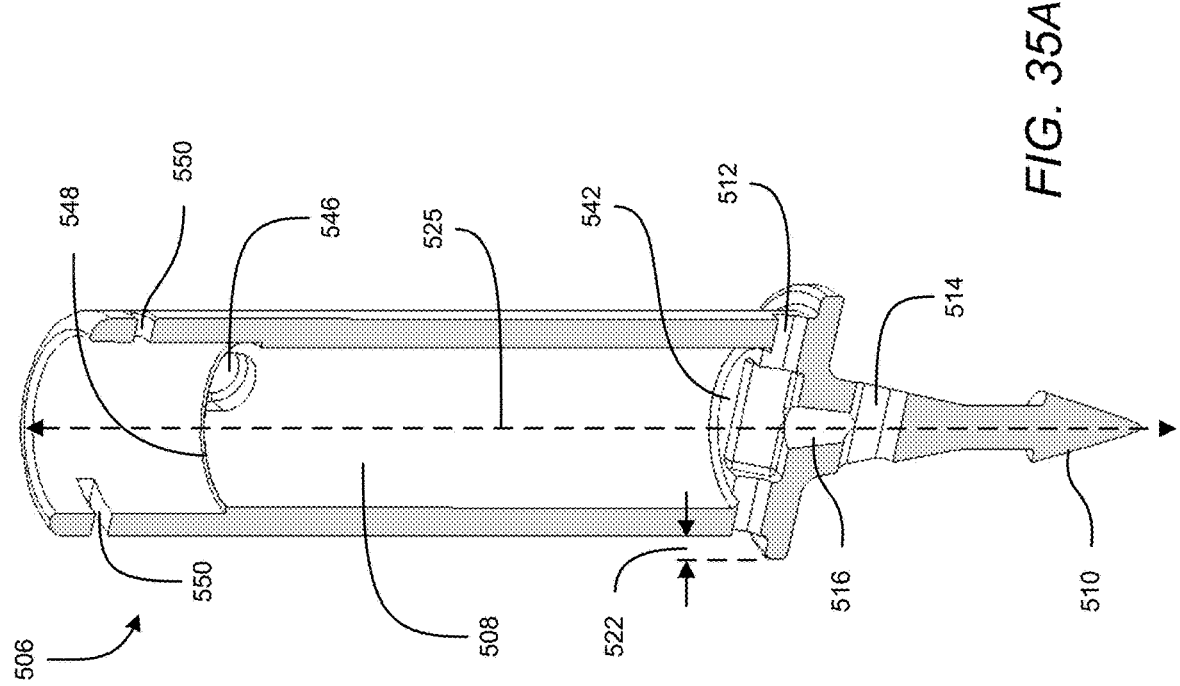
FIG. 35A is a cross-sectional perspective view of an outer shell of the implant of FIG. 32.

FIG. 32 shows a distal perspective view of an example embodiment of a drug delivery ocular implant 500. FIG. 33 shows a proximal perspective view of the implant 500. FIG. 34 shows a side view of the implant 500. The implant 500 can include various features as described in connection with FIGS. 18R-18U, as well as features described in connection with other embodiments disclosed herein. The implant 500 can have a distal end 502 and a proximal end 504. The implant can include an outer shell 506, which can define an interior chamber 508 (e.g., an interior lumen) for holding a drug, as described herein. FIG. 35A shows a cross-sectional perspective view of an example embodiment of a shell 506 for the implant 500. The interior chamber 508 can be generally cylindrical in shape, although other cross-sectional shapes (e.g., square, rectangular, oval, polygonal) can be used. The implant 500 can have a total longitudinal length of less than or equal to about 5 mm, less than or equal to about 3 mm, less than or equal to about 2 mm, less than or equal to about 1.75 mm, less than or equal to about 1.5 mm, less than or equal to about 1.25 mm, less than or equal to about 1.0 mm, at least about 0.5 mm, at least about 0.75 mm, at least about 1.0 mm, at least about 1.25 mm, at least about 1.5 mm, at least about 1.75 mm, and/or at least about 2.0 mm, although the implant 500 may have a length outside of these ranges, in some embodiments. The total longitudinal length of the implant 500 can be between about 1.0 mm and about 2.5 mm, between about 1.5 mm and about 2.0 mm, or between about 1.7 mm and about 1.9 mm.

The implant 500 can include an anchor mechanism 510 (e.g., a retention protrusion) configured to anchor the implant 500 to ocular tissue as described herein (e.g., at or near the trabecular meshwork 23). The anchor mechanism 510 can include a barbed end portion to facilitate retention of the implant 500 after implantation, although various other retention mechanisms can be used, as described herein. For example, the anchor mechanism 510 can include ribs, expandable material, threading, etc. In some embodiments, the anchor mechanism 510 can include a tissue ingress orifice (see orifice 401 in FIG. 18R), which can be configured such that ocular tissue (e.g., scleral tissue) can fill the orifice upon implantation to facilitate retention of the implant. By way of example, the retention protrusion can pass through the trabecular meshwork, through Schlemm's canal, and into the sclera. The barbed end portion can be a scleral anchor.

In some embodiments, the implant 500 can be configured to facilitate drainage of fluid from the anterior chamber 20 of the eye, as discussed herein. The implant 500 can include one or more inlets (e.g., inflow pathway 512), which can be positioned in the anterior chamber 20 upon implantation, and one or more outlets (e.g., outflow pathway 514), which can be positioned in a physiological outflow space, such as Schlemm's canal 22, upon implantation. In some embodiments, the inflow pathway 512 can extend through the implant 500 (e.g., laterally) and can include two inlets positioned on generally opposing sides of the implant 500. Similarly, in some embodiments, the outflow pathway 514 can extend through the implant 500 (e.g., laterally) and can include two outlets positioned on generally opposing sides of the implant 500. As can be seen in FIG. 35, a pathway 516 can extend (e.g., longitudinally) between the inflow pathway 512 and the outflow pathway 514 to provide fluid communication between the inlet(s) and the outlet(s). The outflow pathway 514 can be on the retention protrusion 510 at a location that is configured to position the outflow pathway 514 in Schlemm's canal 22 upon implantation. In some embodiments, the outflow pathway 514 can be elongate in the longitudinal direction to compensate for small differences in the anatomy of different patients and for different implant techniques, to thereby facilitate reliable placement of at least part of the outflow pathway 514 into Schlemm's canal 22. In some embodiments, the inflow pathway 512 can be spaced (e.g., longitudinally) from the outflow pathway 514 by a distance 513. The distance 513 can be less than or equal to about 1.0 mm, less than or equal to about 0.5 mm, less than or equal to about 0.2 mm, less than or equal to about 0.1 mm, less than or equal to about 0.075 mm, less than or equal to about 0.05 mm, at least about 0.025 mm, at least about 0.05 mm, at least about 0.075 mm, at least about 0.1 mm, at least about 0.2 mm, and/or at least about 0.5 mm, although values outside these ranges may also be used in some embodiments. The distance 513 can be between about 0.05 mm and about 0.15 mm or between about 0.075 mm and about 0.125 mm.

Figure 35B:
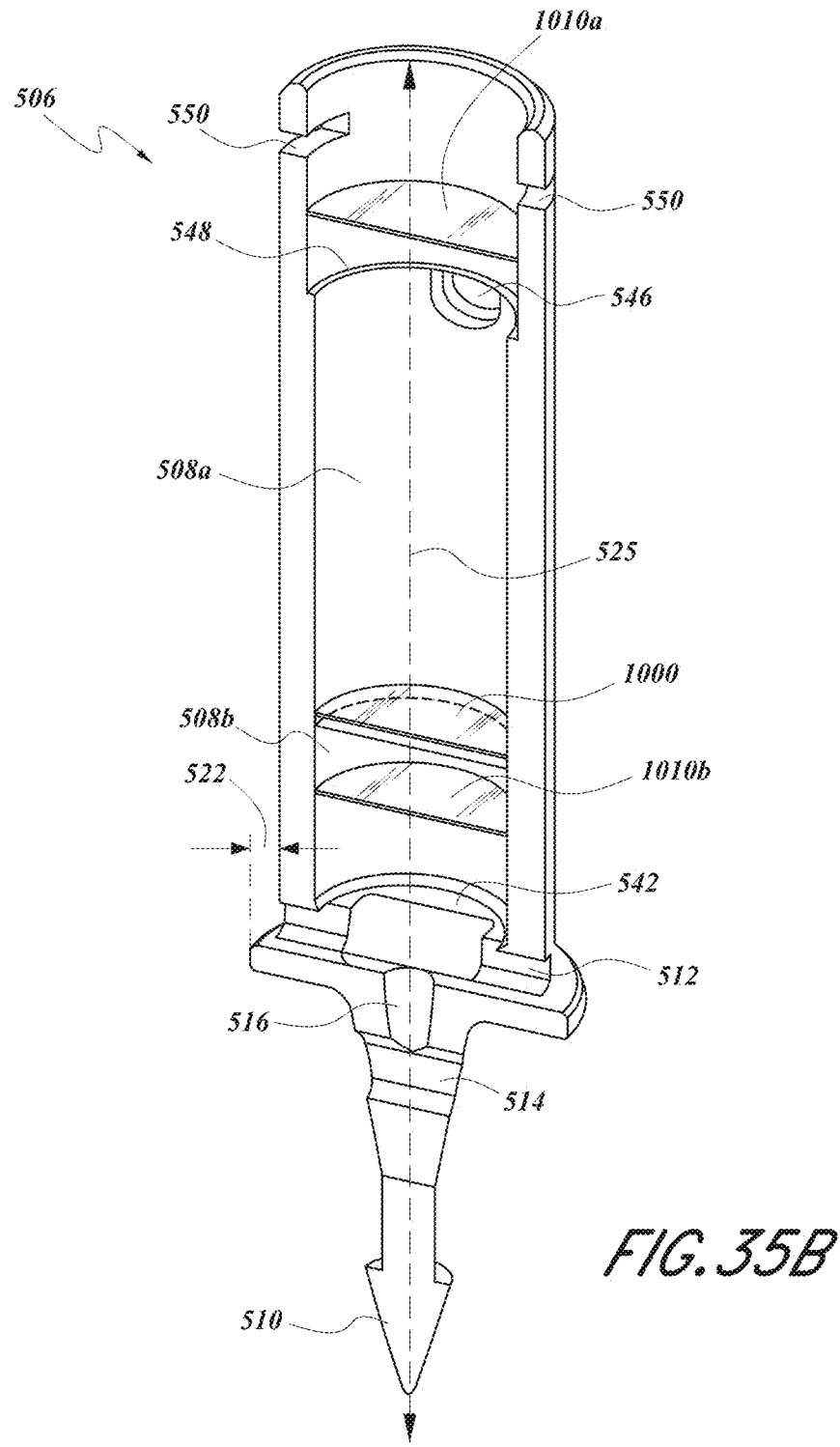
FIG. 35B is a schematic view of an implant that releases two agents from the implant, according to several embodiments.

Many variations are possible. For example, in some embodiments, the implant 500 can include a single inlet and a single outlet. In some embodiments, a single, curved, and/or U-shaped fluid channel can connect an inlet to an outlet to provide a drainage fluid pathway through the implant 500. The one or more inlets and the one or more outlets can be positioned at locations other than those shown in illustrated examples, depending on the desired location of implantation and/or the desired source and destination of the drained fluid. FIG. 35B depicts one such embodiment. FIG. 35B depicts a schematic of an implant wherein the internal lumen is separated by an impermeable barrier 1000 which divides the internal lumen of the implant into two portions, a proximal portion 508a, and a distal portion 508b. As discussed above, implants configured in this manner are able to concurrently deliver a first therapeutic agent to a first region of the eye and a second therapeutic agent to a second region of the eye. In particular embodiments, the first region of the eye is the anterior chamber. In additional particular embodiments, the second region of the eye is a physiological outflow pathway. In some such embodiments, the physiological outflow pathway is the trabecular meshwork or Schlemm's canal. As shown in FIG. 35B, implants allowing for bidirectional elution of drug also comprise two membranes 1010a and 1010b. These membranes regulate the elution of the first and second drug from their respective compartments. Fluid flow into the implant by a an inflow pathway 512 allows ocular fluid to enter the implant and flow into juxtaposition with the more distal drug elution membrane 1010b, thereby allowing drug within the more distal compartment 508b to cross the membrane 1010b and exit the implant via a fluid outflow pathway 514. In this manner the drug positioned in the more distal compartment 508b can advantageously be used to create an effect on the tissue of the outflow pathway. For example, a vasodilator compounds eluting from the more distal chamber can advantageously increase blood and/or fluid flow in and around the physiological outflow pathway. In some embodiments, a vasodilator such as nitric oxide, or a nitric oxide precursor is loaded into the more distal compartment 508b. In some embodiments, a vasodilator is used in conjunction with a prostaglandin analog in the more proximal compartment 508a.

In some embodiments, the position of the inflow pathway 512 along the long axis of the implant body can be varied such that the amount of fluid that comes in contact with the more distal drug elution membrane 1010b can be greater or lesser, depending on the particular drug to be eluted. The more distal drug elution membrane can be positioned at the lower (e.g., distal portion) of the implant body, or anywhere distal of the impermeable barrier in a position where in the membrane is able to be exposed to ocular fluid entering the fluid inlet. Similarly, the position of the impermeable barrier 1000 can be varied from embodiment to embodiment depending on what percentage of the interior volume of the implant is to be dedicated to the more proximal internal chamber 508A versus the more distal internal chamber 508B. In several embodiments, the chambers are equal in size, while in other embodiments the ratio of the proximal chamber volume to the distal chamber volume ranges from about 1:10 to about 10:1.

Figure 35C:
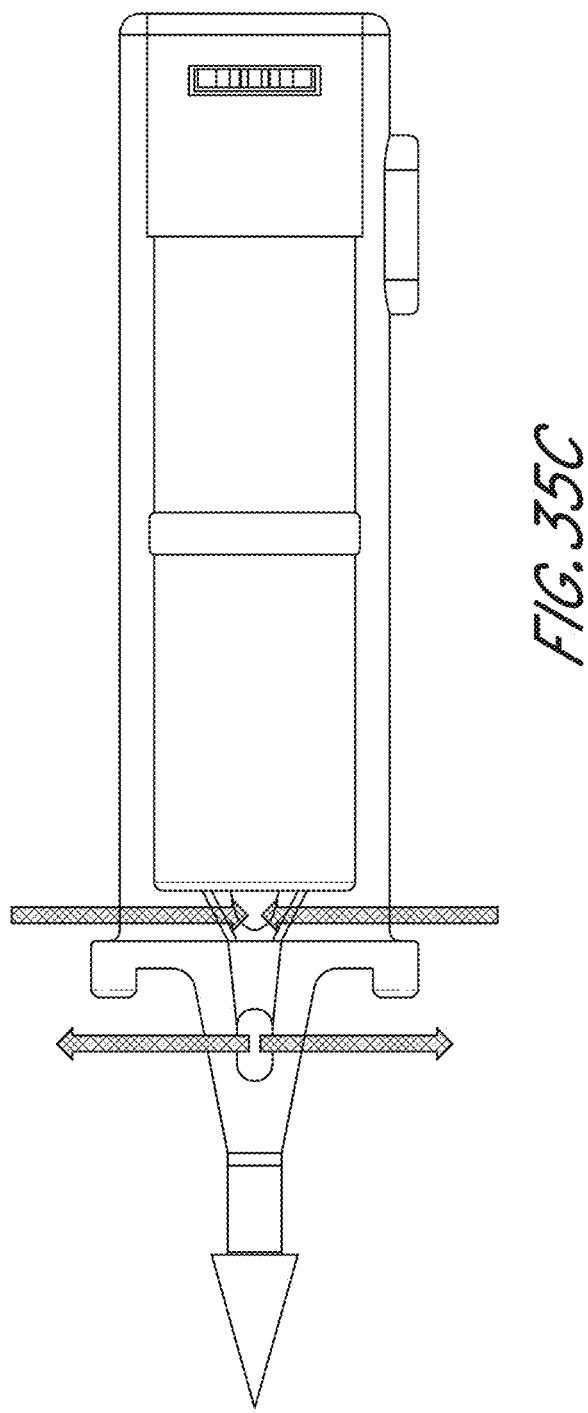
FIG. 35C is an additional schematic view of an implant, according to several embodiments.

In additional embodiments, the implant is optionally configured without a proximal membrane, and comprises only a distal drug eluting membrane. In some such embodiments, the proximal end of the implant is capped or otherwise closed, and the entire (or at least a portion of) the interior lumen is filled with a vasodilator agent (or other agent). In such embodiments, the implant elutes only from the distal portion, e.g., through the fluid outflow pathway and into a physiologic outflow pathway. Thus, depending on the embodiment, implants disclosed herein can elute from the proximal region only, the proximal and the distal regions, or the distal region only. In addition, in some embodiments, one, two, three or more implants are implanted, with the implants being any combination of proximal, distal or proximal+distal elution configurations. FIG. 35C summarizes these various optional configurations schematically in a single implant. For example, in one embodiment, an proximally eluting implant can be anchored in a target tissue in conjunction with a distally eluting implant positioned nearby. In several embodiments this provides the advantage of a single implantation procedure to deliver to the eye two (or more) eluting implants, each of which can be maximized in terms of its drug payload. In several embodiments, the implants are spaced apart a certain distance apart from one another, typically less than 1 mm apart. In additional embodiments a first implant is spaced apart from the second implant by about 0.1 mm, by about 0.2 mm, by about 0.3 mm, by about 0.4 mm, by about 0.5 mm, by about 0.6 mm, by about 0.7 mm, by about 0.8 mm, by about 0.9 mm, or any amount of spacing within those spaces listed including endpoints. In certain embodiments, it is preferable to place for five or six implants in a single surgical procedure within a target region of the eye. In some embodiments, the implants are positioned in a roughly linear pattern with respect to one another, however in other embodiments the implants are positioned randomly or optionally in a nonlinear pattern, depending on the circumstances surrounding a particular subject's ocular anatomy.

In several embodiments, the inflow and/or outflow pathways comprise a mechanism to direct fluid flow, e.g., prevent backflow. In several embodiments a one way valve is used. In several embodiments, the inflow-outflow pathways are unitary (e.g., a single inflow pathway passes by the more distal drug elution membrane and then communicates with a single outflow pathway). Such embodiments reduce and/or eliminate the elution of the second drug to the first ocular tissue (e.g., nitric oxide is not delivered to the anterior chamber, rather it all, or substantially all, elutes to the outflow pathway)

In some embodiments, the first drug comprises a prostaglandin analog. In several embodiments the prostaglandin analog is selected from the group consisting of bimatoprost, latanoprost, travoprost and unoprostone. In several embodiments, the prostaglandin analog is positioned within the more proximally positioned interior chamber of an implant having two chambers and thus, the prostaglandin analog is positioned such that it elutes from the implant into the anterior chamber of the eye. In several embodiments, the second drug positioned within the second interior chamber comprises a vasodilator. Vasodilator compounds that are released from the implant, in several embodiments, act on the trabecular meshwork, and its integrated vasculature, to increase blood flow in and around the trabecular meshwork. In some embodiments, this increased blood flow facilitates passage of ocular fluid through the trabecular meshwork and into a physiological fluid outflow pathway. Suitable vasodilators include, but are not limited to, endothelium derived hyperpolarizing factor (EDHF), cyclic GMP-dependent protein kinase, nitric oxide, epinephrine, histamine, prostacyclin, endothelin, prostaglandin D2, prostaglandin E2, vasoactive intestinal peptide (VIP), adenosine, L-arginine, bradykinin, substance P, niacin, platelet activating factor, or precursors or derivatives of any of the agent listed above. In particular embodiments, nitric oxide, or precursor or derivatives thereof, is released from the implant. In several embodiments, a multicomponent composition suitable for generating nitric oxide in vivo is positioned within the second chamber of an implant. For example, one or more of the enzymes that functions to convert L-arginine to nitric oxide as well as L-arginine can be positioned within the second chamber of an implant. Thus, nitric oxide can be generated in vivo, close to its site of action, which in some embodiments addresses the relatively short half-life of nitric oxide. In several embodiments endothelial nitric oxide synthase, neuronal nitric oxide synthase, and/or inducible nitric oxide synthase positioned within the implant, along with L-arginine. In alternative embodiments the implant can house L-arginine as the second therapeutic agent and the natives enzymes responsible for converting L-arginine to nitric oxide within the eye are leveraged to generate nitric oxide as the L-arginine is eluted from the implant. In several embodiments, S-nitroso-N-acetylpenicillamine (SNAP), hydroxylamine, and/or sodium nitroprusside can be positioned within the implant to generate nitric oxide. Additionally, in several embodiments, supplemental compounds can be included in the implant that facilitates the production of additional nitric oxide, for example, by regeneration of L-arginine (thereby allowing further production of nitric oxide by conversion of the regenerated L-arginine).

The implant 500 can include one or more standoffs 518 to prevent the implant from compressing Schlemm's canal 22 (or other physiological outflow space). The standoffs 518 can extend distally and can be spaced laterally away from the retention protrusion 510. Force applied to the implant 500 in the distal direction (e.g., force from pressing on the implant 500 distally during implantation and/or the distal force from the retention protrusion holding the implant 500 in place) can cause the one or more standoff 518 to press against ocular tissue (e.g., at or near the trabecular meshwork 23) at one or more locations that are spaced away from the outflow space (e.g., Schlemm's canal 22). Accordingly, the standoffs 518 can facilitate sufficiently firm placement of the implant 500 while preventing or reducing compression of the outflow space (e.g., Schlemm's canal 22) to facilitate drainage, as described herein. The standoffs 518 can extend distally beyond the surface 519 between the standoffs 518 and the retention protrusion 510 by a distance of at least about 20 microns, at least about 30 microns, at least about 40 microns, at least about 50 microns, less than or equal to about 100 microns, less than or equal to about 70 microns, less than or equal to about 50 microns, less than or equal to about 40 microns, and/or less than or equal to about 30 microns, although values outside of these ranges can be used in some embodiments. The implant 500 can include two standoffs 518 that are spaced laterally apart by a distance 511, which can be configured such that the two standoffs 518 are positioned on opposing sides of Schlemm's canal 22 upon implantation, such that the standoffs 518 prevent or reduce compression of Schlemm's canal 22 when distal force is applied during implantation and/or during use. The distance 511 can be at least about 0.1 mm, at least about 0.2 mm, at least about 0.3 mm, at least about 0.4 mm, at least about 0.5 mm, less than or equal to about 1.0 mm, less than or equal to about 0.75 mm, less than or equal to about 0.5 mm, less than or equal to about 0.4 mm, and/or less than or equal to about 0.3 mm, although values outside these ranges can be used in some embodiments. The lateral distance 511 can be between about 0.2 mm and about 0.5 mm or between about 0.3 mm and about 0.4 mm.

The longitudinal distance 515 between the surface (e.g., distal surfaces of the standoffs 518) that abuts against the ocular tissue (e.g., at or near the trabecular meshwork 23) and the center of the outflow pathway 514 can be configured to position the outflow pathway 514 in Schlemm's canal 22. For example, the distance 515 can be less than or equal to about 150 microns, less than or equal to about 100 microns, less than or equal to about 75 microns, less than or equal to about 50 microns, at least about 25 microns, at least about 50 microns, at least about 75 microns, and/or at least about 100 microns, although values outside these ranges may be used in some embodiments. The longitudinal distance 515 can be between about 40 microns and about 90 microns or between about 60 microns and about 70 microns.

The implant 500 can include a flange 520 to impede tissue from covering the inflow pathway 512. In some instances, pressing the implant into ocular tissue during implantation can cause the tissue under the implant 500 to compress. If the inflow pathway 512 is positioned adjacent to the tissue being compressed, the surrounding tissue that is less compressed could block part or all of the inflow pathway 512 and impede drainage through the implant 500. Also, in some instances, tissue can grow around the implant 500, especially for implants that are intended to remain implanted for several years. In some instances, tissue that grows around the implant 500 could block part or all of the inflow pathway 512 and impeded drainage through the implant 500. The flange 520 can be disposed between the inflow pathway 512 and the abutting surface (e.g., the distally facing surfaces of the standoffs 518 or the distally facing surface adjacent to the retention protrusion 510) that is configured to abut against the ocular tissue (e.g., the trabecular meshwork 23) when the implant 500 is implanted. In some embodiments, the flange 520 can extend laterally outward from the inflow pathway 512 by a distance 522 (as shown in FIG. 35) to is configured to prevent tissue from blocking the inflow pathway 512, as discussed herein. The distance 522 can be less than or equal to about 150 microns, less than or equal to about 125 microns, less than or equal to about 100 microns, less than or equal to about 90 microns, less than or equal to about 80 microns, less than or equal to about 70 microns, less than or equal to about 60 microns, at least about 40 microns, at least about 50 microns, at least about 60 microns, at least about 70 microns, at least about 80 microns, at least about 90 microns, at least about 100 microns, although values outside these ranges may be used in some embodiments. The distance 522 can be between about 50 microns and about 100 microns or between about 70 and 90 microns.

In some embodiments, the inflow pathway 512 is spaced longitudinally away from the abutting surface (e.g., the distal ends of the standoffs 518) that abuts against the ocular tissue (e.g., at or near the trabecular meshwork 23) by a distance 524 that impedes surrounding tissue from blocking the inflow pathway 512. For example, the distance 524 between the distal ends of the standoffs 518 and the distal end of the inflow pathway can be at least about 50 microns, at least about 75 microns, at least about 90 microns, at least about 100 microns, at least about 110 microns, at least about 125 microns, less than or equal to about 150 microns, less than or equal to about 125 microns, less than or equal to about 110 microns, less than or equal to about 100 microns, less than or equal to about 90 microns, and/or less than or equal to about 80 microns, although values outside these ranges may be sued in some embodiments. The distance 524 can be between about 50 microns and about 150 microns, between about 75 microns and about 125 microns, or between about 90 microns and about 100 microns. Various features of the implant 500 can cooperate to facilitate drainage of the fluid through the inflow pathway 512 and outflow pathway 514. For example, in some instances in which the inflow pathway 512 is positioned further from the standoffs 518, a smaller flange 520 can be used, or the flange 520 can be omitted altogether.

In some embodiments, the inflow pathway 512 and the outflow pathway 514 can extend parallel or substantially parallel through the implant 500. The inlets and outlets can be aligned such that a plane intersecting the central longitudinal axis 525 of the implant 500 (e.g., the plane of the cross-section of FIG. 35) can also intersect the inlets and outlets. The inflow pathway 512 and the outflow pathway 514 can be positioned such that when the outflow pathway 514 is positioned to be in fluid communication with Schlemm's canal 22, the inflow pathway 512 is positioned to be in fluid communication with the anterior chamber 20 of the eye. When implanting the implant 500, the rotational orientation of the implant 500 about the longitudinal axis 525 can be positioned such that inflow pathway 512 can access the anterior chamber 20 and such that the outflow pathway 514 can access Schlemm's canal 22, so that fluid can drain through the implant 500. In some embodiments, misalignment of the implant 500 can interfere with the drainage. For example, if the implant 500 were oriented 90 degrees offset about the longitudinal axis 525 from the desired position, the cornea 12 and/or the iris 13 could block the inflow pathway 512 and/or the outflow pathway 514 could be misaligned with Schlemm's canal 23 such that drainage is impeded or reduced.

In some embodiments, the implant 500 can include a positioning element 526 (e.g., a protrusion) to facilitate proper orientation about the longitudinal axis 525 of the implant 500. In FIGS. 32 and 33, for example, the positioning element 526 is offset by about 90 degrees from the inlets (e.g., of the inflow pathway 512) and the outlets (e.g., of the outflow pathway 514). By orienting the implant 500 with the positioning element 526 facing towards the front of the eye (e.g., towards the cornea 12), the medical practitioner can orient the inlets and outlets at the desired positions, as discussed above. Although the positioning element 526 is shown as a protrusion, various other positioning elements 526 can be used, such as an indentation, a visible marker, etc. In some embodiments, the positioning element 526 (e.g., the protrusion) can interface with a corresponding feature on an implanting tool configured to enable a medical practitioner to rotate the implant 500 about its longitudinal axis 525 to achieve the desired orientation during implantation, as discussed in connection with FIGS. 52 and 53. In some embodiments, the protrusion 526 extends laterally outward from the longitudinal axis 525 by less than or equal to the lateral extension of the flange 520.

In some embodiments, the implant 500 can include inlets that are rotationally offset from each other and/or outlets that are rotationally offset from each other about the longitudinal axis 525 to facilitate drainage through the implant 500. For example, the implant 500 can include four inlets offset by 90 degrees from each other, such that if one or more of the inlets is obstructed (e.g., by the cornea 12 and/or iris 13) one or more additional inlets would be properly oriented to be in fluid communication with the anterior chamber 20. Similarly, the implant 500 can include four outlets offset by 90 degrees from each other, to facilitate drainage into Schlemm's canal 23. Various numbers of inlets can be included (e.g., 1, 2, 3, 4, 5, 6, 7, 8, or more inlets). Various numbers of outlets can be included (e.g., 1, 2, 3, 4, 5, 6, 7, 8, or more outlets).

The shell 506 can be made of various biocompatible materials, as described herein, including metal (e.g., titanium) and ceramic materials. In some embodiments, molding the shell 506 from a ceramic material can be advantageous for reliably forming the small and detailed structure of the implant 500 (e.g., the inflow pathway 512, the outflow pathway 514, the flange 520, and/or the standoffs 518). In some embodiments, the interior chamber 508 of the shell 506, which is a drug reservoir, can be open to the drainage fluid pathway (e.g., open to the inflow pathway 512). For example, when molding the shell 506, a core pin can be used to form the pathway 516, and the core pin can be extracted through the interior chamber 508. Accordingly, in some implementations, to facilitate the manufacturing of the shell 506, the interior chamber 508 of the shell 506 can be open to the inflow pathway 512, pathway 516, and/or outflow pathway 514.

Figure 36:
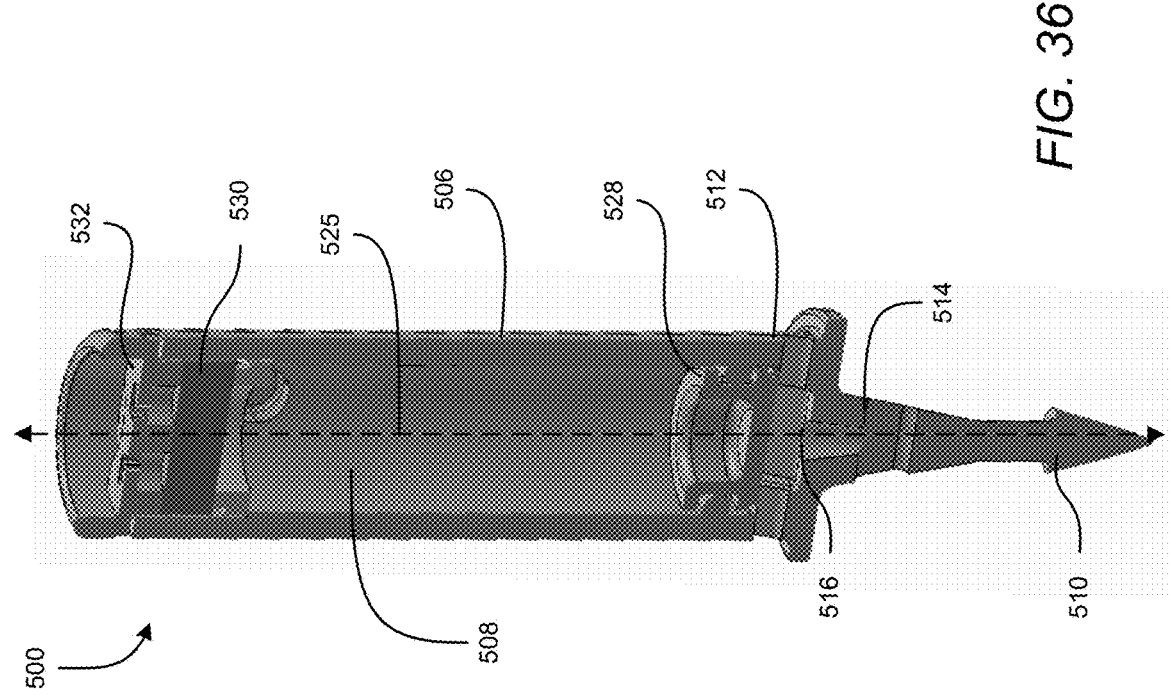
FIG. 36 is a cross-sectional perspective view of the implant of FIG. 32.
Figure 37:
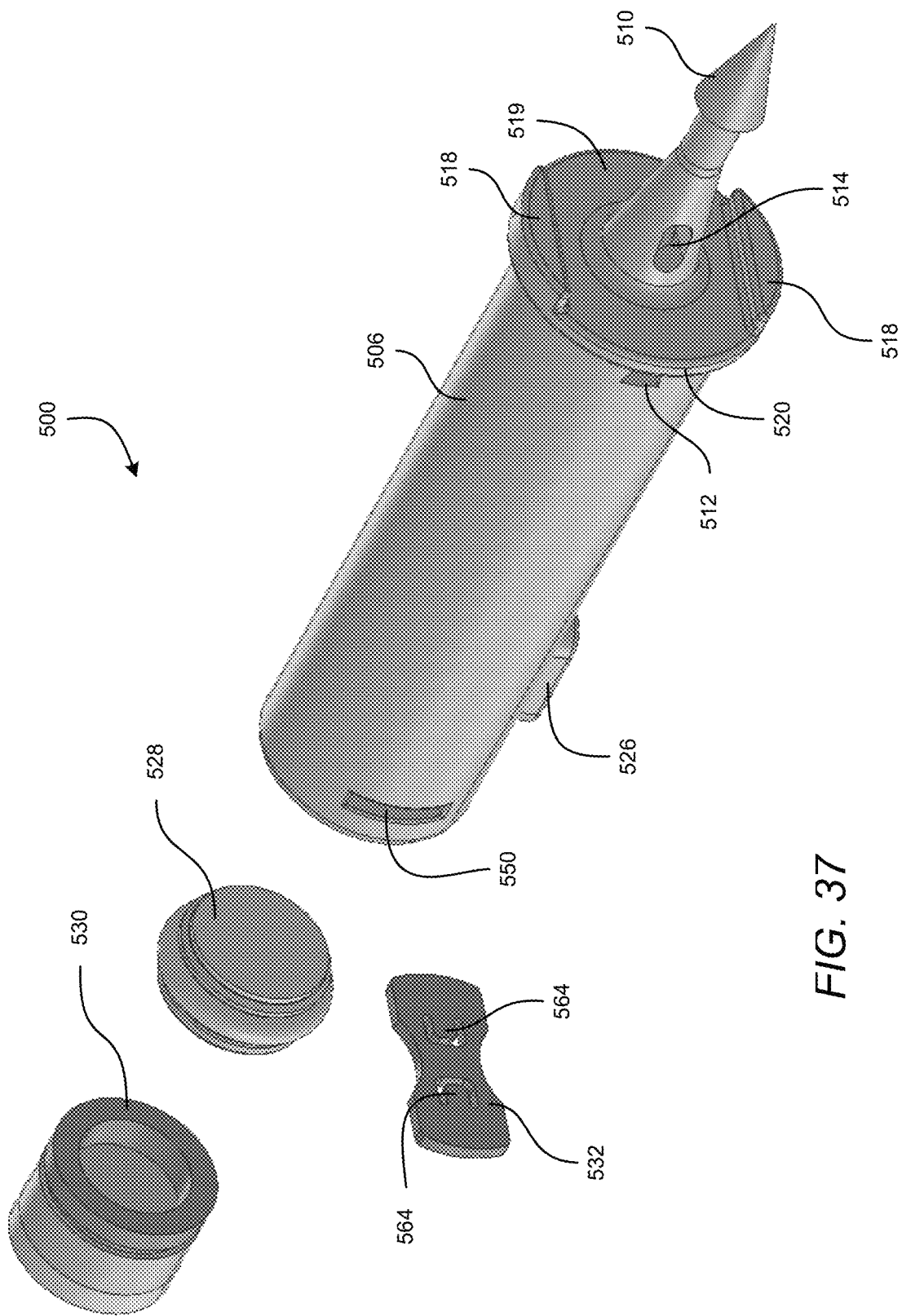
FIG. 37 is a distal exploded perspective view of the implant of FIG. 32.
Figure 38:
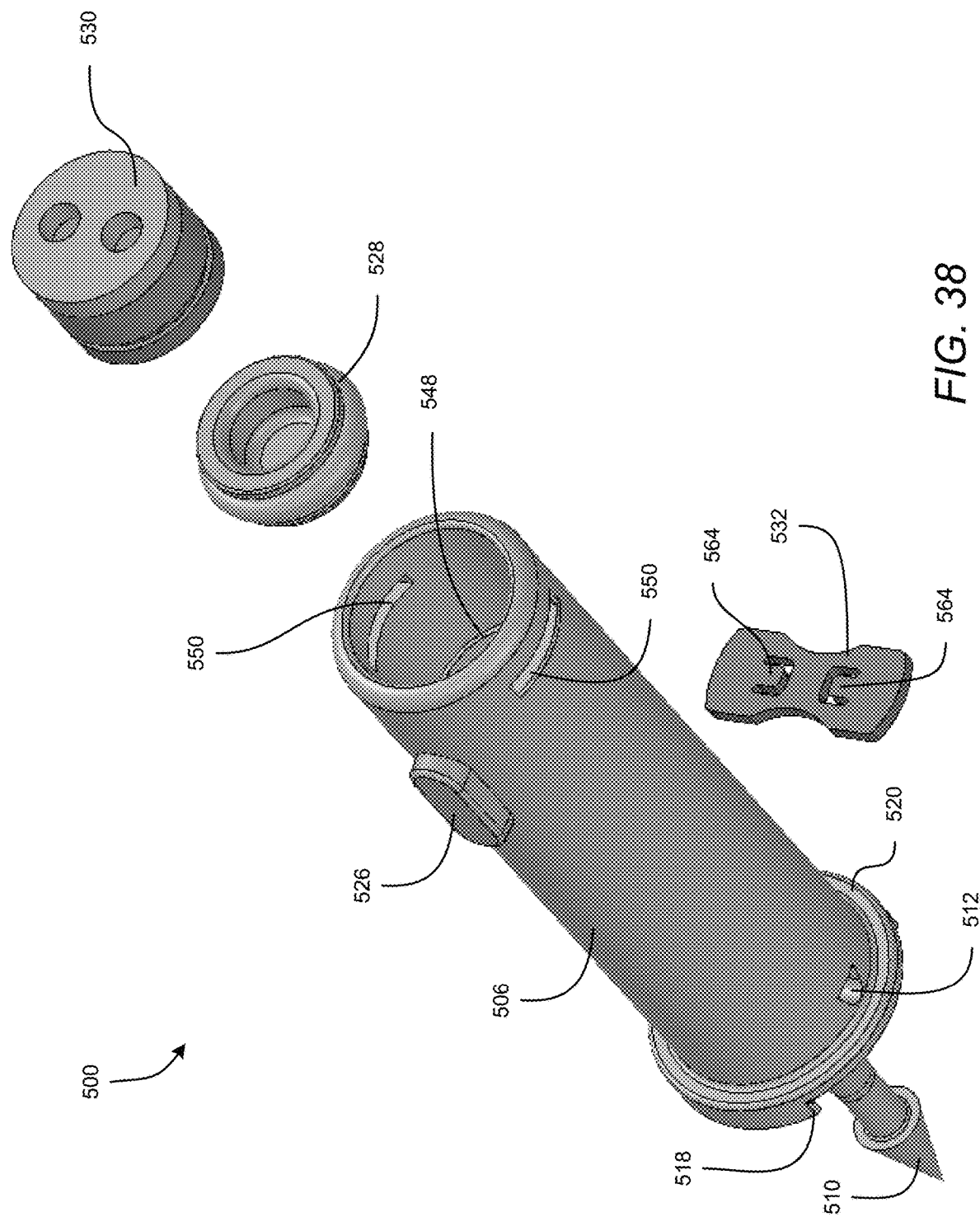
FIG. 38 is a proximal exploded perspective view of the implant of FIG. 32.
Figure 40:
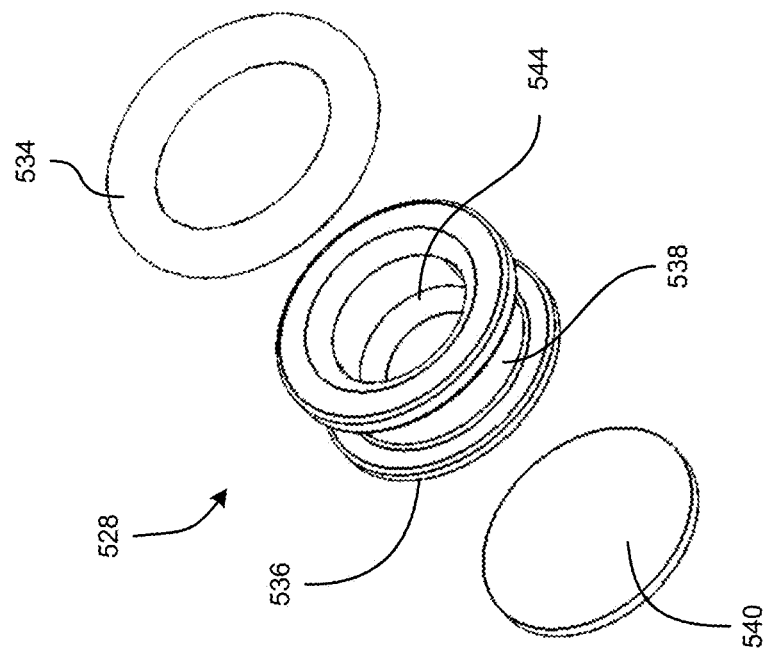
FIG. 40 is a proximal exploded perspective view of the seal of FIG. 39.
Figure 39:
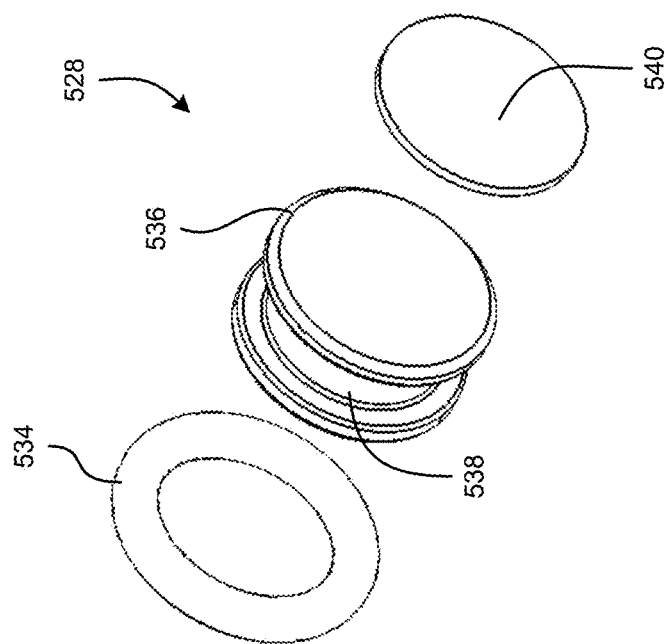
FIG. 39 is a distal exploded perspective view of a seal of the implant of FIG. 32.

The implant 500 can include a seal 528 configured to seal the interior chamber 508 from the inflow pathway 512, to prevent or impede the drug in the interior chamber 508 from escaping via the inflow pathway 512 and/or outflow pathway 514. The implant 500 can also include a drug release element 530, which can be held in place by a retainer 532, as discussed herein. FIG. 36 is a cross-sectional view of the implant 500 showing the seal 528 and the drug release element 530 installed. FIG. 37 is a distal exploded perspective view of the implant 500. FIG. 38 is a proximal exploded perspective view of the implant 500. FIG. 39 is a distal exploded perspective view of the seal 528. FIG. 40 is a proximal exploded perspective view of the seal 528.

The seal 528 can include an O-ring 534. The O-ring 534 can fit into a groove 538 on the seal base 536. The base 536 can be made of various biocompatible materials (e.g., a ceramic material or a metal, such as titanium). The seal base 536 can be rigid. The seal base 536 can have a diameter that is less than the diameter of the internal chamber 508 such that the base 536 can be inserted through the proximal end 504 and pushed longitudinally to the distal end of the interior chamber 508. The O-ring 534 can have an outer diameter that is greater than the diameter of the interior chamber 508, such that the O-ring is compressed and seals against the wall of the interior chamber 508. The O-ring can be made of a compressible material that is impermeable or substantially impermeable to the drug, such as silicone. The groove 538 on the base 536 can be configured to maintain the O-ring 534 on the base 536 as the base 536 slides distally across the interior chamber 508. In some embodiments, a lubricant can be applied to the seal 528 (e.g., to the O-ring) and/or to the interior chamber 508 before insertion of the seal 528.

In some embodiments, the seal 528 can include a distal barrier 540. The distal barrier 540 can be made of a compressible material that is impermeable or substantially impermeable to the drug, such as silicone. The distal barrier 540 can have the shape of a disc. As can be seen in FIG. 35, the shell 506 can include a distal end wall 542 of the interior chamber 508. The distal barrier 540 can be positioned distal of the seal base 536, and can be compressed between the seal base 536 and the distal end wall 542 at the distal end of the interior chamber 508. In some embodiments, the distal end of the base 536 can be substantially flat. The barrier 540 and the O-ring 534 can cooperate to seal the interior chamber 508 from the drainage fluid pathways (e.g., the inflow pathway 512). In some embodiments, the barrier 540 or the O-ring 534 can be omitted.

In some embodiments, the seal base 536 can include a recess 544 on the proximal side thereof. FIG. 43 shows a cross-sectional view of the implant 500 with the seal 528 installed. As can be seen in FIG. 43, the recess 544 can be in fluid communication with the interior chamber 508, such that the drug can fill the recess 544 to provide additional volume for holding a larger capacity of the drug. In some embodiments, as shown in FIG. 35, the positioning protrusion 526 can be hollow forming a recess 546. The recess 546 can be in fluid communication with the interior chamber 508, such that the drug can enter the recess to provide additional volume for holding a larger capacity of the drug. In some embodiments, the recess 546 can be omitted, and the internal wall of the interior chamber 508 can be flush across the area corresponding to the external positioning protrusion 526.

Figure 42:
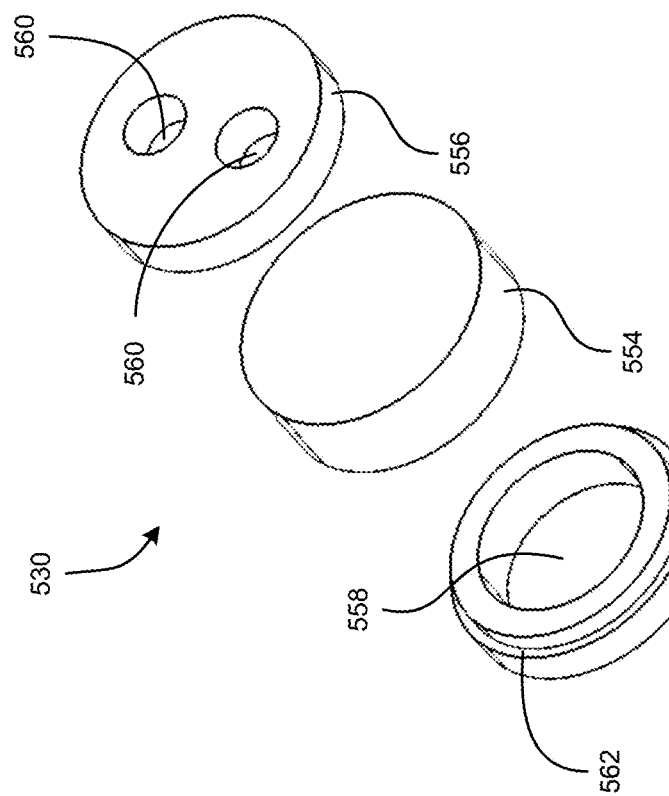
FIG. 42 is a proximal exploded perspective view of the drug release element of FIG. 41.
Figure 41:
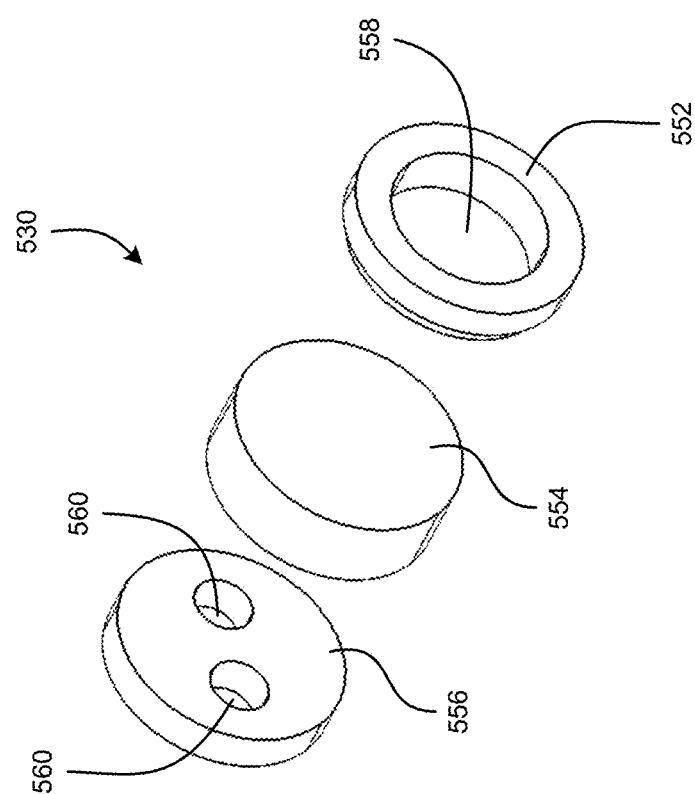
FIG. 41 is a distal exploded perspective view of a drug release element of the implant of FIG. 32.

FIG. 41 shows a distal exploded perspective view of the drug release element 530. FIG. 42 shows a proximal exploded perspective view of the drug release element 530. The drug release element 530 can be configured to slowly elute the drug, as described herein. In some instances, the drug release element 530 is referred to as a cap. The drug release element 530 can be positioned at or near the proximal end 504 of the implant 500. As can be seen in FIGS. 35 and 38, the shell 506 can include a shelf 548. The proximal portion of the shell 506 interior that is proximal of the shelf 548 can have a larger diameter than the portion that is distal of the shelf 548. In some embodiments, the shelf 548 can include a consistent annulus size around its circumference. In some embodiments, the shelf 548 does not have a consistent annulus around its circumference, and in some cases the shelf 548 can be one or more protrusions that create a stop for the distal seal member, as discussed herein. The shell 506 can include one or more slots 550, which can be configured to receive the retainer 532, as described herein. In some embodiments, the shell 506 can include two slots 550 positioned generally opposite each other.

The drug release element 530 can include a distal seal member 552, a membrane 554, and a proximal seal member 556. The distal seal member 552 can be seated against the shelf 548 on the shell 506. The distal seal member 552 can have an outer diameter that is greater than the distal portion of the shell interior (distal of the shelf 548) and that is less than the proximal portion of the shell interior (proximal of the shelf 548). The distal seal member 552 can have a generally annular shape and/or can have an opening 558 extending therethrough. The proximal seal member 556 can have an outer diameter that is greater than the distal portion of the shell interior (distal of the shelf 548) and that is less than the proximal portion of the shell interior (proximal of the shelf 548). The proximal seal member 556 can be inserted into the proximal end 504 of the shell 506. The proximal seal member 556 can be generally disc shaped. The proximal seal member 556 can include at least one opening 560 extending therethrough. In the illustrated embodiment, the proximal seal member 556 includes two openings 560. The membrane 554 can be positioned between the distal seal member 552 and the proximal seal member 556, and in some embodiments, the membrane 554 can be compressed between the distal seal member 552 and the proximal seal member 556. The retainer 532 can retain the drug release element 530 in the compressed state (e.g., with the membrane 554 compressed), as discussed herein. The distal seal member 552 can include a step 562. FIG. 43 shows the membrane 554 in an undeformed state. When compressed, the membrane 554 can deform to fill the space of the step 562.

The distal seal member 552 and/or the proximal seal member 556 can be made of various biocompatible materials, as discussed herein, such as ceramic or metal (e.g., titanium). In some embodiments, forming the members 552 and/or 556 out of a ceramic material can be advantageous for creating small details on the parts. In some embodiments, one or both of the seal members 552 and 556 can be made from a resilient biocompatible material that is impermeable, or substantially impermeable, to the drug (e.g., silicone). The membrane 554 can be made from various suitable materials that allow the drug to elute from the implant 500. In some embodiments, the membrane can be made from ethylene vinyl acetate (EVA). The rate of elution of the drug can depend, at least in part, on the percentage concentration of vinyl acetate in the EVA material. The vinyl acetate concentration can be less than or equal to about 40%, less than or equal to about 30%, less than or equal to about 25%, at least about 10%, at least about 20%, at least about 25%, and/or at least about 30%, although values outside these ranges may be used in some embodiments. The vinyl acetate concentration can be between about 10% and about 30%, between about 20% and about 30%, or between about 25% and about 30% of the EVA material. In some embodiments, the vinyl acetate concentration can be about 25% or about 28% of the EVA material.

As discussed herein, the membrane 554 can be compressed between the distal seal member 552 and the proximal seal member 556. The proximal seal member 556 can be pressed distally to compress the membrane 554, and the retainer 532 can be inserted through the slot 550 such that the retainer is positioned proximally of the proximal seal member 556. The retainer 532 can have a length that is greater than the inner diameter of the proximal portion of the shell interior and a length that is less than or equal to the outer diameter of the shell 506 at the slots 550. When inserted, the retainer 532 can extend into two opposing slots 550. The force from the compressed membrane 554 can press the retainer 532 in the proximal direction, and the slots 550 can hold the retainer in place to maintain the membrane 554 in the compressed configuration. The retainer 532 can have a generally hourglass shape, although other shapes can also be used, in some embodiments. The retainer can include one or more tabs 564, which can be folded down to secure the retainer 532. FIG. 43 is a cross-sectional view that shows the retainer 532 inserted with the tabs 564 up. FIG. 44 is a partial cross-sectional view that shows the retainer 532 inserted with the tabs 564 folded down to engage the proximal seal member 556. When folded down, the tabs 564 can enter the one or more openings 560 and can engage the proximal seal member 556, which can prevent or impede the retainer 532 from moving (e.g., from sliding out of the slot 550). In some embodiments, when the membrane 554 is compressed, a portion of the membrane 554 can be pushed proximally into the one or more openings 560, and the folded tabs 564 can engage the membrane 554, which can facilitate the securement of the membrane 554.

The drug can elute from the proximal end of the implant 500. The drug can pass from the internal chamber 508, through the at least one opening 558 in the distal seal member 552, to the membrane 554. The membrane 554 can be configured to permit the drug to pass through the membrane 554 at a desired elution rate. The drug can pass through the at least one hole 560 in the proximal seal member 556, past the retainer 532, and out of the proximal end 504 of the implant 500. In FIG. 44, the elution of the drug is shown by two arrows. In some embodiments, the thickness and/or compression of the membrane 554 can affect, at least in part, the elution rate of the drug. In some embodiments, the membrane 554 can have a compressed thickness of at least about 50 microns, at least about 75 microns, at least about 80 microns, at least about 90 microns, at least about 95 microns, at least about 100 microns, less than or equal to about 200 microns, less than or equal to about 150 microns, less than or equal to about 125 microns, less than or equal to about 110 microns, less than or equal to about 105 microns, less than or equal to about 100 microns, less than or equal to about 95 microns, and/or less than or equal to about 90 microns, although values outside these ranges may be used in some embodiments. The compressed thickness 566 of the membrane 554 can be between about 75 microns and about 125 microns, between about 85 microns and about 105 microns, or between about 90 microns and about 100 microns. In some embodiments the compressed thickness 566 of the membrane 554 can be about 95 microns. The membrane can be compressed by at least about 10 microns, at least about 20 microns, at least about 30 microns, at least about 40 microns, less than about 50 microns, less than about 40 microns, less than about 30 microns, and/or less than about 20 microns, although values outside these ranges may be used, in some embodiments. The membrane 554 can be compressed by an amount between about 20 microns and about 40 microns, or about 25 microns and about 35 microns. The membrane 554 can be compressed by about 30 microns, in some embodiments. Compression of the membrane 554 can improve the long term operation of the membrane 554 over the course of several years.

The amount of compression applied to the membrane 554 can be applied reliably without dependence on human determinations because the amount of compression applied to the membrane 554 is established by the dimensions of the implant 500 parts, not by a determination made by a human during assembly. By way of example, the longitudinal distance 568 between the shelf 548 and the proximal end of the slot 550 can be about 235 microns. The distal seal member 558 can have a longitudinal thickness 570 of about 65 microns. The proximal seal member 556 can have a longitudinal thickness 572 of about 50 microns. The retainer 532 can have a longitudinal thickness of about 25 microns. A membrane 554 with a longitudinal thickness of about 125 microns can be compressed to a longitudinal thickness 566 of about 95 microns (or less), and a retainer 532 having a longitudinal thickness 574 of about 25 microns can be inserted to maintain the membrane 554 in the compressed form. Accordingly, the dimensions of the respective parts dictate that the membrane 554 will be compressed by 30 microns, from a thickness of 125 microns to a thickness of 95 microns.

Figure 46:
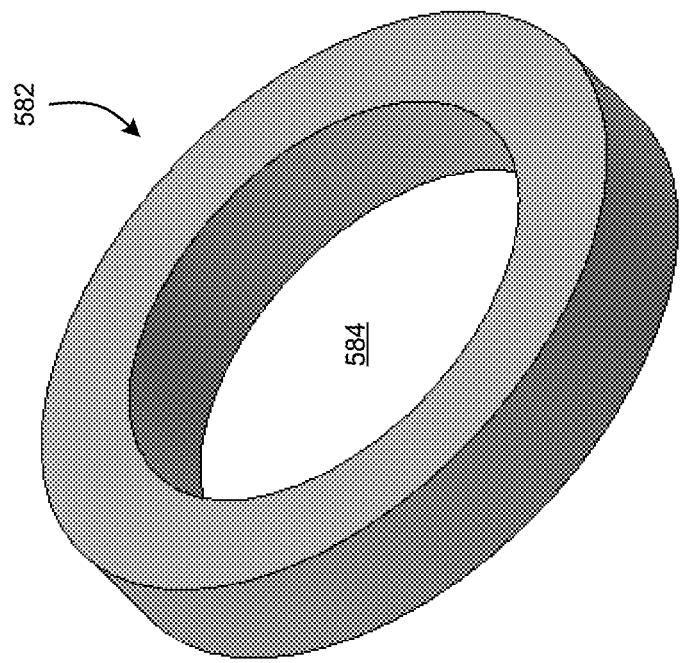
FIG. 46 is a perspective view of an example embodiment of a proximal seal member for use with a drug delivery ocular implant.
Figure 45:
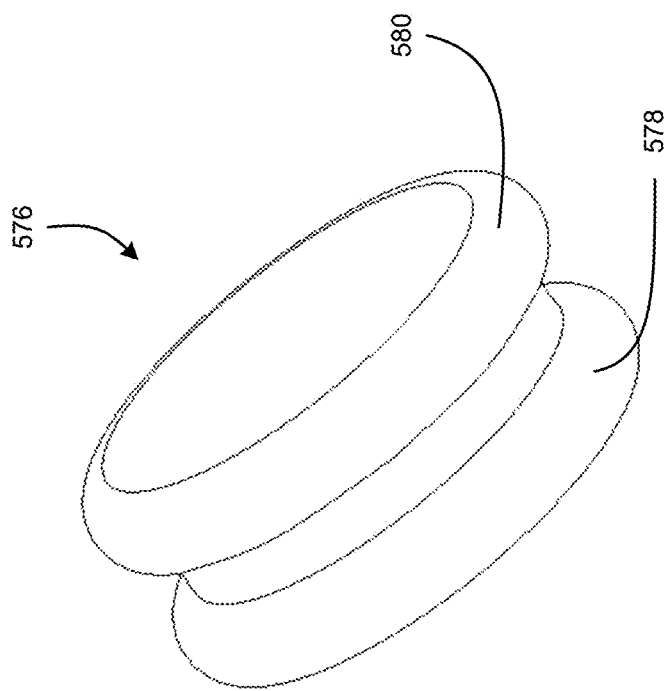
FIG. 45 is a perspective view of an example embodiment of a seal for use with a drug delivery ocular implant.

Many variations are possible. For example, FIG. 45 shows a perspective view of an example embodiment of an alternative seal 576, which can be used in place of the seal 528, in some embodiments. The seal 576 can be a single integral piece, and can be formed of a resilient material (e.g., silicone) that is impermeable or substantially impermeable to the drug. The seal 576 can include a distal bulge 578 and a proximal bulge 580, both of which can be configured to seal against the inside wall of the internal chamber 508. FIG. 46 is a perspective view of an example embodiments of an alternative upper seal member 582, which can be used in place of the upper seal member 556 discussed herein. The upper seal member 582 is generally annular or ring-shaped. The upper seal member 582 includes a single, relatively large hole 584 instead of the two relatively smaller holes 560 of the upper seal member 556 discussed herein. The larger hole 584 can produce a faster elution rate than the two smaller holes 560. Similarly, the size and number of holes in the distal seal member 552 can affect, at least in part, the elution rate of the drug. The implant 500 can be configured to have an elution rate of less than or equal to about 100 nanograms per day, less than or equal to about 75 nanograms per day, less than or equal to about 50 nanograms per day, less than or equal to about 40 nanograms per day, less than or equal to about 30 nanograms per day, less than or equal to about 25 nanograms per day, less than or equal to about 20 nanograms per day, at least about 10 nanograms per day, at least about 15 nanograms per day, at least about 20 nanograms per day, at least about 25 nanograms per day, at least about 30 nanograms per day, and/or at least about 40 nanograms per day, although values outside these ranges may be used, in some embodiments. The elution rate can be between about 15 nanograms per day and about 35 nanograms per day, or between about 20 nanograms per day and about 30 nanograms per day. The elusion rate, in some cases, can be about 25 nanograms per day. The elution rate and volume of the drug can provide drug delivery for a time period of at least about 1 year, at least about 2 year, at least about 3 year, at least about 4 years, at least about 5 years, at least about 6 year, at least about 7 years, at least about 8 years, at least about 9 years, at least about 10 years, less than or equal to about 15 years, less than or equal to about 12 years, less than or equal to about 10 years, less than or equal to about 8 years, less than or equal to about 6 years, and/or less than or equal to about 4 years, although values outside there ranges can be used in some embodiments.

Figure 48:
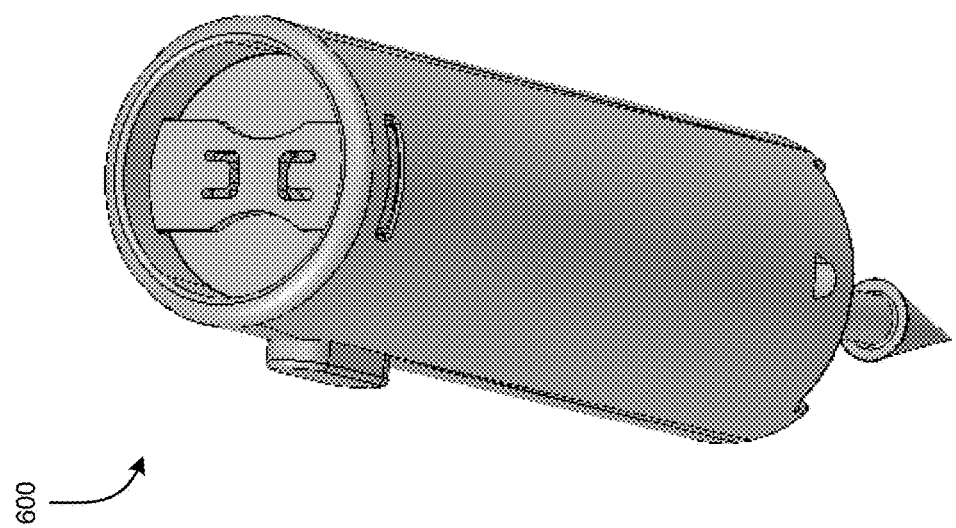
FIG. 48 is a proximal perspective view of the implant of FIG. 47.
Figure 47:
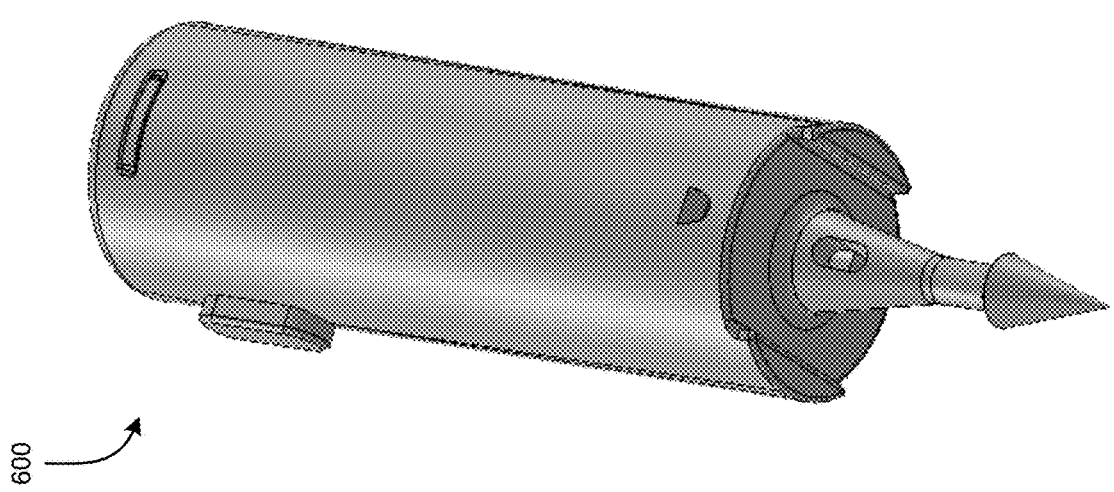
FIG. 47 is a distal perspective view of another example embodiment of a drug delivery ocular implant.
Figure 50:
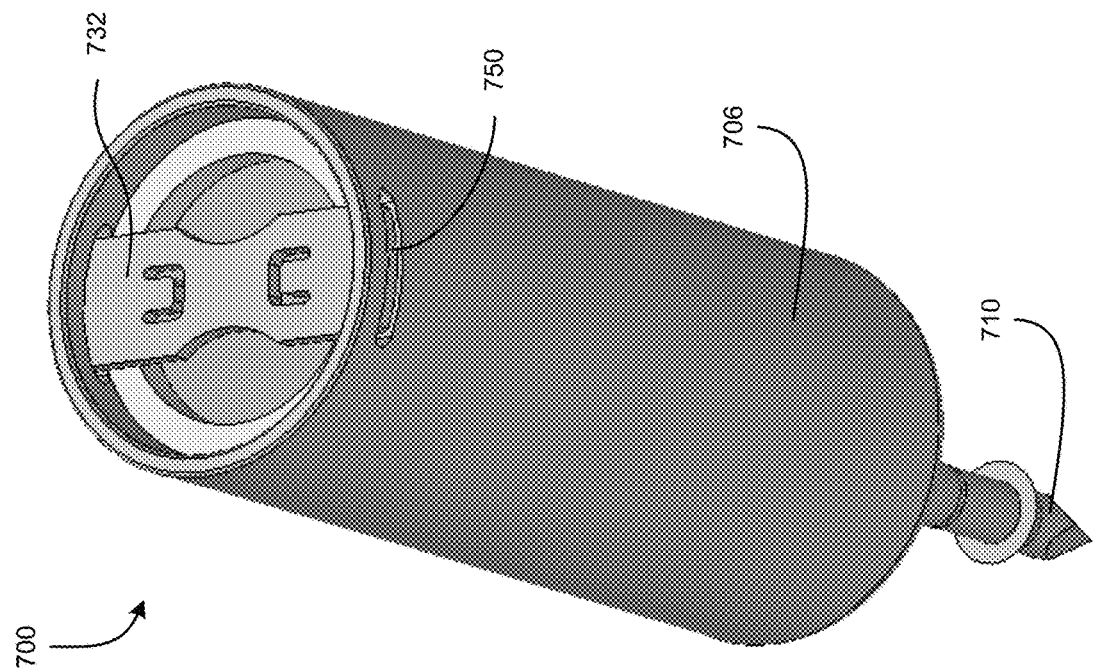
FIG. 50 is a proximal perspective view of the implant of FIG. 49.
Figure 49:
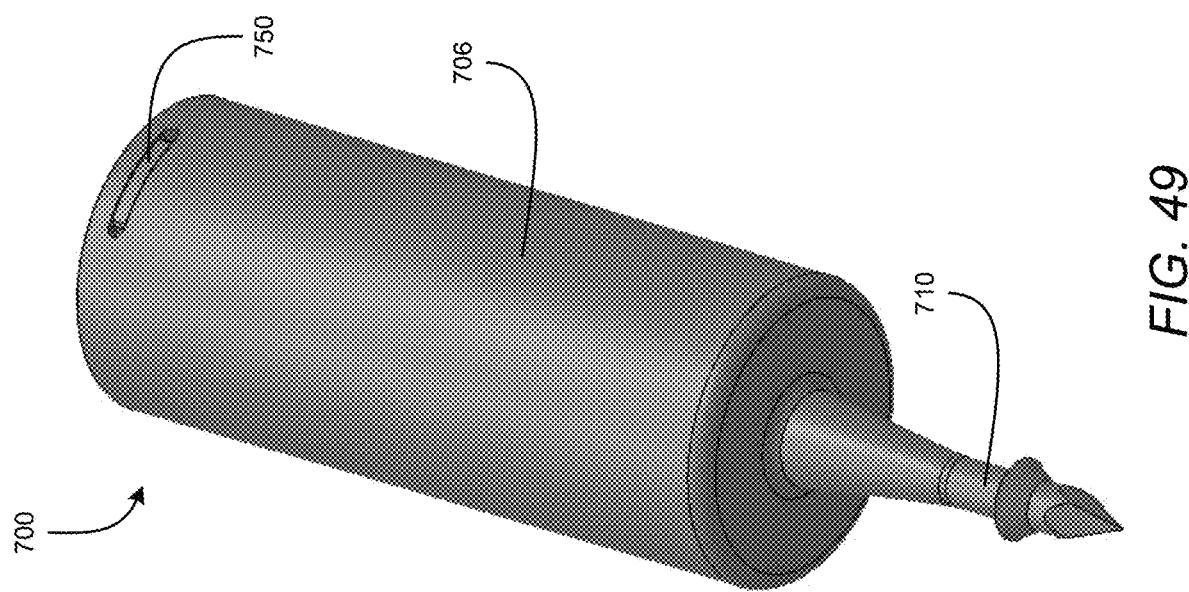
FIG. 49 is a distal perspective view of another example embodiment of a drug delivery ocular implant.

Drug delivery ocular implants such as the implant 500 can be configured to hold various volumes of drugs, as discussed herein. FIGS. 47 and 48 are perspective views of an example embodiment of a drug delivery ocular implant 600, which can include the same features as described in connection with the ocular implant 500, or in connection with other embodiments disclosed herein. In some embodiments, the implant 600 does not include the flange 520 that was included on the implant 500. Accordingly, the implant 600 can have a drug reservoir with a larger diameter than the implant 500, can hold a larger volume of the drug. By way of example, the implant 500 can have an internal diameter of about 0.28 mm and can hold about 58 nanoliters, while the implant 600 can have an internal diameter of about 0.36 mm and can hold about 97 nanoliters. FIGS. 49 and 50 are perspective views of another example embodiment of a drug delivery ocular implant 700, which can include some of the same features as described in connection with the implant 500, the implant 600, or any other embodiment disclosed herein. In some embodiments, the implant 700 does not include the inflow pathway 512 and outflow pathway 514, and the implant 700 also does not include the positioning protrusion 526. Accordingly, the implant 700 can have a drug reservoir that has a larger diameter than the implant 500 and the implant 600, and can hold a larger volume of the drug. By way of example, the implant 700 can have an internal diameter of about 0.41 mm and a volume of about 115 nanoliters. Drug delivery ocular implants can be made to hold a variety of different drug volumes. The implants can hold at least about 30 nanoliters, at least about 40 nanoliters, at least about 50 nanoliters, at least about 60 nanoliters, at least about 70 nanoliters, at least about 80 nanoliters, at least about 90 nanoliters, at least about 100 nanoliters, at least about 110 nanoliters, at least about 120 nanoliters, at least about 130 nanoliters, at least about 140 nanoliters, at least about 150 nanoliters, less than or equal to about 200 nanoliters, less than or equal to about 175 nanoliters, less than or equal to about 150 nanoliters, less than or equal to about 130 nanoliters, less than or equal to about 120 nanoliters, less than or equal to about 110 nanoliters, less than or equal to about 100 nanoliters, less than or equal to about 90 nanoliters, less than or equal to about 80 nanoliters, less than or equal to about 70 nanoliters, less than or equal to about 60 nanoliters, and/or less than about 50 nanoliters, although values outside these ranges may be used, in some embodiments. The implants can hold a volume of drug between about 40 nanoliters and about 150 nanoliters, or between about 50 nanoliters and about 120 nanoliters.

Figure 51:
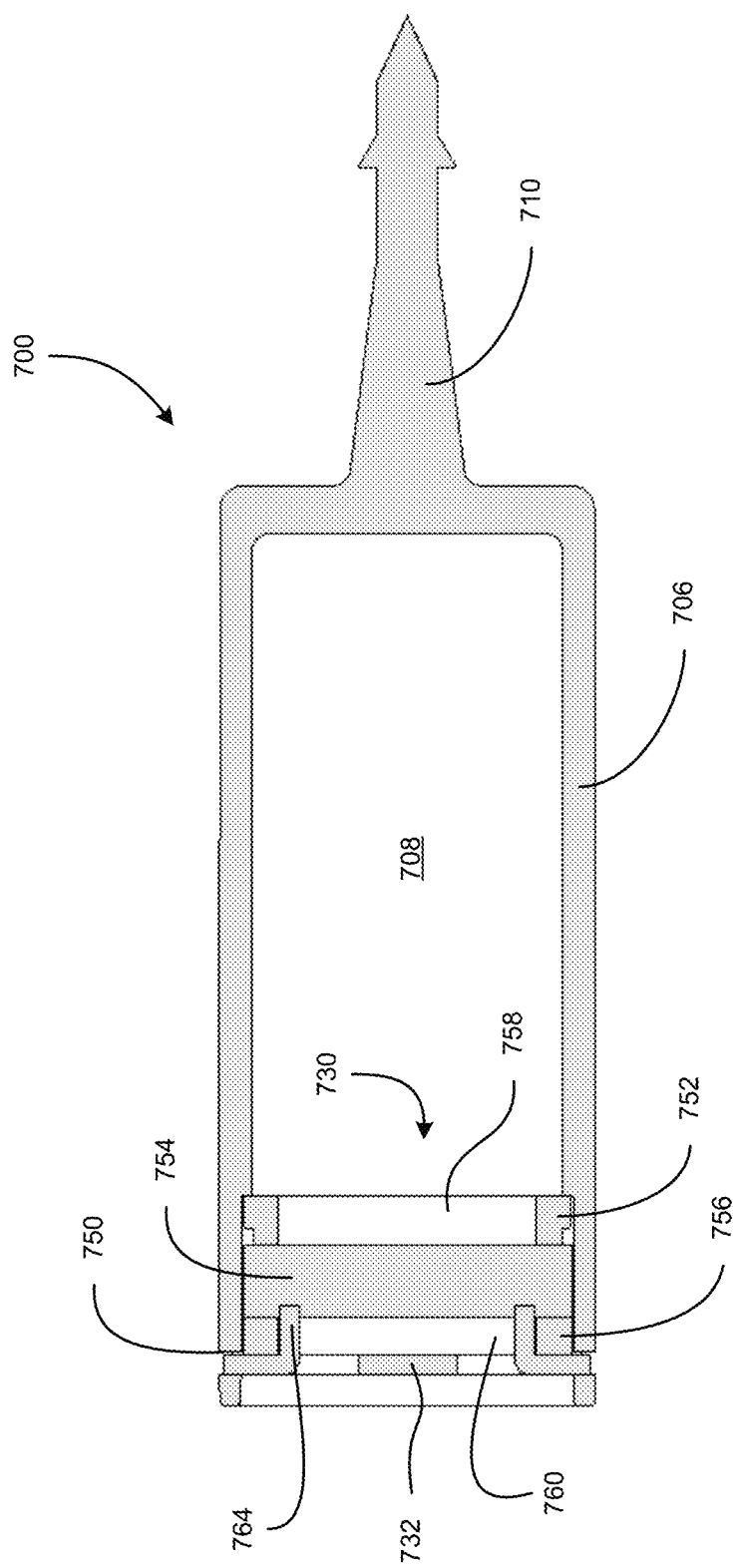
FIG. 51 is a cross-sectional view of the implant of FIG. 49.

FIG. 51 is a cross-sectional view of the implant 700. With reference to FIGS. 49-51, the implant 700 can include an outer shell 706, which can be made from a variety of suitable biocompatible materials, such as ceramic or metal (e.g., titanium). In some embodiments, the implant 700 does not include inflow and outflow passageways, and the shell 706 can be of sufficiently simple shape that it can be constructed of metal (e.g., titanium). In some embodiments, the seal 528 discussed in connection with the implant 500 can be omitted from the implant 700, because the implant 700 does not include the inflow and outflow passages. The implant 700 can include a drug release element 730, retainer 732, retention protrusion 710, and slot 750, which can be similar to the drug release element 530, retainer 532, retention protrusion 710, and slot 550 of the implant 500 discussed herein. As shown in FIG. 51, the tabs 764 of the retainer 732 can engage the membrane 754 when the tabs 764 are bent downward. The upper seal member 756 and the lower seal member 752 can both include a single large opening 760 and 758, respectively, which can have the same or substantially the same size. As discussed above, the internal reservoir 708 can hold more volume of the drug than the internal reservoir 508 of the implant 500. Also, the larger openings 758 and 760 can cause the implant 700 to have a faster elution rate than the implant 500. It should be understood that although the drawings are not necessarily all drawn to scale, the dimensions, proportions, orientations, and other structural aspect shown in the Figures are intended to form part of the disclosure.

Figure 55:
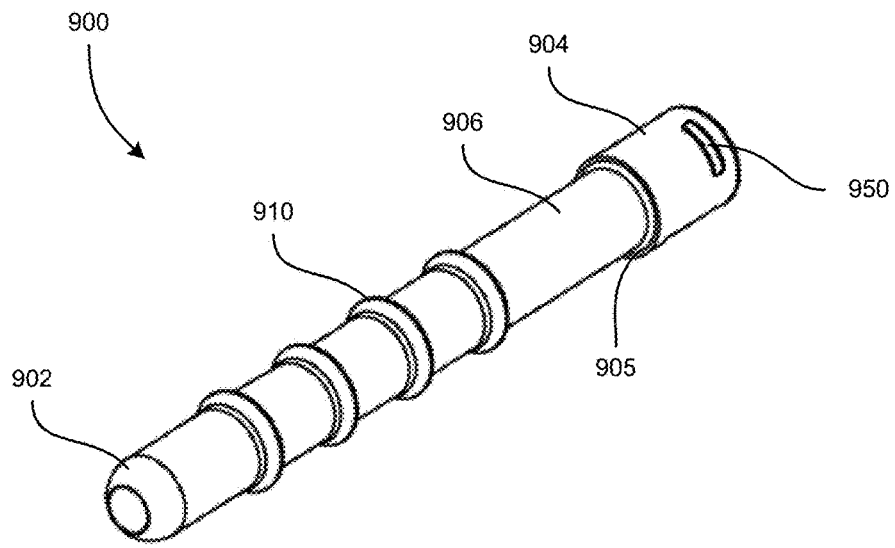
FIG. 55 shows a perspective view of an example embodiment of an ocular implant.
Figure 56:
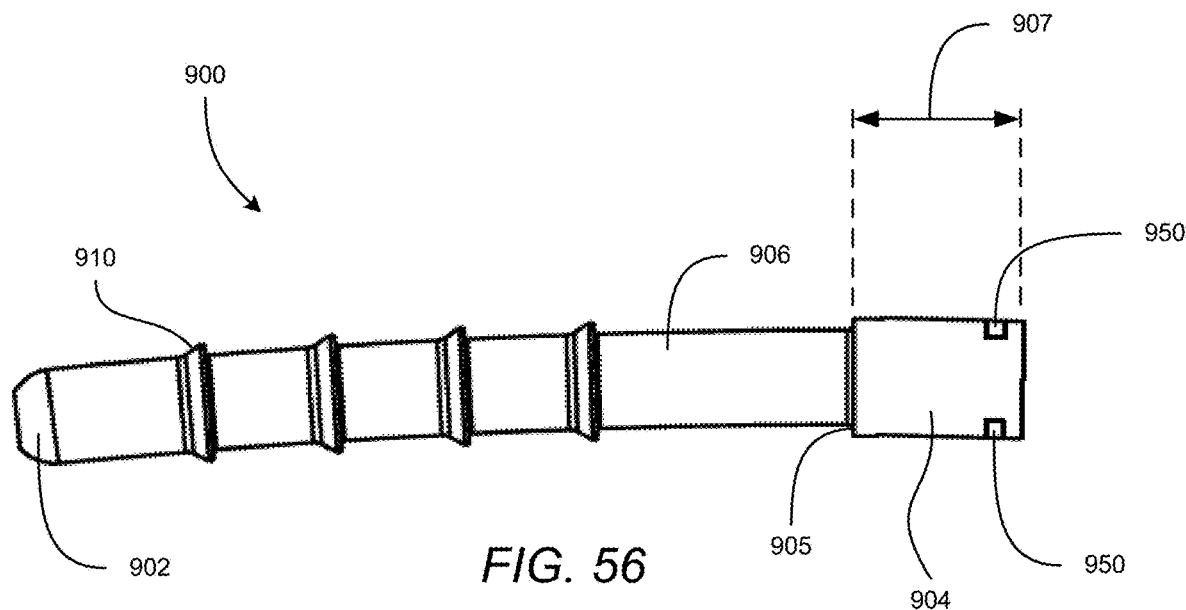
FIG. 56 shows a side view of the example embodiment of an ocular implant of FIG. 55.
Figure 57:
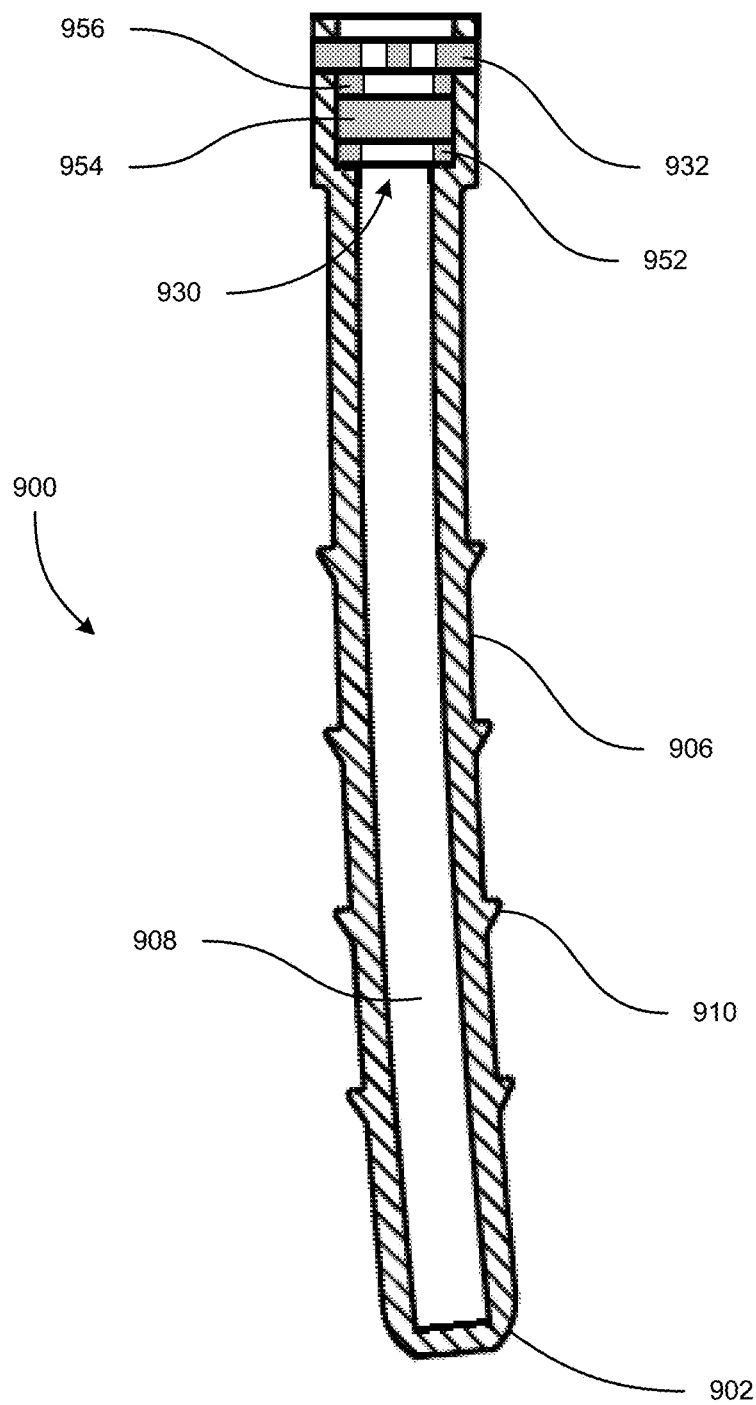
FIG. 57 shows a cross-sectional view of the example embodiment of an ocular implant of FIG. 55.

Various other embodiments disclosed herein can include a drug release element, which can be similar to or the same as the drug release elements 530 and/or 730 or the other drug release elements illustrated and discussed herein. For example, in some embodiments an ocular implant can be configured to be positioned at least partially in the supraciliary space and/or suprachoroidal space and can include a drug release element that has features similar to or the same as the drug release elements disclosed herein (e.g., the drug release elements 530 and/or 730). FIG. 55 shows a perspective view of an example embodiment of an ocular implant 900. FIG. 56 shows a side view of the example embodiment of an ocular implant 900. FIG. 57 shows a cross-sectional view of the example embodiment of an ocular implant 900. Various features of the ocular implant 900 can be similar to or the same as features illustrated by, or described in connection with, FIGS. 12B-12C.

The ocular implant 900 can include an outer shell 906. The outer shell 906 can define an interior chamber 908, which can be a drug reservoir for holding one or more drugs as discussed herein. The outer shell 906 can be configured to be implanted into the supraciliary space and/or suprachoroidal space of a patient's eye. The outer shell 906 can have a generally straight configuration, or the implant can be pre-curved to a curvature that is configured to conform generally to the supraciliary space and/or suprachoroidal space. The outer shell 906 can be flexible, in some embodiments, such as to enable the ocular implant to have a generally straight configuration when positioned in a delivery apparatus and to have a curved configuration when implanted into the eye (e.g., in the supraciliary space and/or the suprachoroidal space). The outer shell 906 can include a distal end 902, which can be tapered to facilitate insertion into the supraciliary space and/or the suprachoroidal space.

The outer shell 906 can include a proximal end portion 904, which can include a drug release element 930. In some embodiments, the proximal end portion 904 can have an increased outer diameter such that a step or ridge 905 is formed between the proximal end portion 904 and the central portion of the outer shell 906. In some embodiments, the ocular implant 900 can be inserted into the eye (e.g., into the supraciliary space and/or the suprachoroidal space) until the step or ridge 905 abuts against eye tissue adjacent to the insertion site (e.g., ciliary tissue). The step or ridge 905 can help impede over-insertion of the ocular implant 900. The ocular implant 900 can be configured to release (e.g., elute) a drug, as discussed herein, such as from the proximal end of the ocular implant 900, for example, into the anterior chamber 20. The drug release location (e.g., the proximal end) can be spaced apart from the step or ridge 905 by a distance 907 to prevent the eye tissue that is adjacent the insertion site from covering or otherwise blocking the drug release location of the ocular implant 900. By way of example, the distance can be about 25 microns, about 50 microns, about 75 microns, about 100 microns, about 150 microns, about 200 microns, about 300 microns, about 400 microns, about 500 microns, about 750 microns, about 1000 microns, about 1250 microns, about 1500 microns, or any values therebetween including ranges that are bound by any of these distances. In some embodiments, the step or ridge 905 can extend laterally outward further than shown in FIGS. 55-57. The step or ridge 905 can extend laterally outward by a distance that can be about 25 microns, about 50 microns, about 75 microns, about 100 microns, about 150 microns, about 200 microns, about 300 microns, about 400 microns, about 500 microns, about 750 microns, about 1000 microns, or any values therebetween including ranges that are bound by any of these distances.

The ocular implant 900 can include one or more retention features 910 configured to anchor the implant in place when implanted in the eye. The one or more retention features 910 can include one or more annular ribs on an outer surface of the outer shell 906. The ribs can have angled distal sides and/or can be barbed to facilitate insertion of the ocular implant 900 into the eye while impeding the ocular implant 900 from unintentionally releasing from the eye tissue. In some embodiments, the ribs can have an outer diameter that is substantially the same as the outer diameter of the proximal end portion 904, to facilitate placement in a delivery apparatus. In some embodiments, the one or more retention features 910 can be configured to engage the eye tissue that is adjacent to the insertion site. For example, the one or more retention features 910 can be on or near the proximal end portion 904 or at or near the step or ridge 905. In some embodiments, the retention features 910 can be omitted, and the outer shell 906 can be held in place by friction against the surrounding eye tissue.

The ocular implant 900 can include a drug release element 930. The drug release element can include a distal seal member 952, a membrane 954, and a proximal seal member 956, which can be the same as, or similar to, the other distal seal members, membranes, and proximal seal members discussed and illustrated herein (e.g., in connection with FIGS. 31-54). The disclosure provided herein for other embodiments that include a drug release element can be applied to the ocular implant 900, and is not repeated here. The membrane 954 can be compressed between the distal seal member 952 and the proximal seal member 956, as discussed herein. A retainer 932 can hold the drug release element 930 in place, as discussed herein. The outer shell 906 can include one or more slots 950, and the retainer 932 can engage the one or more slots 950 proximally of the proximal seal member 956. Two slots 950 can be positioned on opposite sides of the outer shell 906 and the retainer 930 can be inserted through one of the slots 950, across the interior chamber 908, and into the other of the slots 950. The distal seal member 952 can be seated against a shelf in the interior chamber 908. The compressed membrane 954 can apply a force that presses the distal seal member 952 against the shelf and that presses the proximal seal member 956 against the retainer 932.

It will be appreciated that the elements discussed above are not to be read as limiting the implants to the specific combinations or embodiments described. Rather, the features discussed are freely interchangeable to allow flexibility in the construction of a drug delivery implant in accordance with this disclosure.

Delivery Instruments

Another aspect of the systems and methods described herein relates to delivery instruments for implanting an implant for delivering a drug to the eye and optionally for draining fluid from the anterior chamber into a physiologic outflow space. In some embodiments, the implant is inserted into the eye from a site transocularly situated from the implantation site. The delivery instrument is sufficiently long to advance the implant transocularly from the insertion site across the anterior chamber to the implantation site. At least a portion of the instrument may be flexible. The instrument may comprise a plurality of members longitudinally moveable relative to each other. In some embodiments, the plurality of members comprises one or more slideable guide tubes. In some embodiments, at least a portion of the delivery instrument is curved. In some embodiments, a portion of the delivery instrument is rigid and another portion of the instrument is flexible.

In some embodiments, the delivery instrument has a distal curvature. The distal curvature of the delivery instrument may be characterized in some embodiments as a radius of approximately 10 to 30 mm. In some embodiments the distal curvature has a radius of about 20 mm.

Figure 21:
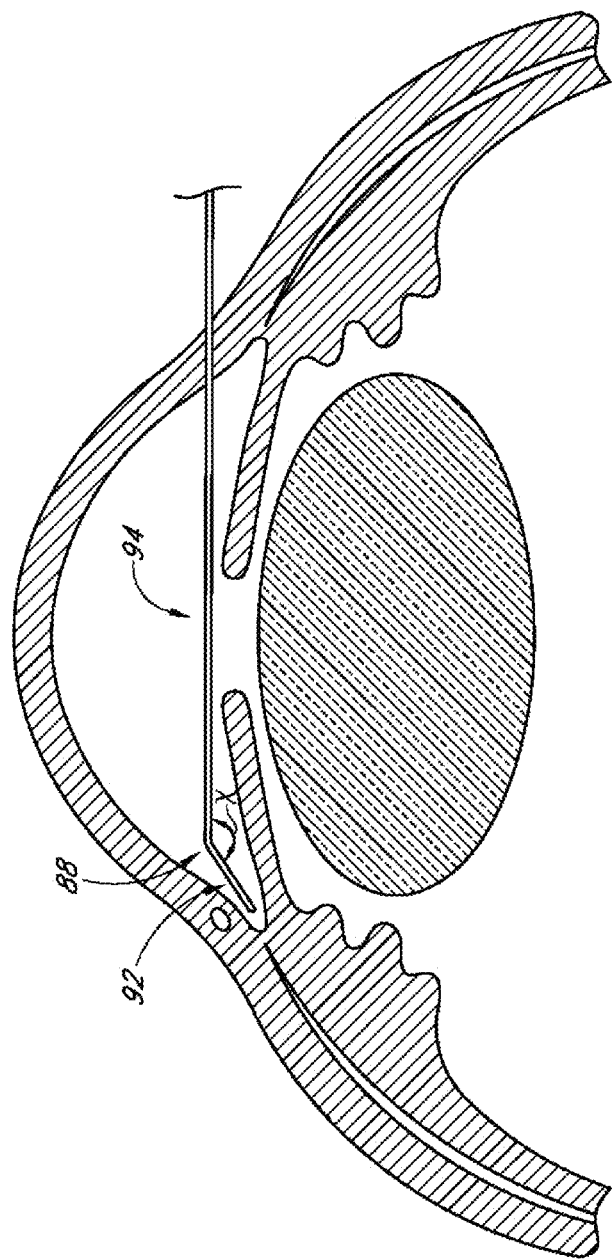
FIG. 21 illustrates an apparatus for implanting a drug delivery device in accordance with embodiments disclosed herein.

In some embodiments, the delivery instrument has a distal angle 88 (with a measure denoted by $\chi$ in FIG. 21). The angle measure $\chi$ may be characterized as approximately 90 to 180 degrees relative to the proximal segment 94 of the delivery instrument. In some embodiments, the angle measure $\chi$ may be characterized as between about 145 and about 170 degrees. In some embodiments the angle measure is between about 150 and about 170 degrees, or between about 155 and about 165 degrees. The angle can incorporate a small radius of curvature at the "elbow" so as to make a smooth transition from the proximal segment of the delivery instrument to the distal segment. The length of the distal segment may be approximately 0.5 to 7 mm in some embodiments, while in some other embodiments, the length of the distal segment is about 2 to 3 mm.

In other embodiments, a curved distal end is preferred. In such embodiments, the height of the delivery instrument/shunt assembly (dimension 90 in FIG. 22) is less than about 3 mm in some embodiments, and less than 2 mm in other embodiments.

In some embodiments, the instruments have a sharpened feature at the forward end and are self-trephinating, i.e., self-penetrating, so as to pass through tissue without pre-forming an incision, hole or aperture. In some embodiments, instruments that are self-trephinating are configured to penetrate the tissues of the cornea and/or limbus only. In other embodiments, instruments that are self-trephinating are configured to penetrate internal eye tissues, such as those in the anterior chamber angle, in order to deliver an implant. Alternatively, a separate trocar, scalpel, spatula, or similar instrument can be used to pre-form an incision in the eye tissue (either the cornea/sclera or more internal tissues) before passing the implant into such tissue. In some embodiments, the implant is blunt at the distal end, to aid in blunt dissection (and hence reduce risk of tissue trauma) of the ocular tissue. In other embodiments, however, the implant is also sharpened, tapered or otherwise configured to penetrate ocular tissues to aid in implantation.

For delivery of some embodiments of the drug eluting ocular implant, the instrument has a sufficiently small cross section such that the insertion site self-seals without suturing upon withdrawal of the instrument from the eye. An outer dimension of the delivery instrument is preferably no greater than about 18 gauge and is not smaller than about 27 or 30 gauge.

For delivery of some embodiments of the drug eluting ocular implant, an incision in the corneal tissue is made with a hollow needle through which the implant is passed. The needle has a small diameter size (e.g., 18 or 19 or 20 or 21 or 22 or 23 or 24 or 25 or 26 or 27 gauge) so that the incision is self-sealing and the implantation occurs in a closed chamber with or without viscoelastic. A self-sealing incision may also be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either may be used to place the ocular implant or may cooperate with a delivery instrument to allow implantation through the same incision without withdrawing the incision-forming instrument. Of course, in other modes, various surgical instruments may be passed through one or more corneal incisions multiple times.

Some embodiments include a spring-loaded pusher system. In some embodiments, the spring-loaded pusher includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the implant. The implant may be delivered over a wire. In some embodiments, the wire is self-trephinating. The wire may also function as a trocar. The wire may be superelastic, flexible, or relatively inflexible with respect to the implant. The wire may be pre-formed to have a certain shape. The wire may be curved. The wire may have shape memory, or be elastic. In some embodiments, the wire is a pull wire. The wire may also be a steerable catheter.

In some embodiments, the wire is positioned within a lumen in the implant. The wire may be axially movable within the lumen. The lumen may or may not include valves or other flow regulatory devices.

In some embodiments, the delivery instrument is a trocar. The trocar may be angled or curved. In some embodiments, the trocar is flexible. In other embodiments the trocar is relatively rigid. In other embodiments, the trocar is stiff. In embodiments where the trocar is stiff, the implant is relatively flexible. The diameter of the trocar is about 0.001 inches to about 0.01 inches. In some embodiments, the diameter of the trocar is 0.001, 0.002, 0.003, 0.004, 0.005, 0.006, 0.007, 0.008, 0.009, or 0.01 inches.

In some embodiments, delivery of the implant is achieved by applying a driving force at or near the proximal end of the implant. The driving force may be a pulling or a pushing applied to the end of the implant.

The instrument may include a seal or coating to prevent aqueous humor from passing through the delivery instrument and/or between the members of the instrument when the instrument is in the eye. The seal aids in preventing backflow. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument may additionally comprise a seal between various members comprising the instrument. The seal may comprise a hydrophobic or hydrophilic coating between slip-fit surfaces of the members of the instrument. The seal may be disposed proximate of the implant when carried by the delivery instrument. In some embodiments, the seal is present on at least a section of each of two devices that are machined to closely fit with one another.

The delivery instrument may include a distal end having a beveled shape. The delivery instrument may include a distal end having a spatula shape. The beveled or spatula shape may or may not include a recess to contain the implant. The recess can include a pusher or other suitable means to push out or eject the implant.

The delivery instrument may be configured to deliver multiple implants. In some such embodiments, the implants may be arranged in tandem (or serially for implant numbers greater than two) within the device.

Figure 52:
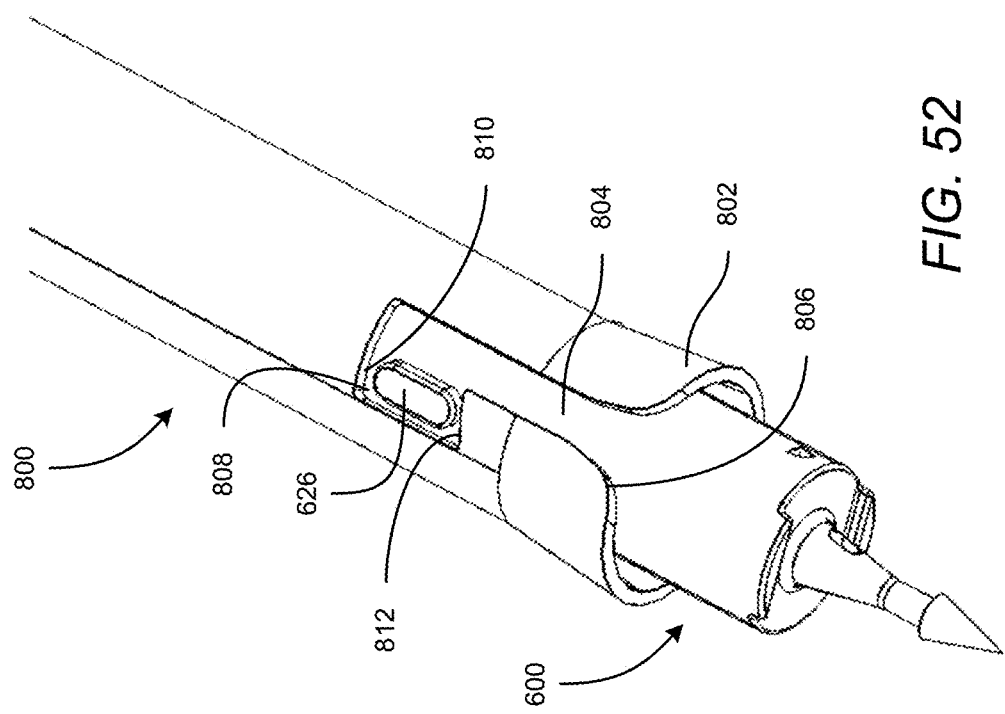
FIG. 52 is a perspective view of an example embodiment of an insertion tube for use with an ocular implant.

FIG. 52 shows an example embodiment of an insertion tube 800 for implanting a drug delivery ocular implant (e.g., implant 600), as discussed herein. The insertion tube 800 can have a flared distal end 802. The insertion tube 800 can include a slit 804 that is configured to receive the positioning protrusion 626 of the implant 600. The slit 804 can have rounded ends 806 to facilitate guiding the positioning protrusion 626 into the slit 804. The slit 804 can include a locking portion 808 that is offset from the main linear path of the slit 804. The locking portion 808 can engage the positioning protrusion 626, for example as shown in FIG. 52 to lock the implant 600 onto the insertion tube 800. In the locked position, movement of the insertion tube 800 in the distal direction can cause the proximal wall 810 to press against the positioning protrusion 626 to drive the implant 600 forward in the distal direction (e.g., for implantation). In the locked position, movement of the insertion tube 800 in the proximal direction can cause the distal wall 812 to press against the positioning protrusion 626 to drive the implant 600 rearward in the proximal direction (e.g., for explanation). The user can rotate the insertion tube 800 in order to rotate the implant 600 via the positioning protrusion 626, as discussed herein.

To remove the implant 600 from the insertion tube 800, the user can rotate the insertion tube 800 until the positioning protrusion 626 is out of the locking portion 808 and is position in the main linear path of the slit 804. Then, the user can withdraw the insertion tube 800 in the proximal direction, and the positioning protrusion 626 can slide along the slit 804 until it exits the insertion tube 800. To engage an implant 600 with the insertion tube 800, a user can align the slit 804 with the positioning protrusion 626 and can move the insertion tube 800 forward, distally so that the positioning protrusion 626 enters the slit 804 and slides back to the location of the turn to the locking portion 808. Then the user can rotate the insertion tube 800 so that the positioning protrusion 626 enters the locking portion 808.

Figure 53:
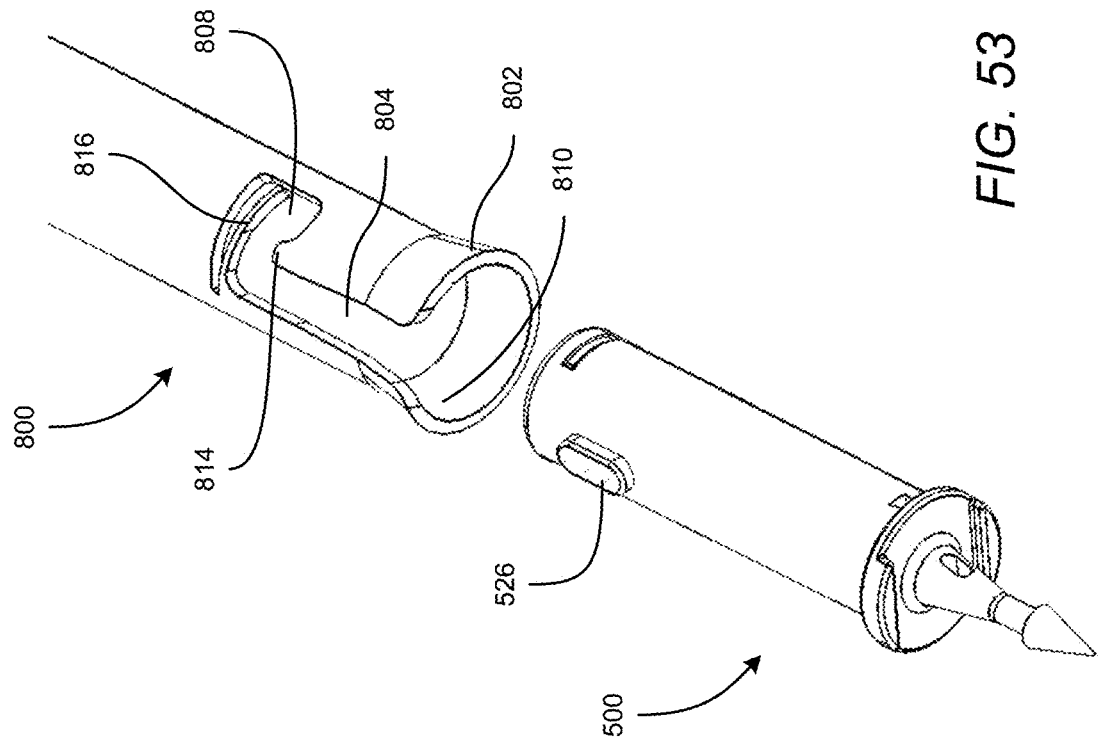
FIG. 53 is a perspective view of another example embodiment of an insertion tube for use with an ocular implant.

FIG. 53 shows another example embodiment of an insertion tube 800 for use with an implant 500, or with various other implants, as discussed herein. The insertion tube 800 can include a notch 814 and a biasing member 816 (e.g., a cantilever spring), which can facilitate the locking of the positioning protrusion 526 into the locking portion 808. To engage the locking portion 808, the positioning protrusion 526 can displace the biasing member 816 so that the positioning protrusion 526 can move past the notch 814 into the locking portion. To disengage from the locking portion 808, the user can press the insertion tube forward to displace the biasing member 816 while rotating the insertion tube 800 so that the positioning protrusion 526 can move past the notch 814 and exit the locking portion 808. Accordingly, the notch 814 and biasing member 816 can prevent or impede accidental disengagement of the locking portion 808.

Procedures

For delivery of some embodiments of the ocular implant, the implantation occurs in a closed chamber with or without viscoelastic.

The implants may be placed using an applicator, such as a pusher, or they may be placed using a delivery instrument having energy stored in the instrument, such as disclosed in U.S. Patent Publication 2004/0050392, filed Aug. 28, 2002, now U.S. Pat. No. 7,331,984, issued Feb. 19, 2008, the entirety of which is incorporated herein by reference and made a part of this specification and disclosure. In some embodiments, fluid may be infused through an applicator to create an elevated fluid pressure at the forward end of the implant to ease implantation.

In one embodiment of the invention, a delivery apparatus (or "applicator") similar to that used for placing a trabecular stent through a trabecular meshwork of an eye is used. Certain embodiments of such a delivery apparatus are disclosed in U.S. Patent Publication 2004/0050392, filed Aug. 28, 2002, now U.S. Pat. No. 7,331,984, issued Feb. 19, 2008; U.S. Publication No. 2002/0133168, entitled APPLICATOR AND METHODS FOR PLACING A TRABECULAR SHUNT FOR GLAUCOMA TREATMENT, now abandoned; and U.S. Provisional Application No. 60/276,609, filed Mar. 16, 2001, entitled APPLICATOR AND METHODS FOR PLACING A TRABECULAR SHUNT FOR GLAUCOMA TREATMENT, now expired, each of which is incorporated by reference and made a part of this specification and disclosure.

In one embodiment, the delivery apparatus 2000 includes a handpiece, an elongate tip, a holder and an actuator, which are schematically depicted in FIG. 20F. The handpiece 1000 has a distal end 1002 and a proximal end 1004. The elongate tip 1010 is connected to the distal end of the handpiece. The elongate tip has a distal portion and is configured to be placed through a corneal incision and into an anterior chamber of the eye. The holder 1020 (e.g., an insertion tube) is attached to the distal portion of the elongate tip. The holder is configured to hold and release the drug delivery implant. The actuator 1040 is on the handpiece and actuates the holder to release the drug delivery implant from the holder. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the drug delivery implant is being held by the holder, the spring being at least partially unloaded upon actuating the actuator, allowing for release of the drug delivery implant from the holder.

In various embodiments, the clamp comprises a plurality of claws configured to exert a clamping force onto at least the proximal portion of the drug delivery implant. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece. The delivery apparatus can further comprise an irrigation port in the elongate tip.

In some embodiments, the method includes using a delivery apparatus that comprises a handpiece having a distal end and a proximal end and an elongate tip connected to the distal end of the handpiece. The elongate tip has a distal portion and being configured to be placed through a corneal incision and into an anterior chamber of the eye. The apparatus further has a holder attached to the distal portion of the elongate tip, the holder being configured to hold and release the drug delivery implant, and an actuator on the handpiece that actuates the holder to release the drug delivery implant from the holder.

The delivery instrument may be advanced through an insertion site in the cornea and advanced either transocularly or posteriorly into the anterior chamber angle and positioned at base of the anterior chamber angle. Using the anterior chamber angle as a reference point, the delivery instrument can be advanced further in a generally posterior direction to drive the implant into the iris, inward of the anterior chamber angle.

Optionally, based on the implant structure, the implant may be laid within the anterior chamber angle, taking on a curved shape to match the annular shape of the anterior chamber angle.

In some embodiments, the implant may be brought into position adjacent the tissue in the anterior chamber angle or the iris tissue, and the pusher tube advanced axially toward the distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

The placement and implantation of the implant may be performed using a gonioscope or other conventional imaging equipment. In some embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

In one embodiment, the drug delivery implant is affixed to an additional portion of the iris or other intraocular tissue, to aid in fixating the implant. In one embodiment, this additional affixation may be performed with a biocompatible adhesive. In other embodiments, one or more sutures may be used. In another embodiment, the drug delivery implant is held substantially in place via the interaction of the implant body's outer surface and the surrounding tissue of the anterior chamber angle.

Figure 23:
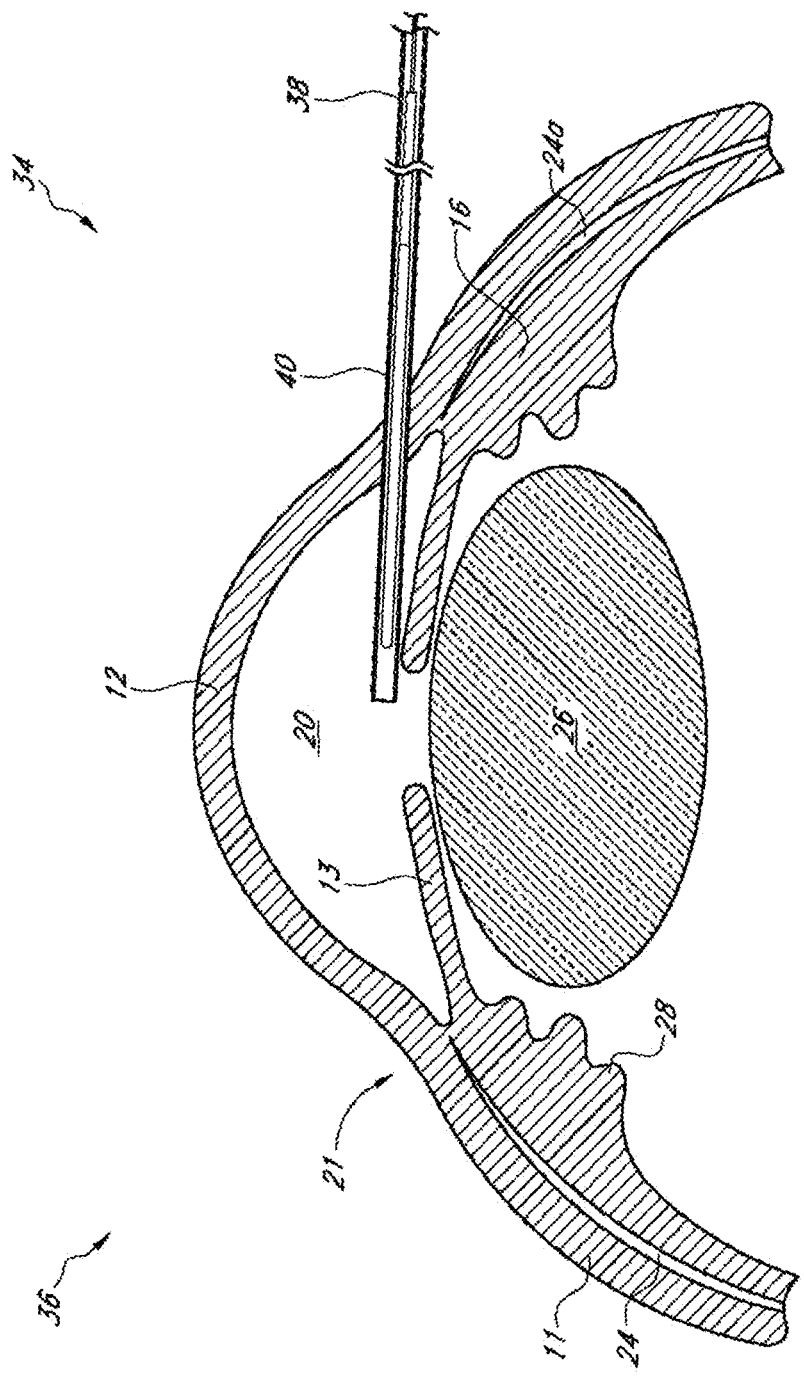
FIG. 23 illustrates a schematic cross-sectional view of an eye with a delivery device containing an implant being advanced across the anterior chamber. The size of the implant is exaggerated for illustration purposes.

FIG. 23 illustrates one embodiment of a surgical method for implanting the drug delivery implant into an eye, as described in the embodiments herein. A first incision or slit is made through the conjunctiva and the sclera 11 at a location rearward of the limbus 21, that is, posterior to the region of the sclera 11 at which the opaque white sclera 11 starts to become clear cornea 12. In some embodiments, the first incision is posterior to the limbus 21, including about 3 mm posterior to the limbus. In some embodiments, the incision is made such that a surgical tool may be inserted into the anterior chamber at a shallow angle (relative to the anteroposterior axis), as shown in FIG. 23. In other embodiments, the first incision may be made to allow a larger angle of instrument insertion (see, e.g. FIGS. 24-26). Also, the first incision is made slightly larger than the width of the drug delivery implant. In one embodiment, a conventional cyclodialysis spatula may be inserted through the first incision into the supraciliary space to confirm correct anatomic position.

A portion of the upper and lower surfaces of the drug delivery implant can be grasped securely by the surgical tool, for example, a forceps, so that the forward end of the implant is oriented properly. The implant may also be secured by viscoelastic or mechanical interlock with the pusher tube or wall of the implant delivery device. In one embodiment, the implant is oriented with a longitudinal axis of the implant being substantially co-axial to a longitudinal axis of the grasping end of the surgical tool. The drug delivery implant is disposed through the first incision.

The delivery instrument may be advanced from the insertion site transocularly into the anterior chamber angle and positioned at a location near the scleral spur. Using the scleral spur as a reference point, the delivery instrument can be advanced further in a generally posterior direction to drive the implant into eye tissue at a location just inward of the scleral spur toward the iris.

Optionally, based on the implant structure, the shearing edge of the insertion head of the implant can pass between the scleral spur and the ciliary body 16 posterior to the trabecular meshwork.

The drug delivery implant may be continually advanced posteriorly until a portion of its insertion head and the first end of the conduit is disposed within the anterior chamber 20 of the eye. Thus, the first end of the conduit is placed into fluid communication with the anterior chamber 20 of the eye. The distal end of the elongate body of the drug delivery implant can be disposed into the suprachoroidal space of the eye so that the second end of the conduit is placed into fluid communication with the suprachoroidal space. Alternatively, the implant may be brought into position adjacent the tissue in the anterior chamber angle, and the pusher tube advanced axially toward the distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

In one embodiment, the drug delivery implant is sutured to a portion of the sclera 11 to aid in fixating the implant. In one embodiment, the first incision is subsequently sutured closed. As one will appreciate, the suture used to fixate the drug delivery implant may also be used to close the first incision. In another embodiment, the drug delivery implant is held substantially in place via the interaction of the implant body's outer surface and the tissue of the sclera 11 and ciliary body 16 and/or choroid 12 without suturing the implant to the sclera 11. Additionally, in one embodiment, the first incision is sufficiently small so that the incision self-seals upon withdrawal of the surgical tool following implantation of the drug delivery implant without suturing the incision.

As discussed herein, in some embodiments the drug delivery implant additionally includes a shunt comprising a lumen configured provide a drainage device between the anterior chamber 20 and the suprachoroidal space. Upon implantation, the drainage device may form a cyclodialysis with the implant providing a permanent, patent communication of aqueous humor through the shunt along its length. Aqueous humor is thus delivered to the suprachoroidal space where it can be absorbed, and additional reduction in pressure within the eye can be achieved.

Figure 24:
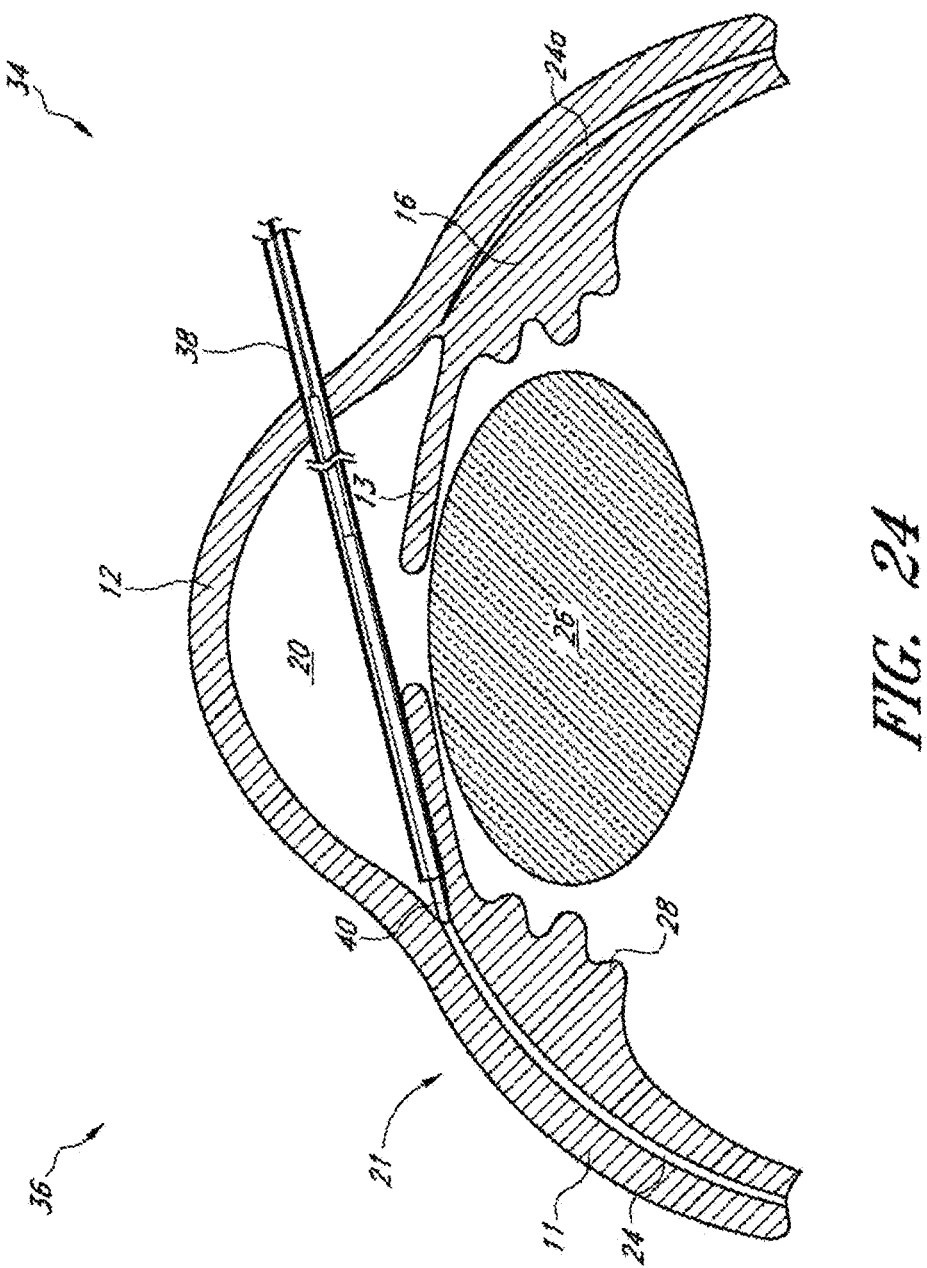
FIG. 24 illustrates an additional implantation procedure according to several embodiments disclosed herein. The size of the implant is exaggerated for illustration purposes.
Figure 25:
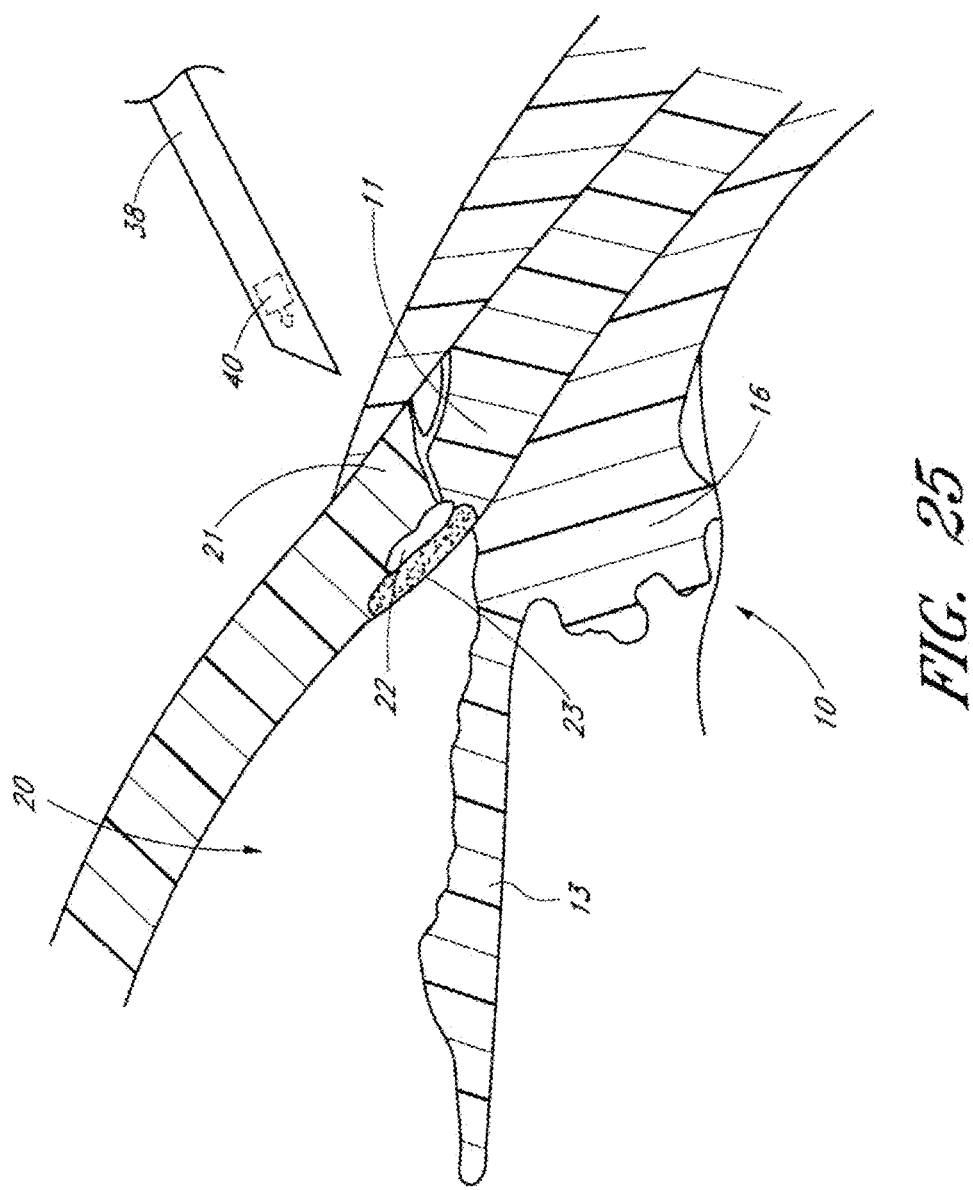
FIG. 25 illustrates a schematic cross-sectional view of an eye with a delivery device being advanced adjacent the anterior chamber angle. The size of the implant is exaggerated for illustration purposes.

In some embodiments it is desirable to deliver the drug delivery implant ab interno across the eye, through a small incision at or near the limbus (FIG. 24). The overall geometry of the system makes it advantageous that the delivery instrument incorporates a distal curvature, or a distal angle. In the former case, the drug delivery implant may be flexible to facilitate delivery along the curvature or may be more loosely held to move easily along an accurate path. In the latter case, the implant may be relatively rigid. The delivery instrument may incorporate an implant advancement element (e.g. pusher) that is flexible enough to pass through the distal angle.

Figure 26:
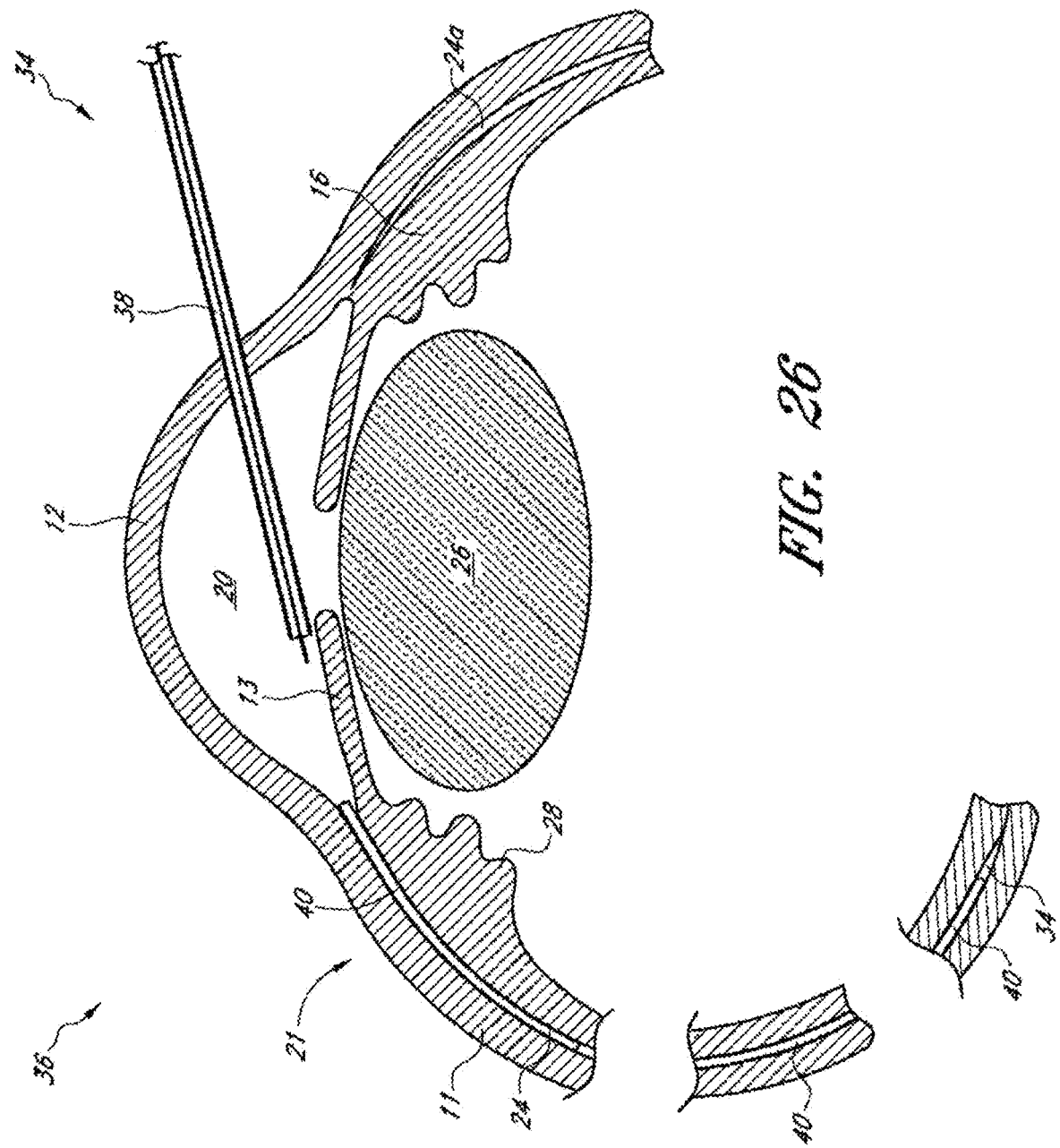
FIG. 26 illustrates a schematic cross-section view of an eye with a delivery device implanting an implant that extends from the anterior chamber through the suprachoroidal space and terminates in close proximity to the macula.

In some embodiments, the implant and delivery instrument are advanced together through the anterior chamber 20 from an incision at or near the limbus 21, across the iris 13, and through the ciliary muscle attachment until the drug delivery implant outlet portion is located in the uveoscleral outflow pathway (e.g. exposed to the suprachoroidal space defined between the sclera 11 and the choroid 12). FIG. 24 illustrates a transocular implantation approach that may be used with the delivery instrument inserted well above the limbus 21. In other embodiments (see, e.g., FIG. 25), the incision may be made more posterior and closer to the limbus 21. In one embodiment, the incision will be placed on the nasal side of the eye with the implanted location of the drug delivery implant 40 on the temporal side of the eye. In another embodiment, the incision may be made temporally such that the implanted location of the drug delivery implant is on the nasal side of the eye. In some embodiments, the operator simultaneously pushes on a pusher device while pulling back on the delivery instrument, such that the drug delivery implant outlet portion maintains its location in the posterior region of the suprachoroidal space near the macula 34, as illustrated in FIG. 26. The implant is released from the delivery instrument, and the delivery instrument retracted proximally. The delivery instrument is withdrawn from the anterior chamber through the incision.

In some embodiments, it is desirable to implant a drug delivery implant with continuous aqueous outflow through the fibrous attachment zone, thus connecting the anterior chamber 20 to the uveoscleral outflow pathway, in order to reduce the intraocular pressure in glaucomatous patients. In some embodiments, it is desirable to deliver the drug delivery implant with a device that traverses the eye internally (ab interno), through a small incision in the limbus 21.

In several embodiments, microinvasive methods of implanting a drug delivery implant are provided. In several such embodiments, an ab externo technique is utilized. In some embodiments, the technique is non-penetrating, thereby limiting the invasiveness of the implantation method. As discussed herein, in some embodiments, the drug delivery device that is implanted comprises a shunt. In some embodiments, such implants facilitate removal of fluid from a first location, while simultaneously providing drug delivery. In some embodiments, the implants communicate fluid from the anterior chamber to the suprachoroidal space, which assists in removing fluid (e.g., aqueous humor) from and reducing pressure increases in the anterior chamber.

In some embodiments (see e.g., FIG. 27), a window (e.g. a slit or other small incision) is surgically made through the conjunctiva and the sclera 11 to the surface of the choroid 28 (without penetration). In some embodiments, the slit is made perpendicular to the optical axis of the eye. In some embodiments, a depth stop is used in conjunction with an incising device. In certain embodiments, the incising device is one of a diamond or metal blade, a laser, or the like. In some embodiments, an initial incision is made with a sharp device, while the final portion of the incision to the choroid surface is made with a less sharp instrument, thereby reducing risk of injury to the highly vascular choroid. In some embodiments, the slit is created at or nearly at a tangent to the sclera, in order to facilitate entry and manipulation of an implant.

In some embodiments, a small core of sclera is removed at or near the pars planar, again, without penetration of the choroid. In order to avoid penetration of the choroid, scleral thickness can optionally be measured using optical coherence tomography (OCT), ultrasound, or visual fixtures on the eye during the surgical process. In such embodiments, the scleral core is removed by a trephining instrument (e.g., a rotary or static trephintor) that optionally includes a depth stop gauge to ensure an incision to the proper depth. In other embodiments, a laser, diamond blade, metal blade, or other similar incising device is used.

Figure 27D:
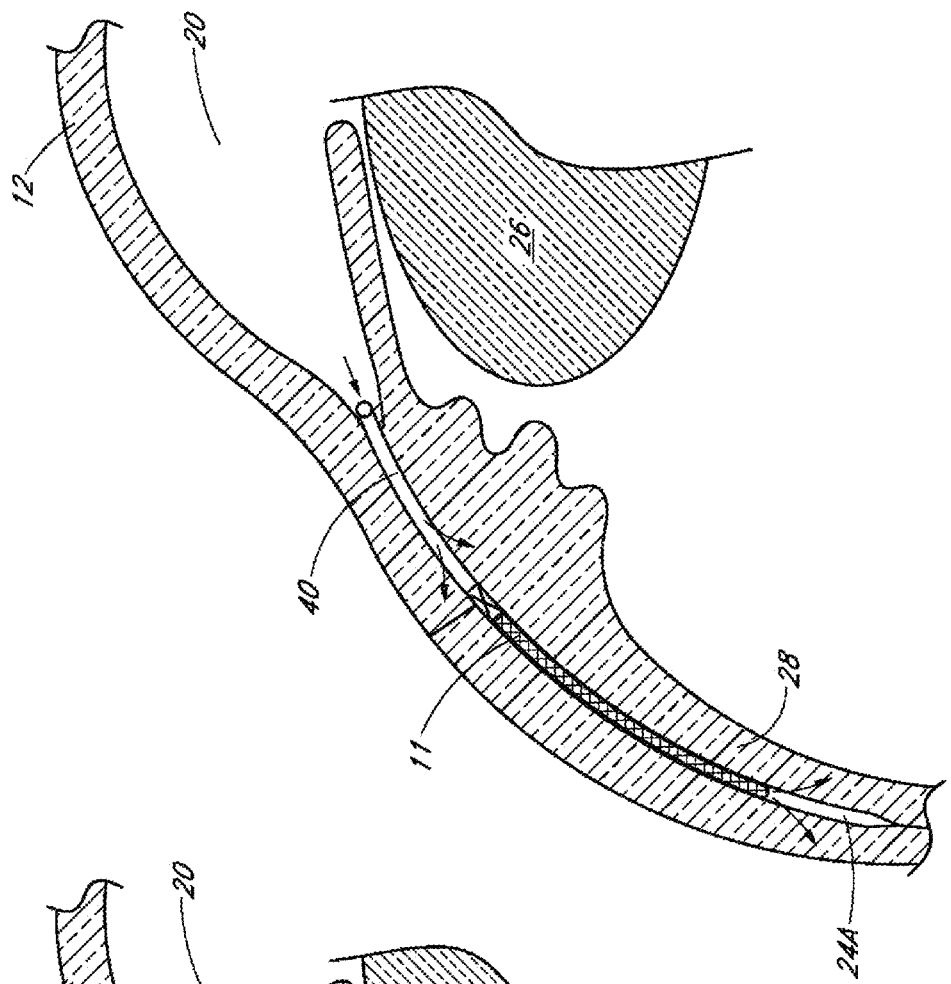
Figure 27C:
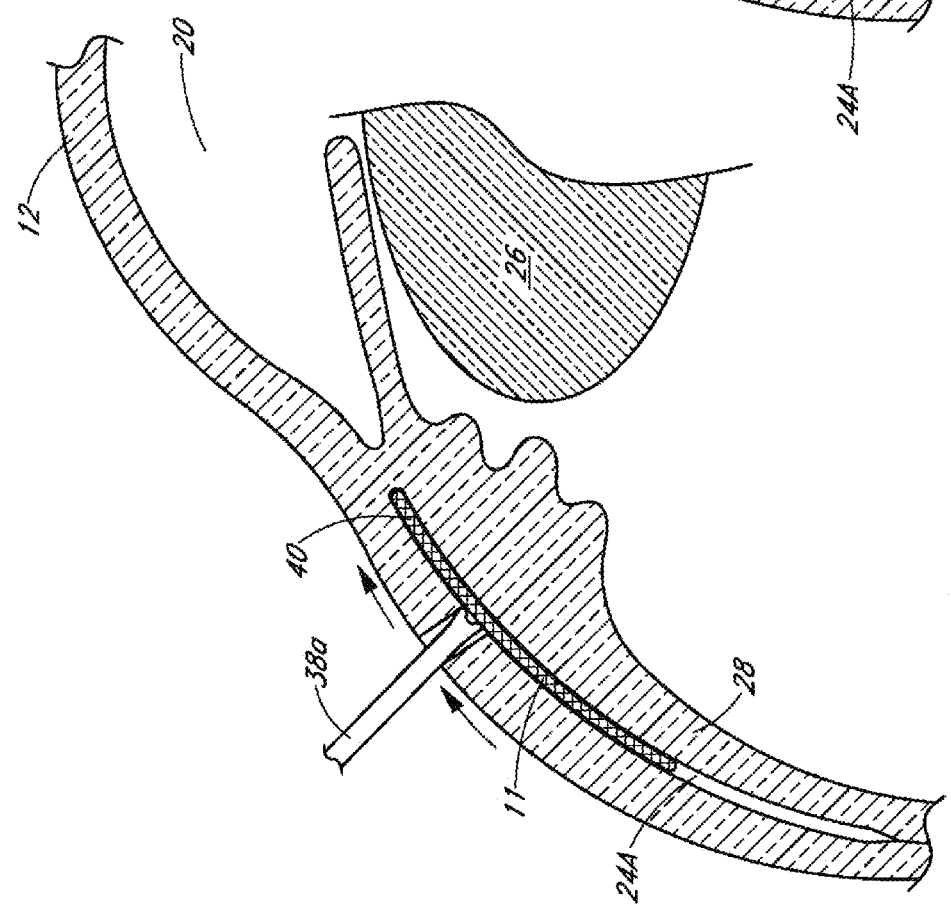

After a window or slit is made in the sclera and the suprachoroidal space is exposed, an implant 40 can be introduced into the window or slit and advanced in multiple directions through the use of an instrument 38a (see e.g., FIG. 27B-27C). Through the use of the instrument 38a, the implant 40 can be maneuvered in a posterior, anterior, superior, or inferior direction. The instrument 38a is specifically designed to advance the implant to the appropriate location without harming the choroid or other structures. The instrument 38a can then be removed and the implant 40 left behind. In some embodiments, the window in the conjunctiva and sclera is small enough to be a self-sealing incision. In some embodiments, it can be a larger window or slit which can be sealed by means of a suture, staple, tissue common wound adhesive, or the like. A slit or window according to these embodiments can be 1 mm or less in length or diameter, for example. In some embodiments, the length of the incision ranges from about 0.2 to about 0.4 mm, about 0.4 to about 0.6 mm, about 0.6 mm to about 0.8 mm, about 0.8 mm to about 1.0 mm, about 1.0 mm to about 1.5 mm, and overlapping ranges thereof. In some embodiments larger incision (slit or window) dimensions are used.

In several embodiments, the implant 40 is tubular or oval tubular in shape. In some embodiments, such a shape facilitates passage of the implant through the small opening. In some embodiments, the implant 40 has a rounded closed distal end, while in other embodiments, the distal end is open. In several embodiments wherein open ended implants are used, the open end is filled (e.g., blocked temporarily) by a portion of the insertion instrument in order to prevent tissue plugging during advancement of the implant (e.g., into the suprachoroidal space). In several embodiments, the implant is an implant as described herein and comprises a lumen that contains a drug which elutes through holes, pores, or regions of drug release in the implant. As discussed herein, drug elution, in some embodiments, is targeted towards the posterior of the eye (e.g., the macula or optic nerve), and delivers therapeutic agents (e.g., steroids or anti VEGFs) to treat retinal or optic nerve disease.

In several embodiments, the implant 40 and implantation instrument 38a is designed with an appropriate tip to allow the implant to be advanced in an anterior direction and penetrate into the anterior chamber without a scleral cut-down. In some embodiments, the tip that penetrates into the anterior chamber is a part of the implant while in some embodiments, it is part of the insertion instrument. In such embodiments, the implant functions as a conduit for aqueous humor to pass from the anterior chamber to the suprachoroidal space to treat glaucoma or ocular hypertension (e.g., a shunt). In several embodiments, the implant is configured to deliver a drug to the anterior chamber to treat glaucoma. In some embodiments, the drug is configured (e.g., produced) to elute over a relatively long period of time (e.g., weeks to months or even years). Non-liming examples of such agents are beta blockers or prostaglandins. In some embodiments, a single implant is inserted, while in other embodiments, two or more implants are implanted in this way, at the same or different locations and in any combination of aqueous humor conduit or drug delivery mechanisms.

Figure 28:
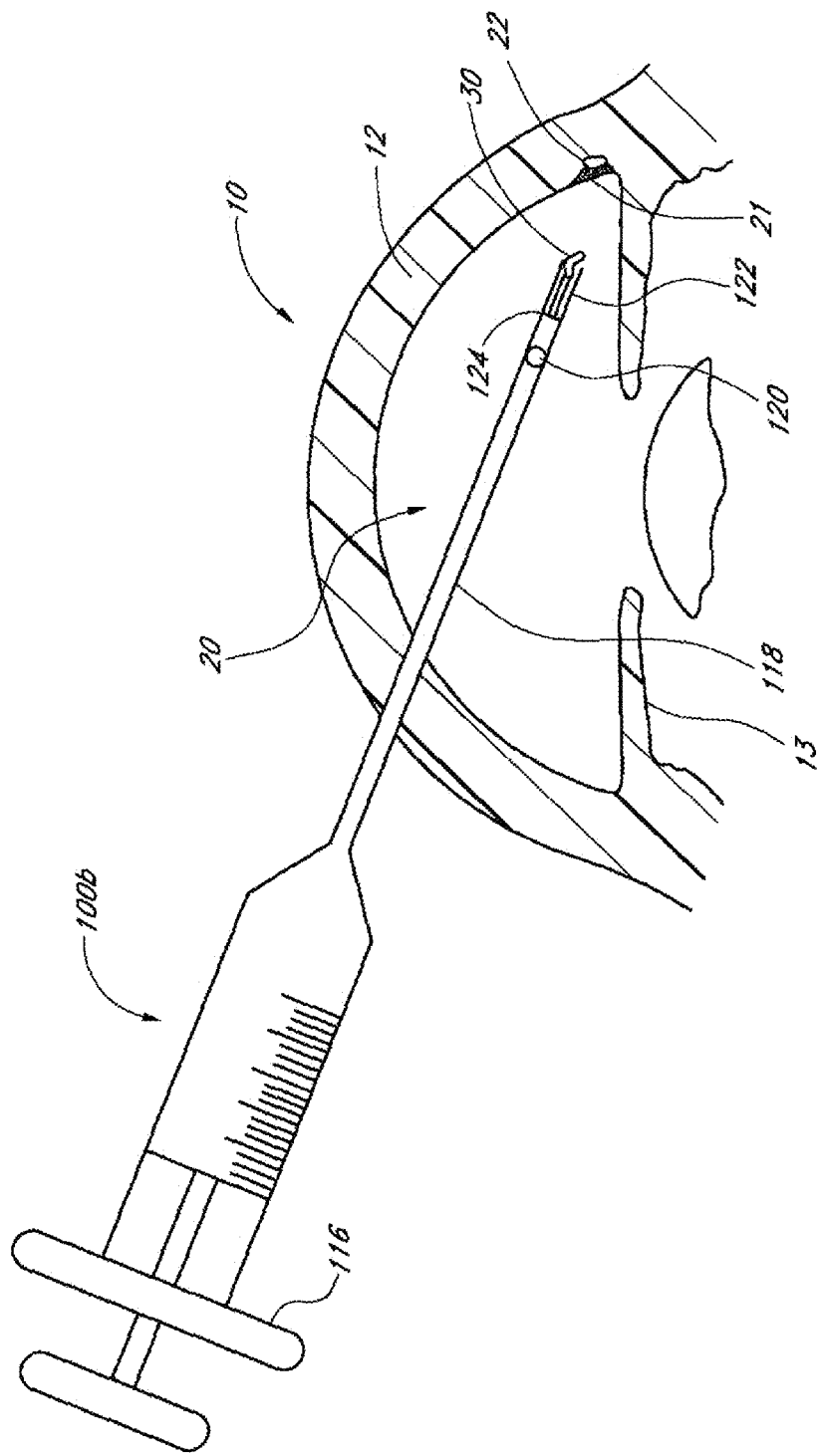
FIG. 28 illustrates a schematic cross-sectional view of an eye with a delivery device being advanced across the eye targeting the iris adjacent to the anterior chamber angle. The size of the shunt is exaggerated for illustration purposes.

FIG. 28 shows an illustrative transocular method for placing any of the various implant embodiments taught or suggested herein at the implant site within the eye 10. A delivery apparatus 100b generally comprises a syringe portion 116 and a cannula portion 118. The distal section of the cannula 118 optionally has at least one irrigating hole 120 and a distal space 122 for holding the drug delivery implant 30. The proximal end 124 of the lumen of the distal space 122 is sealed from the remaining lumen of the cannula portion 118. The delivery apparatus of FIG. 28 may be employed with the any of the various drug delivery implant embodiments taught or suggested herein. In some embodiments, the target implant site is the inferior portion of the iris. It should be understood that the angle of the delivery apparatus shown in FIG. 28 is illustrative, and angles more or less shallow than that shown may be preferable in some embodiments.

Figure 29:
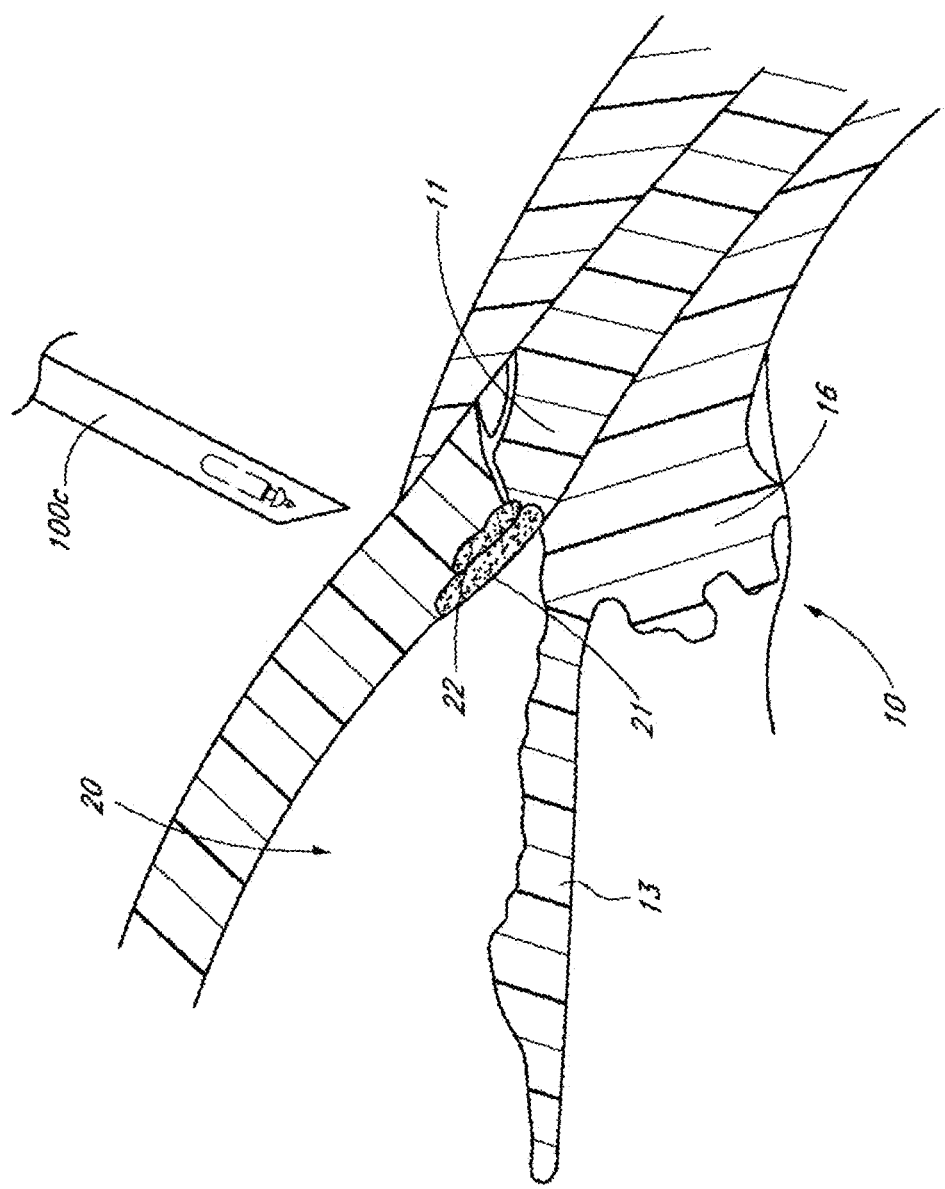
FIG. 29 illustrates a schematic cross-sectional view of an eye with another embodiment of a delivery device targeting the iris adjacent to the anterior chamber angle. The size of the shunt is exaggerated for illustration purposes.

FIG. 29 shows an illustrative method for placing any of the various implant embodiments taught or suggested herein at implant site on the same side of the eye. In one embodiment, the drug delivery implant is inserted into the anterior chamber 20 of the eye 10 to the iris with the aid of an applicator or delivery apparatus 100c that creates a small puncture in the eye from the outside. In some embodiments, the target implant site is the inferior portion of the iris.

Figure 30:
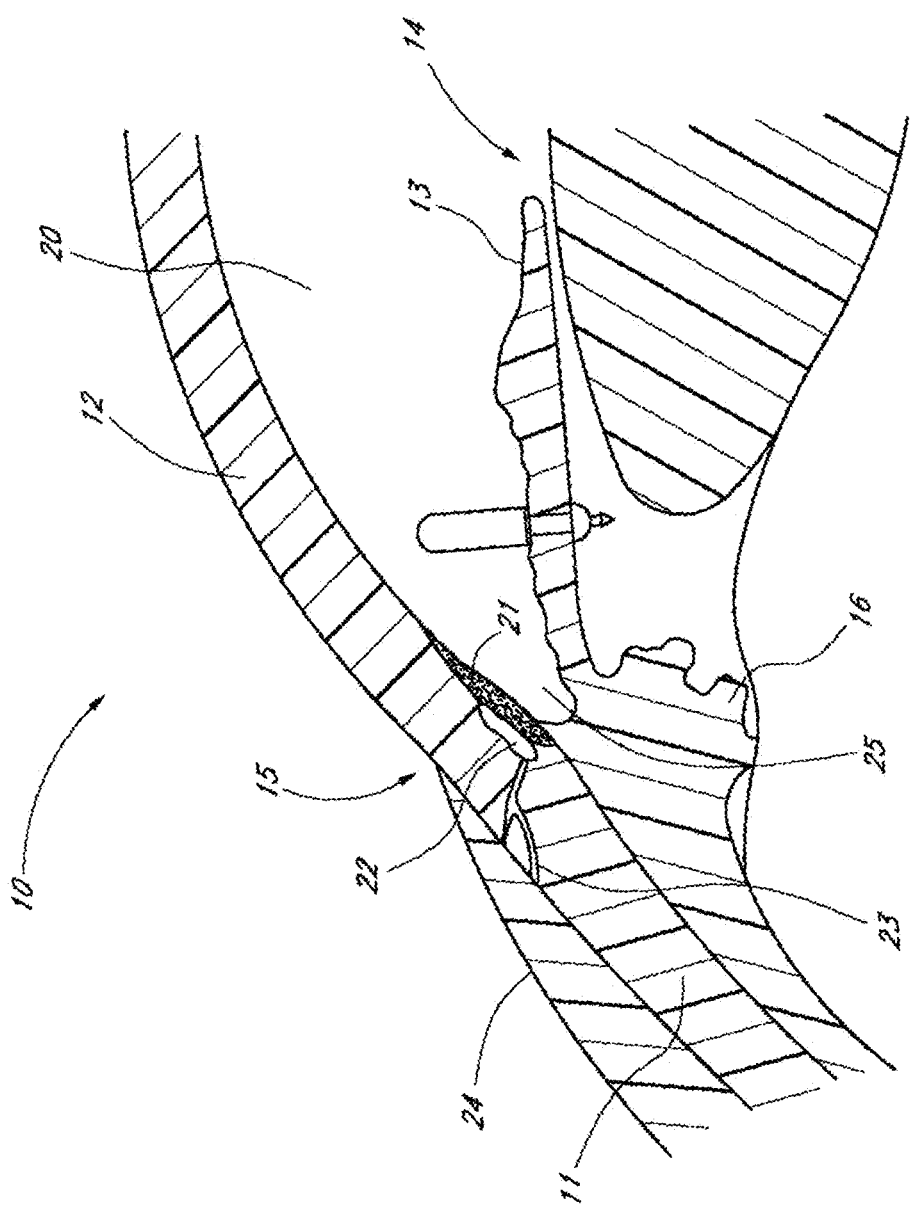
FIG. 30 illustrates a schematic cross-section view of an eye with an implant anchored to the iris.

FIG. 30 illustrates a drug delivery implant consistent with several embodiments disclosed herein affixed to the iris 13 of the eye 10 consistent with several implantation methods disclosed herein. It shall be appreciated that the iris is but one of many tissues that an implant as described here may be anchored to.

Figure 31:
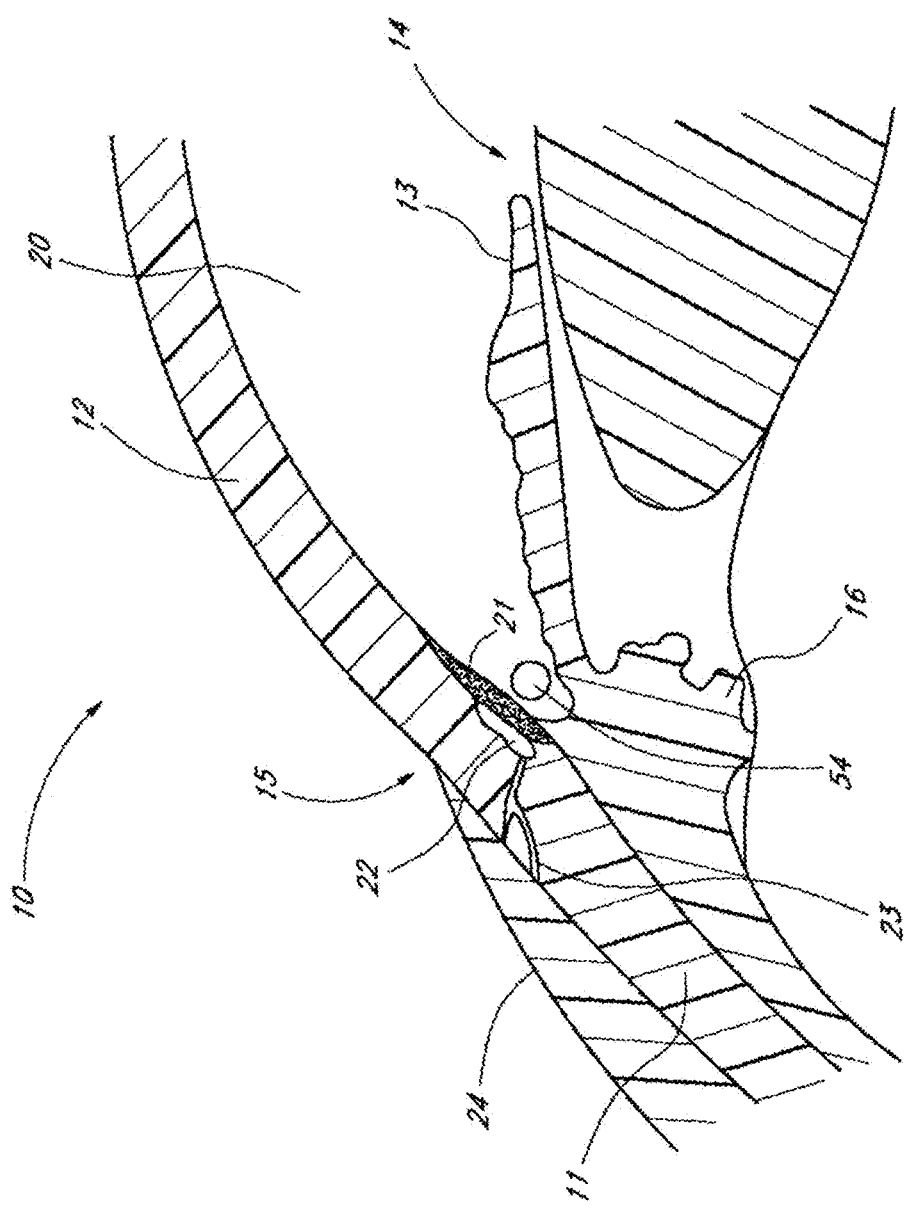
FIG. 31 illustrates a schematic cross-section view of an eye with an implant implanted in the anterior chamber angle.

FIG. 31 illustrates another possible embodiment of placement of a drug delivery implant consistent with several embodiments disclosed herein. In one embodiment, the outer shell 54 of an implant consistent with several embodiments disclosed herein is shown (in cross section) positioned in the anterior chamber angle. In one embodiment, the transocular delivery method and apparatus may be used to position the drug delivery implant wholly within the anterior chamber angle, wherein the drug delivery implant substantially tracks the curvature of the anterior angle. In some embodiments, the implant is positioned substantially within the anterior chamber angle along the inferior portion of the iris.

In some embodiments, the placement of the implant may result in the drug target being upstream of the natural flow of aqueous humor in the eye. For example, aqueous humor flows from the ciliary processes to the anterior chamber angle, which, based on the site of implantation in certain embodiments, may create a flow of fluid against which a drug released from an implant may have to travel in order to make contact with a target tissue. Thus, in certain embodiments, for example when the target tissue is the ciliary processes, eluted drug must diffuse through iris tissue to get from the anterior chamber to target receptors in the ciliary processes in the posterior chamber. The requirement for diffusion of drug through the iris, and the flow of the aqueous humor, in certain instances, may limit the amount of eluted drug reaching the ciliary body.

To overcome these issues, certain embodiments involve placement of a peripheral iridotomy (PI), or device-stented PI, at a location adjacent to a drug eluting implant to facilitate delivery of a drug directly to the intended site of action (i.e., the target tissue). The creation of a PI opens a relatively large communication passage between the posterior and anterior chambers. While a net flow of aqueous humor from the posterior chamber to the anterior chamber still exists, the relatively large diameter of the PI substantially reduces the linear flow velocity. Thus, eluted drug is able to diffuse through the PI without significant opposition from flow of aqueous humor. In certain such embodiments, a portion of the implant is structured to penetrate the iris and elute the drug directly into the posterior chamber at the ciliary body. In other embodiments, the implant is implanted and/or anchored in the iris and elutes drug directly to the posterior chamber and adjacent ciliary body.

Figure 22:
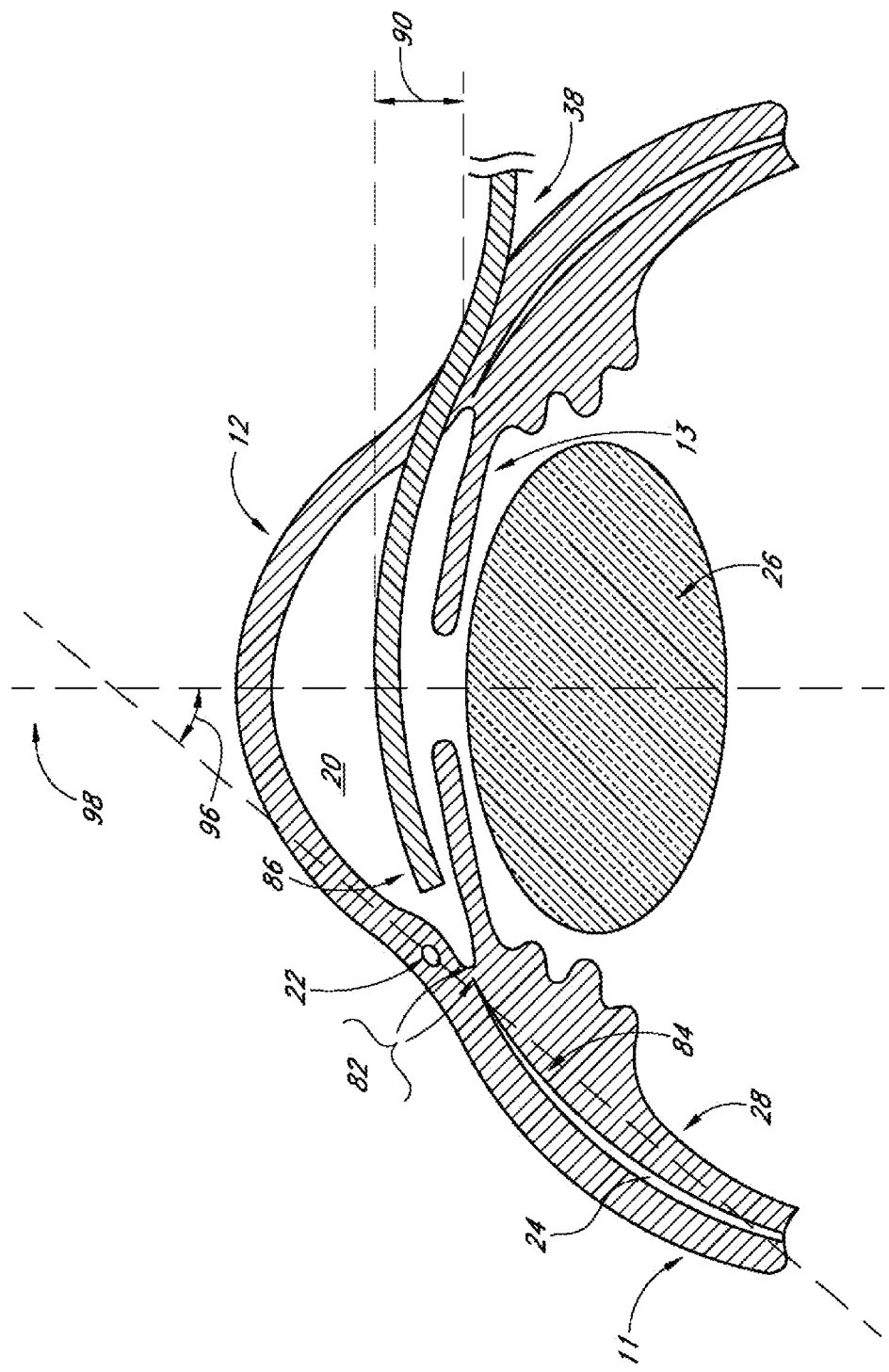
FIG. 22 illustrates another apparatus for implanting a drug delivery device in accordance with embodiments disclosed herein.

FIG. 22 shows a meridional section of the anterior segment of the human eye and schematically illustrates another embodiment of a delivery instrument 38 that may be used with embodiments of drug delivery implants described herein. In FIG. 22, arrows 82 show the fibrous attachment zone of the ciliary muscle 84 to the sclera 11. The ciliary muscle 84 is coextensive with the choroid 28. The suprachoroidal space is the interface between the choroid 28 and the sclera 11. Other structures in the eye include the lens 26, the cornea 12, the anterior chamber 20, the iris 13, and Schlemm's canal 22.

The delivery instrument/implant assembly can be passed between the iris 13 and the cornea 12 to reach the iridocorneal angle. Therefore, the height of the delivery instrument/shunt assembly (dimension 90 in FIG. 22) is less than about 3 mm in some embodiments, and less than 2 mm in other embodiments.

The suprachoroidal space between the choroid 28 and the sclera 11 generally forms an angle 96 of about 55° with the optical axis 98 of the eye. This angle, in addition to the height requirement described in the preceding paragraph, are features to consider in the geometrical design of the delivery instrument/implant assembly.

The overall geometry of the drug delivery implant system makes it advantageous that the delivery instrument 38 incorporates a distal curvature 86, as shown in FIG. 22, a distal angle 88, as shown in FIG. 21, or a combination thereof. The distal curvature (FIG. 23) is expected to pass more smoothly through the corneal or scleral incision at the limbus. In this embodiment, the drug delivery implant may be curved or flexible. Alternatively, in the design of FIG. 21, the drug delivery implant may be mounted on the straight segment of the delivery instrument, distal of the "elbow" or angle 88. In this case, the drug delivery implant may be straight and relatively inflexible, and the delivery instrument may incorporate a delivery mechanism that is flexible enough to advance through the angle. In some embodiments, the drug delivery implant may be a rigid tube, provided that the implant is no longer than the length of the distal segment 92.

The distal curvature 86 of delivery instrument 38 may be characterized as a radius of between about 10 to 30 mm in some embodiments, and about 20 mm in certain embodiments. The distal angle of the delivery instrument in an embodiment as depicted in FIG. 21 may be characterized as between about 90 to 170 degrees relative to an axis of the proximal segment 94 of the delivery instrument. In other embodiments, the angle may be between about 145 and about 170 degrees. The angle incorporates a small radius of curvature at the "elbow" so as to make a smooth transition from the proximal segment 94 of the delivery instrument to the distal segment 92. The length of the distal segment 92 may be approximately 0.5 to 7 mm in some embodiments, and about 2 to 3 mm in certain embodiments.

In some embodiments, a viscoelastic, or other fluid is injected into the suprachoroidal space to create a chamber or pocket between the choroid and sclera which can be accessed by a drug delivery implant. Such a pocket exposes more of the choroidal and scleral tissue area, provides lubrication and protection for tissues during implantation, and increases uveoscleral outflow in embodiments where the drug delivery implant includes a shunt, causing a lower intraocular pressure (IOP). In some embodiments, the viscoelastic material is injected with a 25 or 27 G cannula, for example, through an incision in the ciliary muscle attachment or through the sclera (e.g. from outside the eye). The viscoelastic material may also be injected through the implant itself either before, during or after implantation is completed.

In some embodiments, a hyperosmotic agent is injected into the suprachoroidal space. Such an injection can delay TOP reduction. Thus, hypotony may be avoided in the acute postoperative period by temporarily reducing choroidal absorption. The hyperosmotic agent may be, for example glucose, albumin, HYPAQUE™ medium, glycerol, or poly(ethylene glycol). The hyperosmotic agent can breakdown or wash out as the patient heals, resulting in a stable, acceptably low IOP, and avoiding transient hypotony.

Figure 54:
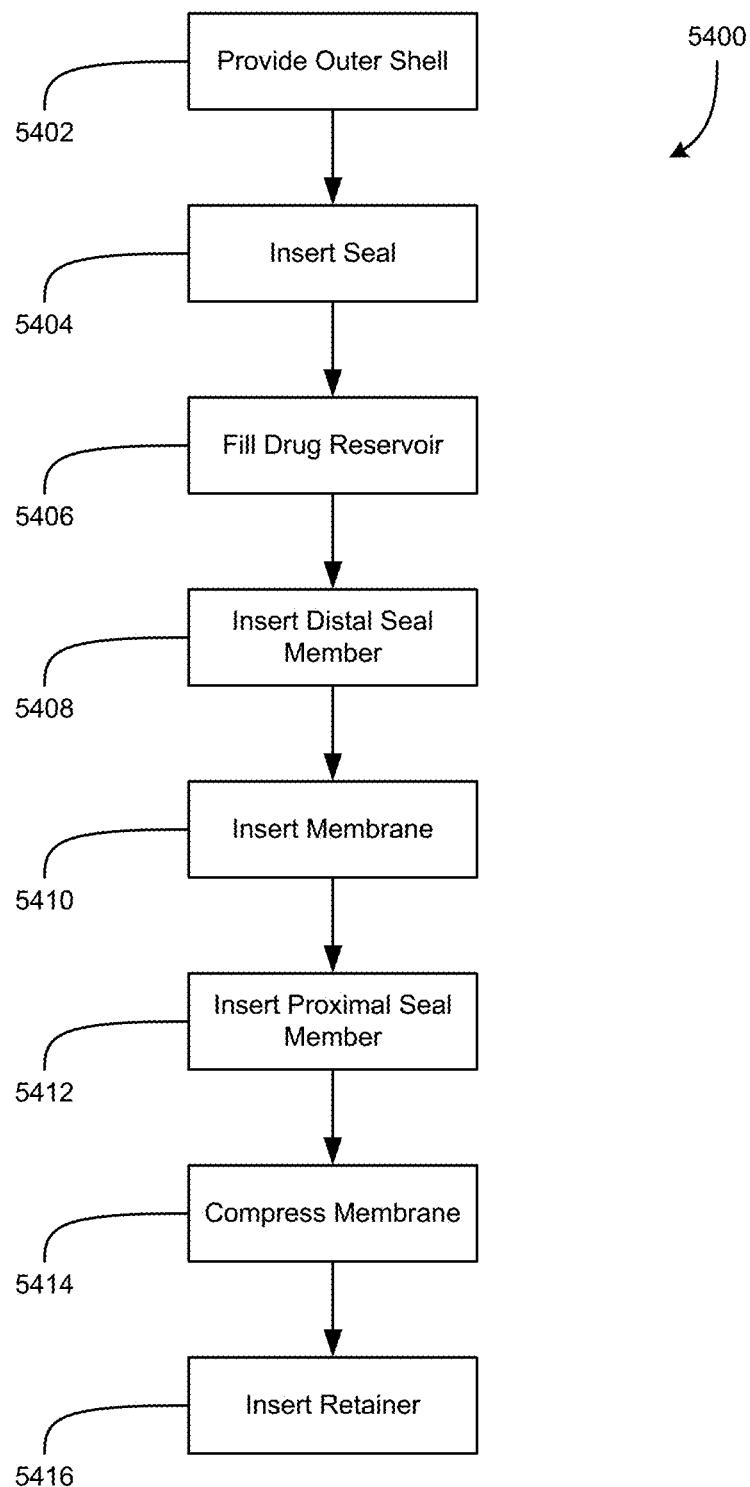
FIG. 54 is a flowchart of an example embodiment of a method for preparing a drug delivery ocular implant.

FIG. 54 is a flowchart showing an example embodiment of a method 5400 for preparing a drug delivery ocular implant, such as the implants 500, 600, or 700 or any other suitable ocular implant disclosed herein. The description of method 5400 will be discussed in connection with the implant 500, although similar methods can be used in connection with implants 600 and 700 as well as with other embodiments disclosed herein. At block 5402 the outer shell 506 is provided. Providing the outer shell 506 can include opening a package and removing an outer shell from its packaging, picking an outer shell 506 out of a container, selecting one of several outer shells for using the method 5400, or otherwise accessing an outer shell 506. Providing the outer shell 506 does not require that the performer of the method 5400 manufacture the outer shell 506. At block 5404, the seal 528 is inserted to seal off the drug reservoir 508 from the drainage pathway (e.g., the inflow pathway 512). In some embodiments, a lubricant can be applied to the seal 528 (e.g., to the O-ring 534) and/or to the interior of the shell 506, to facilitate insertion of the seal 528. In some embodiments, the barrier 540 and the O-ring 534 can be coupled to the seal base 536 and the seal assembly 528 can be inserted into the shell 506, or the barrier 540 can be inserted separately from the base 536 and O-ring 534. In some embodiments, a tool can be used to press the seal 528 distally until it abuts the distal end of the interior chamber 508.

At block 5406 the drug reservoir (e.g., the interior chamber 508) is filled with the drug. In some embodiments, the interior chamber 508 is filled with a precise volume of the drug that is configured to enable the implant to be sealed with no air or substantially no air in the drug reservoir. In some instances, implants with substantially no air in the drug reservoir can refer to implants that include small amounts of air (e.g., air bubbles with a diameter of not more than 10% or 25% of the diameter of the internal chamber 508). It can be undesirable to have air in the drug reservoir. For example, in some instances, air adjacent to the membrane can interfere with elution of the drug (e.g., by interfering with the osmotic pressure across the membrane). In some embodiments, the drug reservoir is not overfilled, such that the drug is not wasted. In some embodiments, the drug reservoir can be overfilled with the drug, which can result in some wasted amount of the drug, but can facilitate preparation of the implants with no air or substantially no air in the drug reservoir.

At block 5408, the distal seal member 552 is inserted. The distal seal member 552 can be seated against the shelf 548, as discussed herein. The membrane 554 can be inserted over the distal seal member 552, at block 5410. At block 5412, the proximal seal member 556 can be inserted over the membrane 554. In some cases, the distal seal member 552, the membrane 554, and/or the proximal seal member 556 can be inserted together (e.g., as an assembly after being coupled together). At block 5414, the membrane 554 can be compressed. For example, a force in the distal direction can be applied to the proximal seal member 556 (e.g., using a tool), which can compress the membrane 554 between the distal seal member 552 and the proximal seal member 556. In some embodiments, the same tool that inserts the proximal seal member 556 into the shell 506 (e.g., along with the membrane 554 and/or distal seal 552 can be used to apply distal force to compress the membrane 554. For example, the tool can advance to insert the proximal seal member 556 into the shell 506 and the tool can continue to advance distally to compress the membrane 554. In some embodiments, in which the drug reservoir was overfilled, blocks 5408, 5410, 5412, and/or 5414 can cause drug to overflow from the drug reservoir (e.g., out of the proximal end of the shell 506).

At block 5416, the retainer 532 is inserted over the proximal seal member 556 (e.g., via one of the slots 550). The slots 550 can engage the retainer 532 to prevent the compressed membrane 554 from pushing the retainer 532 proximally out of the shell 506. The tabs 564 can be bent down to engage the proximal seal member 556 to secure the retainer 532, as discussed herein.

In some cases, the method 5400 can include additional steps, not shown in FIG. 54. For example, if the implant was overfilled and some of the drug overflowed from the drug reservoir, the implant can be cleaned (e.g., wiped, swapped, rinsed). In some embodiments, a heparin coating can be applied to some or all of the implant (e.g., to the retention protrusion 510). In some embodiments, the implant can be sterilized. In some embodiments, steps of the method 5400 can be omitted, combined, divided into multiple steps, and additional steps can be added. In some embodiments that do not include drainage pathways, block 5404 can be omitted.

Many alternatives and variations are possible. For example, in some cases, assembly of the embodiment shown in FIGS. 18R and 18S can include providing an outer shell 54, filling the drug reservoir (e.g., similar to block 5406 of method 5400). A cap 54a with a membrane 60 can be applied over the proximal end of the shell 54. In some embodiments, the cap 54a can be advanced distally until a desired amount of membrane 60 compression (e.g., 30 microns or any other suitable amount as discussed herein) is achieved, and the cap 54a can then be crimped onto the shell 54. In some embodiments, a micrometer can be used to determine the amount of membrane compression. In some embodiments, shell 54 includes a groove, and the cap 54a can be crimped into the groove. In some embodiments, the cap 54a and/or shell 54 can spin during the crimping of the cap 54a onto the shell 54, for example, such that all sides of the cap 54a are crimped.

Controlled Drug Release

The drug delivery implants as described herein, function to house a drug and provide drug elution from the implant in a controlled fashion, based on the design of the various components of the implant, for an extended period of time. Various elements of the implant composition, implant physical characteristics, implant location in the eye, and the composition of the drug work in combination to produce the desired drug release profile.

As described above the drug delivery implant may be made from any biological inert and biocompatible materials having desired characteristics. Desirable characteristics, in some embodiments, include permeability to liquid water or water vapor, allowing for an implant to be manufactured, loaded with drug, and sterilized in a dry state, with subsequent rehydration of the drug upon implantation. Also desirable is an implant constructed of a material comprising microscopic porosities between polymer chains. These porosities may interconnect, which forms channels of water through the implant material. In several embodiments, the resultant channels are convoluted and thereby form a tortuous path which solublized drug travels during the elution process. Implant materials advantageously also possess sufficient permeability to a drug such that the implant may be a practical size for implantation. Thus, in several embodiments, the implant material is sufficiently permeable to the drug to be delivered that the implant is dimensioned to reside wholly contained within the eye of a subject. Implant material also ideally possesses sufficient elasticity, flexibility and potential elongation to not only conform to the target anatomy during and after implantation, but also remain unkinked, untorn, unpunctured, and with a patent lumen during and after implantation. In several embodiments, implant material would advantageously processable in a practical manner, such as, for example, by molding, extrusion, thermoforming, and the like.

Illustrative, examples of suitable materials for the outer shell include polypropylene, polyimide, glass, nitinol, polyvinyl alcohol, polyvinyl pyrolidone, collagen, chemically-treated collagen, polyethersulfone (PES), poly(styrene-isobutyl-styrene), polyurethane, ethyl vinyl acetate (EVA), polyetherether ketone (PEEK), Kynar (Polyvinylidene Fluoride; PVDF), Polytetrafluoroethylene (PTFE), Polymethylmethacrylate (PMMA), Pebax, acrylic, polyolefin, polydimethylsiloxane and other silicone elastomers, polypropylene, hydroxyapetite, titanium, gold, silver, platinum, other metals and alloys, ceramics, plastics and mixtures or combinations thereof. Additional suitable materials used to construct certain embodiments of the implant include, but are not limited to, poly(lactic acid), poly(tyrosine carbonate), polyethylene-vinyl acetate, poly(L-lactic acid), poly(D,L-lactic-co-glycolic acid), poly(D,L-lactide), poly(D,L-lactide-co-trimethylene carbonate), collagen, heparinized collagen, poly(caprolactone), poly(glycolic acid), and/or other polymer, copolymers, or block co-polymers, polyester urethanes, polyester amides, polyester ureas, polythioesters, thermoplastic polyurethanes, silicone-modified polyether urethanes, poly(carbonate urethane), or polyimide. Thermoplastic polyurethanes are polymers or copolymers which may comprise aliphatic polyurethanes, aromatic polyurethanes, polyurethane hydrogel-forming materials, hydrophilic polyurethanes (such as those described in U.S. Pat. No. 5,428,123, which is incorporated in its entirety by reference herein), or combinations thereof. Non-limiting examples include elasthane (poly(ether urethane)) such as Elasthane™ 80A, Lubrizol, Tecophilic™, Pellethane™, Carbothane™, Tecothane™, Tecoplast™, and Estane™. In some embodiments, polysiloxane-containing polyurethane elastomers are used, which include Carbosil™ 20 or Pursil™ 20 80A, Elast-Eon™, and the like. Hydrophilic and/or hydrophobic materials may be used. Non-limiting examples of such elastomers are provided in U.S. Pat. No. 6,627,724, which is incorporated in its entirety by reference herein. Poly(carbonate urethane) may include Bionate™ 80A or similar polymers. In several embodiments, such silicone modified polyether urethanes are particularly advantageous based on improved biostability of the polymer imparted by the inclusion of silicone. In addition, in some embodiments, oxidative stability and thrombo-resistance is also improved as compared to non-modified polyurethanes. In some embodiments, there is a reduction in angiogenesis, cellular adhesion, inflammation, and/or protein adsorption with silicone-modified polyether urethanes. In other embodiments, should angiogenesis, cellular adhesion or protein adsorption (e.g., for assistance in anchoring an implant) is preferable, the degree of silicone (or other modifier) may be adjusted accordingly. Moreover, in some embodiments, silicone modification reduces the coefficient of friction of the polymer, which reduces trauma during implantation of devices described herein. In some embodiments, silicone modification, in addition to the other mechanisms described herein, is another variable that can be used to tailor the permeability of the polymer. Further, in some embodiments, silicone modification of a polymer is accomplished through the addition of silicone-containing surface modifying endgroups to the base polymer. In other embodiments, flurorocarbon or polyethylene oxide surface modifying endgroups are added to a based polymer. In several embodiments, one or more biodegradable materials are used to construct all or a portion of the implant, or any other device disclosed herein. Such materials include any suitable material that degrades or erodes over time when placed in the human or animal body, whether due to a particular chemical reaction or enzymatic process or in the absence of such a reaction or process. Accordingly, as the term is used herein, biodegradable material includes bioerodible materials. In such biodegradable embodiments, the degradation rate of the biodegradable outer shell is another variable (of many) that may be used to tailor the drug elution rate from an implant.

In some embodiments, such as where the drug is sensitive to moisture (e.g. liquid water, water vapor, humidity) or where the drug's long term stability may be adversely affected by exposure to moisture, it may be desirable to utilize a material for the implant or at least a portion of the implant, which is water resistant, water impermeable or waterproof such that it presents a significant barrier to the intrusion of liquid water and/or water vapor, especially at or around human body temperature (e.g. about 35-40° C. or 37° C.). This may be accomplished by using a material that is, itself, water resistant, water impermeable or waterproof.

In some circumstances, however, even materials that are generally considered water impermeable may still allow in enough water to adversely affect the drug within an implant. For example, it may be desirable to have 5% by weight of the drug or less water intrusion over the course of a year. In one embodiment of implant, this would equate to a water vapor transmission rate for a material of about $1 \times 10^{-3}$ g/m$^2$/day or less. This may be as much as one-tenth of the water transmission rate of some polymers generally considered to be water resistant or water impermeable. Therefore, it may be desirable to increase the water resistance or water impermeability of a material.

The water resistance or water impermeability of a material may be increased by any suitable method. Such methods of treatment include providing a coating for a material (including by lamination) or by compounding a material with a component that adds water resistance or increases impermeability. For example, such treatment may be performed on the implant (or portion of the implant) itself, it may be done on the material prior to fabrication (e.g. coating a polymeric tube), or it may be done in the formation of the material itself (e.g. by compounding a resin with a material prior to forming the resin into a tube or sheet). Such treatment may include, without limitation, one or more of the following: coating or laminating the material with a hydrophobic polymer or other material to increase water resistance or impermeability; compounding the material with hydrophobic or other material to increase water resistance or impermeability; compounding or treating the material with a substance that fills microscopic gaps or pores within the material that allow for ingress of water or water vapor; coating and/or compounding the material with a water scavenger or hygroscopic material that can absorb, adsorb or react with water so as to increase the water resistance or impermeability of the material.

One type of material that may be employed as a coating to increase water resistance and/or water impermeability is an inorganic material. Inorganic materials include, but are not limited to, metals, metal oxides and other metal compounds (e.g. metal sulfides, metal hydrides), ceramics, and main group materials and their compounds (e.g. carbon (e.g. carbon nanotubes), silicon, silicon oxides). Examples of suitable materials include aluminum oxides (e.g. $Al_2O_3$) and silicon oxides (e.g. $SiO_2$). Inorganic materials may be advantageously coated onto a material (at any stage of manufacture of the material or implant) using techniques such as are known in the art to create extremely thin coatings on a substrate, including by vapor deposition, atomic layer deposition, plasma deposition, and the like. Such techniques can provide for the deposition of very thin coatings (e.g. about 20 nm-40 nm thick, including about 25 nm thick, about 30 nm thick, and about 35 nm thick) on substrates, including polymeric substrates, and can provide a coating on the exterior and/or interior luminal surfaces of small tubing, including that of the size suitable for use in implants disclosed herein. Such coatings can provide excellent resistance to the permeation of water or water vapor while still being at least moderately flexible so as not to undesirably compromise the performance of an implant in which flexibility is desired.

The drugs carried by the drug delivery implant may be in any form that can be reasonably retained within the device and results in controlled elution of the resident drug or drugs over a period of time lasting at least several days and in some embodiments up to several weeks, and in certain preferred embodiments, up to several years. Certain embodiments utilize drugs that are readily soluble in ocular fluid, while other embodiments utilize drugs that are partially soluble in ocular fluid.

For example, the therapeutic agent may be in any form, including but not limited to a compressed pellet, a solid, a capsule, multiple particles, a liquid, a gel, a suspension, slurry, emulsion, and the like. In certain embodiments, drug particles are in the form of micro-pellets (e.g., micro-tablets), fine powders, or slurries, each of which has fluid-like properties, allowing for recharging by injection into the inner lumen(s). As discussed above, in some embodiments, the loading and/or recharging of a device is accomplished with a syringe/needle, through which the therapeutic agent is delivered. In some embodiments, micro-tablets are delivered through a needle of about 23 gauge to about 32 gauge, including 23-25 gauge, 25 to 27 gauge, 27-29 gauge, 29-30 gauge, 30-32 gauge, and overlapping ranges thereof. In some embodiments, the needle is 23, 24, 25, 26, 27, 28, 29, 30, 31, or 32 gauge.

When more than one drug is desired for treatment of a particular pathology or when a second drug is administered such as to counteract a side effect of the first drug, some embodiments may utilize two agents of the same form. In other embodiments, agents in different form may be used. Likewise, should one or more drugs utilize an adjuvant, excipient, or auxiliary compound, for example to enhance stability or tailor the elution profile, that compound or compounds may also be in any form that is compatible with the drug and can be reasonably retained with the implant.

In some embodiments, treatment of particular pathology with a drug released from the implant may not only treat the pathology, but also induce certain undesirable side effects. In some cases, delivery of certain drugs may treat a pathological condition, but indirectly increase intraocular pressure. Steroids, for example, may have such an effect. In certain embodiments, a drug delivery shunt delivers a steroid to an ocular target tissue, such as the retina or other target tissue as described herein, thereby treating a retinal pathology but also possibly inducing increased intraocular pressure which may be due to local inflammation or fluid accumulation. In such embodiments, the shunt feature reduces undesirable increased intraocular pressure by transporting away the accumulated fluid. Thus, in some embodiments, implants functioning both as drug delivery devices and shunts can not only serve to deliver a therapeutic agent, but simultaneously drain away accumulated fluid, thereby alleviating the side effect of the drug. Such embodiments can be deployed in an ocular setting, or in any other physiological setting where delivery of a drug coordinately causes fluid accumulation which needs to be reduced by the shunt feature of the implant. In some such embodiments, drainage of the accumulated fluid is necessary to avoid tissue damage or loss of function, in particular when the target tissue is pressure sensitive or has a limited space or capacity to expand in response to the accumulated fluid. The eye and the brain are two non-limiting examples of such tissues.

It will be understood that embodiments as described herein may include a drug mixed or compounded with a biodegradable material, excipient, or other agent modifying the release characteristics of the drug. Preferred biodegradable materials include copolymers of lactic acid and glycolic acid, also known as poly (lactic-co-glycolic acid) or PLGA. It will be understood by one skilled in the art that although some disclosure herein specifically describes use of PLGA, other suitable biodegradable materials may be substituted for PLGA or used in combination with PLGA in such embodiments. It will also be understood that in certain embodiments as described herein, the drug positioned within the lumen of the implant is not compounded or mixed with any other compound or material, thereby maximizing the volume of drug that is positioned within the lumen.

It may be desirable, in some embodiments, to provide for a particular rate of release of drug from a PLGA copolymer or other polymeric material. As the release rate of a drug from a polymer correlates with the degradation rate of that polymer, control of the degradation rate provides a means for control of the delivery rate of the drug contained within the therapeutic agent. Variation of the average molecular weight of the polymer or copolymer chains which make up the PLGA copolymer or other polymer may be used to control the degradation rate of the copolymer, thereby achieving a desired duration or other release profile of therapeutic agent delivery to the eye.

In certain other embodiments employing PLGA copolymers, rate of biodegradation of the PLGA copolymer may be controlled by varying the ratio of lactic acid to glycolic acid units in a copolymer.

Still other embodiments may utilize combinations of varying the average molecular weights of the constituents of the copolymer and varying the ratio of lactic acid to glycolic acid in the copolymer to achieve a desired biodegradation rate.

As described above, the outer shell of the implant comprises a polymer in some embodiments. Additionally, the shell may further comprise one or more polymeric coatings in various locations on or within the implant. The outer shell and any polymeric coatings are optionally biodegradable. The biodegradable outer shell and biodegradable polymer coating may be any suitable material including, but not limited to, poly(lactic acid), polyethylene-vinyl acetate, poly(lactic-co-glycolic acid), poly(D,L-lactide), poly(D,L-lactide-co-trimethylene carbonate), collagen, heparinized collagen, poly(caprolactone), poly(glycolic acid), and/or other polymer or copolymer.

As described above, some embodiments of the implants comprise a polymeric outer shell that is permeable to ocular fluids in a controlled fashion depending on the constituents used in forming the shell. For example, the concentration of the polymeric subunits dictates the permeability of the resulting shell. Therefore, the composition of the polymers making up the polymeric shell determines the rate of ocular fluid passage through the polymer and if biodegradable, the rate of biodegradation in ocular fluid. The permeability of the shell will also impact the release of the drug from the shell. Also as described above, the regions of drug release created on the shell will alter the release profile of a drug from the implant. Control of the release of the drug can further be controlled by coatings in or on the shell that either form the regions of drug release, or alter the characteristics of the regions of drug release (e.g., a coating over the region of drug release makes the region thicker, and therefore slows the rate of release of a drug).

In several embodiments as described herein, there are no direct through holes or penetrating apertures needed or utilized to specifically facilitate or control drug elution. As such, in those embodiments, there is no direct contact between the drug core (which may be of very high concentration) and the ocular tissue where adjacent to the site where the implant is positioned. In some cases, direct contact of ocular tissue with high concentrations of drug residing within the implant could lead to local cell toxicity and possible local cell death.

It shall however, be appreciated that, in several other embodiments, disclosed herein, that the number, size, and placement of one or more orifices through the outer shell of the implant may be altered in order to produce a desired drug elution profile. As the number, size, or both, of the orifices increases relative to surface area of the implant, increasing amounts of ocular fluid pass across the outer shell and contact the therapeutic agent on the interior of the implant. Likewise, decreasing the ratio of orifice:outer shell area, less ocular fluid will enter the implant, thereby providing a decreased rate of release of drug from the implant. Additionally, multiple orifices provides a redundant communication means between the ocular environment that the implant is implanted in and the interior of the implant, should one or more orifices become blocked during implantation or after residing in the eye. In other embodiments, the outer shell may contain one (or more) orifice(s) in the distal tip of the implant. As described above, the shape and size of this orifice is selected based on the desired elution profile. In some embodiments, a biodegradable polymer plug is positioned within the distal orifice, thereby acting as a synthetic cork. Tissue trauma or coring of the ocular tissue during the process of implantation is also reduced, which may prevent plugging or partial occlusion of the distal orifice. Additionally, because the polymer plug may be tailored to biodegrade in a known time period, the plug ensures that the implant can be fully positioned before any elution of the drug takes place. Still other embodiments comprise a combination of a distal orifice and multiple orifices placed more proximally on the outer shell, as described above.

Further benefitting the embodiments described herein is the expanded possible range of uses for some ocular therapy drugs. For example, a drug that is highly soluble in ocular fluid may have narrow applicability in treatment regimes, as its efficacy is limited to those pathologies treatable with acute drug administration. However, when coupled with the implants as disclosed herein, such a drug could be utilized in a long term therapeutic regime. A highly soluble drug positioned within the distal portion of the implant containing one or more regions of drug release may be made to yield a particular, long-term controlled release profile.

Alternatively, or in addition to one or more regions of drug release, one or more polymeric coatings may be located outside the implant shell, or within the interior lumen, enveloping or partially enveloping the drug. In some embodiments comprising one or more orifices, the polymeric coating is the first portion of the implant in contact with ocular fluid, and thus, is a primary controller of the rate of entry of ocular fluid into the drug containing interior lumen of the implant. By altering the composition of the polymer coating, the biodegradation rate (if biodegradable), and porosity of the polymer coating the rate at which the drug is exposed to and solublized in the ocular fluid may be controlled. Thus, there is a high degree of control over the rate at which the drug is released from such an embodiment of an implant to the target tissue of the eye. Similarly, a drug with a low ocular fluid solubility may be positioned within an implant coated with a rapidly biodegradable or highly porous polymer coating, allowing increased flow of ocular fluid over the drug within the implant.

In certain embodiments described herein, the polymer coating envelopes the therapeutic agent within the lumen of the implant. In some such embodiments, the ocular fluid passes through the outer shell of the implant and contacts the polymer layer. Such embodiments may be particularly useful when the implant comprises one or more orifices and/or the drug to be delivered is a liquid, slurry, emulsion, or particles, as the polymer layer would not only provide control of the elution of the drug, but would assist in providing a structural barrier to prevent uncontrolled leakage or loss of the drug outwardly through the orifices. The interior positioning of the polymer layer could, however, also be used in implants where the drug is in any form.

In some ocular disorders, therapy may require a defined kinetic profile of administration of drug to the eye. It will be appreciated from the above discussion of various embodiments that the ability to tailor the release rate of a drug from the implant can similarly be used to accomplish achieve a desired kinetic profile. For example the composition of the outer shell and any polymer coatings can be manipulated to provide a particular kinetic profile of release of the drug. Additionally, the design of the implant itself, including the thickness of the shell material, the thickness of the shell in the regions of drug release, the area of the regions of drug release, and the area and/or number of any orifices in the shell provide a means to create a particular drug release profile. Likewise, the use of PLGA copolymers and/or other controlled release materials and excipients, may provide particular kinetic profiles of release of the compounded drug. By tailoring the ratio of lactic to glycolic acid in a copolymer and/or average molecular weight of polymers or copolymers having the drug therein (optionally with one or more other excipients), sustained release of a drug, or other desirable release profile, may be achieved.

In certain embodiments, zero-order release of a drug may be achieved by manipulating any of the features and/or variables discussed above alone or in combination so that the characteristics of the implant are the principal factor controlling drug release from the implant. Similarly, in those embodiments employing PLGA compounded with the drug, tailoring the ratio of lactic to glycolic acid and/or average molecular weights in the copolymer-drug composition can adjust the release kinetics based on the combination of the implant structure and the biodegradation of the PLGA copolymer.

In other embodiments, pseudo zero-order release (or other desired release profile) may be achieved through the adjustment of the composition of the implant shell, the structure and dimension of the regions of drug release, the composition any polymer coatings, and use of certain excipients or compounded formulations (PLGA copolymers), the additive effect over time replicating true zero-order kinetics.

For example, in one embodiment, an implant with a polymer coating allowing entry of ocular fluid into the implant at a known rate may contain a series of pellets that compound PLGA with one or more drugs, wherein the pellets incorporate at least two different PLGA copolymer formulations. Based on the formulation of the first therapeutic agent, each subsequent agent may be compounded with PLGA in a manner as to allow a known quantity of drug to be released in a given unit of time. As each copolymer biodegrades or erodes at its individual and desired rate, the sum total of drug released to the eye over time is in effect released with zero-order kinetics. It will be appreciated that embodiments additionally employing the drug partitions as described herein, operating in conjunction with pellets having multiple PLGA formulations would add an additional level of control over the resulting rate of release and kinetic profile of the drug.

Non-continuous or pulsatile release may also be desirable. This may be achieved, for example, by manufacturing an implant with multiple sub-lumens, each associated with one or more regions of drug release. In some embodiments, additional polymer coatings are used to prevent drug release from certain regions of drug release at a given time, while drug is eluted from other regions of drug release at that time. Other embodiments additionally employ one or more biodegradable partitions as described above to provide permanent or temporary physical barriers within an implant to further tune the amplitude or duration of period of lowered or non-release of drug from the implant. Additionally, by controlling the biodegradation rate of the partition, the length of a drug holiday may be controlled. In some embodiments the biodegradation of the partition may be initiated or enhanced by an external stimulus. In some embodiments, the intraocular injection of a fluid stimulates or enhances biodegradation of the barrier. In some embodiments, the externally originating stimulus is one or more of application of heat, ultrasound, and radio frequency, or laser energy.

Certain embodiments are particularly advantageous as the regions of drug release minimize tissue trauma or coring of the ocular tissue during the process of implantation, as they are not open orifices. Additionally, because the regions are of a known thickness and area (and therefore of a known drug release profile) they can optionally be manufactured to ensure that the implant can be fully positioned before any elution of the drug takes place.

Placement of the drug within the interior of the outer shell may also be used as a mechanism to control drug release. In some embodiments, the lumen may be in a distal position, while in others it may be in a more proximal position, depending on the pathology to be treated. In those embodiments employing a nested or concentric tube device, the agent or agents may be placed within any of the lumens formed between the nested or concentric polymeric shells Further control over drug release is obtained by the placement location of drug in particular embodiments with multiple lumens. For example, when release of the drug is desired soon after implantation, the drug is placed within the implant in a first releasing lumen having a short time period between implantation and exposure of the therapeutic agent to ocular fluid. This is accomplished, for example by juxtaposing the first releasing lumen with a region of drug release having a thin outer shell thickness (or a large area, or both). A second agent, placed in a second releasing lumen with a longer time to ocular fluid exposure elutes drug into the eye after initiation of release of the first drug. This can be accomplished by juxtaposing the second releasing lumen with a region of drug release having a thicker shell or a smaller area (or both). Optionally, this second drug treats side effects caused by the release and activity of the first drug.

It will also be appreciated that the multiple lumens as described above are also useful in achieving a particular concentration profile of released drug. Further, placement location of the drug may be used to achieve periods of drug release followed by periods of no drug release. By way of example, a drug may be placed in a first releasing lumen such that the drug is released into the eye soon after implantation. A second releasing lumen may remain free of drug, or contain an inert bioerodible substance, yielding a period of time wherein no drug is released. A third releasing lumen containing drug could then be exposed to ocular fluids, thus starting a second period of drug release.

It will be appreciated that the ability to alter any one of or combination of the shell characteristics, the characteristics of any polymer coatings, any polymer-drug admixtures, the dimension and number of regions of drug release, the dimension and number of orifices, and the position of drugs within the implant provides a vast degree of flexibility in controlling the rate of drug delivery by the implant.

The drug elution profile may also be controlled by the utilization of multiple drugs contained within the same interior lumen of the implant that are separated by one or more plugs. By way of example, in an implant comprising a single region of drug release in the distal tip of the implant, ocular fluid entering the implant primarily contacts the distal-most drug until a point in time when the distal-most drug is substantially eroded and eluted. During that time, ocular fluid passes through a first semi-permeable partition and begins to erode a second drug, located proximal to the plug. As discussed below, the composition of these first two drugs, and the first plug, as well as the characteristics of the region of drug release may each be controlled to yield an overall desired elution profile, such as an increasing concentration over time or time-dependent delivery of two different doses of drug. Different drugs may also be deployed sequentially with a similar implant embodiment.

Partitions may be used if separation of two drugs is desirable. A partition is optionally biodegradable at a rate equal to or slower than that of the drugs to be delivered by the implant. The partitions are designed for the interior dimensions of a given implant embodiment such that the partition, when in place within the interior lumen of the implant, will seal off the more proximal portion of the lumen from the distal portion of the lumen. The partitions thus create individual compartments within the interior lumen. A first drug may be placed in the more proximal compartment, while a second drug, or a second concentration of the first drug, or an adjuvant agent may be placed in the more distal compartment. As described above, the entry of ocular fluid and rate of drug release is thus controllable and drugs can be released in tandem, in sequence or in a staggered fashion over time.

Partitions may also be used to create separate compartments for therapeutic agents or compounds that may react with one another, but whose reaction is desired at or near ocular tissue, not simply within the implant lumen. As a practical example, if each of two compounds was inactive until in the presence of the other (e.g. a prodrug and a modifier), these two compounds may still be delivered in a single implant having at least one region of drug release associated only with one drug-containing lumen. After the elution of the compounds from the implant to the ocular space the compounds would comingle, becoming active in close proximity to the target tissue. As can be determined from the above description, if more than two drugs are to be delivered in this manner, utilizing an appropriately increased number of partitions to segregate the drugs would be desirable.

In certain embodiments, a proximal barrier serves to seal the therapeutic agent within a distally located interior lumen of the implant. The purpose of such a barrier is to ensure that the ocular fluid from any more distally located points of ocular fluid entry is the primary source of ocular fluid contacting the therapeutic agent. Likewise, a drug impermeable seal is formed that prevents the elution of drug in an anterior direction. Prevention of anterior elution not only prevents dilution of the drug by ocular fluid originating from an anterior portion of the eye, but also reduces potential side effects of drugs delivered by the device. Limiting the elution of the drug to sites originating in the distal region of the implant will enhance the delivery of the drug to the target sites in more posterior regions of the eye. In embodiments that are fully biodegradable, the proximal cap or barrier may comprise a biocompatible biodegradable polymer, characterized by a biodegradation rate slower than all the drugs to be delivered by that implant. It will be appreciated that the proximal cap is useful in those embodiments having a single central lumen running the length of the implant to allow recharging the implant after the first dose of drug has fully eluted. In those embodiments, the single central lumen is present to allow a new drug to be placed within the distal portion of the device, but is preferably sealed off at or near the proximal end to avoid anteriorly directed drug dilution or elution.

Similar to the multiple longitudinally located compartments that may be formed in an implant, drugs may also be positioned within one or more lumens nested within one another. By ordering particularly desirable drugs or concentrations of drugs in nested lumens, one may achieve similarly controlled release or kinetic profiles as described above.

In some embodiments, drugs are variably dimensioned to further tailor the release profile by increasing or limiting ocular fluid flow into the space in between the drug and walls of the interior lumen. For example, if it was optimal to have a first solid or semi solid drug elute more quickly than another solid or semi-solid drug, formation of the first drug to a dimension allowing substantial clearance between the drug and the walls of the interior lumen may be desirable, as ocular fluid entering the implant contacts the drug over a greater surface area. Such drug dimensions are easily variable based on the elution and solubility characteristics of a given drug. Conversely, initial drug elution may be slowed in embodiments with drugs dimensioned so that a minimal amount of residual space remains between the therapeutic agent and the walls of the interior lumen. In still other embodiments, the entirety of the implant lumen is filled with a drug, to maximize either the duration of drug release or limit the need to recharge an implant.

Certain embodiments may comprise a shunt in addition to the drug delivery portion of the implant. For example, once the implant is positioned in the desired intraocular space (in an anterior-posterior direction), a shunt portion of the implant comprising at least one outflow channel can be inserted into a physiological outflow space (for example anchored to the trabecular meshwork and releasing fluid to Schlemm's canal). In some embodiments, a plurality of apertures thus assists in maintaining patency and operability of the drainage shunt portion of the implant. Moreover, as described above, a plurality of apertures can assist in ameliorating any unwanted side effects involving excess fluid production or accumulation that may result from the actions of the therapeutic agent delivered by the implant.

As described above, duration of drug release is desired over an extended period of time. In some embodiments, an implant in accordance with embodiments described herein is capable of delivering a drug at a controlled rate to a target tissue for a period of several (i.e. at least three) months. In certain embodiments, implants can deliver drugs at a controlled rate to target tissues for about 6 months or longer, including 3, 4, 5, 6, 7, 8, 9, 12, 15, 18, and 24 months, without requiring recharging. In still other embodiments, the duration of controlled drug release (without recharging of the implant) exceeds 2 years (e.g., 3, 4, 5, or more years). It shall be appreciated that additional time frames including ranges bordering, overlapping or inclusive of two or more of the values listed above are also used in certain embodiments.

In conjunction with the controlled release of a drug to a target tissue, certain doses of a drug (or drugs) are desirable over time, in certain embodiments. As such, in some embodiments, the total drug load, for example the total load of a steroid, delivered to a target tissue over the lifetime of an implant ranges from about 10 to about 1000 µg. In certain embodiments the total drug load ranges from about 100 to about 900 from about 200 to about 800 from about 300 to about 700 µg, or from about 400 to about 600 µg. In some embodiments, the total drug load ranges from about 10 to about 300 µg, from about 10 to about 500 µg, or about 10 to about 700 µg. In other embodiments, total drug load ranges from about 200 to about 500 µg, from 400 to about 700 µg or from about 600 to about 1000 µg. In still other embodiments, total drug load ranges from about 200 to about 1000 µg, from about 400 to about 1000 µg, or from about 700 to about 1000 µg. In some embodiments total drug load ranges from about 500 to about 700 µg, about 550 to about 700 µg, or about 550 to about 650 µg, including 575, 590, 600, 610, and 625 µg. It shall be appreciated that additional ranges of drugs bordering, overlapping or inclusive of the ranges listed above are also used in certain embodiments.

Similarly, in other embodiments, controlled drug delivery is calculated based on the elution rate of the drug from the implant. In certain such embodiments, an elution rate of a drug, for example, a steroid, is about 0.05 µg/day to about 10 µg/day is achieved. In other embodiments an elution rate of about 0.05 µg/day to about 5 µg/day, about 0.05 µg/day to about 3 µg/day, or about 0.05 µg/day to about 2 µg/day is achieved. In other embodiment, an elution rate of about 2 µg/day to about 5 µg/day, about 4 g/day to about 7 µg/day, or about 6 µg/day to about 10 µg/day is achieved. In other embodiments, an elution rate of about 1 µg/day to about 4 µg/day, about 3 µg/day to about 6 µg/day, or about 7 µg/day to about 10 µg/day is achieved. In still other embodiments, an elution rate of about 0.05 µg/day to about 1 µg/day, including 0.06, 0.07, 0.08, 0.09, 0.1, 0.2, 0.3, 0.4, 0.5, 0.6, 0.7, 0.8, or 0.9 µg/day is achieved. It shall be appreciated that additional ranges of drugs bordering, overlapping or inclusive of the ranges listed above are also used in certain embodiments.

Alternatively, or in addition to one or more of the parameters above, the release of drug from an implant may be controlled based on the desired concentration of the drug at target tissues. In some embodiments, the desired concentration of a drug, for example, a steroid, at the target tissue, ranges from about 1 nM to about 100 nM. In other embodiments the desired concentration of a drug at the site of action ranges from about 10 nM to about 90 nM, from about 20 nM to about 80 nM, from about 30 nM to about 70 nM, or from about 40 nM to about 60 nM. In still other embodiments the desired concentration of a drug at the site of action ranges from about 1 nM to about 40 nM, from about 20 nM to about 60 nM, from about 50 nM to about 70 nM, or from about 60 nM to about 90 nM. In yet other embodiments the desired concentration of a drug at the site of action ranges from about 1 nM to about 30 nM, from about 10 nM to about 50 nM, from about 30 nM to about 70 nM, or from about 60 nM to about 100 nM. In some embodiments, the desired concentration of a drug at the site of action ranges from about 45 nM to about 55 nM, including 46, 47, 48, 49, 50, 51, 52, 53, and 54 nM. It shall be appreciated that additional ranges of drugs bordering, overlapping or inclusive of the ranges listed above are also used in certain embodiments.

Certain embodiments described above are rechargeable.

Optionally, seals for preventing leakage during recharging may be included in the recharging device. Such seals may desirable if, for example, the form of the drug to be refilled is a liquid. Suitable seals for preventing leakage include, for example, an O-ring, a coating, a hydrophilic agent, a hydrophobic agent, and combinations thereof. The coating can be, for example, a silicone coat such as MDX™ silicone fluid.

In other embodiments, recharging entails the advancement of a recharging device through the anterior chamber by way of a one-way valve. See FIGS. 20B and 20C.

Other suitable retention methods may be used to hold the newly placed drug pellet in place. For example, in some embodiments, a deformable O-ring with an inner diameter smaller than the newly placed pellet is used. In such embodiments, the recharging device displaces the O-ring sufficiently to allow passage of the drug pellet through the O-ring. Upon removal of the device, however, the O-ring returns to its original diameter, thereby retaining the pellet within the lumen.

In yet other embodiments a plug made of a "self-healing" material that is penetrable by the recharging device is used. In such embodiments, pressure from the recharging device allows the device to penetrate the plug and deposit a new drug into the interior lumen. Upon withdrawal of the recharging device, the plug re-seals, and retains the drug within the lumen.

The one-way valve may be created of any material sufficiently flexible to allow the insertion and retention of a new drug into the lumen. Such materials include, but are not limited to, silicone, Teflon®, flexible graphite, sponge, silicone rubber, silicone rubber with fiberglass reinforcement, Neoprene®, red rubber, wire inserted red rubber, cork & Neoprene®, vegetable fiber, cork & rubber, cork & nitrile, fiberglass, cloth inserted rubber, vinyl, nitrile, butyl, natural gum rubber, urethane, carbon fiber, fluoroelastomer, and the like.

Drugs

The therapeutic agents utilized with the drug delivery implant, may include one or more drugs provided below, either alone or in combination. The drugs utilized may also be the equivalent of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents may be combined with any number of excipients as is known in the art. In addition to the biodegradable polymeric excipients discussed above, other excipients may be used, including, but not limited to, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silicon dioxide, cornstarch, talc, and the like. The one or more excipients may be included in total amounts as low as about 1%, 5%, or 10% and in other embodiments may be included in total amounts as high as 50%, 70% or 90%.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine); parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluroometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines, immune stimulants, and/or immunosuppressants); MAST cell stabilizer agents such as cromolyn sodium, ketotifen, lodoxamide, nedocrimil, olopadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. Nos. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as *Ginkgo biloba*; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonists such as WIN55-212-2; free radical scavengers such as methoxypolyethylene glycol thioester (MPDTE) or methoxypolyethylene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanoalamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51); and dry eye medications such as cyclosporine, cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; antifungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; antiparasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other antibacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anticoagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; antiplatelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described implant may be combined with embodiments of another illustrated or described shunt. Moreover, the implants described above may be utilized for other purposes. For example, the implants may be used to drain fluid from the anterior chamber to other locations of the eye or outside the eye. Furthermore, various omissions, substitutions and changes in the form of the methods, systems, and devices described herein may be made without departing from the spirit of the disclosure.

One or more of the features illustrated in the drawings and/or described herein may be rearranged and/or combined into a single component or embodied in several components. Additional components may also be added. While certain example embodiments have been described and shown in the accompanying drawings, it is to be understood that such embodiments are merely illustrative of and not restrictive. Thus, the inventions are not limited to the specific constructions and arrangements shown and described, since various other modifications may occur to those ordinarily skilled in the art based on the present disclosure.

Various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Method step and/or actions disclosed herein can be performed in conjunction with each other, and steps and/or actions can be further divided into additional steps and/or actions.

It is to be understood that the claims are not limited to the precise configuration and components illustrated above. Various modifications, changes and variations may be made in the arrangement, operation and details of the methods and apparatus described above.

What is claimed is:

1. A drug delivery ocular implant comprising:
an outer shell having a proximal end and a distal end, the outer shell being shaped to define an interior chamber wherein the outer shell comprises a sidewall extending between the distal end and the proximal end;
a first and a second drug positioned within the outer shell;
a drug barrier within the interior chamber, the drug barrier separating the interior chamber into a first subchamber and a second subchamber, the first drug being positioned within the first subchamber and the second drug being positioned within the second subchamber;
a first drug release element positioned within the interior chamber and extending generally perpendicular to the sidewall, the first drug release element configured to release the first drug from the interior chamber, the first drug release element comprising a first membrane;
a second membrane positioned within the interior chamber and extending generally perpendicular to the sidewall, the second membrane configured to release the second drug from the interior chamber; and
a flange positioned at or near the distal end of the outer shell and extending laterally outward a predetermined distance from a first inlet, the first inlet positioned adjacent the flange and between the flange and the proximal end of the outer shell, the first inlet extending laterally through the sidewall of the outer shell, wherein the flange is configured to impede tissue from covering at least a portion of the first inlet,
wherein the first drug release element is configured such that the first drug passes through the first membrane and out the proximal end of the outer shell,
wherein the second membrane is in fluid communication with the second drug within the interior chamber and in fluid communication with an inlet and outlet fluid flow pathway configured to conduct ocular fluid from an ocular chamber to a physiological fluid outflow pathway, such that the second drug passes through the second membrane, through the inlet and outlet fluid flow pathway, and out the distal end of the outer shell.

2. The ocular implant of claim 1, wherein the first drug release element further comprises:
a distal seal member that includes at least one opening;
a proximal seal member that includes at least one opening; and
the first membrane compressed between the distal seal member and the proximal seal member,
wherein the first drug release element is configured such that the first drug passes through the at least one opening in the distal seal member, through the compressed membrane, through the at least one opening in the proximal seal member, and out the proximal end of the outer shell.

3. The ocular implant of claim 2, further comprising a retainer configured to retain the first drug release element in place relative to the outer shell.

4. The ocular implant of claim 1, wherein the physiological fluid outflow pathway is Schlemm's Canal.

5. The ocular implant of claim 1, wherein the first drug comprises a prostaglandin analog.

6. The ocular implant of claim 5, wherein the prostaglandin analog is selected from the group consisting of bimatoprost, latanoprost, travoprost and unoprostone.

7. The ocular implant of claim 1, wherein the second drug comprises a vasodilator.

8. The ocular implant of claim 7, wherein the vasodilator comprises nitric oxide, a nitric oxide precursor, a nitric oxide analog or a nitric oxide derivative.

9. The ocular implant of claim 8, wherein the nitric oxide precursor comprises L-arginine.

10. The ocular implant of claim 8, wherein the nitric oxide precursor comprises SNAP, hydroxylamine and/or sodium nitroprusside.

11. The ocular implant of claim 1, wherein the implant further includes one or more enzymes that generate nitric oxide.

12. The ocular implant of claim 1, wherein the drug barrier is impermeable to the first and second drug.

13. The ocular implant of claim 1, wherein the drug barrier is positioned to make the first subchamber and the second subchamber equal in volume.

14. The ocular implant of claim 1, wherein the second membrane comprises a material that is semi-permeable or permeable to the second drug.

15. The ocular implant of claim 1, further comprising a second membrane positioned at the distal end of the outer shell, the second membrane configured to release the second drug from the interior chamber.

16. The ocular implant of claim 15, wherein the second membrane comprises a material that is semi-permeable or permeable to the second drug.

17. The ocular implant of claim 15, further comprising a cap having at least one aperture positioned at the proximal end of the outer shell over the first membrane.

18. The ocular implant of claim 1, further comprising a second inlet extending through the sidewall of the outer shell.

19. The ocular implant of claim 1, wherein the first inlet extends through the sidewall of the outer shell in two locations.

20. The ocular implant of claim 1, wherein the inflow and outflow fluid pathway extends generally perpendicular relative to the first inlet and the physiological fluid outflow pathway.

* * * * *